US011053216B2

(12) United States Patent
Rai et al.

(10) Patent No.: US 11,053,216 B2
(45) Date of Patent: *Jul. 6, 2021

(54) COMPOUNDS AND METHODS OF USE

(71) Applicant: Medivation Technologies LLC, New York, NY (US)

(72) Inventors: Roopa Rai, San Francisco, CA (US); Sarvajit Chakravarty, San Francisco, CA (US); Brahmam Pujala, Noida (IN); Bharat Uttam Shinde, Noida (IN); Anjan Kumar Nayak, Noida (IN); Anil Kumar Agarwal, Noida (IN); Sreekanth A. Ramachandran, Noida (IN); Son Minh Pham, San Francisco, CA (US)

(73) Assignee: Medivation Technologies LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/659,775

(22) Filed: Oct. 22, 2019

(65) Prior Publication Data

US 2020/0071296 A1 Mar. 5, 2020

Related U.S. Application Data

(63) Continuation of application No. 15/933,532, filed on Mar. 23, 2018, now Pat. No. 10,501,436, which is a continuation of application No. 15/109,013, filed as application No. PCT/US2014/072922 on Dec. 31, 2014, now Pat. No. 10,030,004.

(30) Foreign Application Priority Data

Jan. 1, 2014 (IN) ................................ 6/DEL/2014

(51) Int. Cl.
*C07D 401/12* (2006.01)
*C07D 401/14* (2006.01)
*C07D 405/14* (2006.01)
*C07D 413/14* (2006.01)
*C07D 471/04* (2006.01)
*C07D 487/04* (2006.01)
*A61K 31/4439* (2006.01)
*A61K 31/444* (2006.01)
*A61K 31/4545* (2006.01)
*A61K 31/4709* (2006.01)
*C07D 213/72* (2006.01)
*C07D 213/73* (2006.01)
*C07D 213/82* (2006.01)
*A61K 45/06* (2006.01)
*A61K 31/506* (2006.01)

(52) U.S. Cl.
CPC .......... *C07D 401/12* (2013.01); *A61K 31/444* (2013.01); *A61K 31/4439* (2013.01); *A61K 31/4545* (2013.01); *A61K 31/4709* (2013.01); *A61K 31/506* (2013.01); *A61K 45/06* (2013.01); *C07D 213/72* (2013.01); *C07D 213/73* (2013.01); *C07D 213/82* (2013.01); *C07D 401/14* (2013.01); *C07D 405/14* (2013.01); *C07D 413/14* (2013.01); *C07D 471/04* (2013.01); *C07D 487/04* (2013.01)

(58) Field of Classification Search
CPC ............. A61K 31/4439; A61K 31/444; A61K 31/4545; A61K 31/4709; A61K 31/506; C07D 213/72; C07D 213/73; C07D 213/82; C07D 401/12; C07D 401/14; C07D 405/14; C07D 413/14; C07D 471/04; C07D 487/04; A61P 11/00; A61P 13/12; A61P 17/00; A61P 19/10; A61P 1/16; A61P 27/02; A61P 29/00; A61P 43/00; A61P 9/00; A61P 9/10; A61P 35/00

See application file for complete search history.

(56) References Cited

U.S. PATENT DOCUMENTS

| | | |
|---|---|---|
| 5,525,604 A | 6/1996 | Lee et al. |
| 5,710,158 A | 1/1998 | Myers et al. |
| 5,714,493 A | 2/1998 | Myers et al. |
| 6,184,226 B1 | 2/2001 | Chakravarty et al. |
| 6,277,989 B1 | 8/2001 | Chakravarty et al. |
| 6,476,031 B1 | 11/2002 | Chakravarty et al. |
| 6,613,776 B2 | 9/2003 | Knegtel et al. |
| 6,645,969 B1 | 11/2003 | Myers et al. |
| 6,660,731 B2 | 12/2003 | Bebbington et al. |
| 6,696,452 B2 | 2/2004 | Davies et al. |

(Continued)

FOREIGN PATENT DOCUMENTS

| | | |
|---|---|---|
| WO | 2004065392 A1 | 8/2004 |
| WO | 2005033105 A2 | 4/2005 |

(Continued)

OTHER PUBLICATIONS

Ananya Mandal, "How to Prevent Cancer", Aug. 29, 2013, pp. 1-4 (Year: 2013).*
Adamali & Maher, "Current and novel drug therapies for idiopathic pulmonary fibrosis," Drug Design, Development and Therapy 2012:6 261-272.
Akhurst & Hata, "Targeting the TGFb signalling pathway in disease," Nature Reviews Drug Discovery, 2012, NIH, vol. 11(10), pp. 790-811.
Bhatia et al., Nature Biotechnology, 2012, Nature Publishing Group, vol. 30(7), pp. 604-610.

(Continued)

*Primary Examiner* — Sarah Pihonak
(74) *Attorney, Agent, or Firm* — Fariba Shoarinejad

(57) ABSTRACT

This disclosure provides compounds and compositions and methods of using those compounds and compositions to treat diseases and disorders associated with excessive transforming growth factor-beta (TGFβ) activity. This disclosure also provides methods of using the compounds in combination with one or more cancer immunotherapies.

19 Claims, No Drawings

(56) References Cited

U.S. PATENT DOCUMENTS

| | | |
|---|---|---|
| 6,903,096 B2 | 6/2005 | Chakravarty et al. |
| 7,008,948 B2 | 3/2006 | Bebbington et al. |
| 7,053,095 B2 | 5/2006 | Munchhof et al. |
| 7,087,603 B2 | 8/2006 | Bebbington et al. |
| 7,098,330 B2 | 8/2006 | Bebbington et al. |
| 7,115,739 B2 | 10/2006 | Bebbington et al. |
| 7,151,110 B2 | 12/2006 | Munchhof et al. |
| 7,153,872 B2 | 12/2006 | Munchhof et al. |
| 7,189,733 B2 | 3/2007 | Scarborough et al. |
| 7,199,123 B2 | 4/2007 | Munchhof |
| 7,223,766 B2 | 5/2007 | Dugar et al. |
| 7,232,824 B2 | 6/2007 | Dugar et al. |
| 7,235,559 B1 | 6/2007 | Mortlock et al. |
| 7,273,936 B2 | 9/2007 | Munchhof et al. |
| 7,314,939 B2 | 1/2008 | Pandey et al. |
| 7,345,045 B2 | 3/2008 | Chakravarty et al. |
| 7,361,669 B2 | 4/2008 | Scarborough et al. |
| 7,368,445 B2 | 5/2008 | Li et al. |
| 7,390,815 B2 | 6/2008 | Davies et al. |
| 7,390,907 B2 | 6/2008 | Chen et al. |
| 7,417,041 B2 | 8/2008 | Blumberg et al. |
| 7,488,740 B2 | 2/2009 | Bakthavatchalam et al. |
| 7,511,056 B2 | 3/2009 | Diefenbacher et al. |
| 7,635,702 B2 | 12/2009 | Munchhof et al. |
| 7,638,537 B2 | 12/2009 | Munchhof et al. |
| 7,691,853 B2 | 4/2010 | Bebbington et al. |
| 7,745,451 B2 | 6/2010 | Kelly et al. |
| 7,767,687 B2 | 8/2010 | Oslob et al. |
| 7,943,640 B2 | 5/2011 | Pandey et al. |
| 7,977,342 B2 | 7/2011 | Simmen et al. |
| 7,982,037 B2 | 7/2011 | Bebbington et al. |
| 8,022,077 B2 | 9/2011 | Simmen et al. |
| 8,030,318 B2 | 10/2011 | Simmen et al. |
| 8,268,857 B2 | 9/2012 | Scarborough et al. |
| 8,426,425 B2 | 4/2013 | Jimenez et al. |
| 8,450,335 B2 | 5/2013 | Singh et al. |
| 8,987,301 B2 | 3/2015 | Jonczyk et al. |
| 9,617,243 B2 | 4/2017 | McMillen et al. |
| 10,030,004 B2 | 7/2018 | Rai et al. |
| 2002/0076799 A1 | 6/2002 | Wang |
| 2003/0225089 A1 | 12/2003 | Jung et al. |
| 2004/0006030 A1 | 1/2004 | Monia et al. |
| 2004/0038856 A1 | 2/2004 | Chakravarty et al. |
| 2004/0106608 A1 | 6/2004 | Munchhof et al. |
| 2004/0110797 A1 | 6/2004 | Munchhof et al. |
| 2004/0110798 A1 | 6/2004 | Munchhof et al. |
| 2004/0116473 A1 | 6/2004 | Munchhof et al. |
| 2004/0116474 A1 | 6/2004 | Munchhof et al. |
| 2004/0127575 A1 | 7/2004 | Ying et al. |
| 2004/0132730 A1 | 7/2004 | Axon et al. |
| 2004/0138188 A1 | 7/2004 | Higgins et al. |
| 2004/0146509 A1 | 7/2004 | Li et al. |
| 2004/0157861 A1 | 8/2004 | Scarborough et al. |
| 2004/0176390 A1 | 9/2004 | Blumberg et al. |
| 2004/0180905 A1 | 9/2004 | Munchhof |
| 2004/0192583 A1 | 9/2004 | Medicherla et al. |
| 2004/0198728 A1 | 10/2004 | Hong et al. |
| 2004/0204431 A1 | 10/2004 | Scarborough et al. |
| 2005/0009815 A1 | 1/2005 | DeVita et al. |
| 2005/0014753 A1 | 1/2005 | Ding et al. |
| 2005/0026933 A1 | 2/2005 | Greenberger et al. |
| 2005/0032835 A1 | 2/2005 | Pandey et al. |
| 2005/0036994 A1 | 2/2005 | Mihara et al. |
| 2005/0171123 A1 | 8/2005 | Chakravarty et al. |
| 2005/0197342 A1 | 9/2005 | Hollingworth et al. |
| 2005/0245508 A1 | 11/2005 | Weller et al. |
| 2005/0267021 A1 | 12/2005 | Schiemann |
| 2006/0025451 A1 | 2/2006 | Munchhof et al. |
| 2006/0128761 A1 | 6/2006 | Munchhof et al. |
| 2006/0217437 A1 | 9/2006 | Burmester |
| 2006/0281763 A1 | 12/2006 | Axon et al. |
| 2007/0043049 A1 | 2/2007 | Bakthavatchalam et al. |
| 2007/0066632 A1 | 3/2007 | Hart et al. |
| 2007/0088037 A1 | 4/2007 | Munchhof et al. |
| 2007/0099950 A1 | 5/2007 | Lim et al. |
| 2007/0117850 A1 | 5/2007 | Munchhof et al. |
| 2007/0142408 A1 | 6/2007 | Scarborough et al. |
| 2007/0155722 A1 | 7/2007 | Li et al. |
| 2008/0038271 A1 | 2/2008 | Amler et al. |
| 2008/0108656 A1 | 5/2008 | Pandey et al. |
| 2008/0262004 A1 | 10/2008 | Diefenbacher et al. |
| 2008/0275235 A1 | 11/2008 | Blumberg et al. |
| 2008/0280891 A1 | 11/2008 | Kelly et al. |
| 2009/0029992 A1 | 1/2009 | Agoston et al. |
| 2009/0074790 A1 | 3/2009 | Reiss et al. |
| 2009/0176870 A1 | 7/2009 | Burmester |
| 2009/0247523 A1 | 10/2009 | Raboisson et al. |
| 2009/0286767 A1 | 11/2009 | Bakthavatchalam et al. |
| 2010/0022507 A1 | 1/2010 | Jimenez et al. |
| 2010/0056571 A1 | 3/2010 | Munchhof et al. |
| 2010/0099642 A1 | 4/2010 | Grainger |
| 2011/0257208 A1 | 10/2011 | Duncton et al. |
| 2012/0101095 A1 | 4/2012 | Hoelzemann et al. |
| 2012/0122212 A1 | 5/2012 | Grskovic et al. |
| 2012/0214233 A1 | 8/2012 | Schiemann |
| 2012/0225875 A1 | 9/2012 | Jonczyk et al. |
| 2012/0316166 A1 | 12/2012 | Jonczyk et al. |
| 2013/0053341 A1 | 2/2013 | Suzuki et al. |
| 2013/0090323 A1 | 4/2013 | Dransfield et al. |
| 2013/0116430 A1 | 5/2013 | Fujiwara et al. |
| 2014/0328860 A1 | 11/2014 | Scandura et al. |
| 2016/0176871 A1 | 6/2016 | Fink et al. |

FOREIGN PATENT DOCUMENTS

| | | | |
|---|---|---|---|
| WO | 2005047279 A1 | 5/2005 | |
| WO | 2005065691 A1 | 7/2005 | |
| WO | 2006037117 A1 | 4/2006 | |
| WO | 2006105222 A2 | 10/2006 | |
| WO | 2008057402 A2 | 5/2008 | |
| WO | 2009012375 A2 | 1/2009 | |
| WO | 2009022171 A1 | 2/2009 | |
| WO | 2010081881 A1 | 7/2010 | |
| WO | 2010129053 A2 | 11/2010 | |
| WO | 2011044181 A1 | 4/2011 | |
| WO | 2011054433 A1 | 5/2011 | |
| WO | 2011146287 A1 | 11/2011 | |
| WO | 2012041476 A1 | 4/2012 | |
| WO | 2012061418 A2 | 5/2012 | |
| WO | 2012119690 A1 | 9/2012 | |
| WO | 2012142329 A1 | 10/2012 | |
| WO | 2012166617 A2 | 12/2012 | |
| WO | WO-2012177624 A2 * | 12/2012 | ........... A61N 5/1042 |
| WO | 2013040863 A1 | 3/2013 | |
| WO | 2013158422 A1 | 10/2013 | |
| WO | 2013175415 A1 | 11/2013 | |
| WO | 2013192125 A1 | 12/2013 | |
| WO | 2014147203 A1 | 9/2014 | |
| WO | 2014181287 A1 | 11/2014 | |
| WO | 2015103453 A1 | 7/2015 | |

OTHER PUBLICATIONS

Bhola, "TGF-b inhibition enhances chemotherapy action against triple-negative breast cancer," J Clin Invest. 2013;123(3):1348-1358.

Buijs et al., "The role of TGF-b in bone metastasis: novel therapeutic perspectives," BoneKEy Reports 1, article No. 96, 10 pages, 2012.

Calone & Souchelnytskyi, "Inhibition of TGFb signaling and its implications in anticancer treatments," Experimental Oncology, 2012, vol. 34, pp. 9-16.

Choi et al., "Pirfenidone inhibits transforming growth factor-b1-induced fibrogenesis by blocking nuclear translocation of Smads in human retinal pigment epithelial cell line ARPE-19," Molecular Vision 2012; 18:1010-1020.

Connolly et al., "Complexities of TGF-b Targeted Cancer Therapy," Int. J. Biol. Sci. 2012, 8, 15 pages.

Gan et al., "Pirfenidone treatment of idiopathic pulmonary fibrosis," Therapeutics and Clinical Risk Management 2011:7 39-47, 2011.

(56) References Cited

OTHER PUBLICATIONS

Gellibert et al., "Design of novel quinazoline derivatives and related analogues as potent and selective ALK5 inhibitors," Bioorganic & Medicinal Chemistry Letters 19, 2277-81, 2009.
Hisatomi et al., "Pirfenidone inhibits TGF-b1-induced overexpression; of collagen type I and heat shock; protein 47 in A549 cells," BMC Pulmonary Medicine 2012, 12:24, 9 pages.
Hong et al., "Diamino-C,N-diarylpyridine positional isomers as inhibitors of lysophosphatidic acid aceyltransferase-b," Bioorganic & Medicinal Chemistry Letters 15, 4703-07, 2005.
International Search Report & Written Opinion for PCT/US2014/072922, dated Feb. 16, 2015, 14 pages.
Izbicki et al., "Time course of bleomycin-induced lung fibrosis," Int. J. Exp. Path. 83, 111-19, 2002.
Kaiser, Science, 2012, AAAS, vol. 337, pp. 282-284.
Lebrun, ISRN Molecular Biology, 2012, International Scholarly Research Network, vol. 2012, pp. 1-29.
Lovering et al., Identification and SAR of squarate inhibitors of mitogen activated protein kinase-activated protein kinase 2 (MK-2), Bioorganic & Medicinal Chemistry 17, 3342-51, 2009.
Mohammad et al., "TGF-b-RI Kinase Inhibitor SD-208 Reduces the Development and Progression of Melanoma Bone Metastases," Cancer Res. 71, 175-84, published online 2010.
Moulder et al., "Epidermal Growth Factor Receptor (HER1) Tyrosine Kinase Inhibitor ZD1839; (Iressa) Inhibits HER2/neu (erbB2)-overexpressing Breast Cancer Cells; in Vitro and in Vivo," Cancer Research 61, 8887-8895, Dec. 15, 2001.
Norman et al., "Novel Vanilloid Receptor-1 Antagonists: 1. Conformationally Restricted Analogues of trans-Cinnamides," J. Med. Chem. 50, 3497-514, 2007.
Peng et al., "Bleomycin Induces Molecular changes Directly Relevant to Idiopathic Pulmonary Fibrosis: A Model for Active Disease," PLoS ONE 8(4), 359348, 15 pages, 2013.
Rai et al., Notice of Allowance and Notice of Allowability for U.S. Appl. No. 15/109,013 dated Mar. 14, 2018, 9 pages.
Rai et al., Response to final office action for U.S. Appl. No. 15/109,013, filed Feb. 26, 2018, 13 pages.
Rai et al., U.S. Appl. No. 15/933,532 allowed claims, 7 pages, Jul. 23, 2019.
Rai et al., U.S. Appl. No. 15/933,532 amendment filed Oct. 21, 2019 under 37 C.F.R. § 1.312, 9 pages.
Rai et al., U.S. Pat. No. 10,030,004 issued claims, 3 pages, Jul. 24, 2018.
Tesseur et al., "Deficiency in neuronal TGF-b signaling promotes neurodegeneration and Alzheimer's pathology," The Journal of Clinical Investigation, 2006, vol. 116(11), pp. 3060-3069.
Williams, "Discontinued drugs in 2012: oncology drugs," Expert Opinion in Investigational Drugs, 2013, Informa Ltd UK, vol. 22(12), pp. 1627-1644.
Wistuba et al., Nature Reviews Clin Oncology, 2011, Nature Publishing Group, vol. 8, pp. 135-141.
Zigmond et al., "Utilization of Murine Colonoscopy for Orthotopic Implantation of Colorectal Cancer," PLoS ONE 6(12), e28858, 7 pages, 2011.
Cook, M., et al., "Tautomeric Pyridine. Part 22. The Effect of Intermolecular Hydrogen Bonding on the Tautomeric Structure of 4-Amino-1, 10-phenanthrolines", Journal of the Chemical Society 1978, vol. 12, pp. 1215-1222.

* cited by examiner

COMPOUNDS AND METHODS OF USE

Each reference cited in this disclosure is incorporated herein by reference in its entirety.

TECHNICAL FIELD

This disclosure relates generally to compounds and compositions useful for treatment (therapy) of conditions associated with excessive transforming growth factor-beta (TGFβ) activity, and can also be used in combination with one or more cancer immunotherapies.

DETAILED DESCRIPTION

The present invention provides compounds processes for their preparation, pharmaceutical compositions containing them, and methods of using those compounds and compositions for the treatment of conditions associated with excessive transforming growth factor-beta (TGFβ) activity, as described below.

TGFβ belongs to a superfamily of multifunctional proteins that includes, for example, TGFβ1, TGFβ2, and TGFβ3, which are pleiotropic modulators of cell growth and differentiation, embryonic and bone development, extracellular matrix formation, hematopoiesis, and immune and inflammatory responses (Roberts and Sporn *Handbook of Experimental Pharmacology* (1990) 95:419-58; Massague, et al., *Ann. Rev. Cell. Biol.* (1990) 6:597-646). For example, TGFβ1 inhibits the growth of many cell types, including epithelial cells, but stimulates the proliferation of various types of mesenchymal cells. Other members of this superfamily include activin, inhibin, bone morphogenic protein, and Mullerian inhibiting substance. The members of the TGFβ family initiate intracellular signaling pathways leading ultimately to the expression of genes that regulate the cell cycle, control proliferative responses, or relate to extracellular matrix proteins that mediate outside-in cell signaling, cell adhesion, migration and intercellular communication.

Therefore, inhibitors of the TGFβ intracellular signaling pathway are recognized as being useful primarily for the treatment of fibroproliferative diseases. Fibroproliferative diseases include kidney disorders associated with unregulated TGFβ activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fasciitis, morphea, or those associated with the occurrence of Raynaud's syndrome. Lung fibroses resulting from excessive TGFβ activity include adult respiratory distress syndrome, chronic obstructive pulmonary disease (COPD), idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Fibroproliferative conditions can be associated with surgical eye procedures. Such procedures include retinal reattachment surgery accompanying proliferative vitreoretinopathy, cataract extraction with intraocular lens implantation, and post glaucoma drainage surgery.

In addition, members of the TGFβ family are associated with the progression of various cancers, M. P. de Caestecker, E. Piek, and A. B. Roberts, *J. National Cancer Inst.*, 92(17), 1388-1402 (2000) and members of the TGFβ family are expressed in large amounts in many tumors. Derynck, *Trends Biochem. Sci.*, 1994, 19, 548-553. For example, it has been found that TGFβ1 inhibits the formation of tumors, probably by inhibition of the proliferation of non-transformed cells. However, once a tumor forms, TGFβ 1 promotes the growth of the tumor. N. Dumont and C. L. Arteaga, *Breast Cancer Res.*, Vol. 2, 125-132 (2000). Thus, inhibitors of the TGFβ pathway are also recognized as being useful for the treatment of many forms of cancer, such as lung cancer, skin cancer, and colorectal cancer. In particular, they are considered to be useful for the treatment of cancers of the breast, pancreas, and brain, including glioma.

For simplicity and illustrative purposes, the principles of the invention are described by referring mainly to specific illustrative embodiments thereof. In addition, in the following description, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

In additional to the compounds that are specifically illustrated, applicants also intend to include any and all stereoisomers, including geometric isomers (cis/trans or E/Z isomers), tautomers, salts, N-oxides, and solvates of the compounds and such alternatives also can be used in the disclosed methods.

Compounds

The compounds disclosed herein fall within formula (I):

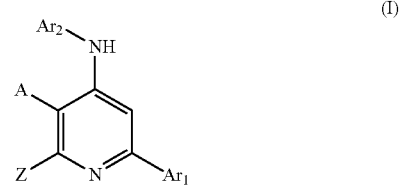

(I)

wherein Ar₁ represents an optionally substituted aryl (such as an optionally substituted phenyl), or an optionally substituted heteroaryl (such as an optionally substituted pyridyl);

A represents H, halogen, amino, alkyl, alkenyl, alkynyl, alkoxy, cycloalkyl, cycloalkenyl, or heterocyclyl wherein the amino, alkyl, alkenyl, alkynyl, alkoxy, cycloalkyl, or heterocyclyl can also be substituted;

Z represents H, halogen, amino, alkyl, alkenyl, alkynyl, alkoxy, cycloalkyl, or heterocyclyl wherein the amino, alkyl, alkenyl, alkynyl, alkoxy, cycloalkyl, or heterocyclyl can also be substituted;

Ar₂ represents an optionally substituted aryl (such as an optionally substituted phenyl), or an optionally substituted heteroaryl (such as an optionally substituted pyridyl, or an optionally substituted pyrazolyl).

The invention also contemplates pharmaceutically acceptable salts of such compounds.

In some embodiments, $Ar_1$ in the compounds of formula (I) can be one of

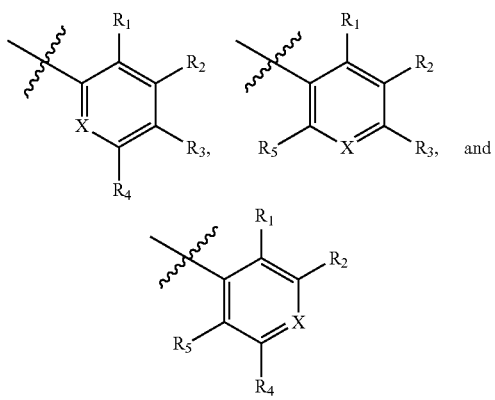

and

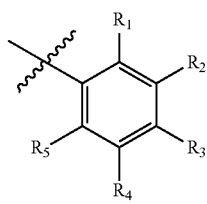

wherein X is N or C—$R_6$ and wherein each of $R_1$, $R_2$, $R_3$, $R_4$, $R_5$, and $R_6$ is independently H, halogen, or alkyl, where the alkyl can also be substituted.

In one embodiment of the compounds of formula (I). $Ar_1$ is

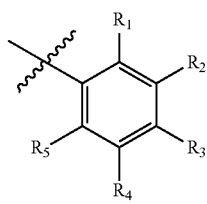

wherein each $R_1$, $R_2$, $R_3$, $R_4$, and $R_5$ is independently selected from H, halogen, or alkyl, where the alkyl can also be substituted. In some embodiments, the alkyl is substituted with a substituent selected from the group consisting of halogen, hydroxy, amino, cyano, mercapto, alkoxy, aryloxy, nitro, oxo, carboxyl, carbamoyl, cycloalkyl, aryl, heterocycloalkyl, heteroaryl, alkylsulfonyl, arylsulfonyl, and —$OCF_3$.

In some embodiments, $R_1$, $R_2$, $R_3$, $R_4$, and $R_5$ independently are selected from the group consisting of halogen, hydroxy, amino, cyano, alkoxy, nitro, mercapto, carboxyl, carbamoyl, alkyl, substituted alkyl. —$OCF_3$, alkylsulfonyl, arylsulfonyl, heterocyclyl, and heteroaryl.

Thus, one subset of structures for $Ar_1$ include:

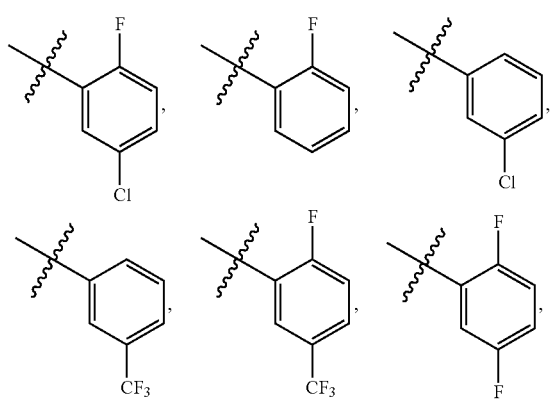

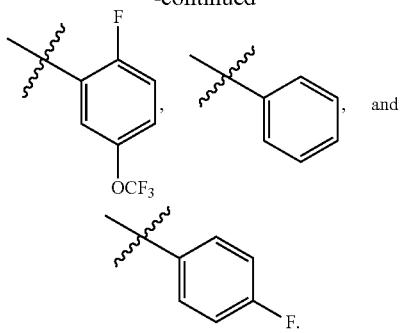

and

In another embodiment of the compounds of formula (I), $Ar_1$ is selected from the group consisting of the following structures:

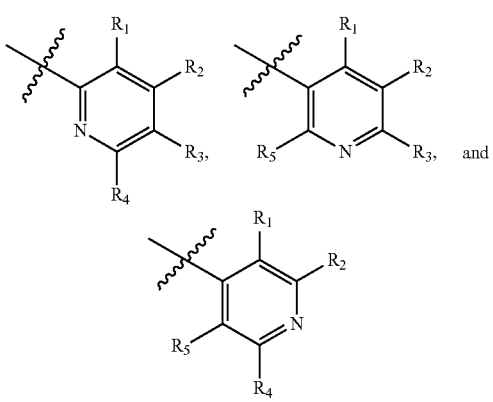

and wherein each of $R_1$, $R_2$, $R_3$, $R_4$, and $R_5$ is independently H, halogen, or alkyl, where the alkyl can also be substituted.

Thus, another subset of structures for $Ar_1$ include the following structures:

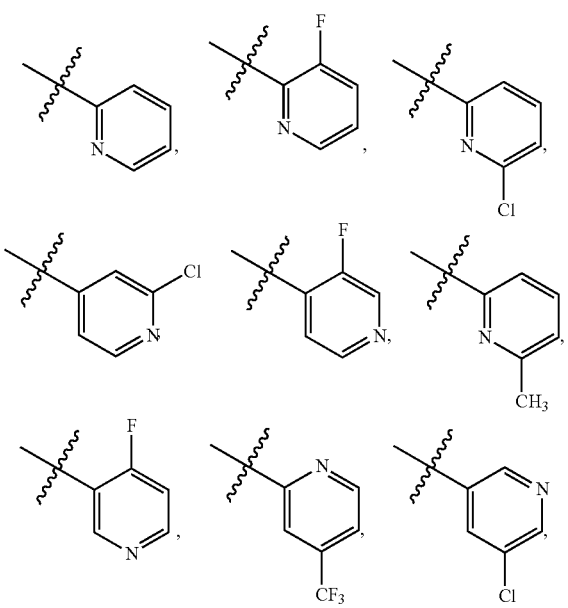

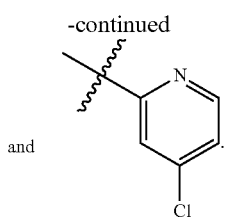

One subset of structures for $Ar_2$ include the following structures:

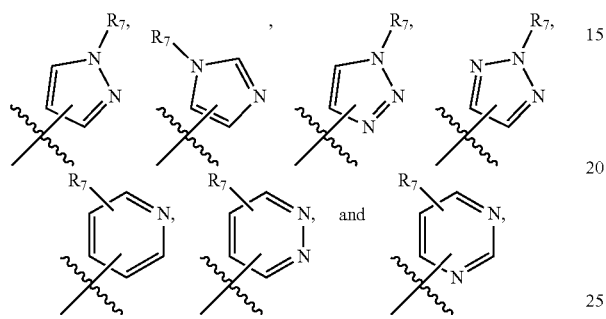

wherein $R_7$ is alkyl, or a substituted alkyl. One particular substituted alkyl for $R_7$, is

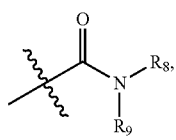

wherein $R_8$ and $R_9$ are independently selected from H, or alkyl, and where the alkyl can also be substituted; or $R_8$ and $R_9$ can be joined together to form an optionally substituted 3-8 membered heterocyclic ring (heterocyclyl).

In particular embodiments. $Ar_2$ can be

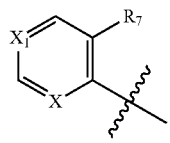

wherein $X_1$ and X are independently N, or CH, and where $R_7$ is alkyl, substituted alkyl, cycloalkyl or heterocyclyl. In one such embodiment, $X_1$ is N, X is CH, and $R_7$ is

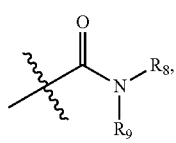

wherein $R_8$ and $R_9$ are independently selected from H, or alkyl, and where the alkyl can also be substituted; or wherein $R_8$ and $R_9$ can be joined together to form an optionally substituted 3-8 membered heterocyclic (heterocyclyl) ring. In another such embodiment, $X_1$ is N, X is CH, and $R_7$ is oxazol-2-yl or thiazol-2-yl.

Table 1 below presents a variety of suitable substituted alkyls for use as $R_7$ in the formulae above.

TABLE 1

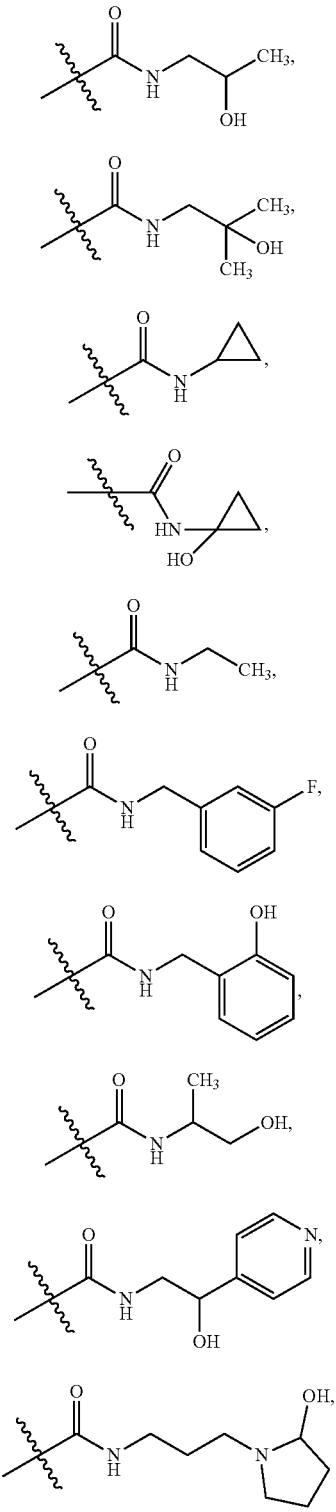

TABLE 1-continued
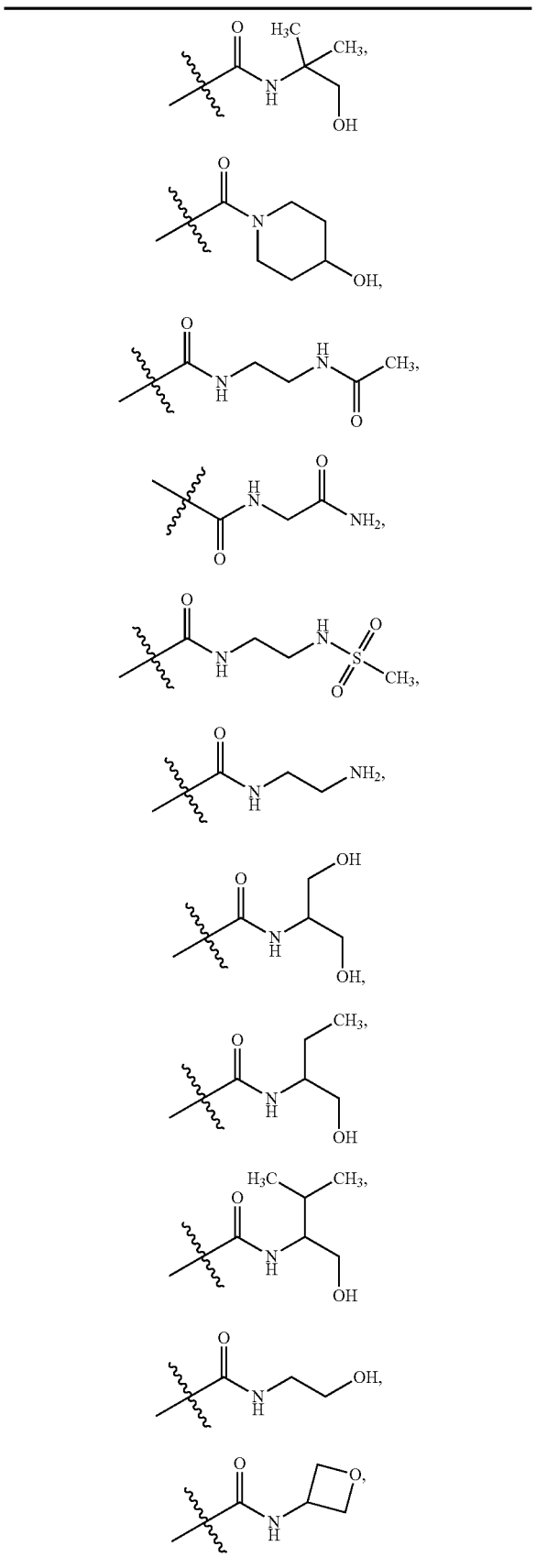
TABLE 1-continued
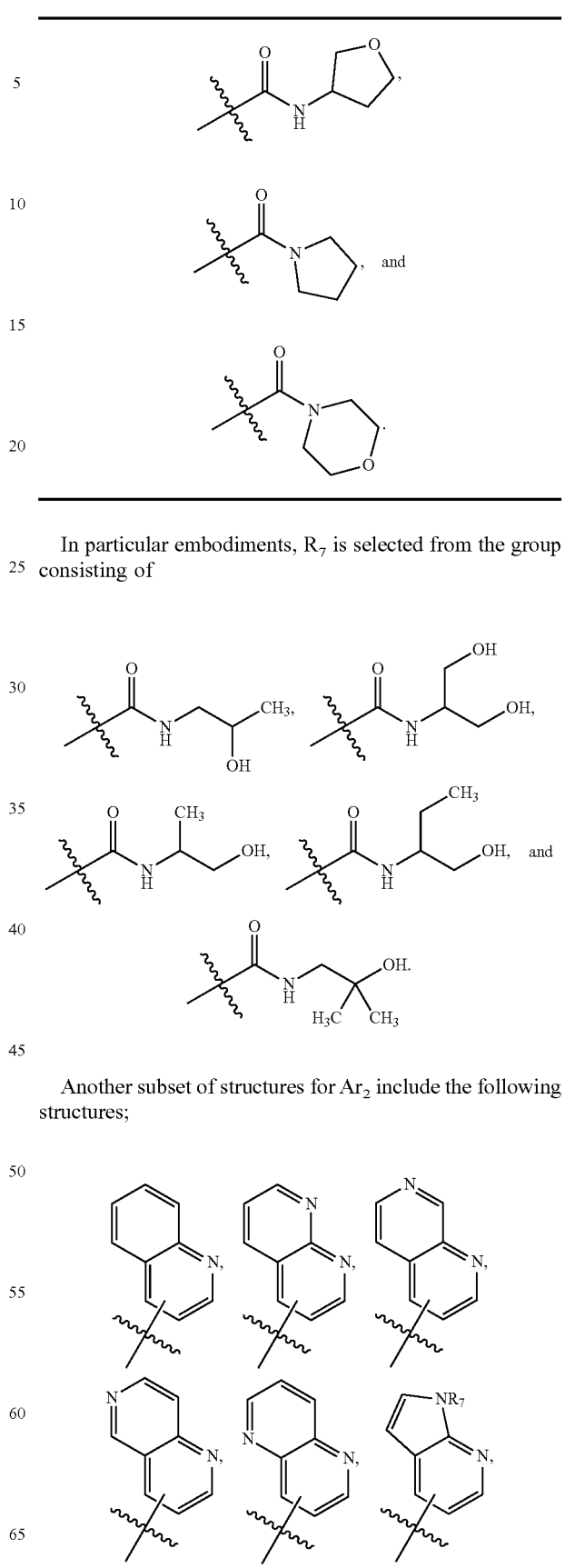
In particular embodiments, $R_7$ is selected from the group consisting of
Another subset of structures for $Ar_2$ include the following structures;

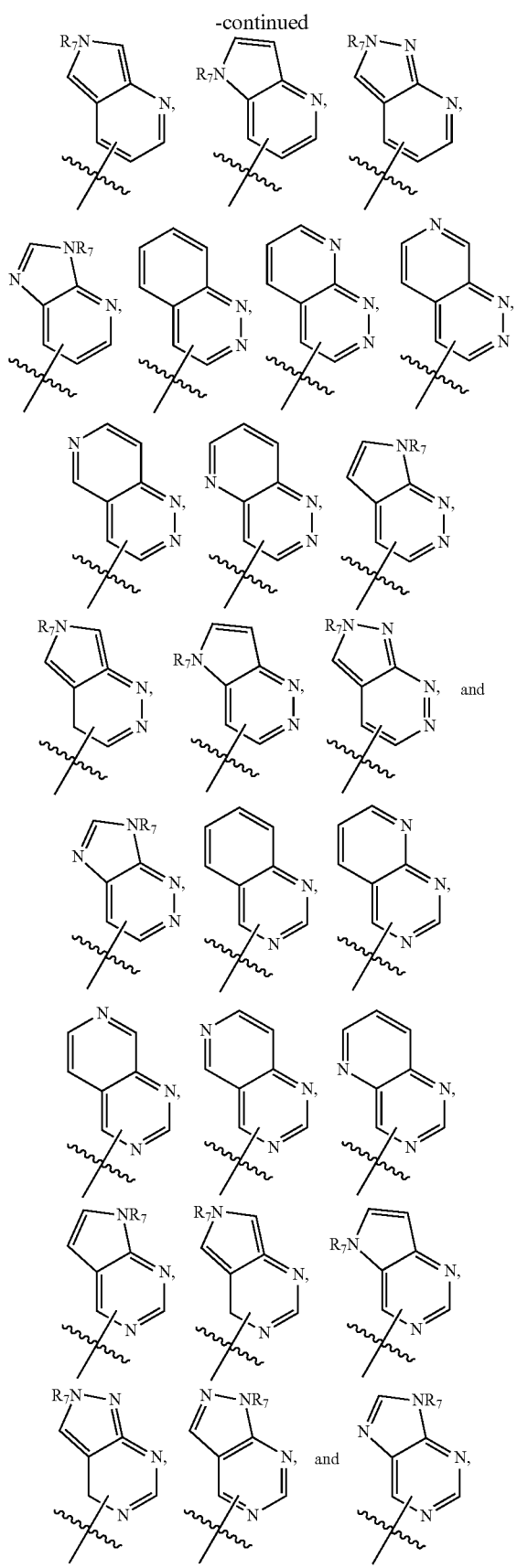
wherein R₇ is H or alkyl.
In particular embodiments, Ar₂ can be a bicyclic heteroaryl selected from the group consisting of
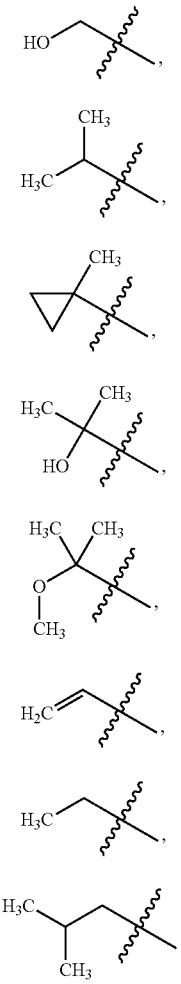
Table 2 below presents a variety of suitable substituents for use as A or Z in the formulae above.
TABLE 2
F, Cl, Br, —CH₃, CF₃ —NH₂,
[structures shown]

TABLE 2-continued
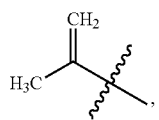
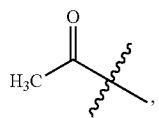
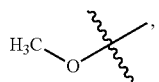
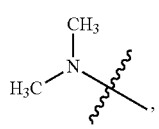
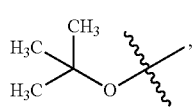
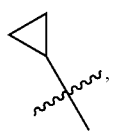
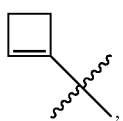
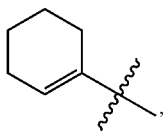 [SMILES: *C1=CCCCC1]
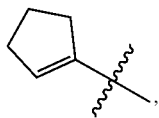 [SMILES: *C1=CCCC1]
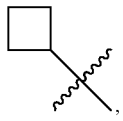
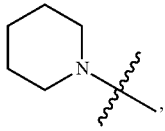 [SMILES: *N1CCCCC1]
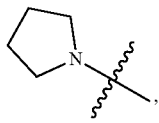 [SMILES: *N1CCCC1]
TABLE 2-continued
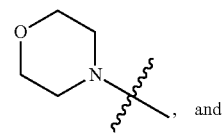 [SMILES: *N1CCOCC1], and
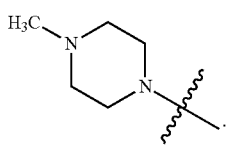 [SMILES: *N1CCN(C)CC1].
In particular embodiments, A is selected from the group consisting of
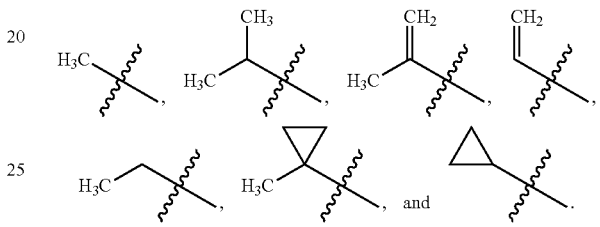
In particular embodiments, Z is H.
In one embodiment, the compound of formula (I) is of the formulae (A), (B), (C), and (D):
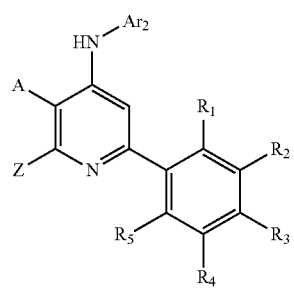 (A)
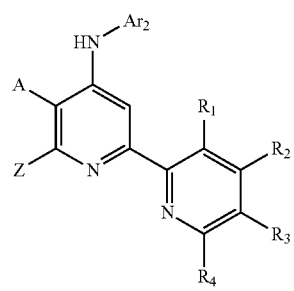 (B)
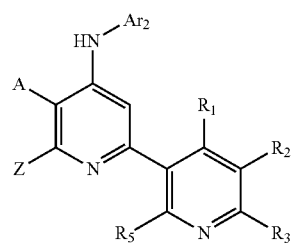 (C)

(D)

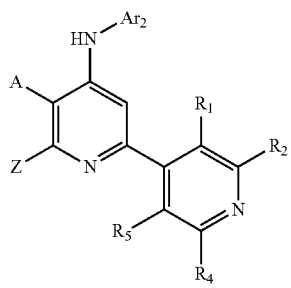

or a salt thereof, wherein A, Z. Ar$_2$. R$_1$, R$_2$, R$_3$, and R$_4$ are as described for formula (I). In some preferred embodiments, the compound is of formula (A). In other preferred embodiments, the compound is of formula (B).

In some embodiments, the compound of formula (A) is of the formulae (Aa), (Ab), (Ac), (Ad), (Ae) and (Af):

(Aa)

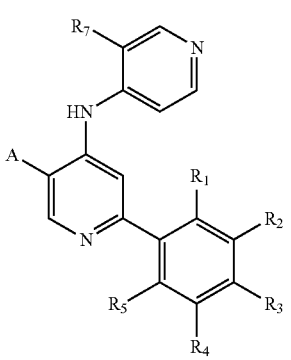

(Ab)

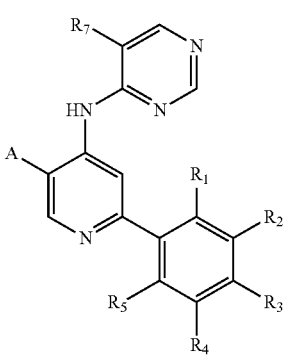

(Ac)

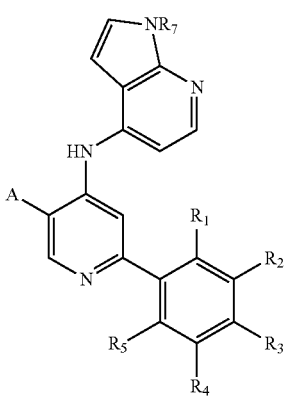

(Ad)

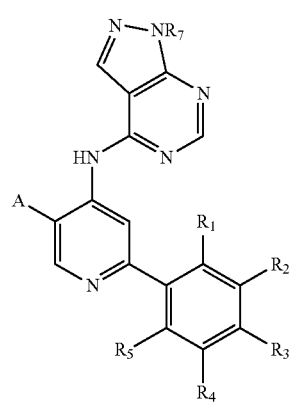

(Ae)

(Af)

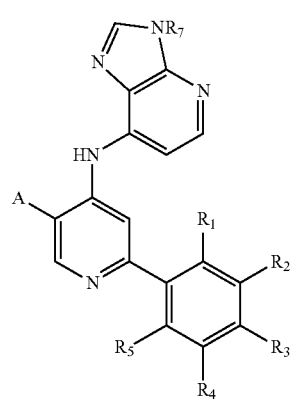

or a salt thereof, where in each of (Aa), (Ab), (Ac), (Ad), (Ae) and (Af), the substituents A, R$_1$, R$_2$, R$_3$, R$_4$, R$_5$ and R$_7$, where present, are as described for formula (I) or any applicable variation thereof. In preferred embodiments, the compound is of formula (Aa).

In some embodiments, the compound of formula (Aa) is of the formulae (Aa-1), (Aa-2). (Aa-3), (Aa-4), (Aa-5). (Aa-6), (Aa-7), (Aa-8), and (Aa-9):

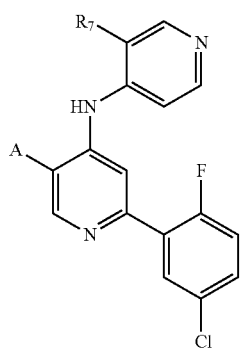 (Aa-1)
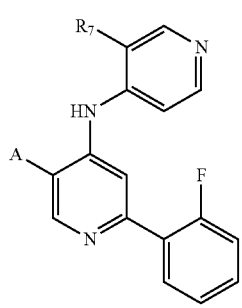 (Aa-2)
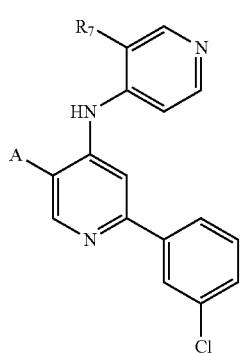 (Aa-3)
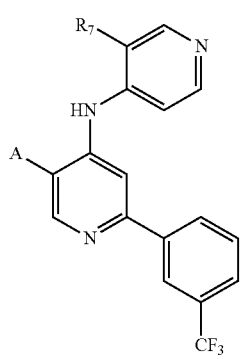 (Aa-4)
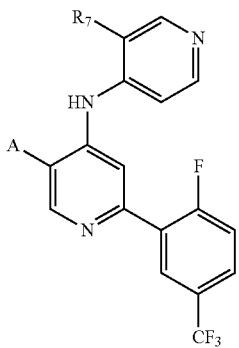 (Aa-5)
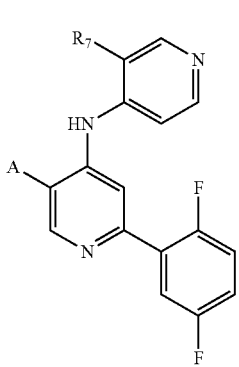 (Aa-6)
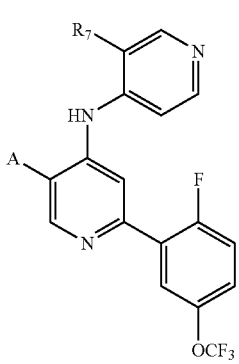 (Aa-7)
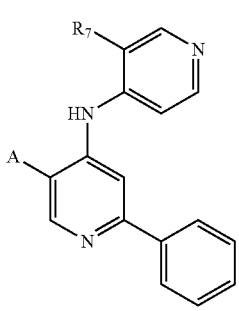 (Aa-8)

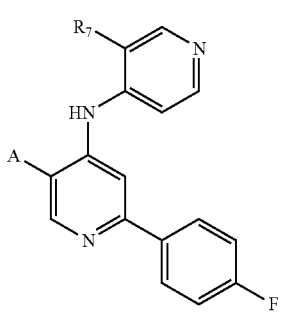
(Aa-9)

or a salt thereof, where in each of (Aa-1), (Aa-2), (Aa-3). (Aa-4), (Aa-5), (Aa-6), (Aa-7). (Aa-8), and (Aa-9), the substituents A and R₇ are as described for formula (I), or any applicable variation thereof. In preferred embodiments, the compound is of formula (Aa-1).

In some embodiments, the compound of formula (Aa-1) is of the formulae (Aa-1a), (Aa-1b), (Aa-1c), (Aa-1d), (Aa-1e), (Aa-1f), and (Aa-1g):

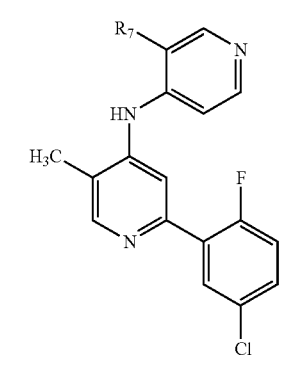
(Aa-1a)

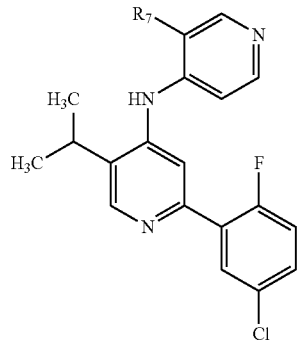
(Aa-1b)

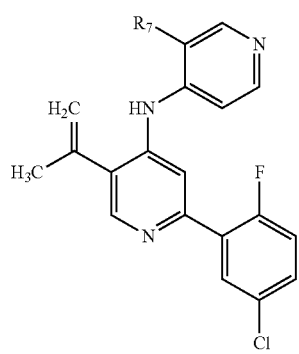
(Aa-1c)

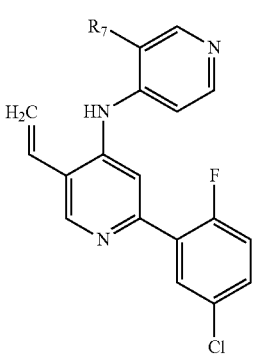
(Aa-1d)

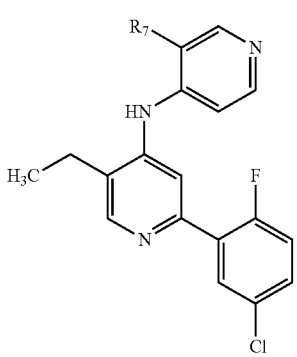
(Aa-1e)

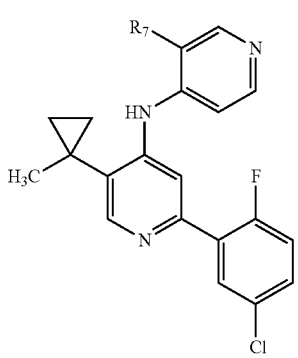
(Aa-1f)

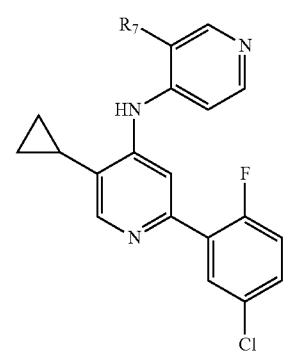
(Aa-1g)

or a salt thereof, where in each of (Aa-1a), Aa-1 b), (Aa-1c), (Aa-1d), (Aa-1e), (Aa-1f), and (Aa-1g), the substituent R₇ is as described for formula (I), or any applicable variation thereof. In preferred embodiments, R₇ is

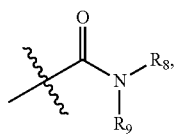

wherein $R_8$ and $R_9$ are independently selected from H. or alkyl, and where the alkyl can also be substituted; or $R_8$ and $R_9$ can be joined together to form an optionally substituted 3-8 membered heterocyclic ring (heterocyclyl). In particular embodiments, $R_7$ is selected from the group consisting of

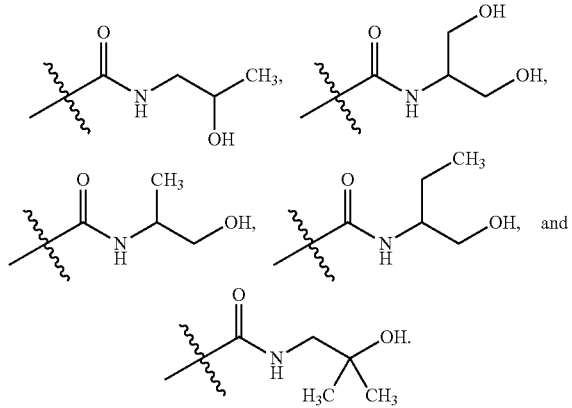

In some embodiments, the compound is of the formula (Aa-1a), wherein $R_7$ is

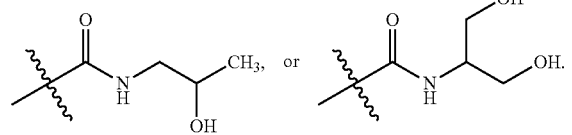

In some embodiments, the compound is of the formula (Aa-1b), wherein $R_7$ is

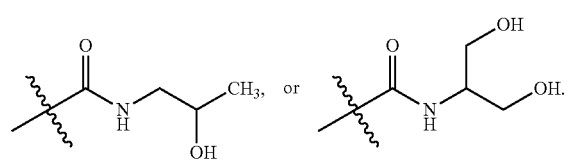 [SMILES: *C(=O)NCC(C)O ; "or" ; *C(=O)NC(CO)CO]

In some embodiments, the compound is of the formula (Aa-1c), wherein $R_7$ is

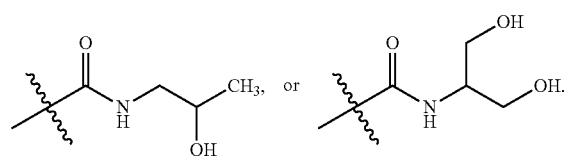 [SMILES: *C(=O)NCC(C)O ; "or" ; *C(=O)NC(CO)CO]

In some embodiments, the compound is of the formula (Aa-1d), wherein $R_7$ is

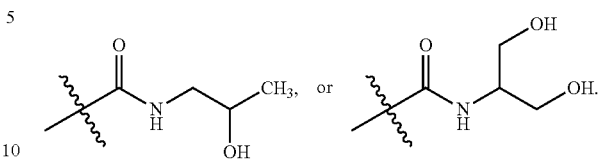

In some embodiments, the compound is of the formula (Aa-1e), wherein R; is

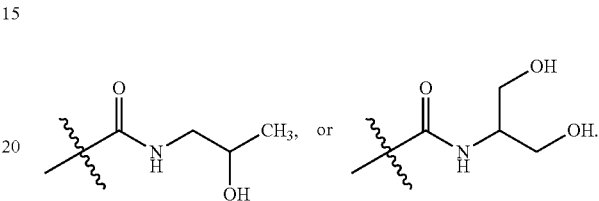

In some embodiments, the compound is of the formula (Aa-1 f), wherein $R_7$ is

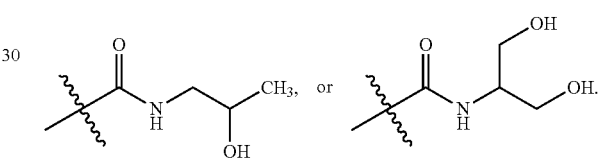

In some embodiments, the compound is of the formula (Aa-1g), wherein $R_7$ is

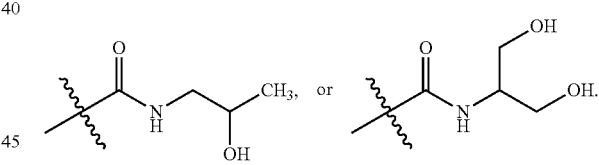

In some embodiments, the compound of formulae (Ab), (Ac), (Ad), (Ae) and (Af) is of the formulae (Ab-1), (Ac-1), (Ad-1), (Ae-1) and (Af-1):

(Ab-1)

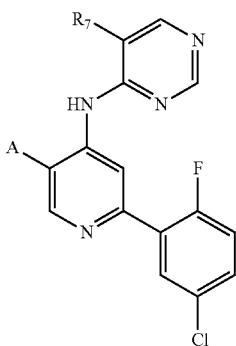

-continued (Ac-1)
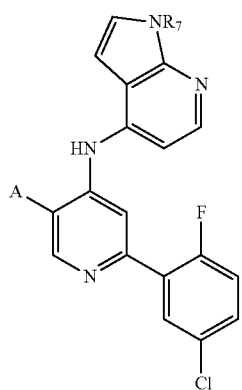

(Ad-1)
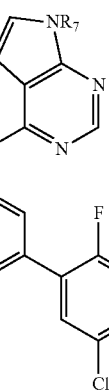

(Ae-1)
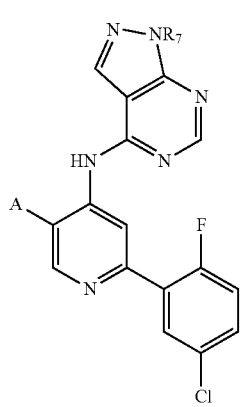

(Af-1)
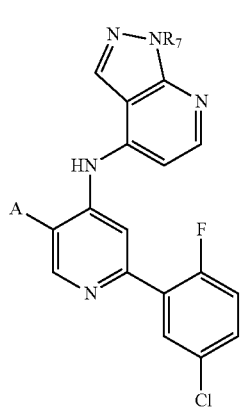

or a salt thereof, wherein each of (Ab-1), (Ac-1), (Ad-1), (Ae-1) and (Af-1), the substituents A and $R_7$, where present, are as described for formula (I) or any applicable variation thereof. In particular embodiments, $R_7$ is H or $CH_3$.

In some embodiments, the compound is of formula (Ab-1), wherein A is

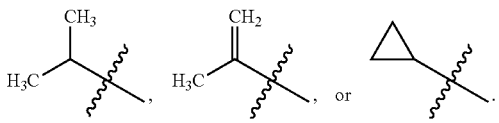

In some embodiments, the compound is of formula (Ac-1), wherein A is

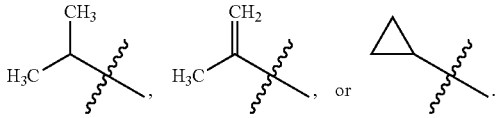

In some embodiments, the compound is of formula (Ad-1), wherein A is

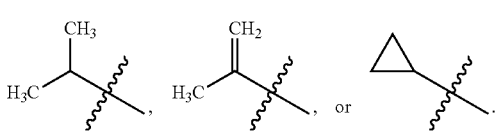

In some embodiments, the compound is of formula (Ae-1), wherein A is

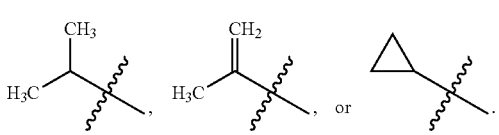

In some embodiments, the compound is of formula (Af-1), wherein A is

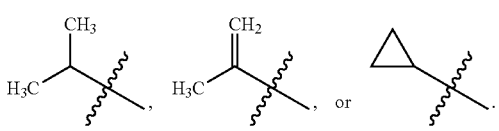

In some embodiments, the compound of formula (B) is of the formulae (Ba), (Bb), (Bc), (Bd), (Be) and (Bf):

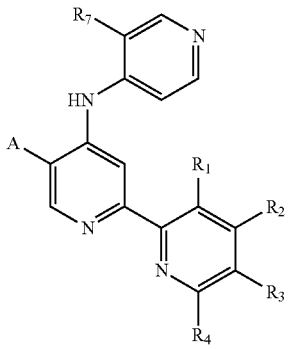
(Ba)

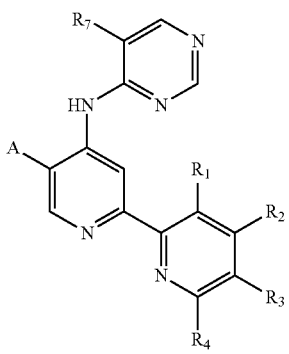
(Bb)

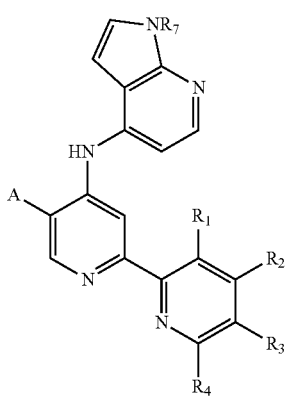
(Bc)

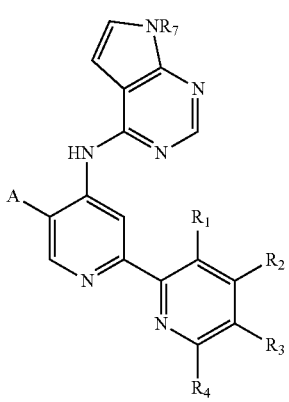
(Bd)

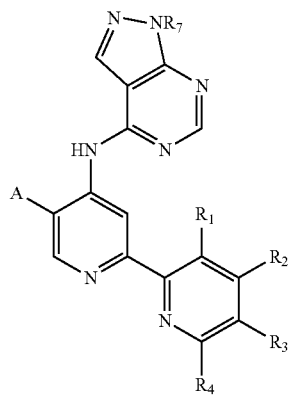
(Be)

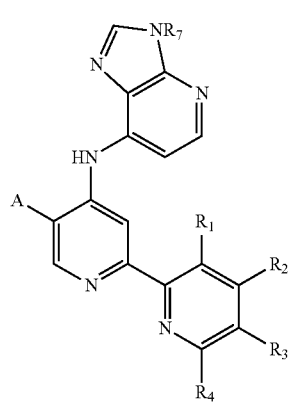
(Bf)

or a salt thereof, where in each of (Ba), (Bb), (Bc), (Bd), (Be) and (Bf), the substituents A, $R_1$, $R_2$, $R_3$, $R_4$, and $R_7$, where present, are as described for formula (I) or any applicable variation thereof. In particular embodiments, $R_7$ is H or $CH_3$.

In some embodiments, the compound of formulae (Ba), (Bb), (Bc), (Bd), (Be), and (Bf) is of the formulae (Ba-1), (Bb-1), (Bc-1), (Bd-1), (Be-1) and (Bf-1):

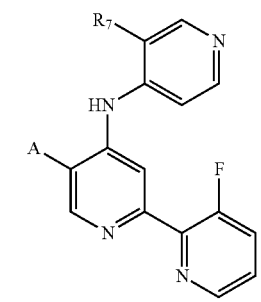
(Ba-1)

(Bb-1) 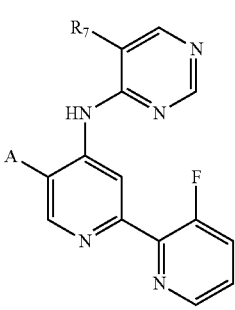

(Bc-1) 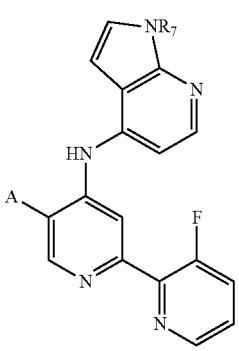

(Bd-1) 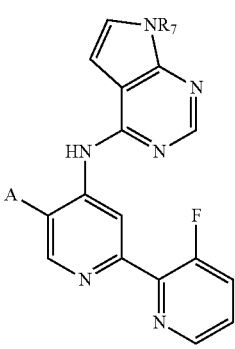

(Be-1) 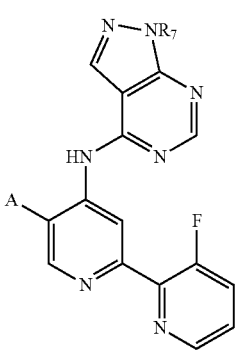

(Bf-1) 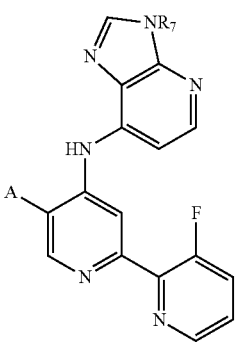

or a salt thereof, where in each of (Ba-1), (Bb-1), (Bc-1), (Bd-1), (Be-1) and (Bf-1), the substituents A and $R_7$, where present, are as described for formula (I) or any applicable variation thereof. In particular embodiments, $R_7$ is H or $CH_3$.

The embodiments and variations described herein are suitable for compounds of any formulae detailed herein, where applicable. As such, variations of formula (I) detailed throughout where applicable apply to formulae (A), (B), (C), and (D), the same as if each and every variation were specifically listed for formulae (A), (B), (C), and (D). Variations of formulae (A), (B), (C), and (D), detailed throughout, where applicable, apply to formulae (Aa), (Ab), (Ac), (Ad), (Ae), and (Af), the same as if each and every variation were specifically listed for formulae (Aa), (Ab), (Ac), (Ad), (Ae), and (Af). Variations of formulae (Aa), (Ab), (Ac), (Ad), (Ae), and (Af), detailed throughout, where applicable, apply to formulae (Aa-1), (Aa-2), (Aa-3), (Aa-4), (Aa-5), (Aa-6), (Aa-7), (Aa-8), and (Aa-9), the same as if each and every variation were specifically listed for formulae (Aa-1), (Aa-2), (Aa-3), (Aa-4), (Aa-5), (Aa-6), (Aa-7), (Aa-8), and (Aa-9). Variations of formulae (Aa-1), (Aa-2), (Aa-3), (Aa-4), (Aa-5), (Aa-6), (Aa-7), (Aa-8), and (Aa-9), detailed throughout, where applicable, apply to formulae (Aa-1a), (Aa-1b), (Aa-1c), (Aa-1d), (Aa-1e), (Aa-1f), and (Aa-1g), the same as if each and every variation were specifically listed for formulae (Aa-1a), (Aa-1b), (Aa-1c), (Aa-1d), (Aa-1e), (Aa-1f), and (Aa-1g). Variations of formulae (Ab), (Ac), (Ad), (Ae), and (Af), detailed throughout, where applicable, apply to formulae (Ab-1), (Ac-1), (Ad-1), (Ae-1), and (Af-1), the same as if each and every variation were specifically listed for formulae (Ab-1), (Ac-1), (Ad-1), (Ae-1), and (Af-1). Variations of formula (B), detailed throughout, where applicable, apply to formulae (Ba), (Bb), (Bc), (Bd), (Be), and (Bf), the same as if each and every variation were specifically listed for formulae (Ba), (Bb), (Bc), (Bd), (Be), and (Bf). Variations of formula (Ba), (Bb), (Bc), (Bd), (Be), and (Bf), detailed throughout, where applicable, apply to formulae (Ba-1), (Bb-1), (Bc-1), (Bd-1), (Be-1), and (Bf-1), the same as if each and every variation were specifically listed for formulae (Ba-1), (Bb-1), (Bc-1), (Bd-1), (Be-1), and (Bf-1).

Particular compounds described below are not intended to be limiting; rather, these embodiments and variations are intended to provide examples of compounds within the scope of formula (I).

Definitions

"Alkyl" (monovalent) and "alkylene" (divalent) when used alone or as part of another term (e.g., alkoxy) mean a branched or unbranched, saturated aliphatic hydrocarbon group, having up to 12 carbon atoms unless otherwise specified. Examples of particular alkyl groups include, but are not limited to, methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The term, "lower," when used to modify alkyl or alkylene, means 1 to 4 carbon atoms, so that, e.g., the terms "lower alkyl," "$C_1$-$C_4$ alkyl" and "alkyl of 1 to 4 carbon atoms" are synonymous and may be used interchangeably to mean methyl, ethyl, i-propyl, isopropyl, 1-butyl, sec-butyl or t-butyl. Examples of alkylene groups include, but are not limited to, methylene, ethylene, n-propylene, n-butylene and 2-methyl-butylene.

The term "substituted alkyl" refers to an alkyl moiety having substituents replacing one or more hydrogens on one or more (often no more than four) carbon atoms of the hydrocarbon backbone. Such substituents are independently selected from the group consisting of: halogens (e.g., iodo (I), bromo (Br), chloro (Cl), or fluoro (F), particularly fluoro (F)), hydroxy, amino, cyano, mercapto, alkoxy (such as a $C_1$-$C_6$ alkoxy, or a lower ($C_1$-$C_4$) alkoxy, e.g., methoxy or ethoxy to yield an alkoxyalkyl), aryloxy (such as phenoxy to yield an aryloxyalkyl), nitro, oxo ((=O), e.g., to form a carbonyl), carboxyl (which is actually the combination of an oxo and hydroxy substituent on a single carbon atom), carbamoyl (an aminocarbonyl such as $NR_2C(O)$—, which is the substitution of an oxo and an amino (as defined hereafter) on a single carbon atom), cycloalkyl (e.g., to yield a cycloalkylalkyl), aryl (resulting for example in an aralkyl such as benzyl or phenylethyl), heterocycloalkyl (e.g., resulting in a heterocycloalkylalkyl), heteroaryl (e.g., resulting in a heteroarylalkyl), alkylsulfonyl (including lower alkylsulfonyl such as methylsulfonyl), arylsulfonyl (such as phenylsulfonyl), and —$OCF_3$ (which is a halogen substituted alkoxy).

The invention further contemplates that several of these alkyl substituents, including specifically alkoxy, cycloalkyl, aryl, heterocyclyalkyl and heteroaryl, themselves can be optionally further substituted as defined in connection with each of their respective definitions provided below.

In addition, as noted above, certain alkyl substituent moieties result from a combination of such substitutions on a single carbon atom. For example, an ester moiety, e.g., an alkoxycarbonyl such as methoxycarbonyl, or tert-butoxycarbonyl (Boc) results from such multiple substitutions. In particular, methoxycarbonyl is a substituted alkyl that results from the substitution, on a methyl group (—$CH_3$), of both an oxo (=O) and an unsubstituted alkoxy, e.g., a methoxy ($CH_3$—O—). Tert-butoxycarbonyl (Boc) results from the substitution on a methyl group (—$CH_3$) of both an oxo (=O) and an unsubstituted alkoxy, e.g., a tert-butoxy (($CH_3)_3$ C—O—). In both cases, the oxo substituent and the unsubstituted alkoxy substituent replace all three hydrogens on the methyl group. Similarly, an amide moiety, e.g., an alkylaminocarbonyl, such as dimethylaminocarbonyl or methylaminocarbonyl, is a substituted alkyl that results from the substitution on a methyl group (—$CH_3$) of both an oxo (=O) and a mono-substituted alkylamino or, a di-substituted alkylamino, e.g., dimethylamino (—N—($CH_3)_2$), or methylamino (—NH—($CH_3$)), replacing the three methyl hydrogens (similarly an arylaminocarbonyl such as diphenylaminocarbonyl is a substituted alkyl that results from the substitution on a methyl group (—$CH_3$) of both an oxo (=O) and a mono-substituted aryl(phenyl)amino). Exemplary substituted alkyl groups further include cyanomethyl, nitromethyl, hydroxyalkyls such as hydroxymethyl, trityloxymethyl, propionyloxymethyl, aminoalkyls such as aminomethyl, carboxylalkyls such as carboxymethyl, carboxyethyl, carboxypropyl, 2,3-dichloropentyl, 3-hydroxy-5-carboxyhexyl, acetyl (e.g., an alkanoyl, where in the case of acetyl the two hydrogen atoms on the —$CH_2$ portion of an ethyl group are replaced by an oxo (=O)), 2-aminopropyl, pentachlorobutyl, trifluoromethyl, methoxyethyl, 3-hydroxypentyl, 4-chlorobutyl, 1,2-dimethyl-propyl, pentafluoroethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro (n-butyl), 2-amino (iso-propyl), cycloalkylcarbonyl (e.g., cuclopropylcarbonyl) and 2-carbamoyloxyethyl. Particular substituted alkyls are substituted methyl groups. Examples of substituted methyl group include groups such as hydroxymethyl, protected hydroxymethyl (e.g., tetrahydropyranyloxymethyl), acetoxymethyl, carbamoyloxymethyl, trifluoromethyl, chloromethyl, carboxymethyl, carboxyl (where the three hydrogen atoms on the methyl are replaced, two of the hydrogens are replaced by an oxo (=O) and the other hydrogen is replaced by a hydroxy (—OH)), tert-butoxycarbonyl (where the three hydrogen atoms on the methyl are replaced, two of the hydrogens are replaced by an oxo (=O) and the other hydrogen is replaced by a tert-butoxy (—O—C(($CH_3)_3$), bromomethyl and iodomethyl. When the specification and especially the claims refer to a particular substituent for an alkyl, that substituent can potentially occupy one or more of the substitutable positions on the alkyl. For example, reciting that an alkyl has a fluoro substituent, would embrace mono-, di-, and possibly a higher degree of substitution on the alkyl moiety.

"Alkoxy" is an —O-alkyl. A "substituted alkoxy" is an —O-substituted alkyl, where the alkyl portion of the alkoxy is similarly substituted with groups as set forth above for alkyl. One substituted alkoxy is acetoxy where two of the hydrogens in ethoxy (e.g., —O—$CH_2$—$CH_3$) are replaced by an oxo, i.e., (=O), to yield —O—C(O)—$CH_3$; another substituted alkoxy is an aralkoxy where one of the hydrogens in the alkoxy is replaced by an aryl. One such example is benzyloxy where one of the hydrogens on methoxy is replaced with phenyl. Another substituted alkoxy is a carbamate where two of the hydrogens for example on methoxy (e.g., —O—$CH_3$) are replaced by oxo (=O) and the other hydrogen is replaced by an amino (e.g., —$NH_2$, —NHR or —NRR) to yield, for example, —O—C(O)—$NH_2$. A lower alkoxy is an —O-lower alkyl.

"Alkenyl" (monovalent) and "alkenylene" (divalent) when alone or as part of another term mean an unsaturated hydrocarbon group containing one or more carbon-carbon double bonds, typically 1 or 2 carbon-carbon double bonds, and usually only one double bond. The hydrocarbon group may be linear or branched and may have at least 2 and up to 12 carbon atoms unless otherwise specified. Representative alkenyl groups include, by way of example, vinyl, allyl, isopropenyl, but-2-enyl, n-pent-2-enyl, and n-hex-2-enyl.

The terms "substituted alkenyl" and "substituted alkenylene" refer to alkenyl and alkenylene moieties having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), aryloxy (such as phenoxy), nitro, mercapto, carboxyl, oxo, carbamoyl, cycloalkyl, aryl, heterocyclyl, heteroaryl, alkylsulfonyl, arylsulfonyl and —$OCF_3$.

"Alkynyl" means a monovalent unsaturated hydrocarbon group containing one or more carbon-carbon triple bonds, typically only 1 carbon-carbon triple bond, which may be linear or branched and which may have at least 2 and up to 12 carbon atoms unless otherwise specified. Representative alkynyl groups include, by way of example, ethynyl, propargyl, and but-2-ynyl.

"Cycloalkyl," when alone or as part of another term, means a saturated or partially unsaturated cyclic aliphatic hydrocarbon group (carbocycle group), having at least 3 and up to 12 carbon atoms unless otherwise specified, such as cyclopropyl, cyclobutyl, cyclopentyl and cyclohexyl, and further includes polycyclic, including fused cycloalkyls such as 1,2,3,4-tetrahydonaphthalenyls (1,2,3,4-tetrahydonaphthalen-1-yl, and 1,2,3,4-tetrahydonaphthalen-2-yl), indanyls (indan-1yl, and indan-2-yl), isoindenyls (isoinden-1-yl, isoinden-2-yl, and isoinden-3-yl) and indenyls (inden-1-yl, inden-2-yl and inden-3-yl). A lower cycloalkyl has from 3 to 6 carbon atoms and includes cyclopropyl, cyclobutyl, cyclopentyl and cyclohexyl.

The term "substituted cycloalkyl" refers to a cycloalkyl moiety having substituents replacing one or more hydrogens on one or more (often no more than four) carbon atoms of the hydrocarbon backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, mercapto, carboxyl, oxo, carbamoyl, alkyl, substituted alkyls such as trifluoromethyl, aryl, substituted aryls, heterocyclyl, heteroaryl, alkylsulfonyl, arylsulfonyl and —$OCF_3$. When the specification and especially the claims refer to a particular substituent for a cycloalkyl, that substituent can potentially occupy one or more of the substitutable positions on the cycloalkyl. For example, reciting that a cycloalkyl has a fluoro substituent, would embrace mono-, di-, and a higher degree of fluoro substitution on the cycloalkyl moiety.

"Amino" denotes primary (i.e., —$NH_2$), secondary (i.e., —NHR) and tertiary (i.e., —NRR) amines, where the R groups can be the same or different and can be selected from a variety of moieties, usually an alkyl, an aryl, or a cycloalkyl, and especially a lower alkyl and an aryl (phenyl). Secondary and tertiary aminos thus include alkylamino, dialkylamino, arylamino, diarylamino, aralkylamino and diaralkylamino. Particular secondary and tertiary amines are methylamino, ethylamino, propylamino, isopropylamino, phenylamino, benzylamino dimethylamino, diethylamino, dipropylamino and disopropylamino. A substituted amino includes an amino where the alkyl, aryl, or cycloalkyl is/are substituted with halo (e.g., I, Br, Cl, F), hydroxy, cyano, alkoxy (such as $C_1$-$C_6$ alkoxy), aryloxy (such as phenoxy), nitro, mercapto, carboxyl, oxo, carbamoyl, heterocyclyl, heteroaryl, alkylsulfonyl, arylsulfonyl and —$OCF_3$ "Aryl," when used alone or as part of another term, means an aromatic carbocyclic group whether or not fused having the number of carbon atoms designated, or if no number is designated, from 6 up to 14 carbon atoms. Particular aryl groups include phenyl, naphthyl, biphenyl, phenanthrenyl, naphthacenyl, and the like (see e. g. Lang's Handbook of Chemistry (Dean, J. A., ed) 13$^{th}$ ed. Table 7-2 [1985]). Phenyl and naphthyl groups are generally preferred and phenyl is by far the most commonly employed aryl.

The term "substituted aryl," such as substituted phenyl, refers to an aryl moiety having substituents replacing one or more hydrogens on one or more (usually no more than six) carbon atoms of the aromatic hydrocarbon core. Such substituents are independently selected from the group consisting of: halogens (e.g., I, Br, Cl, F), hydroxy, amino, cyano, alkoxy (such as $C_1$-$C_6$ alkoxy and particularly lower alkoxy), substituted alkoxy, aryloxy (such as phenoxy), nitro, mercapto, carboxyl, carbamoyl, alkyl, substituted alkyl (such as trifluoromethyl), aryl, —$OCF_3$, alkylsulfonyl (including lower alkylsulfonyl), arylsulfonyl, heterocyclyl and heteroaryl. Examples of such substituted phenyls include but are not limited to a mono- or di (halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl; 3-fluorophenyl, 4-fluorophenyl, a mono- or di (hydroxy) phenyl group such as 4-hydroxyphenyl, 3-hydroxyphenyl, 2,4-dihydroxyphenyl, the protected-hydroxy derivatives thereof; a nitrophenyl group such as 3- or 4-nitrophenyl; a cyanophenyl group, for example, 4-cyanophenyl; a mono- or di (lower alkyl) phenyl group such as 4-methylphenyl, 2,4-dimethylphenyl, 2-methylphenyl, 4-(iso-propyl)phenyl, 4-ethylphenyl, 3-(n-propyl) phenyl; a mono or di (alkoxy) phenyl group, for example, 3,4-dimethoxyphenyl, 3-methoxy-4-benzyloxyphenyl, 3-methoxy-4-(1-chloromethyl) benzyloxy-phenyl, 3-ethoxyphenyl, 4-(isopropoxy) phenyl, 4-(t-butoxy) phenyl, 3-ethoxy-4-methoxyphenyl; 3- or 4-trifluoromethylphenyl; a mono- or dicarboxyphenyl or (protected carboxy) phenyl group such 4-carboxyphenyl; a mono- or di (hydroxymethyl) phenyl or (protected hydroxymethyl) phenyl such as 3-(protected hydroxymethyl) phenyl or 3,4-di (hydroxymethyl) phenyl; a mono- or di (aminomethyl) phenyl or (protected aminomethyl) phenyl such as 2-(aminomethyl) phenyl or 2, 4-(protected aminomethyl) phenyl; or a mono- or di (N-(methylsulfonylamino)) phenyl such as 3-(N-methylsulfonylamino) phenyl. Also, the substituents, such as in a di-substituted or higher substituted phenyl group, can be the same or different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl. When the specification and especially the claims refer to a particular substituent for an aryl, that substituent can potentially occupy one or more of the substitutable positions on the aryl. For example, reciting that an aryl has a fluoro substituent, would embrace mono-, di-, tri, tetra and a higher degree of substitution on the aryl moiety. Fused aryl rings may also be substituted with the substituents specified herein, for example with 1, 2 or 3 substituents, in the same manner as substituted alkyl groups. The terms aryl and substituted aryl do not include moieties in which an aromatic ring is fused to a saturated or partially unsaturated aliphatic ring.

"Aryloxy" is —O-aryl. A "substituted aryloxy" is —O-substituted aryl, where the suitable substituents are those described for a substituted aryl.

"Heterocyclic ring," "heterocyclic group," "heterocyclic," "heterocycle," "heterocyclyl," "heterocycloalkyl" or "heterocycle," alone and when used as a moiety in a complex group, are used interchangeably and refer to any mono-, bi-, or tricyclic, saturated or unsaturated, non-aromatic hetero-atom-containing ring system having the number of atoms designated, or if no number is specifically designated then from 5 to about 14 atoms in the ring, where the ring atoms are carbon and at least one heteroatom and usually not more than four heteroatoms (i.e., nitrogen, sulfur or oxygen). Included in the definition are any bicyclic groups where any of the above heterocyclic rings are fused to an aromatic ring (i.e., an aryl (e.g., benzene) or a heteroaryl ring). In a particular embodiment, the group incorporates 1 to 4 heteroatoms. Typically, a 5-membered ring has 0 to 1 double bonds and a 6- or 7-membered ring has 0 to 2 double bonds and the nitrogen or sulfur heteroatoms may optionally be oxidized (e.g. NO, SO, SO$_2$), and any nitrogen heteroatom may optionally be quaternized. Particular unsubstituted non-aromatic heterocycles include morpholinyl (morpholino), pyrrolidinyls, oxiranyl, indolinyls, 2,3-dihydoindolyl, isoindolinyls, 2,3-dihydoisoindolyl, tetrahydroquinolinyls, tetrahydroisoquinolinyls, oxetanyl, tetrahydrofuranyls, 2,3-dihydrofuranyl, 2H-pyranyls, tetrahydropyranyls, aziridinyls, azetidinyls, 1-methyl-2-pyrrolyl, piperazinyls, and piperidinyls.

The term "substituted heterocyclo" refers to heterocyclo moieties having substituents replacing one or more hydrogens on one or more (usually no more than six) atoms of the heterocyclo backbone. Such substituents are independently selected from the group consisting of: halo (e.g., I, Br, Cl, F), hydroxy, amino, cyano, alkoxy (such as $C_1$-$C_6$ alkoxy), substituted alkoxy, aryloxy (such as phenoxy), nitro, carboxyl, oxo, carbamoyl, alkyl, substituted alkyl (such as trifluoromethyl), —OCF$_3$, aryl, substituted aryl, alkylsulfonyl (including lower alkylsulfonyl), and arylsulfonyl. When the specification and especially the claims refer to a particular substituent for a heterocycloalkyl, that substituent can potentially occupy one or more of the substitutable positions on the heterocycloalkyl. For example, reciting that a heterocycloalkyl has a fluoro substituent, would embrace mono-, di-, tri, tetra, and a higher degree of substitution on the heterocycloalkyl moiety.

"Heteroaryl," alone and when used as a moiety in a complex group, refers to any mono-, bi-, or tricyclic aromatic ring system having the number of atoms designated, or if no number is specifically designated then at least one ring is a 5-, 6- or 7-membered ring and the total number of ring atoms is from 5 to about 14 and containing from one to four heteroatoms selected from the group consisting of nitrogen, oxygen, and sulfur. Included in the definition are any bicyclic groups where any of the above embraced or below-noted heteroaryl rings are fused to a benzene ring or to a heterocycle ring. The following ring systems are examples of the heteroaryl groups denoted by the term "heteroaryl"; thienyls (alternatively called thiophenyl), furyls, imidazolyls, pyrazolyls, thiazolyls, isothiazolyls, oxazolyls, isoxazolyls, triazolyls, thiadiazolyls, oxadiazolyls, tetrazolyls, thiatriazolyls, oxatriazolyls, pyridyls (including 1H-pyrrolo[2,3-b]pyridyls, and 3H-imidazo[4,5-b]pyridyls), pyrimidinyls (e.g., pyrimidin-2-yl), pyrazinyls, pyridazinyls, thiazinyls, oxazinyls, triazinyls, thiadiazinyls, oxadiazinyls, dithiazinyls, dioxazinyls, oxathiazinyls, tetrazinyls, thiatriazinyls, oxatriazinyls, dithiadiazinyls, imidazolinyls, dihydropyrimidyls, tetrahydropyrimidyls, tetrazolo [1, 5-b] pyridazinyl and purinyls. The following benzo-fused derivatives, for example benzoxazolyls, benzofuryls, benzothienyls, benzothiazolyls, benzothiadiazolyl, benzotriazolyls, benzoimidazolyls, isoindolyls, indazolyls, indolizinyls, indolyls, naphthyridines, pyridopyrimidines, phthalazinyls, quinolyls, isoquinolyls, and quinazolinyls are also embraced under the definition of heteroaryl.

The term "substituted heteroaryl" refers to heteroaryl moieties (such as those identified above, such as substituted pyridyl, or substituted pyrazolyl) having substituents replacing one or more hydrogens on one or more (usually no more than six) atoms of the heteroaryl backbone. Such substituents are independently selected from the group consisting of: halogen (e.g., I, Br, Cl, F), hydroxy, amino, cyano, alkoxy (such as $C_1$-$C_6$ alkoxy), aryloxy (such as phenoxy), nitro, mercapto, carboxyl, carbamoyl, alkyl, substituted alkyl (such as trifluoromethyl), —OCF$_3$, aryl, substituted aryl, alkylsulfonyl (including lower alkylsulfonyl), and arylsulfonyl. When the specification and especially the claims refer to a particular substituent for a heteroaryl, that substituent can potentially occupy one or more of the substitutable positions on the heteroaryl. For example, reciting that a heteroaryl has a fluoro substituent, would embrace mono-, di-, tri, tetra, and a higher degree of substitution on the heteroaryl moiety.

Examples of "heteroaryls" (including "substituted heteroaryls") include; 1H-pyrrolo[2,3-b]pyridine; 1,3-thiazol-2-yl; 4-(carboxymethyl)-5-methyl-1,3-thiazol-2-yl; 1,2,4-thiadiazol-5-yl; 3-methyl-1,2,4-thiadiazol-5-yl; 1,3,4-triazol-5-yl; 2-methyl-1,3,4-triazol-5-yl; 2-hydroxy-1,3,4-triazol-5-yl; 2-carboxy-4-methyl-1,3,4-triazol-5-yl; 1,3-oxazol-2-yl; 1,3,4-oxadiazol-5-yl; 2-methyl-1,3,4-oxadiazol-5-yl; 2-(hydroxymethyl)-1,3,4-oxadiazol-5-yl; 1,2,4-oxadiazol-5-yl; 1,3,4-thiadiazol-5-yl; 2-thiol-1,3,4-thiadiazol-5-yl; 2-(methylthio)-1,3,4-thiadiazol-5-yl; 2-amino-1,3,4-thiadiazol-5-yl; 1H-tetrazol-5-yl; 1-methyl-1H-tetrazol-5-yl; 1-(1-(dimethylamino)eth-2-yl)-1H-tetrazol-5-yl; 1-(carboxymethyl)-1H-tetrazol-5-yl; 1-(methylsulfonic acid)-1H-tetrazol-5-yl; 2-methyl-1H-tetrazol-5-yl; 1,2,3-triazol-5-yl; 1-methyl-1,2,3-triazol-5-yl; 2-methyl-1,2, 3-triazol-5-yl; 4-methyl-1,2,3-triazol-5-yl; pyrid-2-yl N-oxide; 6-methoxy-2-(n-oxide)-pyridaz-3-yl; 6-hydroxypyridaz-3-yl; 1-methlpyrid-2-yl; 1-methylpyrid-4-yl; 2-hydroxypyrimid-4-yl; 1H-Pyrazolo[3,4-d]pyrimidine; 1,4, 5,6-tetrahydro-5,6-di oxo-4-methyl-as-triazin-3-yl; 1,4,5,6-tetrahydro-4-(formylmethyl)-5,6-dioxo-as-triazin-3-yl; 2,5-dihydro-5-oxo-6-hydroxy-astriazin-3-yl; 2,5-dihydro-5-oxo-6-hydroxy-as-triazin-3-yl; 2,5-dihydro-5-oxo-6-hydroxy-2-methyl-astriazin-3-yl; 2,5-dihydro-5-oxo-6-hydroxy-2-methyl-as-triazin-3-yl; 2,5-dihydro-5-oxo-6-methoxy-2-methyl-as-triazin-3-yl; 2,5-dihydro-5-oxo-as-triazin-3-yl; 2,5-dihydro-5-oxo-2-methyl-as-triazin-3-yl; 2,5-dihydro-5-oxo-2,6-dimethyl-as-triazin-3-yl; tetrazolo[1, 5-b]pyridazin-6-yl; 8-aminotetrazolo[1,5-b]-pyridazin-6-yl; quinol-2-yl; quinol-3-yl; quinol-4-yl; quinol-5-yl; quinol-6-yl; quinol-8-yl; 2-methyl-quinol-4-yl; 6-fluoro-quinol-4-yl; 2-methyl,8-fluoro-quinol-4-yl; isoquinol-5-yl; isoquinol-8-yl; isoquinol-1-yl; and quinazolin-4-yl; An alternative group of "heteroaryl" includes: 5-methyl-2-phenyl-2H-pyrazol-3-yl; 4-(carboxymethyl)-5-methyl-1,3-thiazol-2-yl; 1,3,4-triazol-5-yl; 2-methyl-1,3,4-triazol-5-yl; 1H-tetrazol-5-yl; 1-methyl-1H-tetrazol-5-yl; 1-(1-(dimethylamino)eth-2-yl)-1H-tetrazol-5-yl; 1-(carboxymethyl)-1H-tetrazol-5-yl; 1-(methylsulfonic acid)-1H-tetrazol-5-yl; 1,2,3-triazol-5-yl; 1,4,5,6-tetrahydro-5,6-dioxo-4-methyl-as-triazin-3-yl; 1,4, 5,6-tetrahydro-4-(2-formylmethyl)-5,6-dioxo-as-triazin-3-yl; 2,5-dihydro-5-oxo-6-hydroxy-2-methyl-as-triazin-3-yl; 2,5-dihydro-5-oxo-6-hydroxy-2-methyl-as-triazin-3-yl; tetrazolo[1,5-b]pyridazin-6-yl; and 8-aminotetrazolo[1,5-b]pyridazin-6-yl.

As used in the specification, the terms "a compound of the present invention" and "compounds of the present invention" are intended to include the pharmaceutically acceptable salts of compounds having acidic and/or basic moieties.

As used herein, the terms "pharmaceutically acceptable." "physiologically tolerable" and grammatical variations thereof, as they refer to compositions, excipients, carriers, diluents and reagents, are used interchangeably and represent that the materials can be safely administered to a subject or patient, especially a human patient.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound disclosed herein in its free acid or base form with a suitable organic or inorganic base or acid, respectively, and isolating the salt thus formed during subsequent purification.

In accordance with the present invention, the compounds and their pharmaceutically acceptable salts also include the solvent addition forms and/or crystal forms thereof, particularly solvates or polymorphs. Solvates contain either stoichiometric or non-stoichiometric amounts of a solvent, and are often formed during the process of crystallization. Hydrates are formed when the solvent is water, while alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Unless otherwise specified, the terms "treating," "treat," or "treatment" and the like include preventative (e.g., prophylactic) and palliative treatment. In some embodiments, "treating" does not require prevention.

As used herein "subject" or "patient" refers to an animal or mammal including, but not limited to, human, dog, cat, horse, cow, pig, sheep, goat, chicken, monkey, rabbit, rat, and mouse.

Unless otherwise specified, as used herein, the term "therapeutic" refers to the amelioration of, the prevention of, an improvement of, or a delay in the onset of one or more symptoms of an unwanted condition or disease of a patient. Embodiments of the present invention are directed to therapeutic treatments by inhibiting TGFβ activity.

The terms "therapeutically effective amount" or "effective amount," as used herein, means an amount of a compound, or a pharmaceutically acceptable salt thereof, often as part of a pharmaceutical composition, sufficient to inhibit, halt, ameliorate, attenuate, delay the onset of, or cause an improvement in one or more symptoms of the disease being treated when administered alone or in conjunction with another pharmaceutical agent for treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "excipient" means any pharmaceutically acceptable additive, carrier, diluent, adjuvant, or other ingredient, other than the active pharmaceutical ingredient (API), which is typically included in a pharmaceutical composition for formulation and/or administration to a patient.

In some embodiments, the salts of the compounds of the invention are pharmaceutically acceptable salts. Where one or more tertiary amine moiety is present in the compound, the N-oxides are also provided and described. For example, exemplary N-oxide compounds could include:

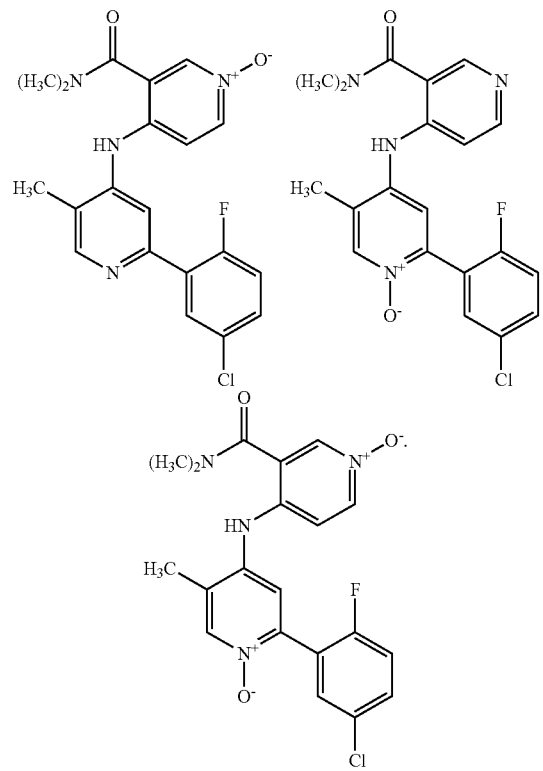

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) are useful in compound or substrate tissue distribution study. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound.

The compounds of the present invention may also be supplied in the form of a "prodrug" which is designed to release the compound of the present invention when administered to a subject. Prodrug designs are well known in the art, and depend on the substituents contained in any particular compound of the present invention. For example, a substituent containing sulfhydryl could be coupled to a carrier which renders the compound biologically inactive until removed by endogenous enzymes or, for example, by enzymes targeted to a particular receptor or location in the subject. Similarly, ester and amide linkages may be employed to mask hydroxyl, amino, or carboxyl groups on an active molecule within the scope of the invention, and such groups may be enzymatically cleaved in vivo to release the active molecule.

In particular prodrug embodiments, compounds having a hydroxyl group in the $Ar_2$ substituent may be acylated or phosphorylated with groups that can be hydrolyzed under physiological conditions at an appreciable rate. Suitable acyl groups may include C1-C8 acyl groups, which may be substituted, and which can include cyclic and/or aryl groups; for example, benzoyl, acetyl, formyl, and methoxyacetyl esters of a hydroxyl group in $Ar_2$. Similarly, phosphate esters of hydroxyl groups on $Ar_2$ may also be suitable for use as prodrugs, including the mono- and di- and tri-alkyl esters. Any of the phosphate oxygens not alkylated can be OH or OM, where M represents a pharmaceutically acceptable cation. Furthermore, a hydroxyl of $Ar_2$ can be acylated with the carboxylic acid portion of an amino acid or of a dipeptide formed from two amino acids; such esters are particularly susceptible to in vivo hydrolysis by esterase activity. Accordingly, such esters can often also serve as prodrugs that release the corresponding alcohol in vivo. These compounds may also possess intrinsic activity as inhibitors of TGFβ activity; accordingly, they may also be useful as drugs themselves.

Compounds according to the present invention are typically provided in a pharmaceutical composition comprising a pharmaceutically acceptable carrier and/or excipient. A "pharmaceutically acceptable" carrier or excipient is a material that is not biologically or otherwise undesirable, e.g., the material may be incorporated into a pharmaceutical composition administered to an individual without causing significant undesirable biological effects or interacting in a deleterious manner with any of the other components of the composition, wherein it is contained. Pharmaceutically acceptable carriers or excipients meet the required standards of toxicological and manufacturing testing and/or are included on the Inactive Ingredient Guide prepared by the U.S. Food and Drug administration or an equivalent regulatory agency.

A pharmaceutical composition can comprise one or more compounds of the present invention, but in most instances only one compound of the present invention is present in a pharmaceutical composition. In some embodiments, a pharmaceutical composition further comprises other pharmacological active adjuvants, as described below.

Preferably a compound of the present invention selected for use in a pharmaceutical composition is bioavailable orally. However, the compounds of this invention may also be formulated for parenteral (e.g., intravenous) administration.

A compound of the present invention can be used in the preparation of a medicament by combining the compound or compounds as an active ingredient with a pharmacologically acceptable carrier, which is known in the art. Depending on the therapeutic form of the medication, the carrier may be in various forms. In one variation, the manufacture of a medicament is for use in any of the methods disclosed herein.

Methods as provided herein may comprise administering to an individual a pharmacological composition that contains an effective amount of a compound of the present invention and a pharmaceutically acceptable carrier. The effective amount of the compound may in one aspect be a dose of between about 0.001-100 mg/kg total body weight, preferably from 0.01-50 mg/kg and more preferably about 0.01 mg/kg-10 mg/kg.

The manner of administration and formulation of the compounds of the present invention will depend on the nature of the condition, the severity of the condition, the particular subject to be treated, and the judgment of the practitioner; formulation will depend on mode of administration.

Thus, compounds of the present invention may be formulated for any available delivery route, including an oral, mucosal (e.g., nasal, sublingual, vaginal, buccal or rectal), parenteral (e.g., intramuscular, subcutaneous or intravenous), topical or transdermal. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

A compound of the present invention can be used in the preparation of a formulation, such as a pharmaceutical composition, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical compositions may contain preservatives, solubilizers, stabilizers, re-wetting agents, emulgators, sweeteners, dyes, adjusters, salts for the adjustment of osmotic pressure, buffers, coating agents or antioxidants. Compositions/formulations comprising the compound may also contain other substances which have valuable therapeutic properties. Pharmaceutical compositions may be prepared by known pharmaceutical methods. Suitable formulations can be found, e.g., in *Remington's Pharmaceutical Sciences*, Mack Publishing Company, Philadelphia. Pa., $20^{th}$ ed. (2000), which is incorporated herein by reference.

A compound of the present invention may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

Compounds of the present invention can be formulated in a tablet in any dosage form described. For example, a compound as described herein or a pharmaceutically acceptable salt thereof can be formulated as a 10 mg tablet.

The dose of a compound administered to an individual (such as a human) may vary with the particular compound or salt thereof, the method of administration, and the particular stage of disease being treated. The amount should be sufficient to produce a desirable response, such as a therapeutic or prophylactic response against fibrosis. In some embodiments, the amount of the compound or salt thereof is a therapeutically effective amount. In some embodiments, the amount of the compound or salt thereof is a prophylactically effective amount. In some embodiments, the amount of compound or salt thereof is below the level that induces a toxicological effect (e.g., an effect above a clinically acceptable level of toxicity) or is at a level where a potential side effect can be controlled or tolerated when the composition is administered to the individual.

In some embodiments, the amount of compound or salt thereof is an amount sufficient to inhibit a TGFβ kinase, inhibit fibrosis, inhibit cancer cell growth and/or proliferation or increase apoptosis of cancer cells.

A compound of the present invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, a compound of the present invention is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

In some embodiments, a pharmaceutical composition is provided as a unit dosage form, such as a tablet, capsule, or individually packaged container (e.g., an ampoule, syringe, or vial).

In some embodiments, the unit dosage form contains a daily dose of a compound of the present invention. In some embodiments, the unit dosage form contains a daily sub-dose of the compound.

In some embodiments, the unit dosage form contains a daily dose of each of two or more compounds of the present invention. In some embodiments, the unit dosage form contains a daily sub-dose of each of two or more compounds.

In some embodiments, the unit dosage form contains a daily dose of a compound of the present invention and a daily dose of each of one or more additional chemotherapeutic agents. In some embodiments, the unit dosage form contains a daily sub-dose of the compound and a daily sub-dose of each of one or more additional chemotherapeutic agents.

In some embodiments, the unit dosage form contains a daily dose of each of two or more compounds of the present invention and a daily dose of each of one or more additional chemotherapeutic agents. In some embodiments, the unit dosage form contains a daily sub-dose of each of two or more compounds of the present invention and a daily dose of each of one or more additional chemotherapeutic agents.

Kits and Articles of Manufacture

This disclosure also provides kits and articles of manufacture comprising one or more compounds of the present invention or a pharmacological composition comprising a compound of the present invention or a pharmaceutically acceptable salt thereof. The kits may employ any of the compounds disclosed herein. In one variation, the kit employs a compound described herein or a pharmaceutically acceptable salt thereof.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the disclosed methods. The instructions included with the kit generally include information as to the components and their administration to an individual.

Therapeutic Uses

Compounds of the present invention can be used to treat disorders and conditions associated with fibroproliferation, particularly conditions characterized by excessive activity of TGFβ. A "fibroproliferation disorder" includes fibroproliferative diseases that affect many tissues and organ systems. Diseases in which fibrosis is a major cause of morbidity and mortality include the interstitial lung diseases, osteoporosis, myelofibrosis (also known as myeloid metaplasia), liver cirrhosis, liver fibrosis resulting from chronic hepatitis B or C infection, kidney disease, heart disease especially cardiac fibrosis occurring after infarction and progressive heart failure and in hypertensive vasculopathy, and systemic sclerosis. Fibroproliferative disorders also include nasal polyposis, systemic and local scleroderma, keloids and hypertrophic scars, atherosclerosis, restenosis, and eye diseases including macular degeneration and retinal and vitreal retinopathy. Additional fibrotic disorders include keloid formation, excessive scarring occurring during the healing of wounds including surgical wounds and traumatic lacerations, chemotherapeutic drug-induced fibrosis, radiation-induced fibrosis, and injuries and burns Fibrotic tissue remodeling can also influence cancer metastasis and accelerate chronic graft rejection in transplant recipients.

Specific diseases benefited by TGFβ inhibition thus include cardiovascular diseases such as congestive heart failure, dilated cardiomyopathy, myocarditis, or vascular stenosis associated with atherosclerosis, angioplasty treatment, or surgical incisions or mechanical trauma; kidney diseases associated with fibrosis and/or sclerosis, including glomerulonephritis of all etiologies, diabetic nephropathy, and all causes of renal interstitial fibrosis, including hypertension, complications of drug exposure, such as cyclosporin. HIV-associated nephropathy, transplant nephropathy, chronic ureteral obstruction; hepatic diseases associated with excessive scarring and progressive sclerosis, including cirrhosis due to all etiologies, disorders of the biliary tree, and hepatic dysfunction attributable to infections such as hepatitis virus or parasites; syndromes associated with pulmonary fibrosis with consequential loss of gas exchange or ability to efficiently move air into and out of the lungs, including adult respiratory distress syndrome, idiopathic pulmonary fibrosis, or pulmonary fibrosis due to infectious or toxic agents such as smoke, chemicals, allergens, or autoimmune disease; all collagen vascular disorders of a chronic or persistent nature including progressive systemic sclerosis, polymyositis, scleroderma, dermatomyositis, fascists, or Raynaud's syndrome, or arthritic conditions such as rheumatoid arthritis; eye diseases associated with fibroproliferative states, including proliferative vitreoretinopathy of any etiology or fibrosis associated with ocular surgery such as retinal reattachment, cataract extraction, or drainage procedures of any kind; excessive or hypertrophic scar formation in the dermis occurring during wound healing resulting from trauma or surgical wounds; disorders of the gastrointestinal tract associated with chronic inflammation, such as Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis, or surgical wounds; neurological conditions characterized by TGFβ production or enhanced sensitivity to TGFβ, including conditions post-traumatic or hypoxic injury, Alzheimer's disease, and Parkinson's disease; diseases of the joints involving scarring sufficient to impede mobility or produce pain, including conditions post-mechanical or surgical trauma, osteoarthritis and rheumatoid arthritis; and cancer, including lung cancer, skin cancer, colorectal cancer and cancers of the breast, pancreas, and brain, including glioma.

The modulation of the immune and inflammation systems by TGFβ (Wahl et al., *Immunol. Today* (1989) 10:258-61) includes stimulation of leukocyte recruitment, cytokine production, and lymphocyte effector function, and inhibition of T-cell subset proliferation, B-cell proliferation, antibody formation, and monocytic respiratory burst. TGFβ is a stimulator for the excess production of extracellular matrix proteins, including fibronectin and collagen. It also inhibits the production of enzymes that degrade these matrix proteins. The net effect is the accumulation of fibrous tissue which is the hallmark of fibroproliferative diseases.

In one aspect, the invention provides a method of inhibiting a TGFβ3 receptor kinase receptor, comprising administering to an individual an effective amount of one or more compounds of the invention, or a salt thereof (e.g., a pharmaceutically acceptable salt). In one aspect of the method, a compound of the invention or salt thereof inhibits binding of a ligand to the TGFβ receptor and/or reduces or eliminates or increases or enhances or mimics an activity of the TGFβ receptor in a reversible or irreversible manner. In some aspects, a compound of the invention inhibits binding of a ligand to the TGFβ3 receptor by at least about or by about any one of 10%, 20%, 30%, 40%, 50%, 60%, 70%, 80%, 90%, 95% or 100% as determined by an assay described herein. In some aspects, a compound of the invention reduces an activity of the TGFβ receptor by at least about or about any of 10%, 20%, 30%, 40%, 50%, 60%, 70%, 80%, 90%, 95% or 100% as compared to the corresponding activity in the same subject prior to treatment with the receptor modulator or compared to the corresponding activity in other subjects not receiving the compound. In one aspect, the individual has or is believed to have a disorder in which the TGFβ receptor is implicated. In certain variations, a compound or composition of the invention is used to treat or prevent a TGFβ receptor related disorder, such as cancer (e.g., neuroblastoma, pancreatic cancer and colon cancer). In one aspect, the method comprises administering to the individual a compound provided herein, or a pharmaceutically acceptable salt thereof, including but not limited to a compound of the invention such as a compound according to any one or more of formulae I. (A) to (D); (Aa) to (Af); (Aa-1) to (Aa-9); (Aa-1a) to (Aa-1g); (Ab-1) to (Af-1); (Ba) to (Bf); (Ba-1) to (Bf-1); or a compound of Tables 3 or 4, or an isomer thereof, or a salt (such as a pharmaceutically acceptable salt) of any of the foregoing. In one aspect, the individual is a human in need of cancer treatment.

In some embodiments, the amount of the compound or pharmaceutically acceptable salt thereof that is administered to an individual is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

Examples of in vitro and cell-based assays are provided in the Examples, below. A variety of appropriate and accepted animal models are well known in the art and include, for example, bleomycin-induced pulmonary fibrosis models (e.g., Peng et al., *PLoS ONE* 8(4), e59348, 2013; Izbicki et al., *Int. J. Exp. Path.* 83, 111-19, 2002); colorectal cancer models (e.g., Zigmond et al., *PLoS ONE* 6(12), e28858, 2011); and bone metastasis models (e.g., Mohammad et al., *Cancer Res.* 71, 175-84, 2011; Buijs et al., *BoneKEy Reports* 1, Article number: 96, 2012).

In some embodiments, the cancer that may be treated is a solid tumor such as sarcomas and carcinomas. In some embodiments, the cancer that may be treated is a liquid tumor such as leukemia. Examples of cancers that may be treated by methods of the invention include, but are not limited to, breast cancer, prostate cancer, ovarian cancer, lung cancer, colon cancer, brain tumors, gastric cancer, liver cancer, thyroid cancer, endometrial cancer, gallbladder cancer, kidney cancer, adrenocortical cancer, sarcoma, skin cancer, head and neck cancer, leukemia, bladder cancer, colorectal cancer, hematopoietic cancer and pancreatic cancer. In some embodiments, the breast cancer is breast carcinoma (ER negative or ER positive), primary breast ductal carcinoma, mammary adenocarcinoma, mammary ductal carcinoma (ER positive, ER negative or HER2 positive), HER2 positive breast cancer, luminal breast cancer or triple negative breast cancer (TNBC). In some embodiments, the breast cancer is unclassified. In some embodiments, the triple negative breast cancer is a basal-like TNBC, a mesenchymal TNBC (mesenchymal or mesenchymal stem-like), an immunomodulatory TNBC, or a luminal androgen receptor TNBC. In some embodiments, the prostate cancer is prostate adenocarcinoma. In some embodiments, the ovarian cancer is ovary adenocarcinoma. In some embodiments, the lung cancer is lung carcinoma, non-small lung carcinoma, adenocarcinoma, mucoepidermoid, anaplastic, large cell, or unclassified. In some embodiments, the colon cancer is colon adenocarcinoma, colon adenocarcinoma from a metastatic site lymph node, metastatic colorectal cancer, or colon carcinoma. In some embodiments, a brain tumor is glioblastoma, astrocytoma, meduloblastoma, meningioma or neuroblastoma. In some embodiments, gastric cancer is stomach cancer. In some embodiments, liver cancer is hepatocellular carcinoma, hepatoblastoma or cholangiocarcinoma. In some embodiments, liver cancer is hepatitis B virus derived. In some embodiments, liver cancer is virus negative. In some embodiments, thyroid cancer is papillary thyroid carcinoma, follicular thyroid cancer or medullary thyroid cancer. In some embodiments, endometrial cancer is high grade endometroid cancer, uterine papillary serous carcinoma or uterine clear cell carcinoma. In some embodiments, gallbladder cancer is gallbladder adenocarcinoma or squamous cell gallbladder carcinoma. In some embodiments, kidney cancer is renal cell carcinoma or urothelial cell carcinoma. In some embodiments, adrenocortical cancer is adrenal cortical carcinoma. In some embodiments, sarcoma is synovial sarcoma, osteosarcoma, rhabdomiosarcoma, fibrosarcoma or Ewing's sarcoma. In some embodiments, skin cancer is basal cell carcinoma, squamous carcinoma or melanoma. In some embodiments, head and neck cancer is oropharyngeal cancer, nasopharyngeal cancer, laryngeal cancer and cancer of the trachea. In some embodiments, the leukemia is acute promyelocytic leukemia, acute lymphoblastic leukemia, chronic lymphocytic leukemia, chronic myelogenous leukemia, mantle cell lymphoma or multiple myeloma. In some embodiments, the leukemia is acute promyelocytic leukemia, acute lymphoblastic leukemia, chronic lymphocytic leukemia, chronic myelogenous leukemia, mantle cell lymphoma or multiple myeloma.

The invention additionally provides a method for treating a tumor comprising contacting the tumor with an effective amount of one or more compounds of the invention, or a salt thereof. In one aspect of the method, a compound or salt thereof is administered to an individual in need of tumor treatment. Exemplary tumors are derived from carcinomas of the breast, prostate, ovary, lung, or colon. In one aspect, the treatment results in a reduction of the tumor size. In another aspect, the treatment slows or prevents tumor growth and/or metastasis.

The invention further provides methods for treating a hematopoietic malignancy comprising administering an effective amount of one or more compounds of the invention to an individual in need thereof. In some embodiments, the hematopoietic malignancy is acute promyelocytic leukemia.

Any of the methods of treatment provided herein may be used to treat a primary tumor. Any of the methods of treatment provided herein may also be used to treat a metastatic cancer (that is, cancer that has metastasized from the primary tumor). Any of the methods of treatment provided herein may be used to treat cancer at an advanced stage. Any of the methods of treatment provided herein may be used to treat cancer at a locally advanced stage. Any of the methods of treatment provided herein may be used to treat early stage cancer. Any of the methods of treatment provided herein may be used to treat cancer in remission. In some of the embodiments of any of the methods of treatment provided herein, the cancer has reoccurred after remission. In some embodiments of any of the methods of treatment provided herein, the cancer is progressive cancer.

Any of the methods of treatment provided herein may be used to treat an individual (e.g., human) who has been diagnosed with or is suspected of having cancer. In some embodiments, the individual may be a human who exhibits one or more symptoms associated with cancer. In some embodiments, the individual may have advanced disease or a lesser extent of disease, such as low tumor burden. In some embodiments, the individual is at an early stage of a cancer. In some embodiments, the individual is at an advanced stage of cancer. In some of the embodiments of any of the methods of treatment provided herein, the individual may be a human who is genetically or otherwise predisposed (e.g., has one or more so-called risk factors) to developing cancer who has or has not been diagnosed with cancer. In some embodiments, these risk factors include, but are not limited to, age, sex, race, diet, history of previous disease, presence of precursor disease, genetic (e.g., hereditary) considerations, and environmental exposure. In some embodiments, the individuals at risk for cancer include, e.g., those having relatives who have experienced this disease and those whose risk is determined by analysis of genetic or biochemical markers. In some embodiments, the individual does not have type I diabetes. In some embodiments, the individual does not have type II diabetes with sustained hyperglycemia or type II diabetes with hyperglycemia for prolonged duration (e.g., for several years).

Any of the methods of treatment provided herein may be practiced in an adjuvant setting. In some embodiments, any of the methods of treatment provided herein may be used to treat an individual who has previously been treated for cancer, e.g., with one or more other therapies such as radiation, surgery or chemotherapy. Any of the methods of treatment provided herein may be used to treat an individual who has not previously been treated for cancer. Any of the methods of treatment provided herein may be used to treat an individual at risk for developing cancer, but who has not been diagnosed with cancer. Any of the methods of treatment provided herein may be used as a first line therapy. Any of the methods of treatment provided herein may be used as a second line therapy.

Any of the methods of treatment provided herein in one aspect reduce the severity of one or more symptoms associated with cancer by at least about any of 10%, 20%, 30%, 40%, 50% 60%, 70%, 80%, 90%, 95% or 100% compared to the corresponding symptom in the same subject prior to treatment or compared to the corresponding symptom in other subjects not receiving a compound or composition of the invention.

Any of the methods of treatment provided herein may be used to treat, stabilize, prevent, and/or delay any type or stage of cancer. In some embodiments, the individual is at least about any of 40, 45, 50, 55, 60, 65, 70, 75, 80, or 85 years old. In some embodiments, one or more symptoms of the cancer are ameliorated or eliminated. In some embodiments, the size of a tumor, the number of cancer cells, or the growth rate of a tumor decreases by at least about any of 10%, 20%, 30%, 40%, 50%, 60%, 70%, 80%, 90%, 95% or 100%. In some embodiments, the cancer is delayed or prevented.

In some embodiments, a compound or composition of the invention may be used to treat or prevent cancer in conjunction with a second therapy useful to reduce one or more side effects associated with administering the compound or composition of the invention. In some embodiments, the second compound for such combination therapy is selected from agents used for the treatment of glucose-related disorders such as Type 2 diabetes mellitus, impaired glucose tolerance, Insulin Resistance Syndrome and hyperglycemia. Examples of such agents include oral antidiabetic compounds from the classes of sulfonylureas, biguanides, thiazolidinediones, alpha-glucosidase inhibitors, meglitinides, other insulin-sensitizing compounds and/or other antidiabetic agents. Particular examples comprise Metformin (N,N-dimethylimidodicarbonimidic diamide), sulfonylureas and the like, or a salt of the foregoing. Testing of glucose concentration levels in an individual receiving a compound of the present invention may be followed by the co-administration of such a second agent (e.g., Metformin) as part of a combination therapy where appropriate (e.g., where the results of a glucose concentration level test in an individual indicate that such combination therapy will be or is expected to be beneficial for the individual).

In some embodiments, the compounds and compositions of the invention may be used to treat or prevent cancer in conjunction with a second therapy useful for cancer treatment. The second therapy includes, but is not limited to, surgery, radiation, and/or chemotherapy.

Use of Compounds of the Invention in Combination with Cancer Immunotherapies

In some embodiments, a compound of the invention is administered to a patient in combination with one or more cancer immunotherapies, including cell-based therapies ("cancer vaccines"), antibody therapies, cytokine therapies, and other immunosuppressive mediators such as indoleamine 2,3-dioxygenase (IDO). Unless otherwise indicated, "in combination" as used herein includes substantially simultaneous administration of the compound of the invention and one or more cancer immunotherapies (either in the same composition or in separate compositions) as well as sequential administration.

Cell-based therapies include, but are not limited to, natural killer cells, lymphokine-activated killer cells, cytotoxic T cells, regulatory T cells, and dendritic cells. In some embodiments, a compound of the invention is used in combination with sipuleucel-T (e.g., PROVENGE®), to treat prostate cancer. In some embodiments, adjuvants, such as GM-CSF, are used to attract and/or activate dendritic cells.

Antibody therapies include, but are not limited to, antibodies to cell surface receptors, such as epidermal growth factor receptor and HER2, as well as antibodies which block immune checkpoints (e.g., antibodies which bind to molecules such as PD-1, PD-L1, and CTLA-4). The term "antibody" as used herein includes monoclonal antibodies, humanized or chimeric antibodies, bispecific antibodies (e.g., BiTE), single chain antibodies, and binding fragments such as Fab, Fab' F(ab')$_2$, Fabc, and Fv. Antibodies may be used alone or may be conjugated, for example, to a moiety which is either toxic to cells (antibody drug conjugate, or ADC) or is radioactive. Examples of antibody therapies include Pidilizumab, Alemtuzumab, Bevacizumab, Brentuximab vedotin, Cetuximab, Gemtuzumab ozogamicin, Ibritumomab tiuxetan, Ipilimumab, Ofatumumab, Panitumumab, Rituximab, Tositumomab, and Trastuzumab.

Cytokine therapies include, but are not limited to, GM-CSF, interleukins (e.g., IL-2, IL-7, IL-10, IL-12, IL-15, IL-18, IL-21), and interferons (e.g., interferon α).

Examples of compounds of formula (I) are shown in Table 3 and Table 4. Specific synthetic methods for preparing the compounds of Table 3 are provided in the following examples.

In one embodiment, the invention relates to Compounds presented in Tables 3 and 4, and uses thereof, other than Compound Nos. C-E 1, C-E 1a and C-E 1b.

In another embodiment, the invention relates to Compound Nos. 1, 1a, 1b, 2, 2a, 2b, 3, 3a, 3b, 4, 4a, 4b, 5, 5a, 5b, 6, 6a, 6b, 7, 7a, 7b, 8, 9, 10, 10a, 10b, 11, 1a, 11b, 12, 12a, 12b, 13, 13a, 13b, 14, 15, 16, 16a, 16b, 17, 17a, 17b, 18, 19, 20, 20a, 20b, 21, 21a, 21b, 22, 23, 23a, 23b, 24, 24a, 24b, 25, 25a, 25b, 26, 27, 28, 28a, 28b, 29, 30, 31, 31a, 31b, 32, 33, 34, 35, 36, 37, 37a, 37b, 38, 38a, 38b, 39, 39a, 39b, 40, 40a, 40b, 41, 42, 43, 43a, 43b, 44, 44a, 44b, 45, 46, 46a, 46b, 47, 47a, 47b, 48, 49, 50, 51, 51a, 51b, 52, 52a, 52b, 53, 53a, 53b, and 54, and uses thereof.

In another embodiment, the invention relates to Compound Nos. 2.1, 2.1a, 2.1b, 2.2, 2.2a, 2.2b, 2.3, 2.3a, 2.3b, 2.4, 2.4a, 2.4b, 2.5, 2.6, 2.6a, 2.6b, 2.7, 2.7a, 2.7b, 2.8, 2.8a, 2.8b, 2.9, 2.9a, 2.9b, 2.10, 2.10a, 2.10b, 2.11, 2.11a, 2.11b, 2.12, 2.12a, 2.12b, 2.13, 2.13a, 2.13b, 2.14, 2.14a, 2.14b, 2.15, 2.15a, 2.15b, 2.16, 2.16a, 2.16b, 2.17, 2.17a, 2.17b, 2.18, 2.18a, 2.18b, 2.19, 2.19a, 2.19b, 2.20, 2.20a, 2.20b, 2.21, 2.21a, 2.21b, 2.22, 2.22a, 2.22b, 2.23, 2.23a, 2.23b, 2.24, 2.24a, 2.24b, 2.25, 2.26, 2.27, 2.28, 2.29, 2.29a, 2.29b, 2.30, 2.30a, 2.30b, 2.31, 2.31a, 2.31b, 2.32, 2.32a, 2.32b, 2.33, 2.34, 2.35, 2.36, 2.37, 2.38, 2.38a, 2.38b, 2.39, 2.40, 2.41, 2.41a, 2.41b, 2.42, 2.42a, 2.42b, 2.43, 2.44, 2.45, 2.46, 2.47, and 2.48, and uses thereof.

TABLE 3

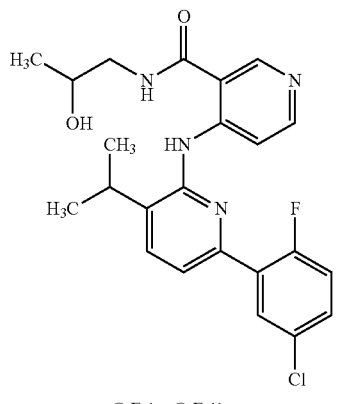

C-E 1

C-E 1a, C-E 1b

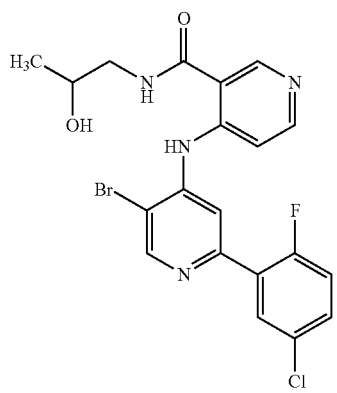

1

1a, 1b

TABLE 3-continued
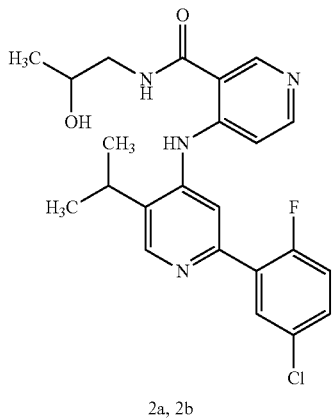 [SMILES: CC(O)CNC(=O)c1cnccc1Nc1cc(-c2cc(Cl)ccc2F)ncc1C(C)C]
2a, 2b
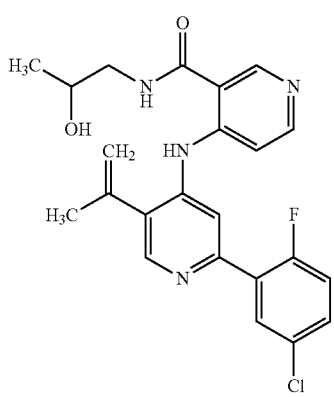
3a, 3b
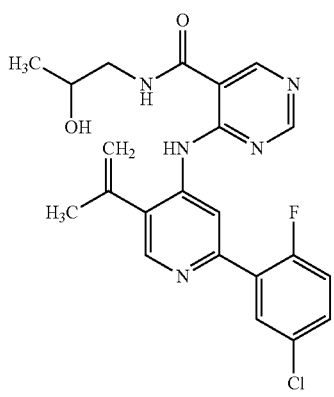
4a, 4b
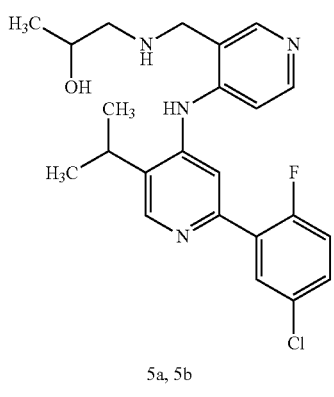 [SMILES: CC(O)CNCc1cnccc1Nc1cc(-c2cc(Cl)ccc2F)ncc1C(C)C]
5a, 5b
TABLE 3-continued
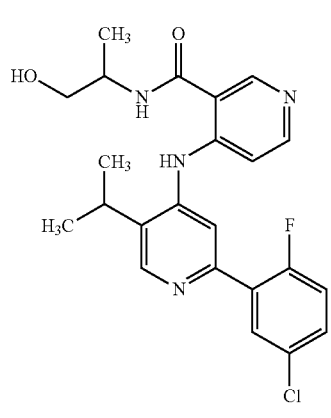
6a, 6b
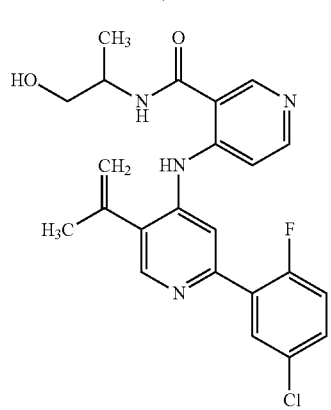
7a, 7b
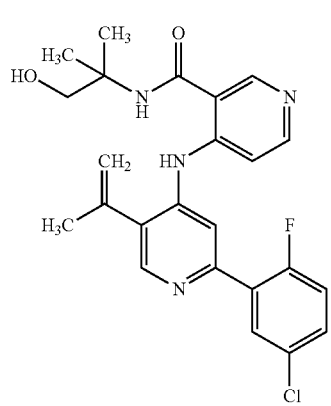 [SMILES: C=C(C)c1cnc(-c2cc(Cl)ccc2F)cc1Nc1ccncc1C(=O)NC(C)(C)CO]
8
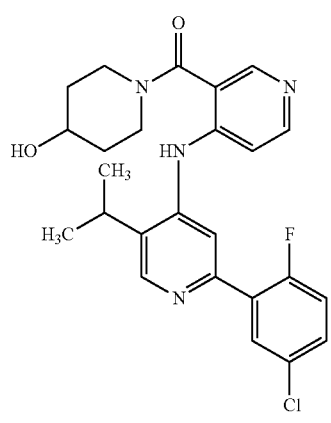 [SMILES: CC(C)c1cnc(-c2cc(Cl)ccc2F)cc1Nc1ccncc1C(=O)N1CCC(O)CC1]
9

TABLE 3-continued
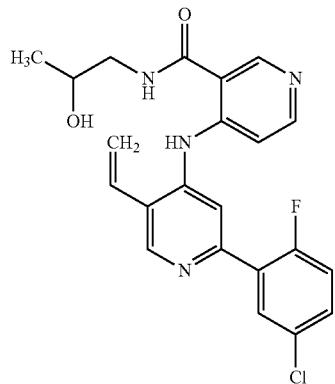
10a, 10b
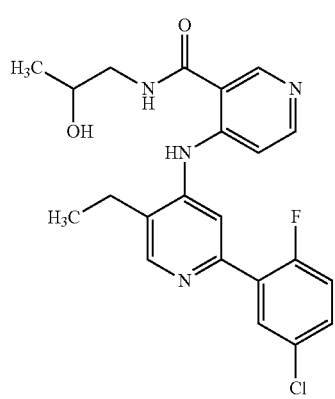
11a, 11b
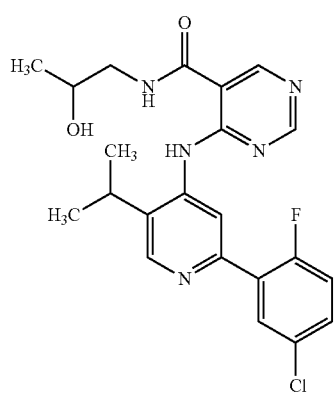
12a, 12b
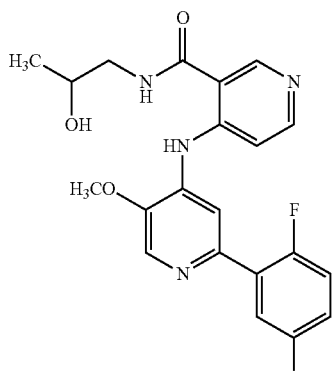
13a, 13b
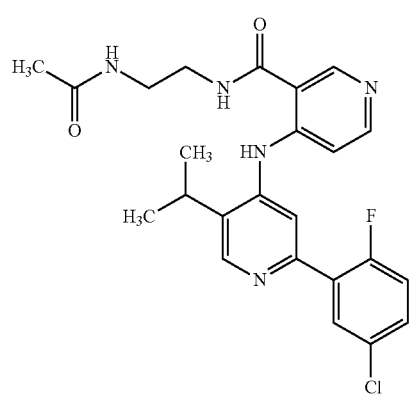 [SMILES: CC(=O)NCCNC(=O)c1cnccc1Nc1cc(-c2cc(Cl)ccc2F)ncc1C(C)C]
14
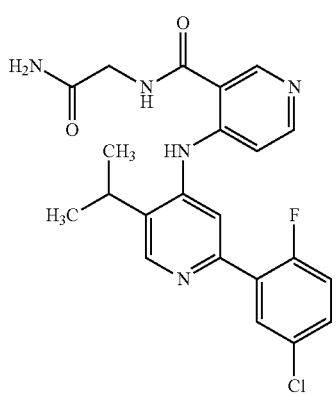 [SMILES: CC(C)c1cnc(-c2cc(Cl)ccc2F)cc1Nc1ccncc1C(=O)NCC(N)=O]
15
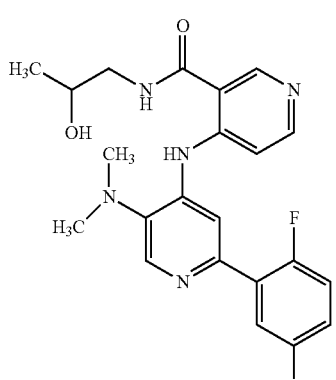
16a, 16b TABLE 3-continued
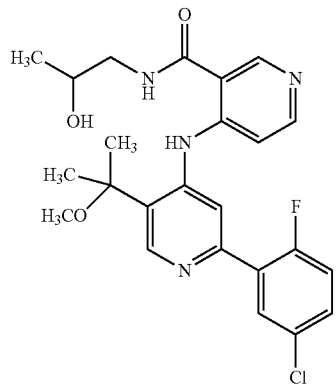
17a, 17b
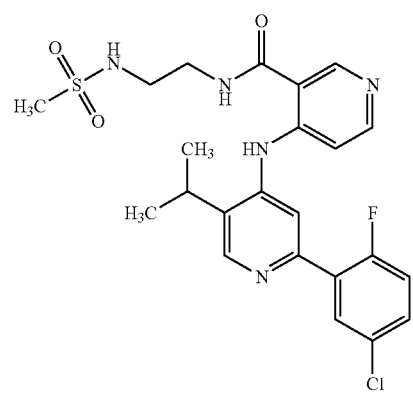 [SMILES: CC(C)c1cnc(-c2cc(Cl)ccc2F)cc1Nc1ccncc1C(=O)NCCNS(C)(=O)=O]
18
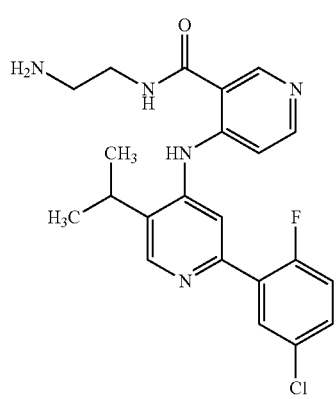 [SMILES: CC(C)c1cnc(-c2cc(Cl)ccc2F)cc1Nc1ccncc1C(=O)NCCN]
19
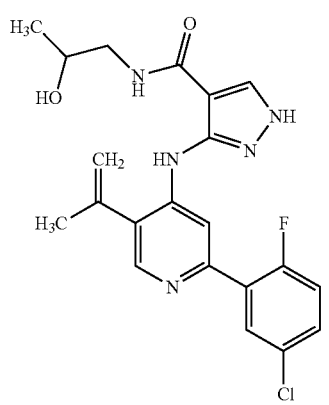
20a, 20b
TABLE 3-continued
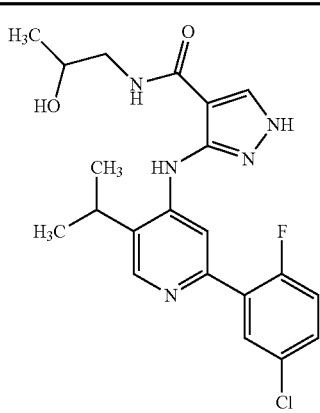
21a, 21b
22
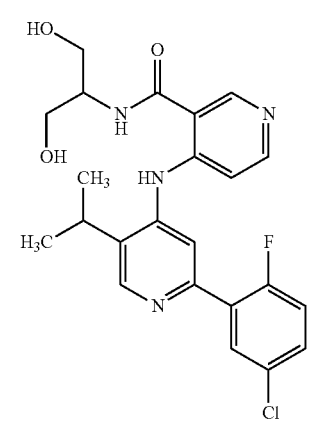
23
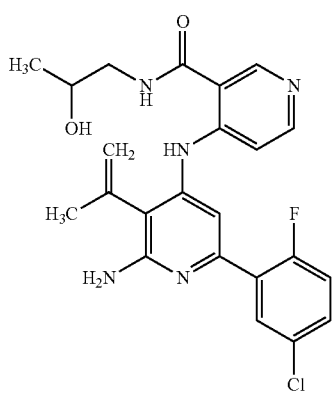
23a, 23b TABLE 3-continued
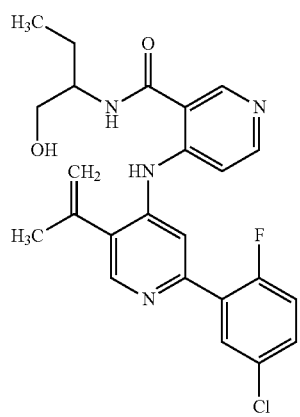 [SMILES: CC(C)c1cnc(-c2cc(Cl)ccc2F)cc1Nc1ccncc1C(=O)NC(CO)CO]
24a, 24b
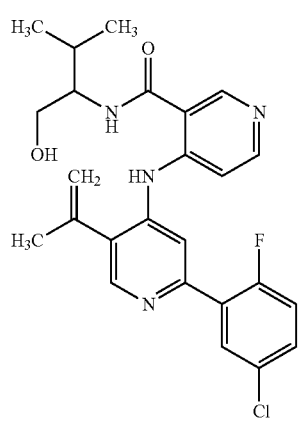
25a, 25b
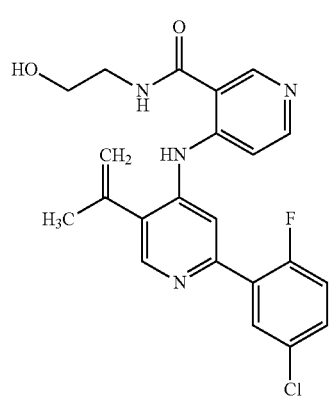 [SMILES: C=C(C)c1cnc(-c2cc(Cl)ccc2F)cc1Nc1ccncc1C(=O)NCCO]
TABLE 3-continued
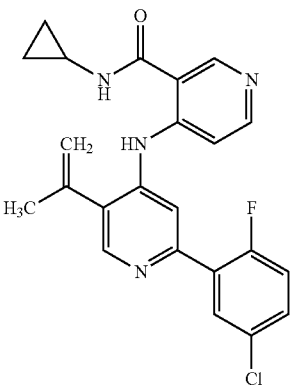 [SMILES: C=C(C)c1cnc(-c2cc(Cl)ccc2F)cc1Nc1ccncc1C(=O)NC1CC1]
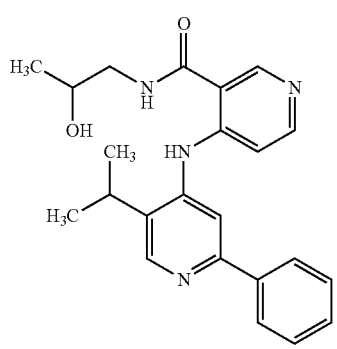
28a, 28b
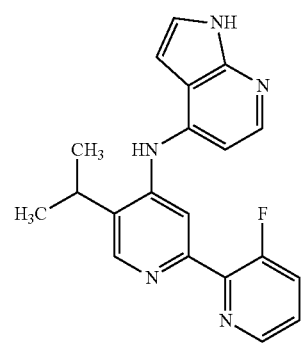 [SMILES: CC(C)c1cnc(-c2ncccc2F)cc1Nc1ccnc2[nH]ccc12]
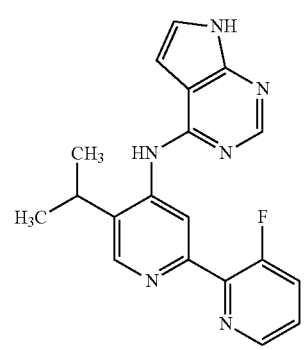 [SMILES: CC(C)c1cnc(-c2ncccc2F)cc1Nc1ncnc2[nH]ccc12]

TABLE 3-continued
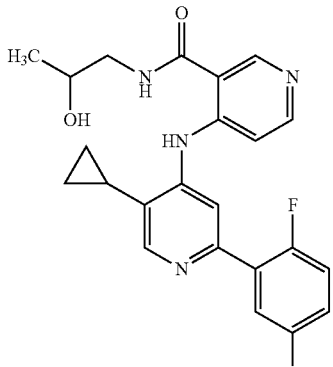
31
31a, 31b
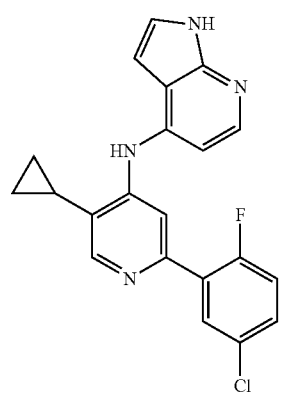 [SMILES: Fc1ccc(Cl)cc1-c1cc(Nc2ccnc3[nH]ccc23)c(C2CC2)cn1]
32
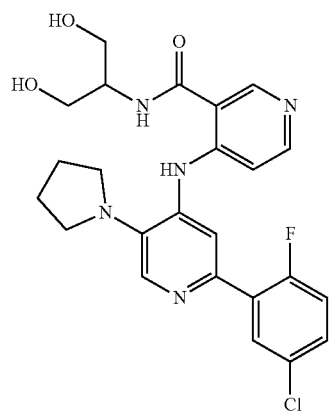 [SMILES: O=C(NC(CO)CO)c1cnccc1Nc1cc(-c2cc(Cl)ccc2F)ncc1N1CCCC1]
33
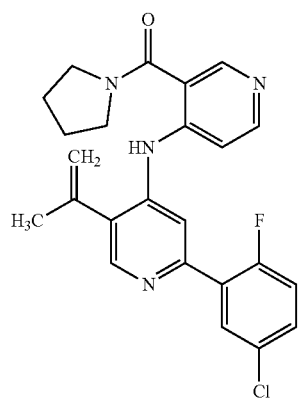 [SMILES: C=C(C)c1cnc(-c2cc(Cl)ccc2F)cc1Nc1ccncc1C(=O)N1CCCC1]
34
TABLE 3-continued
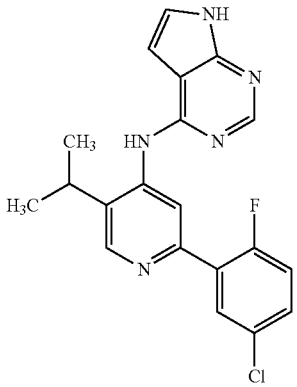 [SMILES: CC(C)c1cnc(-c2cc(Cl)ccc2F)cc1Nc1ncnc2[nH]ccc12]
35
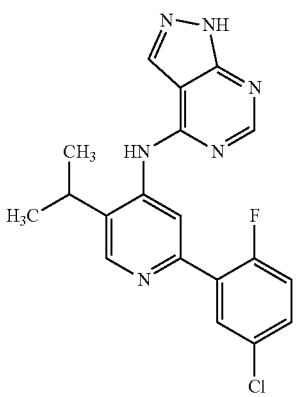 [SMILES: CC(C)c1cnc(-c2cc(Cl)ccc2F)cc1Nc1ncnc2[nH]ncc12]
36
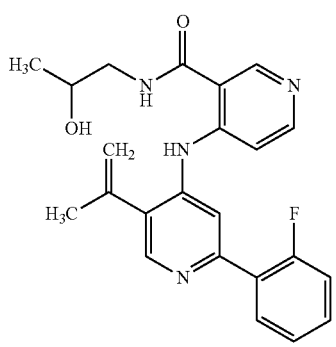
37
37a, 37b
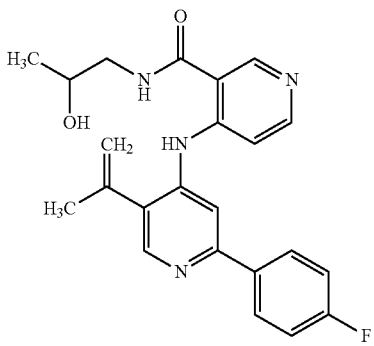
38
38a, 38b TABLE 3-continued
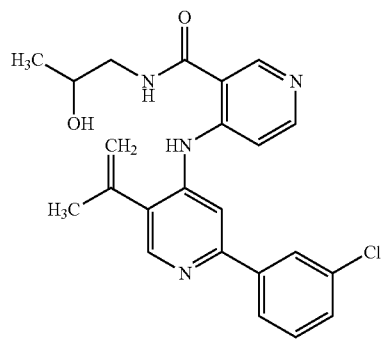
39a, 39b
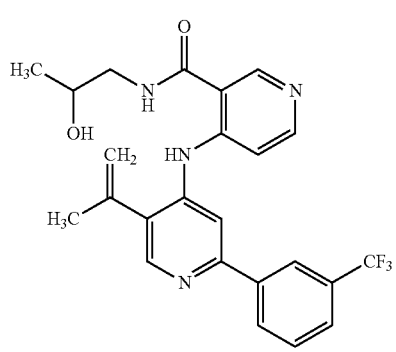
40a, 40b
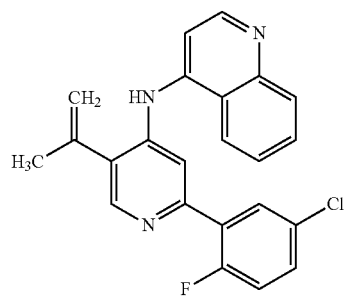 [SMILES: C=C(C)c1cnc(-c2cc(Cl)ccc2F)cc1Nc1ccnc2ccccc12]
41
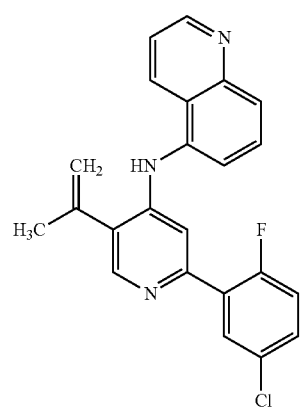 [SMILES: C=C(C)c1cnc(-c2cc(Cl)ccc2F)cc1Nc1cccc2ncccc12]
42
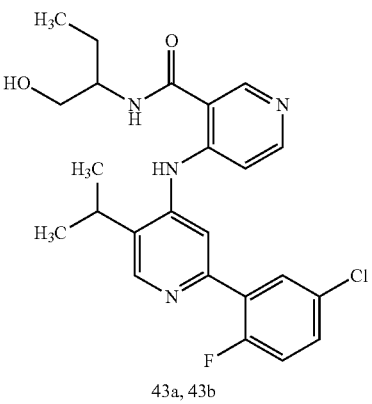 [SMILES: CCC(CO)NC(=O)c1cnccc1Nc1cc(-c2cc(Cl)ccc2F)ncc1C(C)C]
43a, 43b
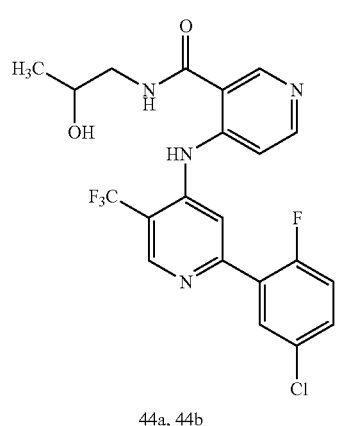 [SMILES: CC(O)CNC(=O)c1cnccc1Nc1cc(-c2cc(Cl)ccc2F)ncc1C(F)(F)F]
44a, 44b
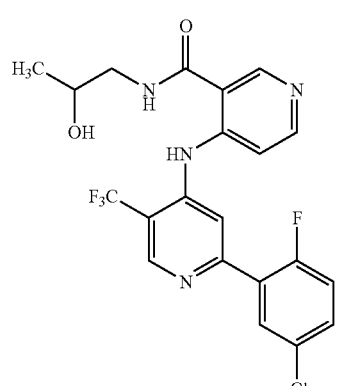
45
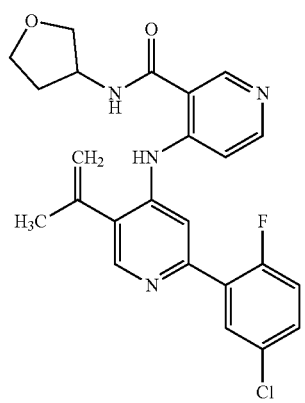
46a, 46b TABLE 3-continued
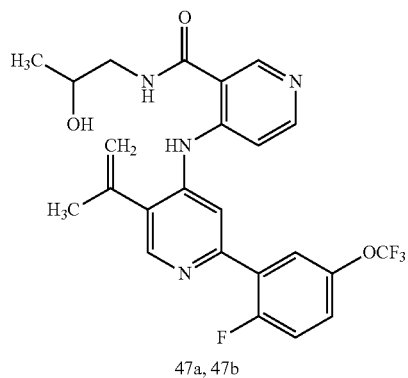 [SMILES: C=C(C)c1cnc(-c2cc(OC(F)(F)F)ccc2F)cc1Nc1ccncc1C(=O)NCC(C)O]
47
47a, 47b
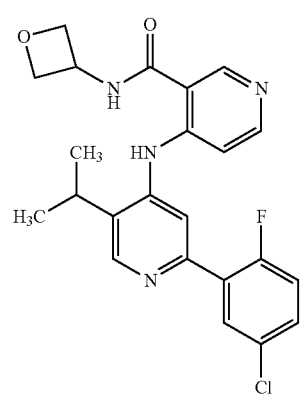 [SMILES: CC(C)c1cnc(-c2cc(Cl)ccc2F)cc1Nc1ccncc1C(=O)NC1COC1]
48
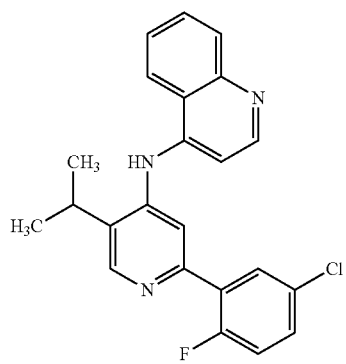 [SMILES: CC(C)c1cnc(-c2cc(Cl)ccc2F)cc1Nc1ccnc2ccccc12]
49
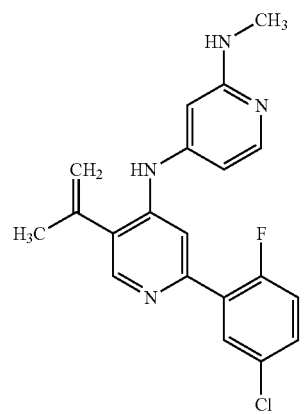 [SMILES: C=C(C)c1cnc(-c2cc(Cl)ccc2F)cc1Nc1ccnc(NC)c1]
50
TABLE 3-continued
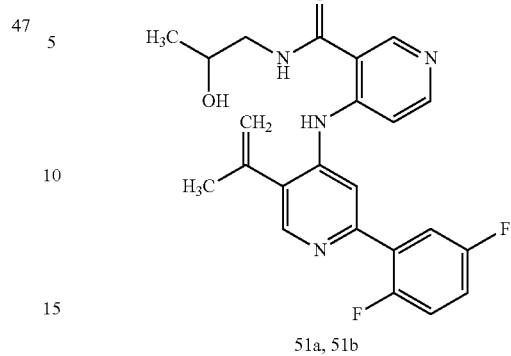
51
51a, 51b
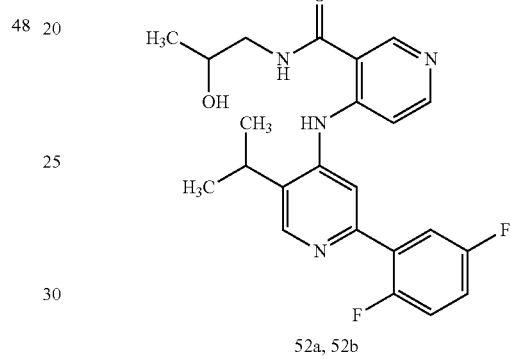
52
52a, 52b
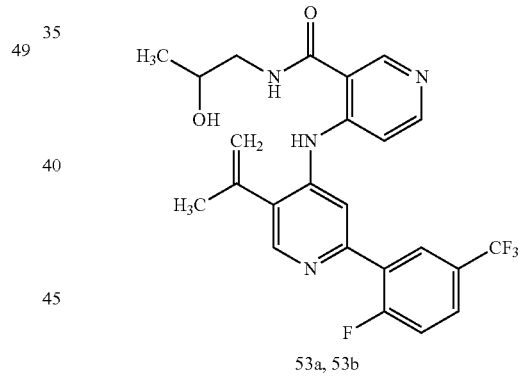
53
53a, 53b
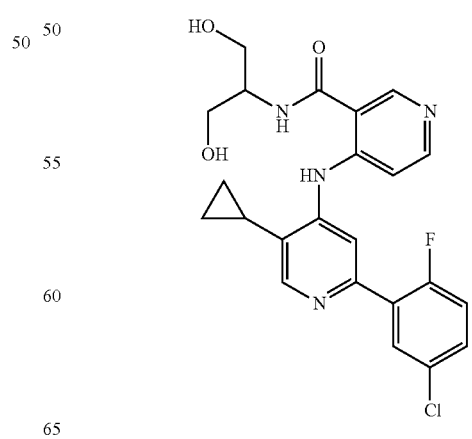
54

Those entries with additional a and b entries are intended to designate the stereoisomers of the illustrated structure. It is understood that such stereoisomers may be resolved into the respective enantiomers. The compounds of the invention include the enantiomers in its isomerically pure form or in a composition comprising mixtures of compounds of the invention in any ratio including two stereochemical forms, such as in a racemic or non-racemic mixture. Individual enantiomers can be prepared, for example, by either chiral separation of racemic mixtures using techniques known to those skilled in the art, or by employing chirally pure enantiomeric reagents during the synthetic process. As an example, racemic compound 1, bearing one chiral center, can be resolved into its individual enantiomers 1a and 1b.

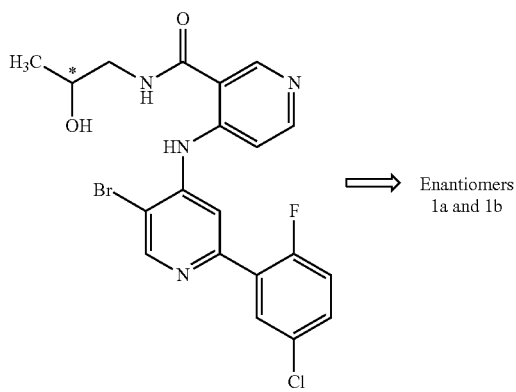

\* = chiral center

Enantiomers 1a and 1b

The compounds illustrated in Table 4 can be prepared in a manner analogous to the techniques used in connection with the preparation of the Table 3 compounds and in accordance, using appropriate, analogous starting materials and by utilizing the general synthetic schemes illustrated below.

TABLE 4

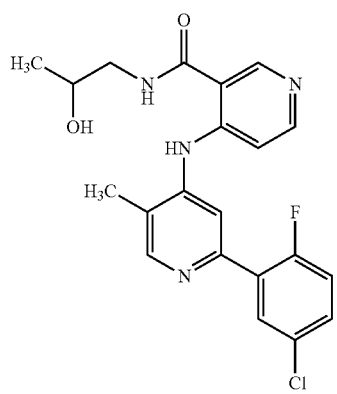

2.1

2.1a, 2.1b

TABLE 4-continued

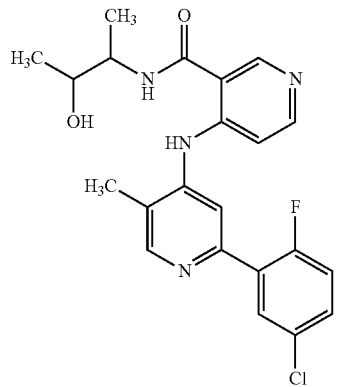

2.2

2.2a, 2.2b

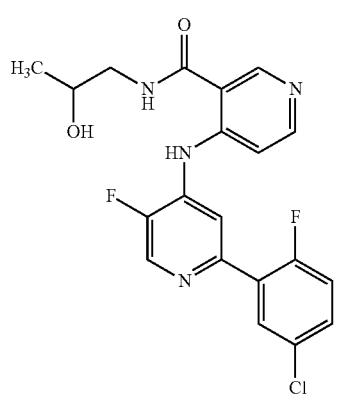

2.3

2.3a, 2.3b

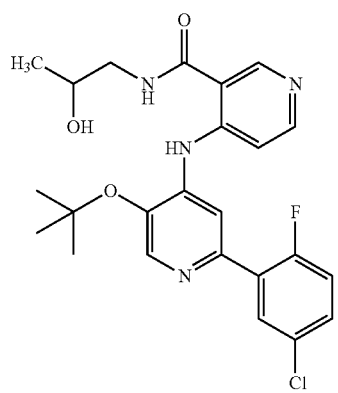

2.4

2.4a, 2.4b

TABLE 4-continued
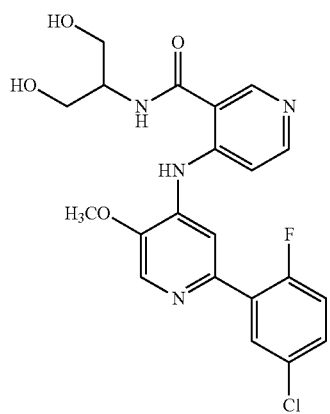 [SMILES: COc1cnc(-c2cc(Cl)ccc2F)cc1Nc1ccncc1C(=O)NC(CO)CO]
2.5
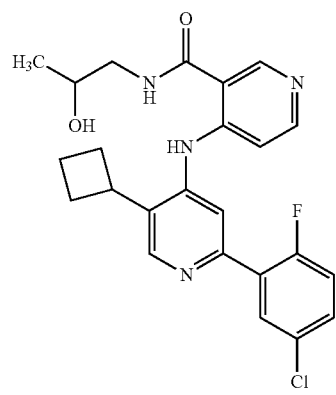
2.6a, 2.6b
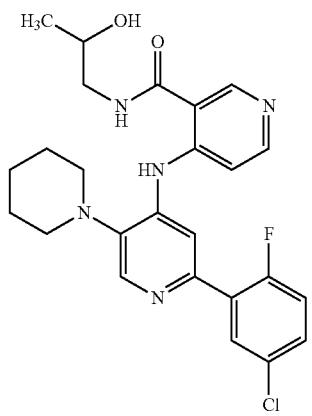
2.7a, 2.7b
TABLE 4-continued
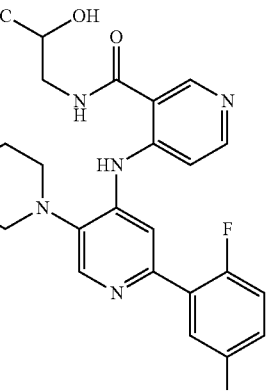
2.8a, 2.8b
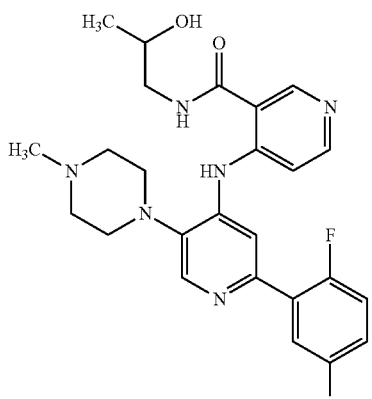
2.9a, 2.9b
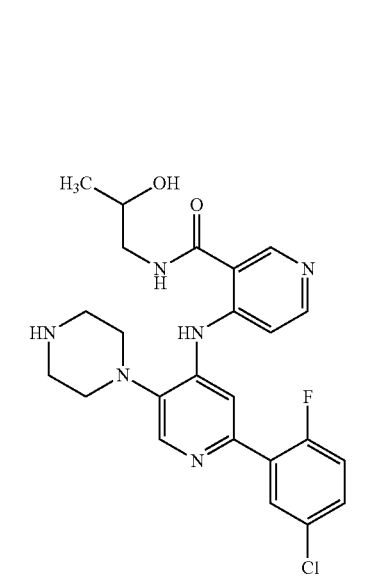
2.10a, 2.10b TABLE 4-continued
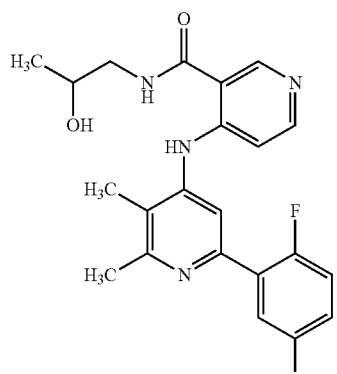
2.11a, 2.11b
2.11
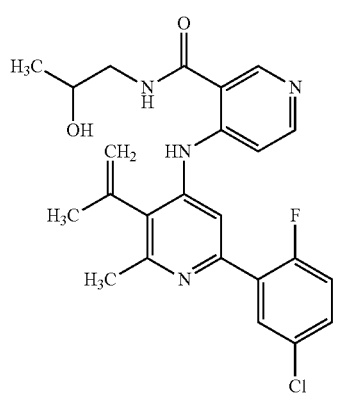
2.12a, 2.12b
2.12
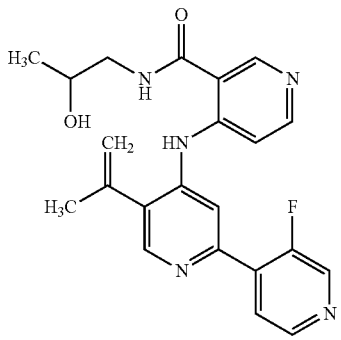
2.13a, 2.13b
2.13
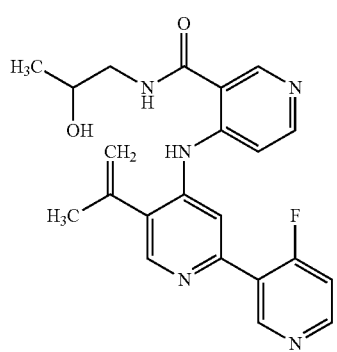
2.14a, 2.14b
2.14
TABLE 4-continued
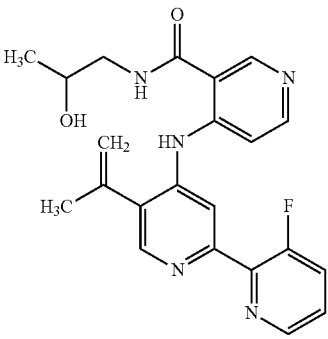
2.15a, 2.15b
2.15
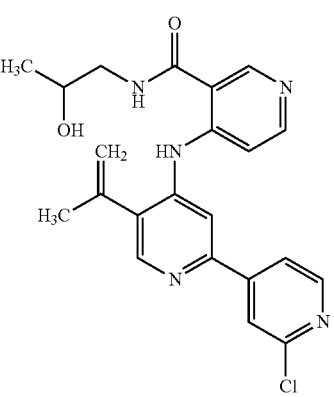
2.16a, 2.16b
2.16
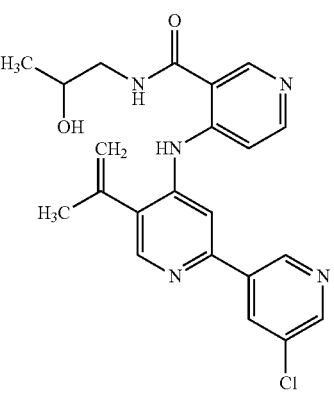
2.17a, 2.17b
2.17
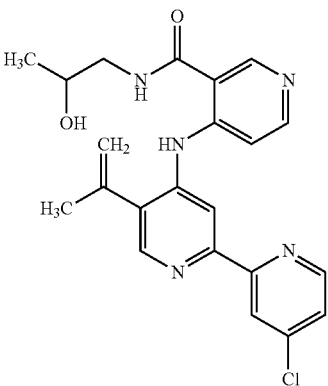
2.18a, 2.18b
2.18

TABLE 4-continued
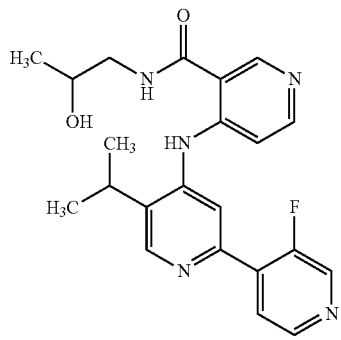
2.19a, 2.19b    2.19
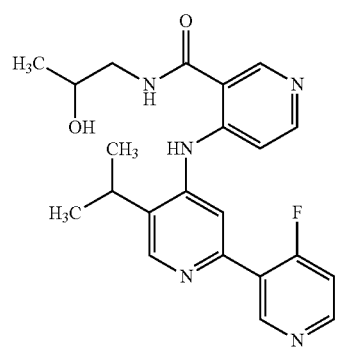
2.20a, 2.20b    2.20
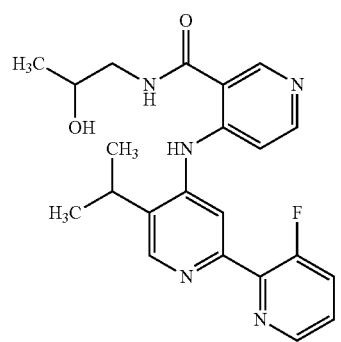
2.21a, 2.21b    2.21
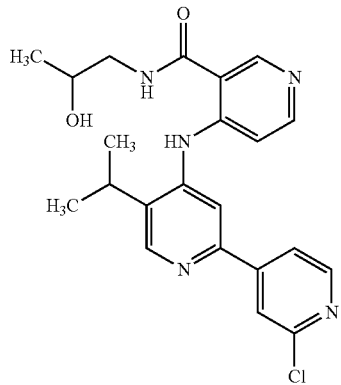
2.22a, 2.22b    2.22
TABLE 4-continued
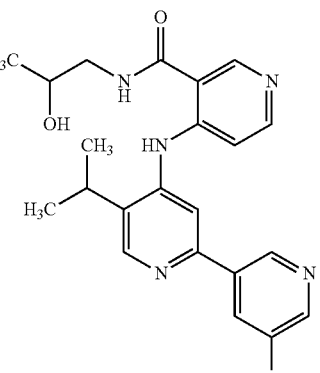
2.23a, 2.23b    2.23
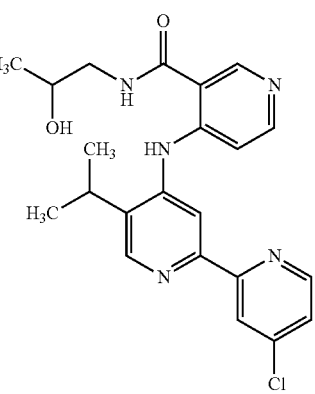
2.24a, 2.24b    2.24
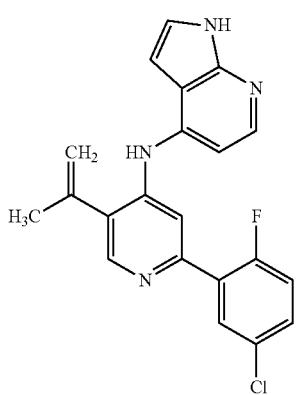
2.25
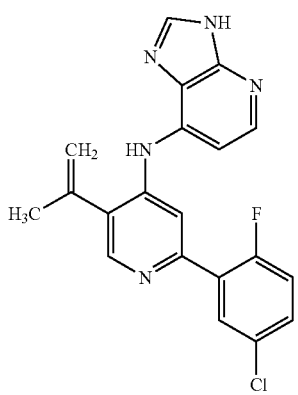 [SMILES: C=C(C)c1cnc(-c2cc(Cl)ccc2F)cc1Nc1ccnc2[nH]cnc12]
2.26

TABLE 4-continued
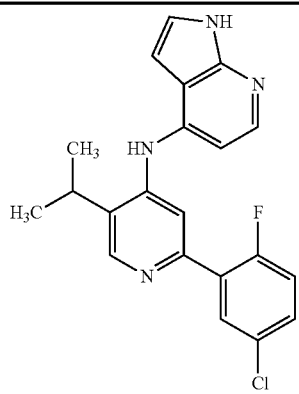
2.27
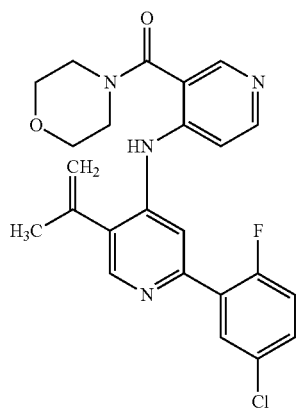 [SMILES: C=C(C)c1cnc(-c2cc(Cl)ccc2F)cc1Nc1ccncc1C(=O)N1CCOCC1]
2.28
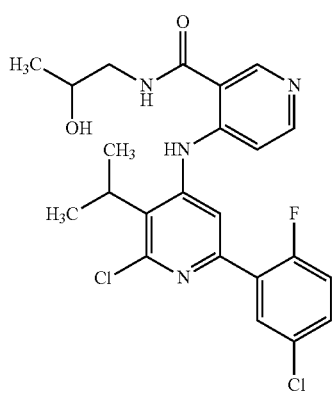
2.29a, 2.29b
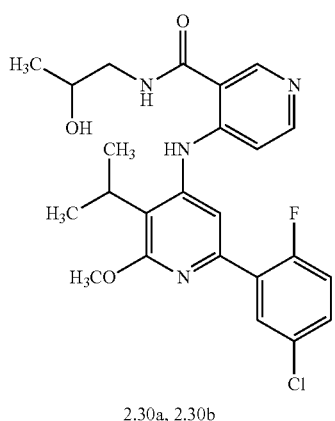 [SMILES: COc1nc(-c2cc(Cl)ccc2F)cc(Nc2ccncc2C(=O)NCC(C)O)c1C(C)C]
2.30a, 2.30b
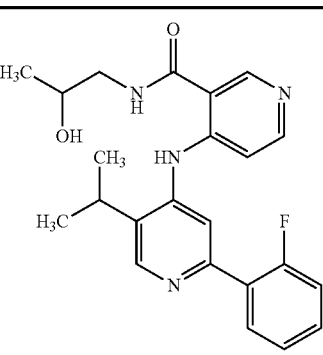
2.31a, 2.31b
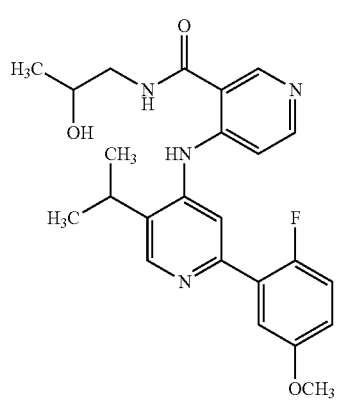
2.32a, 2.32b
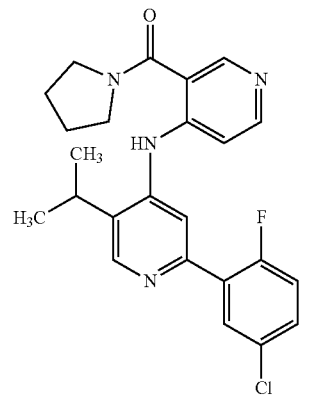 [SMILES: CC(C)c1cnc(-c2cc(Cl)ccc2F)cc1Nc1ccncc1C(=O)N1CCCC1]
2.33
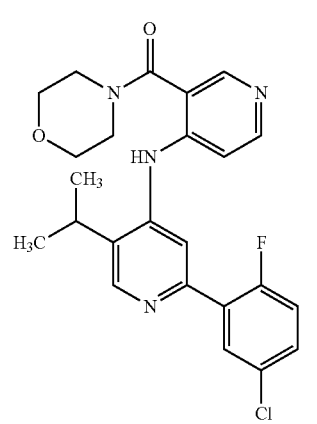 [SMILES: CC(C)c1cnc(-c2cc(Cl)ccc2F)cc1Nc1ccncc1C(=O)N1CCOCC1]
2.34

TABLE 4-continued
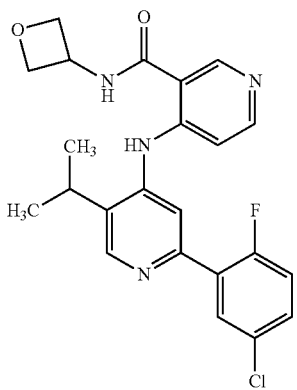 [SMILES: CC(C)c1cnc(-c2cc(Cl)ccc2F)cc1Nc1ccncc1C(=O)NC1COC1]
2.35
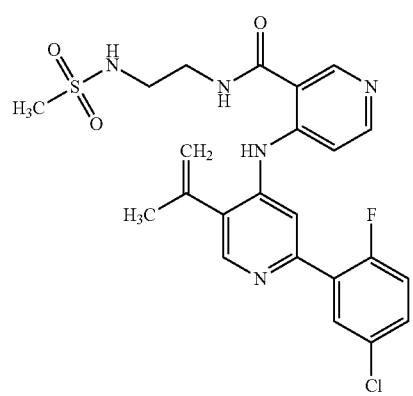 [SMILES: C=C(C)c1cnc(-c2cc(Cl)ccc2F)cc1Nc1ccncc1C(=O)NCCNS(C)(=O)=O]
2.36
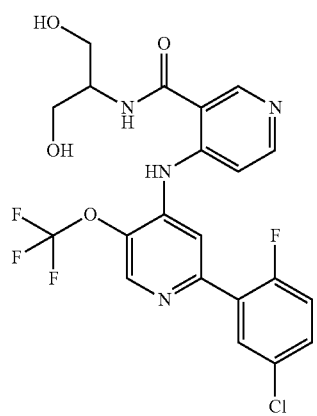 [SMILES: O=C(NC(CO)CO)c1cnccc1Nc1cc(-c2cc(Cl)ccc2F)ncc1OC(F)(F)F]
2.37
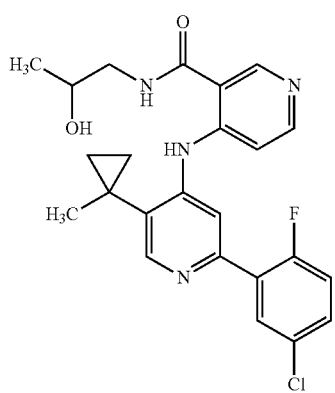
2.38
2.38a, 2.38b
TABLE 4-continued
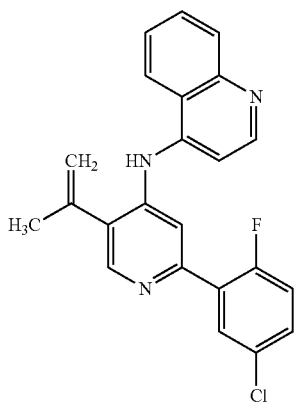 [SMILES: C=C(C)c1cnc(-c2cc(Cl)ccc2F)cc1Nc1ccnc2ccccc12]
2.39
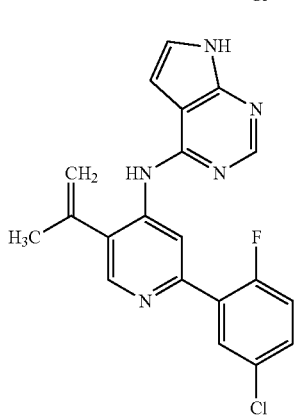
2.40
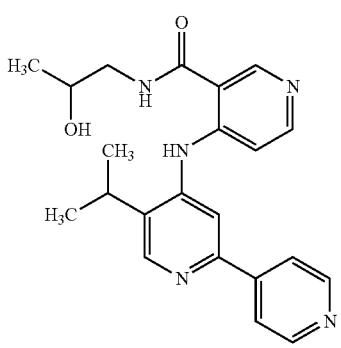
2.41
2.41a, 2.41b
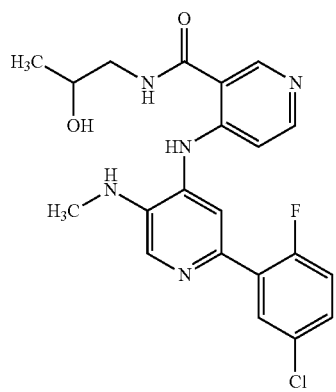
2.42
2.42a, 2.42b TABLE 4-continued

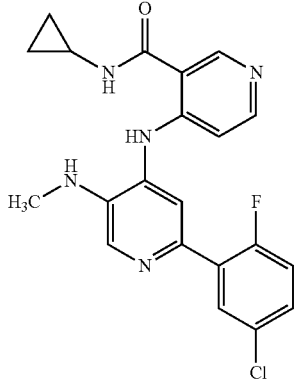 [SMILES: CNc1cnc(-c2cc(Cl)ccc2F)cc1Nc1ccncc1C(=O)NC1CC1]
2.43

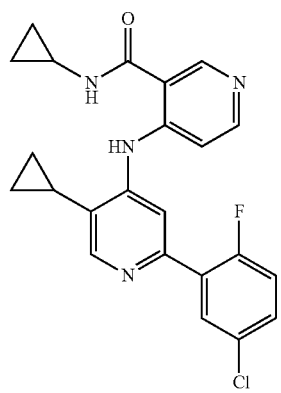 [SMILES: O=C(NC1CC1)c1cnccc1Nc1cc(-c2cc(Cl)ccc2F)ncc1C1CC1]
2.44

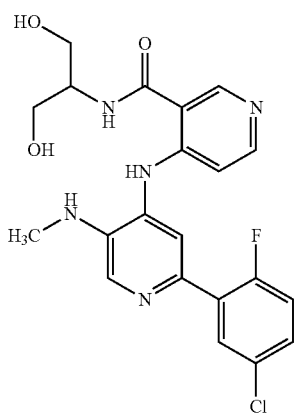 [SMILES: CNc1cnc(-c2cc(Cl)ccc2F)cc1Nc1ccncc1C(=O)NC(CO)CO]
2.45

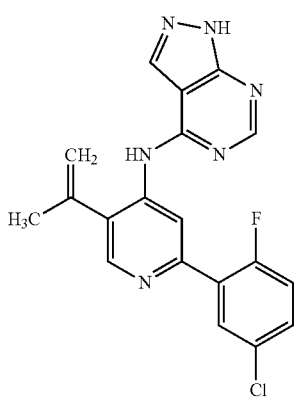 [SMILES: C=C(C)c1cnc(-c2cc(Cl)ccc2F)cc1Nc1ncnc2[nH]ncc12]
2.46

TABLE 4-continued

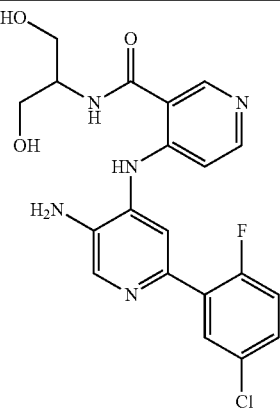
2.47

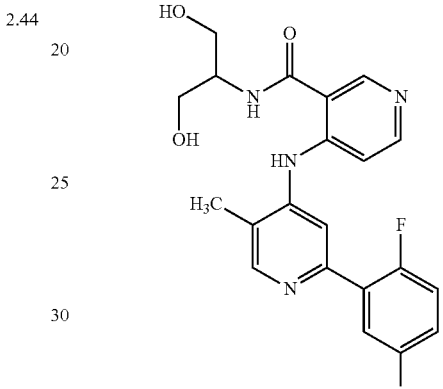
2.48

General Synthetic Methods

A number of synthetic routes may be employed to produce compounds of the present invention. In general, the compounds may be synthesized from conventional starting materials using reactions known in the art. In particular, compounds may be prepared by a number of processes as generally described below in the General Synthetic Schemes and more specifically in the Examples hereinafter. In the following process descriptions, the symbols when used in the formulae depicted are to be understood to represent those groups described above in relation to the formulae herein.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); hour (h); minute (min); second (sec); ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); ethyl acetate (EtOAc); Retention factor (Rf); room temperature (RT); acetyl (Ac); 4,5-Bis(diphenylphosphino)-9,9-dimethylxanthene (Xantphos); 1-[Bis(dimethylamino)methylene]-1H-1,2,3-triazolo[4,5-b]pyridinium 3-oxid hexafluorophosphate (HATU); N,N-diisopropylamine (DIPEA); methyl (Me); ethyl (Et); phenyl (Ph); para-toluenesulfonic acid (PTSA); Diisobutylaluminium hydride (DiBAL-H); Diphenyl phosphoryl azide (DPPA); Tetrakis(triphenylphosphine)palladium(0) (Pd[P(C$_6$H$_5$)$_3$]$_4$, and (tetrakis); meta-Chloroperoxybenzoic acid (m-CPBA), 2,2'-Bis(diphenylphosphino)-1,1'-binaphthyl (BINAP).

The following General Synthetic Schemes and Examples are provided to illustrate but not to limit the invention. Those skilled in the art will be familiar with many of the reaction steps described. Particular publications are presented to assist with the understanding of certain steps of the synthetic route. In some of the reaction schemes that follow a terminal methyl (CH$_3$) and a terminal methylene (=CH$_2$) are shown without the providing the text for these groups (due to space limitations), as is a common convention and well understood by those skilled in the chemical arts.

General Synthetic Scheme 1

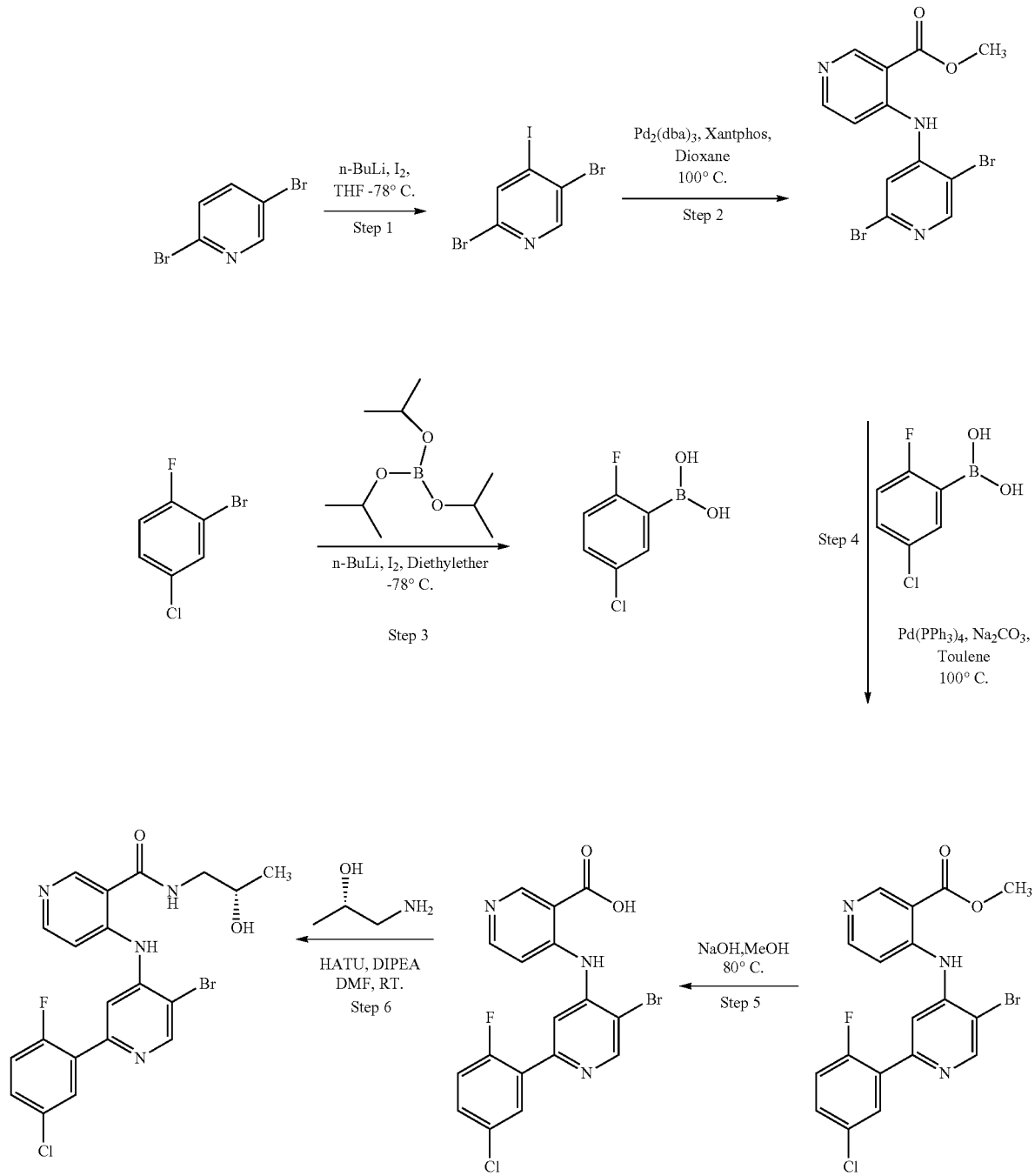

In General Synthetic Scheme 1, one route to compounds of formula (I) commences with a di-halo substituted pyridine that is further functionalized with iodine, under base-mediated iodination conditions, in step 1. The iodo group is selectively substituted under palladium-mediated amination conditions with amines, such as the methyl 4-aminonicotinate shown here, in step 2 to give the 4-amino intermediate. Separately, in step 3, appropriately functionalized aromatic, or heteroaromatic, rings can be treated under base-mediated boronation conditions to provide the boronic acid intermediate which, when applied to the Suzuki coupling conditions of step 4, provide the regioselectively coupled product. Basic hydrolysis conditions of step 5, convert the ester group to its acid which, when subjected to amine coupling conditions of step 6 in the presence of various amines including chiral amines, such as (S)-1-aminopropan-2-ol shown, yields the final desired product. Each step presented in General Synthetic Scheme 1 is amenable to a variety of appropriately functionalized reagents as appropriate to the embodiments provided herein, and will be familiar to those skilled in the art.

General Synthetic Scheme 2

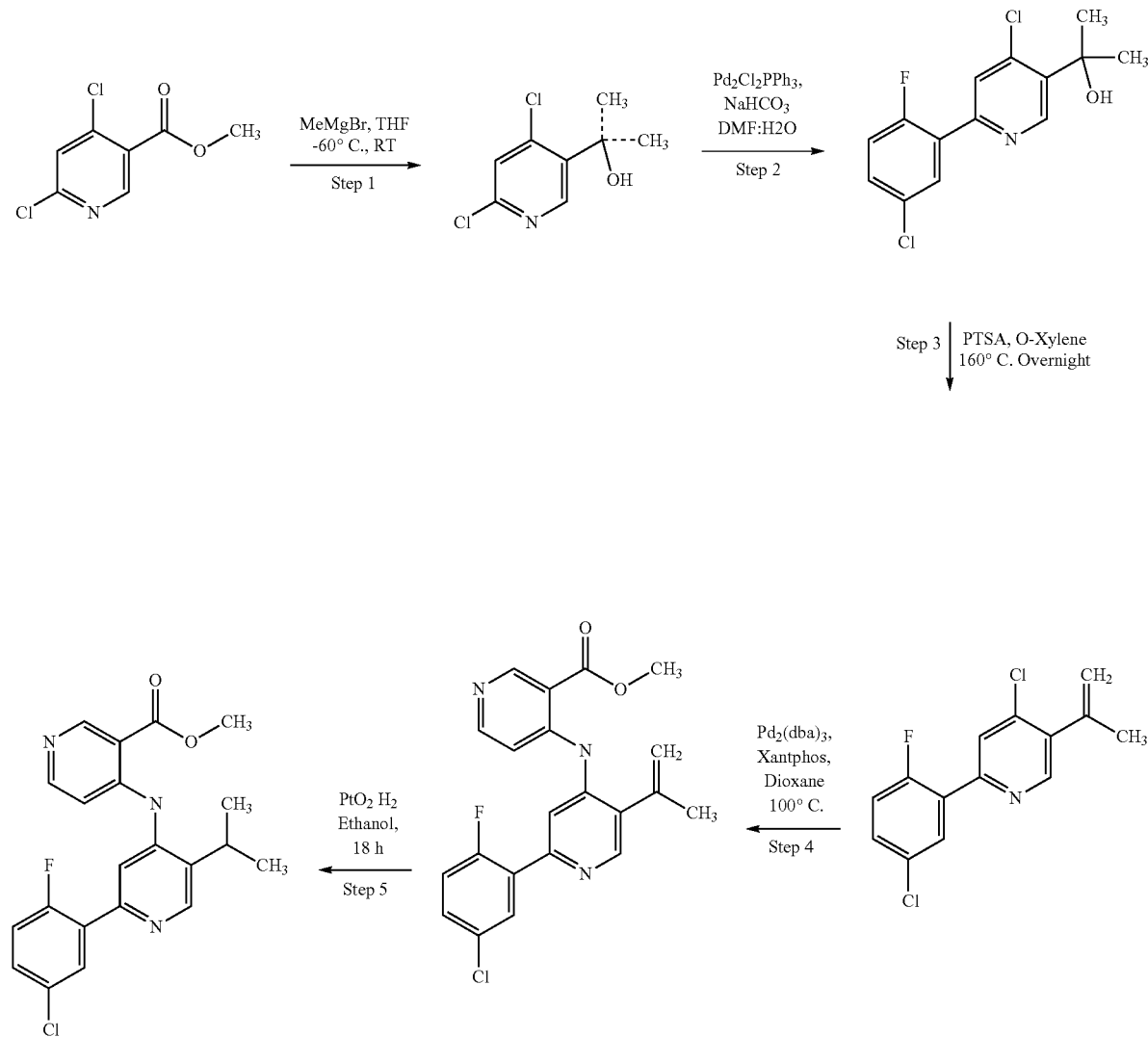

General Synthetic Scheme 2 presents a route to analogs of the products of step 4 in General Synthetic Scheme 1, wherein the substituent A of formula (I) can now be for example a prop-2-enyl or an isopropyl group. Step 1 commences with treatment of an appropriately functionalized aromatic or heteroaromatic ring bearing an ester, with a Grignard reagent such as methylmagnesium bromide, and results in the addition product—a tertiary alcohol. Regioselective coupling in step 2 under palladium-mediated conditions with various boronic acids, similar to those in step 4 of General Synthetic Scheme 1, provides the coupled product. Acid based dehydration conditions of step 3 results in the alkene intermediate which can be subjected to amine coupling conditions of step 4 to provide the 4-aminopyridyl product. If necessary, the propene group can be reduced under hydrogenation conditions of step 5 to yield the propyl substituted derivative. The products of steps 4 and 5 can be utilized as described above in steps 5 and 6 of General Synthetic Scheme 1.

General Synthetic Scheme 3

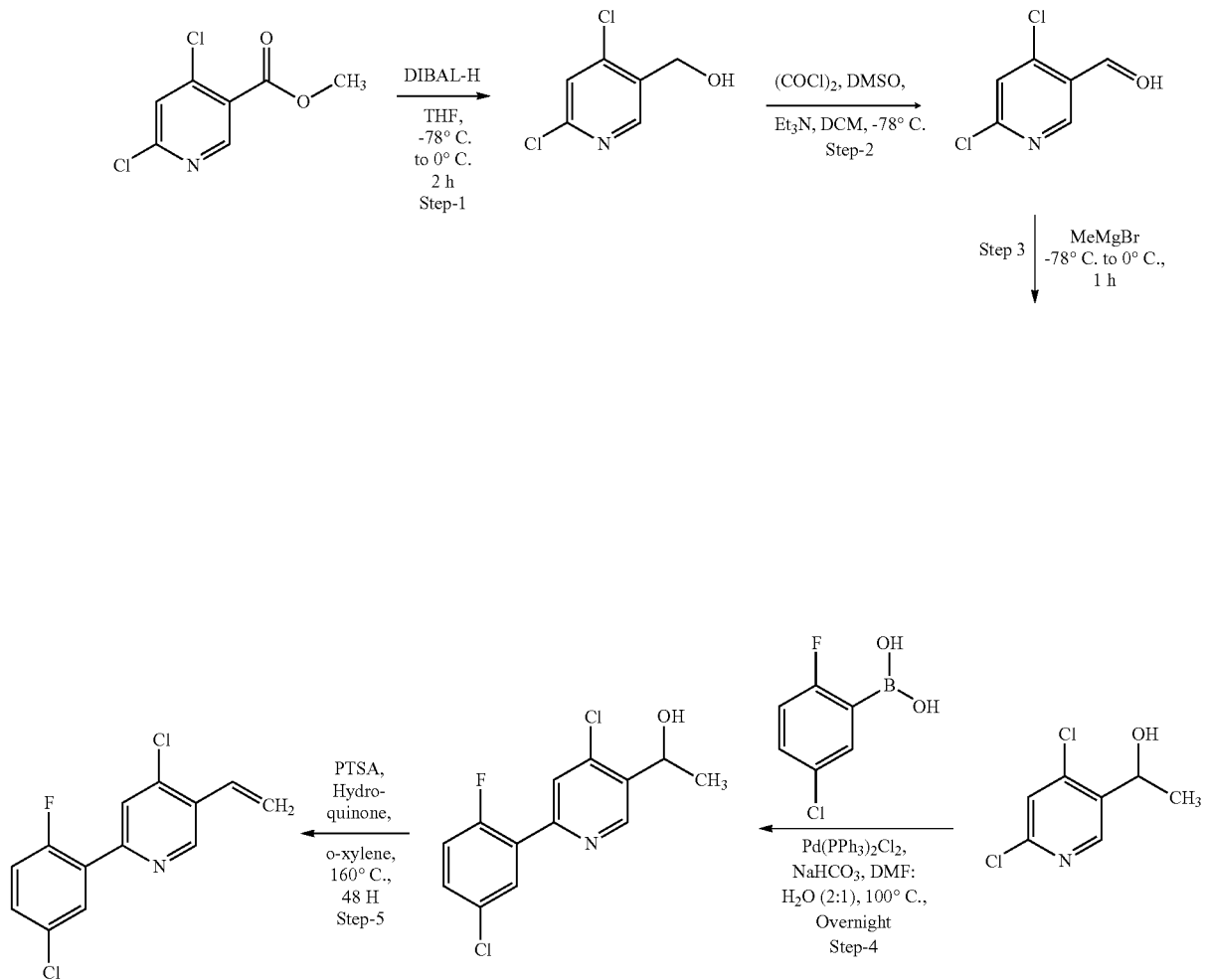

General Synthetic Scheme 3 presents a route to other analogs of the products of step 1 in General Synthetic Scheme 1, wherein the substituent A of formula (I) can now be for example a vinyl group. Step 1 commences with reduction of an appropriately functionalized aromatic or heteroaromatic ring bearing an ester, to afford the primary alcohol which, when subjected to Swern oxidation conditions of step 2, yields the aldehyde. Subjecting the aldehyde to various Grignard reagents in step 3, such as methylmagnesium bromide, provides the secondary alcohol which can undergo regioselective coupling in step 4 with various boronic acids as described in the previous General Synthetic Schemes, to provide the coupled product. The alcohol group can be dehydrated in step 5 under similar conditions as presented in step 3 of General Synthetic Scheme 2, to yield the vinyl product. This product can be utilized as described in step 2 of General Synthetic Scheme 1.

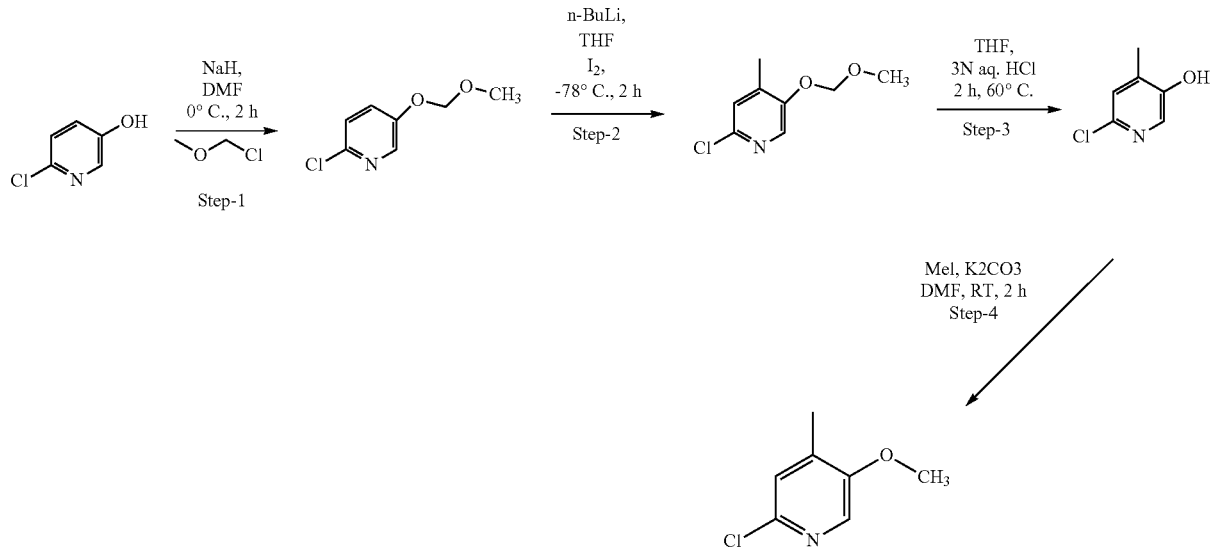

General Synthetic Scheme 4 also presents a route to other analogs of the products of step 1 in General Synthetic Scheme 1, wherein the substituent A of formula (I) can now be for example a methoxy group. This route commences with protection of the alcohol group attached to an appropriately functionalized aromatic or heteroaromatic ring, in the example provided in step 1 to give the methoxymethoxy ("MOM") derivative. Base-mediated iodination conditions of step 2 yield the regioisomeric iodo intermediate, which can be treated to acid hydrolysis conditions of step 3 to deprotect the alcohol group, and finally in step 4, alkylation with various alkyl iodides such as methyl iodide, results in the methoxy substituted product. This product can be utilized as described in step 2 of General Synthetic Scheme 1.

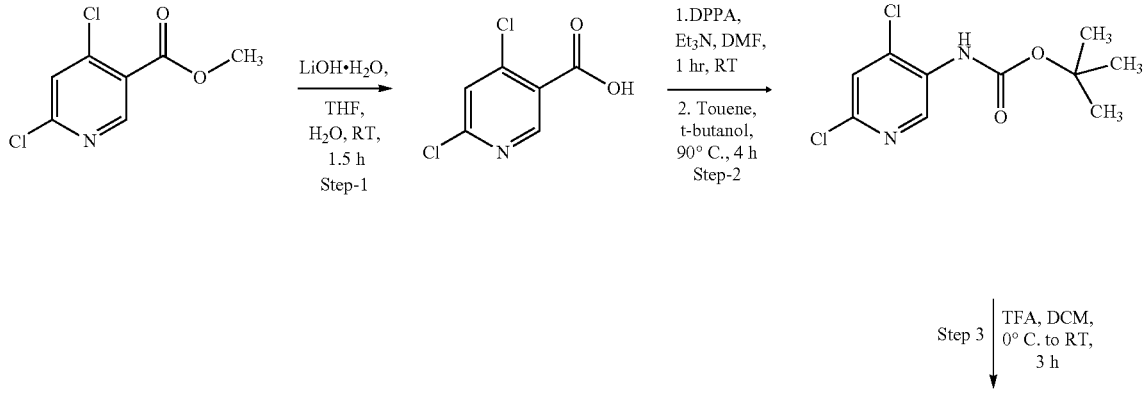

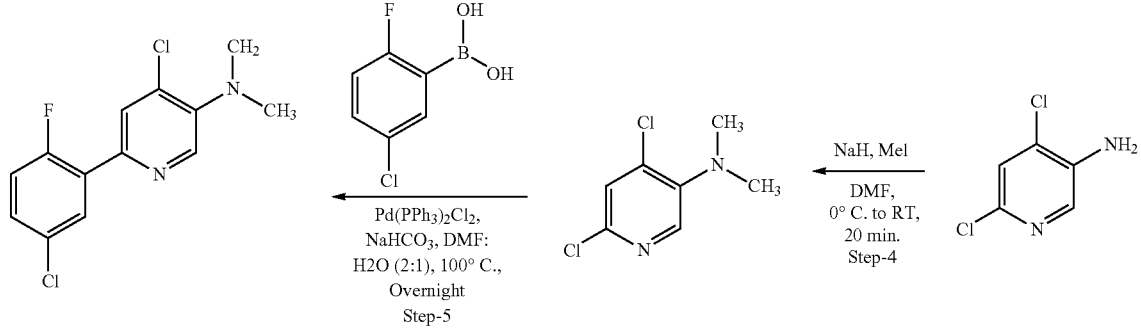

General Synthetic Scheme 5 also presents a route to other analogs of the products of step 1 in General Synthetic Scheme 1, wherein the substituent A of formula (I) can now be for example an amino group. Step 1 presents the hydrolysis of an appropriately functionalized methyl nicotinate ester to its acid derivative, followed in step 2 by a Curtius rearrangement to provide the Boc-protected amine group. Deprotection of the amine under mild acidic conditions of step 3 provides the free amine which, in step 4, can be alkylated with various alkyl halides such as methyl iodide to give the dimethylamino product. Regioselective coupling under Suzuki conditions with various boronic acids presented in step 5 provides an appropriate intermediate that can be utilized in step 2 of General Synthetic Scheme 1.

It is understood that General Synthetic Schemes 1 to 5 present synthetic routes involving steps clearly familiar to those skilled in the art, wherein the substituents described in compounds of formula (I) herein can be varied with a choice of appropriate starting materials and reagents utilized in the steps presented.

EXAMPLES

Comparative Example 1

Synthesis of 4-[[6-(5-chloro-2-fluoro-phenyl)-3-isopropyl-2-pyridyl]amino]-N-(2-hydroxy propyl) pyridine-3-carboxamide

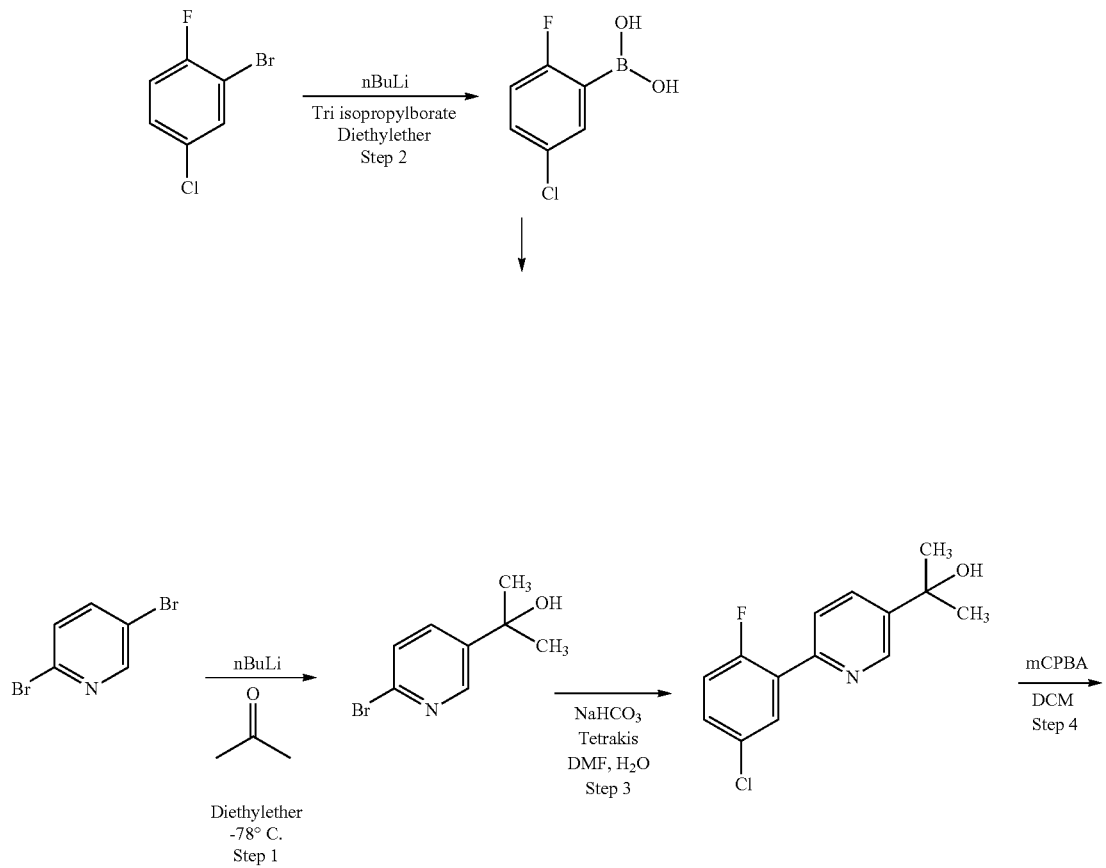

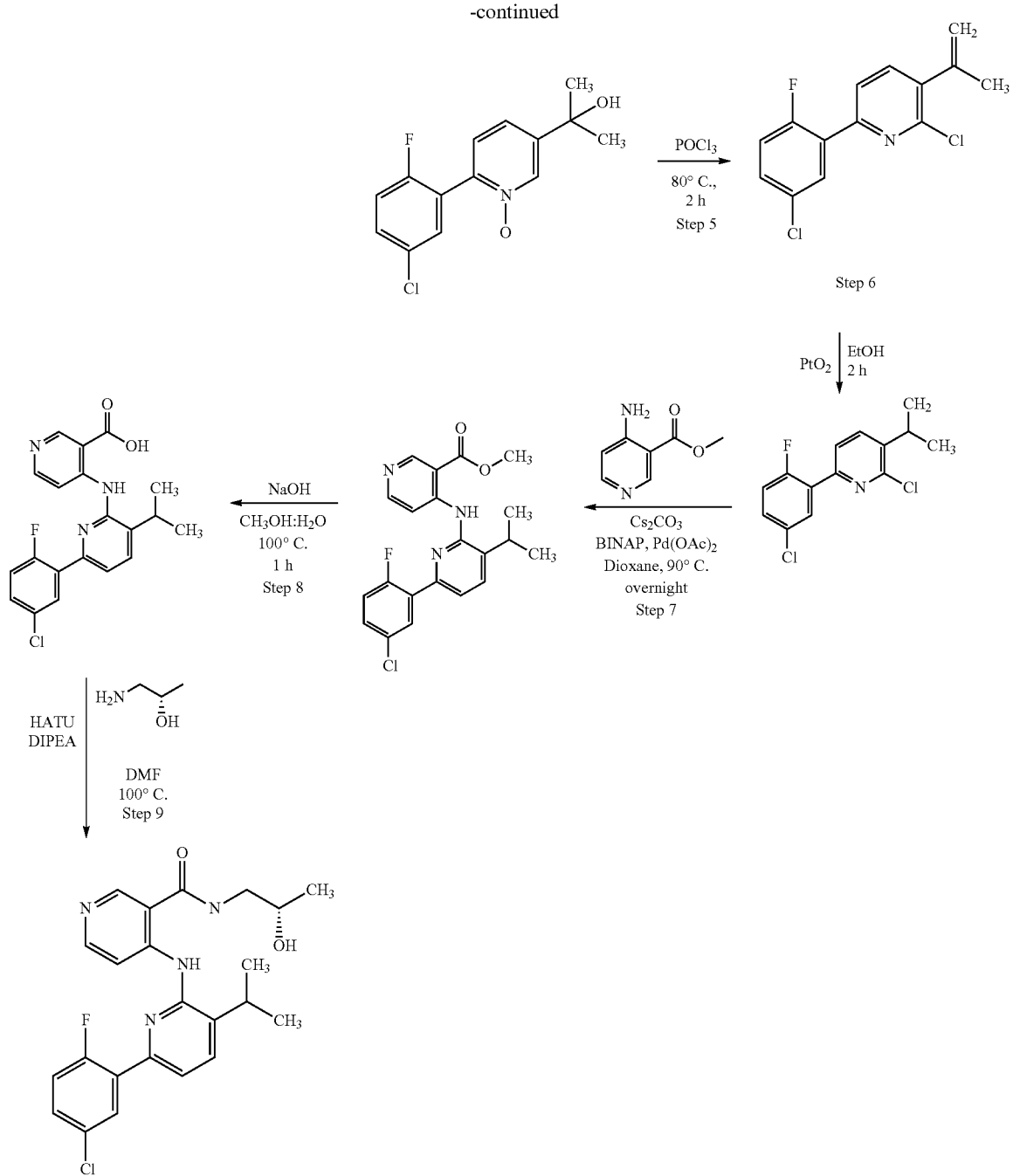

Step 1: Synthesis of 2-(6-bromo-3-pyridyl)propan-2-ol

To a stirred solution of 2,5-dibromopyridine (20 g, 84.4 mmol) in diethyl ether (300 mL) was added a 2.5M solution of n-BuLi in hexane (8.8 mL, 22.16 mmol) at −78° C. and the reaction mixture was stirred at the same temperature for 1 h. To this stirred reaction mixture was added acetone (8 mL, 109.7 mmol) dropwise and the reaction mixture was stirred at −78° C. for 45 min. The progress of reaction was monitored by TLC. After completion of reaction, the mixture was quenched with an aqueous solution of ammonium chloride (100 mL) and extracted by adding more diethyl ether (1000 mL). The organic layer was dried over sodium sulfate, and concentrated under reduced pressure to give a crude product. The crude product was purified by column chromatography on silica gel (100-200 mesh) using 8% EtOAc-hexane system as eluent to afford 2-(6-bromo-3-pyridyl)propan-2-ol (9.9 g).

Step 2: Synthesis of (5-chloro-2-fluoro-phenyl)boronic acid

To a solution of 2-bromo-4-chloro-1-fluoro-benzene (5 g, 0.0238 mol) in anhydrous diethyl ether (30 mL) was added a 2M solution of n-BuLi in n-hexane (13 mL, 0.0262 mol) at −70° C. under nitrogen atmosphere. The reaction mixture was stirred at the same temperature for 30 min. Then, to this reaction mixture was added triisopropyl borate (4.93 g, 0.0262 mol) dropwise. The reaction mixture turned into a white slurry, which was further stirred at −70° C. for 30 min and then warmed to RT and stirred for 1 h. The progress of reaction was monitored by TLC and 1H NMR. After completion of the reaction, the mixture was hydrolyzed with 6 N HCl, stirred for 1 h and the product was extracted with EtOAc (50 mL). The organic layer was washed with brine and concentrated under reduced pressure to obtain a sticky compound which was triturated with n-pentane to afford (5-chloro-2-fluoro-phenyl)boronic acid (2.2 g) as an off white solid.

Step 3: Synthesis of 2-[6-(5-chloro-2-fluoro-phenyl)-3-pyridyl]propan-2-ol

To a solution 2-(6-bromo-3-pyridyl)propan-2-ol (1.5 g, 6.94 mmol) and (5-chloro-2-fluoro-phenyl)boronic acid (1.81 g, 10.41 mmol) in DMF (20 mL) and water (20 mL) was added $NaHCO_3$ (1.16 g, 0.013 mmol). The reaction mixture was purged with nitrogen for 30 min. To this reaction mixture was added tetrakis(triphenylphosphine)palladium(0) (401 mg, 0.347 mmol) and then the reaction mixture was heated at 100° C. overnight. The progress of reaction was monitored by LCMS. After completion of the reaction, to the reaction mixture was added water (75 mL) and the product was extracted with EtOAc (2×250 mL). The combined organic layer was washed with water (4×100 mL), dried over sodium sulfate and concentrated under reduced pressure to give a crude product. The crude product was purified by column chromatography on silica gel (100-200 mesh) using 20-60% EtOAc-hexane to afford 2-[6-(5-chloro-2-fluoro-phenyl)-3-pyridyl]propan-2-ol (1.1 g).

Step 4: Synthesis of 2-[6-(5-chloro-2-fluoro-phenyl)-3-pyridyl]propan-2-ol

To a stirred solution of 2-[6-(5-chloro-2-fluoro-phenyl)-3-pyridyl]propan-2-ol (2 g, 7.54 mmol) in DCM (12 mL) was added mCPBA (1.95 g, 11.32 mmol) in portions at 0° C. The reaction mixture was stirred at RT overnight. The progress of reaction was monitored by TLC and LCMS. After completion of the reaction, the DCM layer was washed with 1 N HCl (2×100 mL). The aqueous layer was then concentrated under reduced pressure to give N-oxide of 2-[6-(5-chloro-2-fluoro-phenyl)-3-pyridyl]propan-2-ol as HCl salt (1.9 g) as an off white solid.

Step 5: Synthesis of 2-chloro-6-(5-chloro-2-fluoro-phenyl)-3-isopropenyl-pyridine A mixture of the N-oxide of 2-[6-(5-chloro-2-fluoro-phenyl)-3-pyridyl]propan-2-ol (1.9 g, 6.76 mmol) and $POCl_3$ (9.7 mL, 101.4 mmol) was heated to reflux at 80° C. for 2 h. The progress of reaction was monitored by LCMS. After completion of the reaction, the $POCl_3$ was evaporated under reduced pressure. An aqueous solution of $NaHCO_3$ was added to the residue, and the product was extracted with EtOAc (2×250 mL). The combined organic layer was dried over sodium sulfate and concentrated under reduced pressure to give a pale yellow liquid compound that was purified by column chromatography on silica gel (100-200 mesh) using 0.5% EtOAc-hexane system as eluent to afford 2-chloro-6-(5-chloro-2-fluoro-phenyl)-3-isopropenyl-pyridine (600 mg) as a yellow oily liquid.

Step 6: Synthesis of 2-chloro-6-(5-chloro-2-fluoro-phenyl)-3-isopropyl-pyridine To a stirred solution of 2-chloro-6-(5-chloro-2-fluoro-phenyl)-3-isopropenyl-pyridine (600 mg, 2.13 mmol) in ethanol (5 mL) was added $PtO_2$ (100 mg). The reaction mixture was hydrogenated using hydrogen bladder for 4 h. The progress of reaction was monitored by NMR After completion of the reaction, the mixture was filtered through a celite bed and the celite bed washed with MeOH (200 mL). The filtrate was concentrated under reduced pressure to obtain 2-chloro-6-(5-chloro-2-fluoro-phenyl)-3-isopropyl-pyridine (570 mg) as a pale yellow liquid.

Step 7: Synthesis of 4-[[6-(5-chloro-2-fluoro-phenyl)-3-isopropyl-2-pyridyl]amino]pyridine-3-carboxylate acid To a solution of 2-chloro-6-(5-chloro-2-fluoro-phenyl)-3-isopropyl-pyridine (570 mg, 2.01 mmol) and methyl 4-aminopyridine-3-carboxylate (306 mg, 2.01 mmol) in dioxane (3 mL) was added $Cs_2CO_3$ (918 mg, 2.8 mmol). The reaction mixture was purged with nitrogen for 1 h. Then, to this reaction mixture was added BINAP (175 mg, 0.281 mmol) and $Pd(OAc)_2$. The reaction mixture was heated at 90° C. overnight. The progress of reaction was monitored by LCMS and TLC. After completion of the reaction, the product was extracted with EtOAc (2×200 mL). The combined organic layer was concentrated under reduced pressure to give a crude product. The crude product was purified by column chromatography on silica gel (100-200 mesh) using 20% EtOAc-hexane system as eluent to afford methyl 4-[[6-(5-chloro-2-fluoro-phenyl)-3-isopropyl-2-pyridyl]amino]pyridine-3-carboxylate acid (360 mg) as a white solid compound.

Step 8: Synthesis of 4-[[6-(5-chloro-2-fluoro-phenyl)-3-isopropyl-2-pyridyl]amino]pyridine-3-carboxylic acid To a solution of methyl 4-[[6-(5-chloro-2-fluoro-phenyl)-3-isopropyl-2-pyridyl]amino]pyridine-3-carboxylate (360 mg, 0.90 mmol) in MeOH (6 mL) was added sodium hydroxide (72 mg, 1.30 mmol) in water (1 mL). The reaction mixture was heated at reflux for 1 h. The progress of reaction was monitored by TLC and NMR. After completion of the reaction, the mixture was concentrated and toluene was added to give 4-[[6-(5-chloro-2-fluoro-phenyl)-3-isopropyl-2-pyridyl]amino]pyridine-3-carboxylic acid (350 mg) as sodium salt as an off white solid.

Step 9: Synthesis of 4-[[6-(5-chloro-2-fluoro-phenyl)-3-isopropyl-2-pyridyl]amino]-N-(2-hydroxypropyl) pyridine-3-carboxamide To a solution of 4-[[6-(5-chloro-2-fluoro-phenyl)-3-isopropyl-2-pyridyl]amino]pyridine-3-carboxylic acid (50 mg, 0.123 mmol) in DMF (1.5 mL) was added DIPEA (0.06 mL, 0.369 mmol) followed by addition of HATU (93 mg, 0.246 mmol). After 15 min, to this reaction mixture was added (S)-1-aminopropan-2-ol (18 mg, 0.23 mmol). The reaction mixture was heated at 100° C. overnight. The progress of reaction was monitored by LCMS. After completion of the reaction, the mixture was quenched by addition of water (5 mL) and the product was extracted with EtOAc (2×50 mL). The combined organic layer was dried over sodium sulfate and concentrated under reduced pressure to give a crude product. The crude product was purified by reverse phase preparative HPLC to afford 4-[[6-(5-chloro-2-fluoro-phenyl)-3-isopropyl-2-pyridyl]amino]-N-(2-hydroxy propyl) pyridine-3-carboxamide (11.89 mg) as an off white solid.

NMR: $^1$H NMR (400 MHz, $CD_3OD$) δ (ppm): 8.84-8.69 (m, 2H), 8.34 (d, J=6.1 Hz, 1H), 8.00 (dd, J=6.8, 2.7 Hz 1H), 7.79 (d, J=8.0 Hz, 1H), 7.57-7.49 (m, 1H), 7.42 (m, 1H), 7.25 (dd, J=10.9, 8.9 Hz, 1H), 4.01 (q, J=6.1 Hz, 1H), 3.45 (d, J=4.7 Hz, 2H), 3.37 (dd, J=13.3, 6.9 Hz, 2H), 3.23 (dd, J=13.7, 6.8 Hz, 1H), 1.37 (d, J=6.8 Hz, 6H), 1.24 (d, J=6.3 Hz, 3H).

Example 1. Preparation of Compound Nos. 1, 1a and 1b
Synthesis of 4-[[5-bromo-2-(5-chloro-2-fluoro-phenyl)-4-pyridyl]amino]-N-(2-hydroxypropyl) pyridine-3-carboxamide
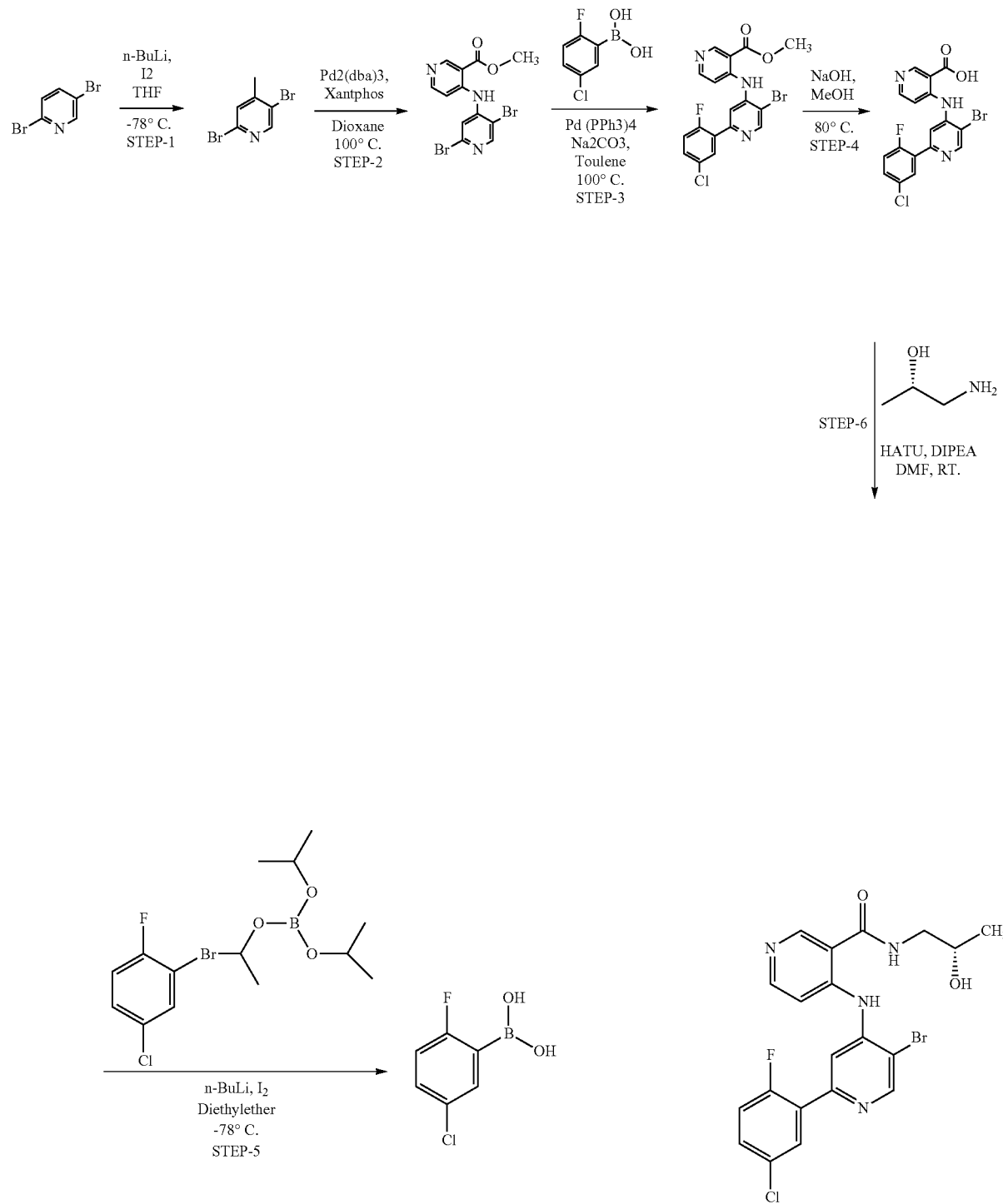

Step 1: Synthesis of 2,5-dibromo-4-iodo-pyridine

To a solution of diisopropylamine (3.24 mL, 0.023 mol) in anhydrous THF (50 mL) was added a 2M solution of n-BuLi in n-hexane (11.6 mL, 0.023 mol) at −70° C. under nitrogen atmosphere. The reaction mixture was stirred at −70° C. for 30 min. To this reaction mixture was added 2,5-dibromopyridine (5 g, 0.021 mol) in THF (30 mL) dropwise. The reaction mixture was stirred at −70° C. for 4 h. To the reaction mixture, then was added a solution of iodine (6.96 g, 0.0274 mol) in THF (20 mL) and stirred for 30 min at the same temperature. The progress of reaction was monitored by TLC & $^1$H NMR After completion of reaction, the mixture was quenched using aqueous Sodium thiosulfate solution and the product was extracted with EtOAc. The organic layer was washed with aqueous sodium thiosulfate solution and brine solution. The organic layer was dried over anhydrous sodium sulfate and concentrated under reduced pressure to afford 2,5-dibromo-4-iodo-pyridine (7.3 g) as a yellow solid pure compound.

Step 2: Synthesis of methyl 4-[(2,5-dibromo-4-pyridyl)amino]pyridine-3-carboxylate To a suspension of 2,5-dibromo-4-iodo-pyridine (3.5 g, 0.0096 mol) methyl 4-aminopyridine-3-carboxylate (1.615 g, 0.0106 mol) and potassium phosphate tribasic (4.095 g, 0.0193 mol) in dioxane (20 mL) was purged with nitrogen for 45 min at RT. Then, to this reaction mixture was added Xantphos (0.837 g, 0.00144 mol) and Pd$_2$(dba)$_3$ (1.397 g, 0.00144 mol) and purging with nitrogen was continued for 10 min. The reaction mixture was heated at 110° C. overnight. The progress of reaction was monitored by TLC and LCMS. After completion of reaction, the mixture was filtered through a celite bed and the celite bed was washed with EtOAc. The filtrate was concentrated under reduced pressure to obtain crude compound that was purified by column chromatography on silica (100:200 mesh) using 40% EtOAc-hexane system as eluent to afford methyl 4-[(2,5-dibromo-4-pyridyl)amino]pyridine-3-carboxylate pure compound (1.510 g) as a yellow solid.

Step 3: Synthesis of methyl 4-[[5-bromo-2-(5-chloro-2-fluoro-phenyl)-4-pyridyl]amino]pyridine-3-carboxylate To a suspension of methyl 4-[(2,5-dibromo-4-pyridyl)amino]pyridine-3-carboxylate (1.5 g, 0.0038 mol), (5-chloro-2-fluoro-phenyl) boronic acid (1.014 g, 0.0058 mol) and sodium carbonate (0.823 g, 0.0077 mol) in toluene (20 mL) was purged with nitrogen for 45 min at RT. To this reaction mixture was added Pd(PPh$_3$)$_4$ (0.224 g, 0.00019 mol) and purging with nitrogen was continued for a further 10 min. The reaction mixture was heated at 100° C. overnight. After completion of reaction, the mixture was diluted with water and the product was extracted with EtOAc. The organic layer was washed with water and brine solution, dried over anhydrous sodium sulfate and concentrated under reduced pressure to obtain crude compound that was purified by column chromatography on silica (100:200 mesh) using 35-40% EtOAc-hexane system as eluent to afford methyl 4-[[5-bromo-2-(5-chloro-2-fluoro-phenyl)-4-pyridyl]amino]pyridine-3-carboxylate (1.07 g) in pure form.

Step 4: Synthesis of 4-[[5-bromo-2-(5-chloro-2-fluoro-phenyl)-4-pyridyl]amino]pyridine-3-carboxylic acid To a suspension of methyl 4-[[5-bromo-2-(5-chloro-2-fluoro-phenyl)-4-pyridyl]amino]pyridine-3-carboxylate (665 mg, 1.522 mmol) in MeOH (5 mL) was added a solution of NaOH (91 mg, 2.284 mmol) in water (1 mL). The reaction mixture was heated at 80° C. for 1 h. The progress of reaction was monitored by TLC. After completion of reaction, the mixture was concentrated under reduced pressure to obtain a sticky compound. To this reaction mixture was added toluene (3×10 mL) to obtain a solid compound which was triturated with diethyl ether (10 mL) to afford 4-[[5-bromo-2-(5-chloro-2-fluoro-phenyl)-4-pyridyl]amino]pyridine-3-carboxylic acid (550 mg) as a light yellow solid.

Step 5: Synthesis of (5-chloro-2-fluoro-phenyl)boronic acid

To a solution of 2-bromo-4-chloro-1-fluoro-benzene (5 g, 0.0238 mol) in anhydrous diethyl ether (30 mL) was added a 2M solution of n-BuLi in n-hexane (13 mL, 0.0262 mole) at −70° C. under nitrogen atmosphere. The solution was stirred for 30 min at the same temperature, and then triisopropyl borate (4.93 g, 0.0262 mol) was added dropwise in to the solution. The white slurry that formed was stirred for 30 min at −70° C. and then warmed to RT and stirred for 1 h. The reaction was monitored by TLC and $^1$H NMR. After completion of reaction, the reaction mixture was hydrolyzed with 6 N NaOH and stirred for 1 h. The reaction mixture was extracted with EtOAc. The organic layer was washed with brine and concentrated under reduced pressure to obtain a sticky compound that was triturated with n-Pentane and dried to afford (5-chloro-2-fluoro-phenyl)boronic acid (2.2 g) as an off white solid.

Step 6: Synthesis of 4-[[5-bromo-2-(5-chloro-2-fluoro-phenyl)-4-pyridyl]amino]-N-(2-hydroxypropyl)pyridine-3-carboxamide To a solution of 4-[[5-bromo-2-(5-chloro-2-fluoro-phenyl)-4-pyridyl]amino]pyridine-3-carboxylic acid (550 mg, 1.241 mmol) in DMF (5 mL) was added N,N-diisopropylethyl amine (0.65 mL, 3.725 mmol) and HATU (755 mg, 1.986 mmol). The reaction mixture was stirred at RT for 15 min under nitrogen atmosphere. Then, to this reaction mixture was added (S)-1-aminopropan-2-ol (233 mg, 3.104 mmol) and the reaction mixture was stirred at 35° C. overnight. The progress of reaction was monitored by TLC. After completion of reaction, the mixture was diluted with water and extracted with EtOAc (100 mL). The organic layer was washed with water (100 mL) and brine solution (100 mL), dried over anhydrous sodium sulfate and concentrated under reduced pressure to obtain crude product. The crude product was purified by reverse phase HPLC to afford 4-[[5-bromo-2-(5-chloro-2-fluoro-phenyl)-4-pyridyl]amino]-N-(2-hydroxypropyl) pyridine-3-carboxamide (11 mg) as a white solid. The (R) enantiomer can be synthesized utilizing (R)-1-aminopropan-2-ol in this step.

NMR: $^1$H NMR (400 MHz. CDCl$_3$) δ (ppm): 10.62 (s, 1H), 8.75 (d, J=5.7 Hz, 2H), 8.50 (d, J=5.9 Hz, 1H), 8.03 (dd, J=6.8, 2.7 Hz, 1H), 7.88 (s, 1H), 7.47 (d, J=5.8 Hz, 1H), 7.35 (m, 1H), 7.11 (dd, J=10.8, 8.7 Hz, 1H), 6.76 (s, 1H), 4.09 (m, 1H), 3.76 (m, 1H), 3.31 (m, 1H), 1.34-1.23 (d, 3H).

Example 2. Preparation of Compound Nos. 2, 2a and 2b

Synthesis of (S)-4-[[2-(5-chloro-2-fluoro-phenyl)-5-isopropyl-4-pyridyl]amino]-N-(2-hydroxy propyl) pyridine-3-carboxamide

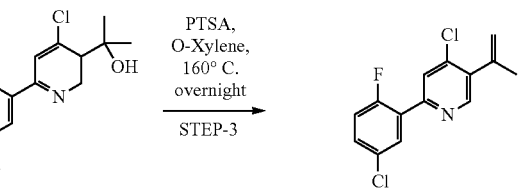

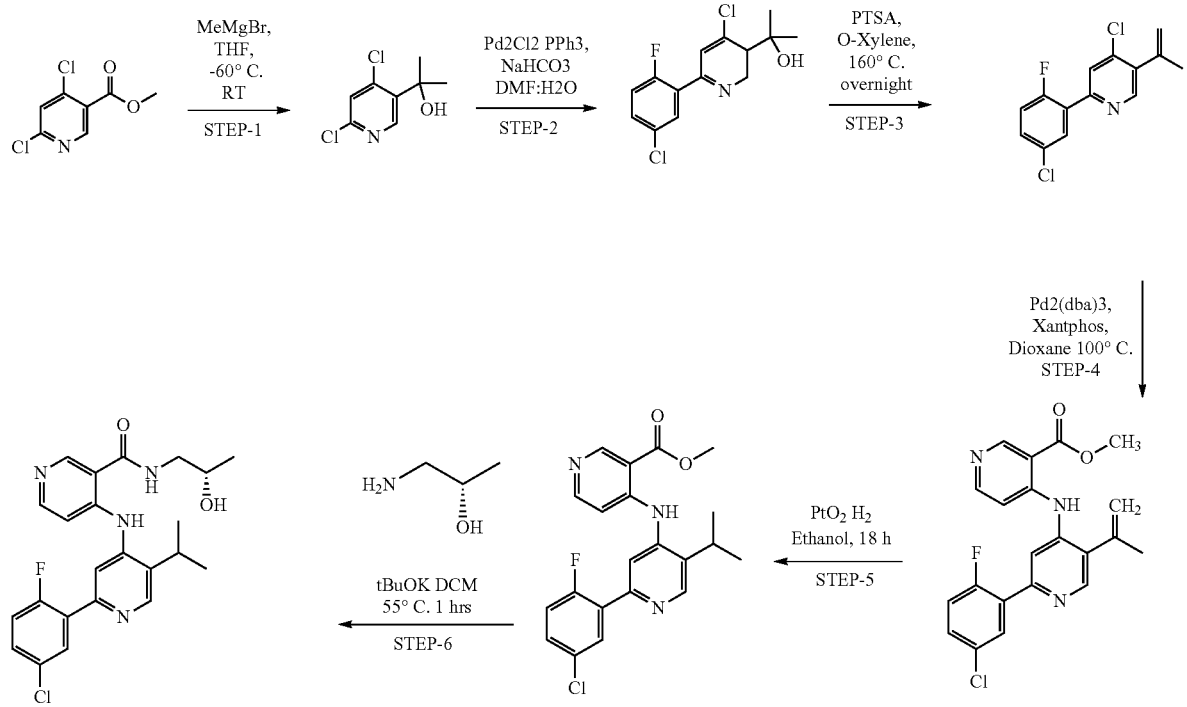

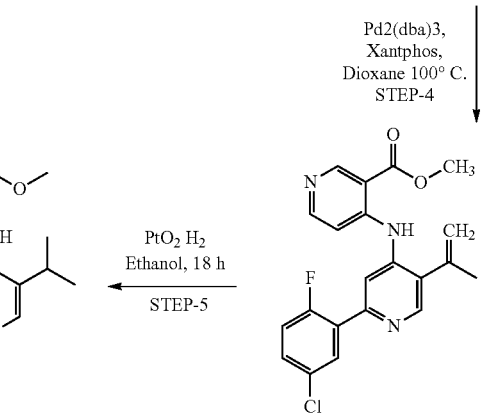

Step 1: Synthesis of 2-(4,6-dichloro-3-pyridyl)propan-2-ol

To a solution of (5 g, 0.0243 mol) in dry THF (60 mL) was added a 3M solution of methylmagnesium bromide in diethyl ether (28.3 mL, 0.0848 mol) dropwise under nitrogen at −60° C. The reaction mixture was stirred at −60° C. to 0° C. for 2 h. The progress of reaction was monitored by TLC & $^1$H NMR. After completion of the reaction, the mixture was quenched with a saturated aqueous solution of ammonium chloride and extracted with EtOAc. The organic layer was washed water and brine solution, dried over anhydrous sodium sulfate and concentrated under reduced pressure to afford 2-(4,6-dichloro-3-pyridyl)propan-2-ol (4.96 g) in pure form as a yellow oily substance.

Step 2: Synthesis of 2-[4-chloro-6-(5-chloro-2-fluoro-phenyl)-3-pyridyl]propan-2-ol A suspension of 2-(4,6-dichloro-3-pyridyl)propan-2-ol (4.96 g, 0.024 mole), (5-chloro-2-fluoro-phenyl)boronic acid (6.284 g, 0.036 mol) and sodium bicarbonate (4.045 g, 0.048 mol) in a 2:1 mixture of DMF:H$_2$O (60 mL) was purged with nitrogen for 45 min. Then, to this reaction mixture was added Pd(PPh$_3$)$_4$ (500 mg) and purging continued with nitrogen for 10 min. The reaction mixture was heated at 80° C. overnight. After completion of reaction, the reaction mixture was diluted with water, and the product was extracted with EtOAc. The organic layer was washed with water and brine solution, then dried over anhydrous sodium sulfate and concentrated under reduced pressure to obtain crude product. The crude product was purified by column chromatography on silica gel (100:200 mesh) using 7% EtOAc-hexane system as eluent to afford 2-[4-chloro-6-(5-chloro-2-fluoro-phenyl)-3-pyridyl]propan-2-ol (4.931 g) pure compound as an off white solid.

Step 3: Synthesis of 4-chloro-2-(5-chloro-2-fluoro-phenyl)-5-isopropenyl-pyridine To a solution of 2-[4-chloro-6-(5-chloro-2-fluoro-phenyl)-3-pyridyl]propan-2-ol (4.931 g, 0.0165 mol) in O-xylene (60 mL) was added PTSA.H$_2$O (0.313 g, 0.00165 mol) and hydroquinone (0.181 g, 0.00165 mol) and heated at 160° C. in Dean Stark apparatus overnight. The progress of reaction was monitored by TLC and $^1$H NMR. After completion of reaction, the mixture was concentrated under reduced pressure to obtain crude product. The crude product was purified by column chromatography on silica gel (100:200 mesh) using 10% EtOAc-hexane to afford 4-chloro-2-(5-chloro-2-fluoro-phenyl)-5-isopropenyl-pyridine (4 g) pure compound.

Step 4: Synthesis of 4-[[2-(5-chloro-2-fluoro-phenyl)-5-isopropenyl-4-pyridyl]amino]pyridine-3-carboxylate To a suspension of 4-chloro-2-(5-chloro-2-fluoro-phenyl)-5-isopropenyl-pyridine (1 g, 3.55 mmol), methyl 4-aminopyridine-3-carboxylate (0.595 g, 0.0039 mol) and potassium phosphate tribasic (1.510 g, 0.0071 mol) in dioxane (20 mL) was purged with nitrogen for 45 min. To this reaction mixture was added Xantphos (0.308 g, 0.0053 mol) and Pd$_2$(dba)$_3$ (0.552 g, 0.0053 mol) and purging continued with nitrogen for 10 min. The reaction mixture was heated at 100° C. for 16 h. The progress of reaction was monitored by TLC and LCMS. After completion of reaction, the reaction mixture was filter through a celite bed, and the celite bed was washed with EtOAc. The filtrate was concentrated under reduced pressure to obtain the crude product. The crude product was purified by column chromatography on silica gel (100:200 mesh) using 30-35% EtOAc-hexane as eluent to afford methyl 4-[[2-(5-chloro-2-fluoro-phenyl)-5-isopropenyl-4-pyridyl]amino]pyridine-3-carboxylate (0.7 g) pure compound as a yellow solid.

Step 5: Synthesis of methyl 4-[[2-(5-chloro-2-fluoro-phenyl)-5-isopropyl-4-pyridyl]amino]pyridine-3-carboxylate To a stirred solution of methyl 4-[[2-(5-chloro-2-fluoro-phenyl)-5-isopropenyl-4-pyridyl]amino]pyridine-3-carboxylate (360 mg, 0.906 mmol) in ethanol (5 mL) was added $PtO_2$ (80 mg). The reaction mixture was stirred at RT for 18 h under hydrogen atmosphere using a hydrogen bladder. The progress of reaction was monitored by $^1H$ NMR. After completion of reaction, the mixture was filtered through a celite bed, and the celite bed was washed with EtOAc (2×50 mL). The filtrate was collected and concentrated under reduced pressure to afford methyl 4-[[2-(5-chloro-2-fluoro-phenyl)-5-isopropyl-4-pyridyl]amino]pyridine-3-carboxylate (350 mg) as a sticky oily substance.

Step 6: Synthesis of (S)-4-[[2-(5-chloro-2-fluoro-phenyl)-5-isopropyl-4-pyridyl]amino]-N-(2-hydroxypropyl)pyridine-3-carboxamide To a stirred solution of (S)-1-aminopropan-2-ol (86 mg, 1.14 mmol) in DCM (10 mL) was added potassium tert-butoxide (128 mg, 1.14 mmol). The reaction mixture was stirred at RT for 10 min under nitrogen atmosphere. Then, to this reaction mixture was added a solution of methyl 4-[[2-(5-chloro-2-fluoro-phenyl)-5-isopropyl-4-pyridyl]amino] pyridine-3-carboxylate (350 mg, 0.877 mmol) in DCM (10 mL) dropwise. The reaction mixture was heated at 55° C. for 1 h. The progress of reaction was monitored by TLC and LCMS. After completion of reaction, the mixture was diluted with DCM (50 mL) and washed with water (30 mL) and brine solution (20 mL). The organic layer was dried over anhydrous sodium sulfate, and concentrated under reduced pressure to obtain the crude product. The crude product was purified by reverse phase HPLC to afford (S)-4-[[2-(5-chloro-2-fluoro-phenyl)-5-isopropyl-4-pyridyl]amino]-N-(2-hydroxypropyl)pyridine-3-carboxamide (13 mg) as the TFA salt. The (R) enantiomer can be synthesized utilizing (R)-1-aminopropan-2-ol in this step.

NMR: $^1H$ NMR (400 MHz, $CD_3OD$) δ (ppm): 8.92 (s, 1H), 8.77 (s, 1H), 8.37 (d, J=7.1 Hz, 1H), 7.99-7.90 (m, 2H), 7.54 (m, 1H), 7.46 (d, J=7.0 Hz, 1H), 7.31 (t, J=9.7 Hz, 1H), 4.07-3.94 (m, 1H), 3.49 (m, 1H), 3.37 (m, 1H), 3.32-3.21 (m, 1H), 1.40 (d, J=6.9 Hz, 6H), 1.24 (d, J=6.3 Hz, 3H).

Example 3. Preparation of Compound Nos. 3, 3a and 3b

Synthesis of (S)-4-(2-(5-chloro-2-fluorophenyl)-5-(prop-1-en-2-yl)pyridin-4-ylamino)-N-(2-hydroxypropyl)pyridine-5-carboxamide

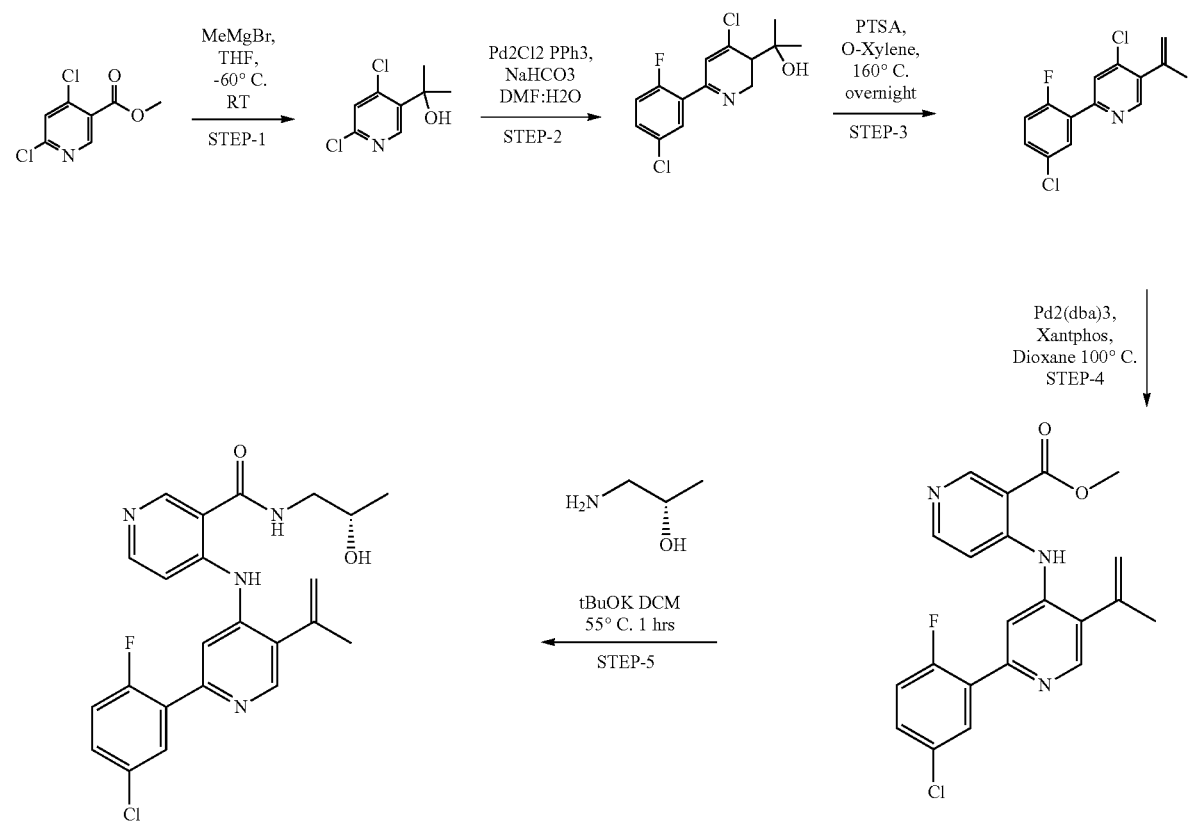

Steps 1 to 4 are the same as in Example 2.

Step 5: Synthesis of (S)-4-(2-(5-chloro-2-fluorophenyl)-5-(prop-1-en-2-yl)pyridin-4-ylamino)-N-(2-hydroxypropyl)pyridine-5-carboxamide To a stirred solution of (S)-1-aminopropan-2-ol (92 mg, 1.227 mmol) in DCM (10 mL) was added potassium tertiary butoxide (138 mg, 1.227 mmol). The reaction mixture was stirred at RT for 10 min under nitrogen atmosphere. Then, to this stirred reaction mixture was added a solution of methyl 4-[[2-(5-chloro-2-fluoro-phenyl)-5-isopropenyl-4-pyridyl]amino]pyridine-3-carboxylate (375 mg, 0.944 mmol) in DCM (10 mL) dropwise. The reaction mixture was heated at 55° C. for 1 h. The progress of reaction was monitored by TLC and LCMS. After completion of reaction, the mixture was diluted with DCM (60 mL), washed with water (40 mL) and brine solution (20 mL). The organic layer was dried over anhydrous sodium sulfate and concentrated under reduced pressure to obtain the crude product. The crude product was purified by reverse phase HPLC to afford (S)-4-(2-(5-chloro-2-fluorophenyl)-5-(prop-1-en-2-yl)pyridin-4-ylamino)-N-(2-hydroxypropyl)pyridine-5-carboxamide (31 mg) as a white solid. The (R) enantiomer can be synthesized utilizing (R)-1-aminopropan-2-ol in this step.

NMR: $^1$H NMR (400 MHz, CDCl$_3$) δ (ppm): 10.21 (s, 1H), 8.68 (s, 1H), 8.50 (s, 1H), 8.44-8.37 (m, 1H), 8.03 (dd, J=6.8, 2.8 Hz, 1H), 7.81 (d, J=1.8 Hz, 1H), 7.43-7.24 (m, 2H), 7.10 (t, J=9.7 Hz, 1H), 6.76 (s, 1H), 5.51 (s, 1H), 5.23 (s, 1H), 4.13-4.00 (m, 1H), 3.70 (m, 1H), 3.29 (m, 1H), 2.14 (d, J=1.4 Hz, 3H), 1.29 (d, J=6.3 Hz, 3H).

Example 4. Preparation of Compound Nos. 4, 4a and 4b

Synthesis of (S)-4-(2-(5-chloro-2-fluorophenyl)-5-(prop-1-en-2-yl)pyridin-4-ylamino)-N-(2-hydroxypropyl)pyrimidine-5-carboxamide

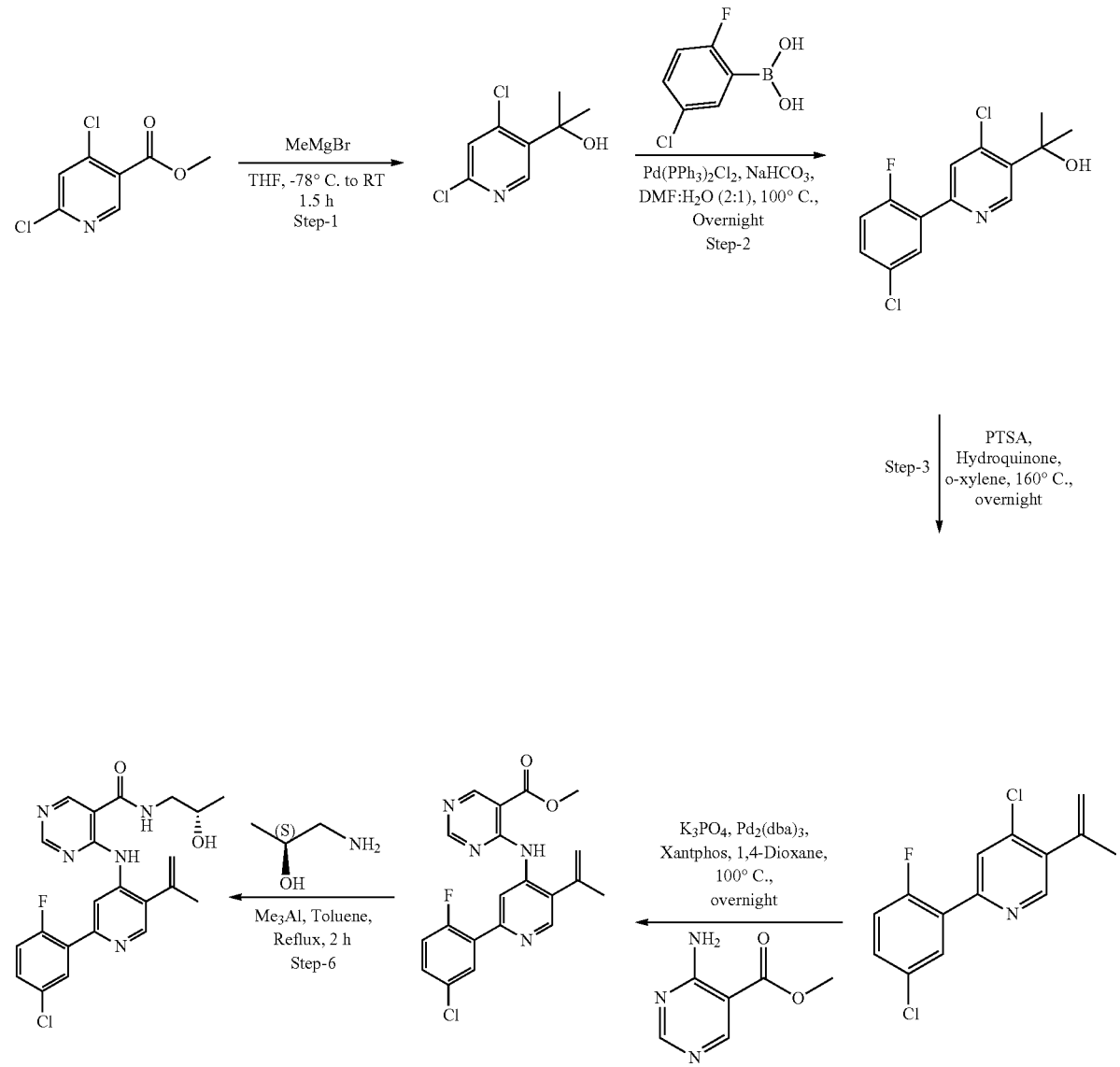

-continued

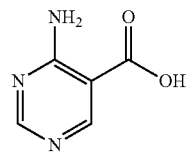

Steps 1 to 3 are the same as in Example 2.

Step 4: Synthesis of 4-aminopyrimidine-5-carboxylic acid

To a stirred solution of 4-aminopyrimidine-5-carboxylic acid (1 g, 7.188 mmol) in MeOH (20 mL) was added concentrated sulfuric acid (4 mL) dropwise at 0° C. The reaction mixture was heated to reflux at 85° C. in a reagent bottle overnight. The progress of reaction was monitored by $^1$H NMR. After completion of reaction, the mixture was concentrated under reduced pressure to remove MeOH. To the residue was added ice-water (10 mL) and the pH of the aqueous mixture was made neutral by the addition of a saturated solution of sodium bicarbonate. The product was extracted with EtOAc (2×50 mL). The organic layer was again washed with brine solution (40 mL). The organic layer was separated, dried over anhydrous sodium sulfate and concentrated under reduced pressure to afford 4-aminopyrimidine-5-carboxylic acid (780 mg) as an off-white solid.

Step 5: Synthesis of methyl 4-[[2-(5-chloro-2-fluoro-phenyl)-5-isopropenyl-4-pyridyl]amino]pyrimidine-5-carboxylate A solution of 4-chloro-2-(5-chloro-2-fluoro-phenyl)-5-isopropenyl-pyridine (440 mg, 1.559 mmol), methyl 4-aminopyrimidine-5-carboxylate (263 mg, 1.715 mmol) and potassium phosphate (tribasic) (662 mg, 3.118 mmol) in 1,4-dioxane (20 mL) was purged with nitrogen for 30 min. Then, to this reaction mixture was added tris(dibenzylideneacetone)dipalladium(0) (143 mg, 0.156 mmol) and Xantphos (135 mg, 0.233 mmol). Then, to this reaction mixture was purged with nitrogen gas for another 5 min. The reaction mixture was heated at 100° C. overnight. The progress of reaction was monitored by TLC and LCMS. After completion of reaction, the mixture was diluted with EtOAc (50 mL) and filtered through a celite bed. The filtrate was washed with water (20 mL) and finally with brine solution (20 mL). The organic layer was separated, dried over anhydrous sodium sulfate and concentrated under reduced pressure to afford crude product which was purified by CombiFlash® chromatography using 20% EtOAc-hexane system as eluent to afford methyl 4-[[2-(5-chloro-2-fluoro-phenyl)-5-isopropenyl-4-pyridyl]amino]pyrimidine-5-carboxylate (325 mg) as a light yellow solid.

Step 6: Synthesis of (S)-4-(2-(5-chloro-2-fluorophenyl)-5-(prop-1-en-2-yl)pyridin-4-ylamino)-N-(2-hydroxypropyl)pyrimidine-5-carboxamide To a stirred solution of methyl 4-[[2-(5-chloro-2-fluoro-phenyl)-5-isopropenyl-4-pyridyl]amino]pyrimidine-5-car-boxylate (100 mg, 0.250 mmol) and (S)-1-amino-propan-2-ol (28 mg, 0.376 mmol) in toluene (8 mL) was added a 1 M solution of trimethylaluminium in heptane (1 mL, 1.00 mmol) at RT. The reaction mixture was heated at reflux for 2 h. The progress of reaction was monitored by TLC. After completion of reaction, the mixture was diluted with EtOAc (30 mL) and washed with saturated solution of sodium bicarbonate (15 mL), water (15 mL) and brine (15 mL). The organic layer was separated, dried over anhydrous sodium sulfate, and concentrated under reduced pressure to afford crude product. The crude product was purified by precipitating in DCM-Pentane system and dried to afford (S)-4-(2-(5-chloro-2-fluorophenyl)-5-(prop-1-en-2-yl)pyridin-4-ylamino)-N-(2-hydroxypropyl)pyrimidine-5-carboxamide (90 mg) as an off-white solid. The (R) enantiomer can be synthesized utilizing (R)-1-aminopropan-2-ol in this step.

NMR: $^1$H NMR (400 MHz, CD$_3$OD) δ (ppm): 9.56 (s, 1H), 9.15 (d, J=9.8 Hz, 2H), 8.63 (s, 1H), 7.88 (dd, J=6.3, 2.7 Hz, 1H), 7.75 (ddd, J=9.1, 4.5, 2.7 Hz, 1H), 7.48 (t, J=9.5 Hz, 1H), 5.88-5.64 (s, 1H), 5.45 (s, 1H), 3.99 (td, J=6.8, 4.6 Hz, 1H), 3.52-3.34 (m, 2H), 2.72 (s, 9H), 2.25 (s, 3H), 1.23 (d, J=6.3 Hz, 3H). LCMS: 442.2 (M+1).

Example 5. Preparation of Compound Nos. 5, 5a and 5b

Synthesis of (S)-1-((4-(2-(5-chloro-2-fluorophenyl)-5-isopropylpyridin-4-ylamino)pyridin-3-yl)methylamino)propan-2-ol

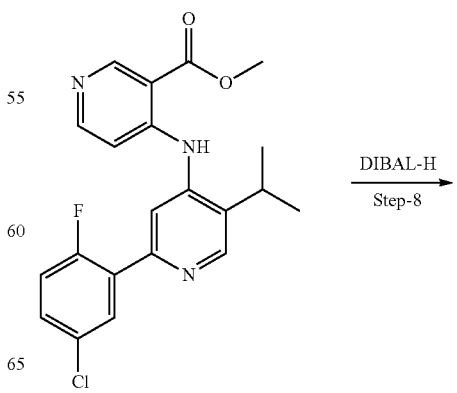

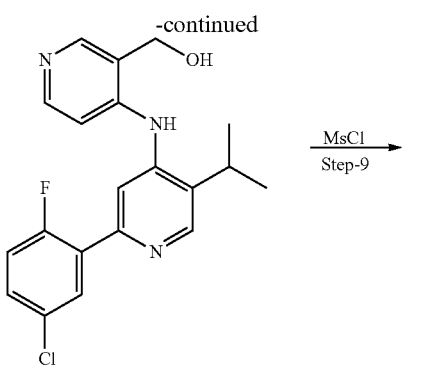

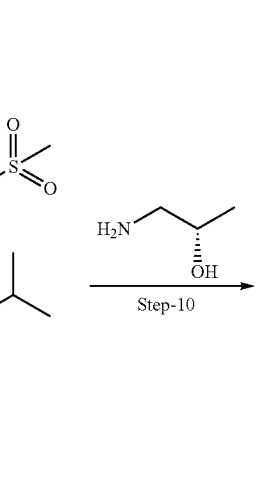

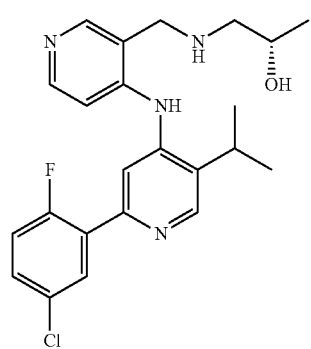

Steps 1 to 7 are the same as in Comparative Example 1

Step 8: Synthesis of (S)-1-((4-(2-(5-chloro-2-fluoro-phenyl)-5-isopropylpyridin-4-ylamino)pyridin-3-yl) methylamino)propan-2-ol To a solution of methyl 4-[[2-(5-chloro-2-fluoro-phenyl)-5-isopropyl-4-pyridyl]amino]pyridine-3-carboxylate (100 mg, 0.25 mmol) in THF (10 mL) was added a 1 M solution of DIBAL-H (1.25 mL, 1.25 mmol) in toluene at 0° C. The reaction mixture was stirred at RT overnight. The progress of reaction was monitored by TLC and LCMS. After completion of reaction, the mixture was quenched with an aqueous solution of $NH_4Cl$ and extracted with EtOAc (50 mL). The combined organic layer was washed with water (20 mL), dried over anhydrous sodium sulfate and concentrated under reduced pressure to obtain [4-[[2-(5-chloro-2-fluoro-phenyl)-5-isopropyl-4-pyridyl]amino]-3-pyridyl] methanol (70 mg).

Step 9: Synthesis of [4-[[2-(5-chloro-2-fluoro-phenyl)-5-isopropyl-4-pyridyl]amino]-3-pyridyl]methyl methanesulfonate To a solution of [4-[[2-(5-chloro-2-fluoro-phenyl)-5-isopropyl-4-pyridyl]amino]-3-pyridyl]methanol (70 mg, 0.188 mmol) in DCM (5 mL) was added triethylamine (0.13 mL, 0.94 mmol) at 0° C. After 10 min, to this reaction mixture was added methane sulfonyl chloride (0.03 mL, 0.376 mmol). The reaction mixture was stirred at the same temperature for 2 h. The progress of reaction was monitored by TLC and LCMS. After completion of the reaction, the mixture was diluted with DCM (15 mL) and washed with water (10 mL). The organic layer was separated and further washed with water (20 mL). The organic layer was dried over anhydrous sodium sulfate, and concentrated under reduced pressure to give [4-[[2-(5-chloro-2-fluoro-phenyl)-5-isopropyl-4-pyridyl]amino]-3-pyridyl]methyl methanesulfonate (40 mg).

Step 10: Synthesis of 1-[[4-[[2-(5-chloro-2-fluoro-phenyl)-5-isopropyl-4-pyridyl]amino]-3-pyridyl]methylamino]propan-2-ol To a solution of (2S)-1-aminopropan-2-ol (33 mg, 0.444 mmol) in DMF (3 mL) was added NaH (10 mg, 0.22 mmol) at 0° C. The reaction mixture was stirred for 30 min at the same temperature. To this stirred reaction mixture was added a solution of [4-[[2-(5-chloro-2-fluoro-phenyl)-5-isopropyl-4-pyridyl]amino]-3-pyridyl]methyl methanesulfonate (100 mg, 0.22 mmol) in DMF (2 mL). Then, the reaction mixture was stirred at 0° C. for 2 h. The progress of reaction was monitored by LCMS. After completion of the reaction, the mixture was quenched with ice-cold water (10 mL) and extracted with EtOAc (50 mL). The organic layer was dried over anhydrous sodium sulfate and concentrated under reduced pressure to obtain the crude product. The crude product was purified by reverse phase HPLC to give 1-[[4-[[2-(5-chloro-2-fluoro-phenyl)-5-isopropyl-4-pyridyl] amino]-3-pyridyl]methylamino]propan-2-ol (8.9 mg). The (R) enantiomer can be synthesized utilizing (R)-1-amino-propan-2-ol in this step.

NMR: $^1$H NMR (400 MHz, $CDCl_3$) δ (ppm): 8.83 (s, 1H), 8.75 (s, 1H), 8.09-7.91 (m, 2H), 7.61 (s, 1H), 7.42-7.29 (m, 1H), 7.11-6.95 (m, 2H), 6.71 (d, J=6.7 Hz, 1H), 4.52 (s, 2H), 4.25 (s, 1H), 3.23 (m, 1H), 3.11 (m, 1H), 2.40 (m, 1H), 1.35 (m, 3H), 1.28 (m, 6H).

Example 6. Preparation of Compound Nos. 6, 6a and 6b

Synthesis of (S)-4-(2-(5-chloro-2-fluorophenyl)-5-isopropylpyridin-4-ylamino)-N-(1-hydroxypropan-2-yl)nicotinamide

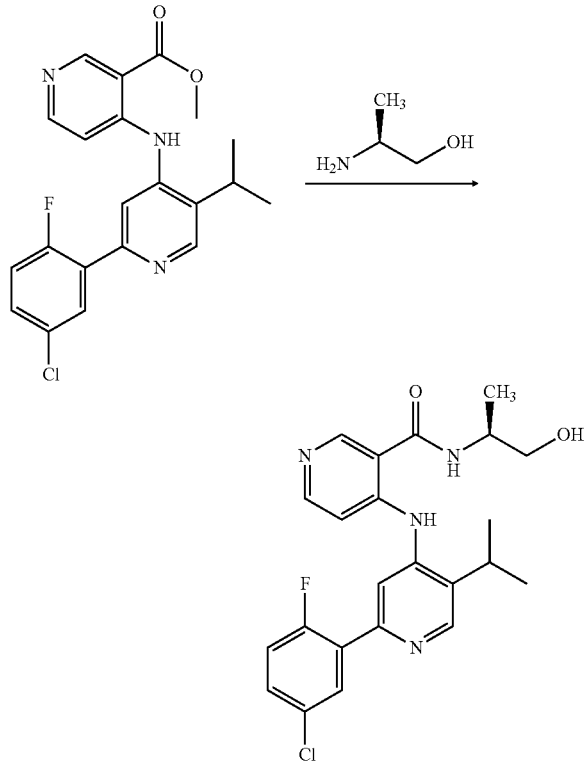

Steps 1 to 7 are the same as in Comparative Example 1

Step 8: Synthesis of (S)-4-(2-(5-chloro-2-fluorophenyl)-5-isopropylpyridin-4-ylamino)-N-(1-hydroxypropan-2-yl)nicotinamide A suspension of (S)-2-aminopropan-1-ol (45 mg, 0.601 mmol), potassium tert-butoxide (68 mg, 0.601 mmol) in DCM (5 mL) was stirred for 5 min. The reaction mixture turned yellow. To this reaction mixture was added a solution of methyl 4-[[2-(5-chloro-2-fluoro-phenyl)-5-isopropyl-4-pyridyl]amino]pyridine-3-carboxylate (200 mg, 0.503 mmol) in DCM (5 mL). Then, this reaction mixture was heated in a closed reagent bottle at 55° C. for 1 h. The progress of reaction was monitored by TLC and LCMS. After completion of the reaction, the reaction mixture was diluted with DCM (15 mL) and water (5 mL). The DCM layer was separated. The aqueous layer was again extracted with DCM (15 mL). The combined organic layer was dried over anhydrous sodium sulfate, and concentrated under reduced pressure to afford a crude product which was purified by reverse phase HPLC to afford (S)-4-(2-(5-chloro-2-fluorophenyl)-5-isopropylpyridin-4-ylamino)-N-(1-hydroxypropan-2-yl)nicotinamide (42.12 mg) as a white solid. The (R) enantiomer can be synthesized utilizing (R)-2-aminopropan-1-ol in this step.

NMR: $^1$H NMR (400 MHz, CD$_3$OD) δ (ppm): 8.76 (s, 1H), 8.59 (s, 1H), 8.32 (d, J=6.0 Hz, 1H), 7.89 (dd, J=6.7, 2.7 Hz, 1H), 7.80 (s, 1H), 7.45 (t, J=5.2 Hz, 1H), 7.37 (d, J=6.1 Hz, 1H), 7.25 (t, J=9.75 Hz, 1H), 4.24 (h, J=6.4 Hz, 1H), 3.62 (m, 2H), 3.25 (m, 1H), 1.40 (dd, J=7.0, 1.6 Hz, 6H), 1.26 (d, J=6.8 Hz, 3H).

Example 7a. Preparation of Compound No. 7a

Synthesis of (S)-4-(2-(5-chloro-2-fluorophenyl)-5-(prop-1-en-2-yl)pyridin-4-ylamino)-N-(1-hydroxypropan-2-yl)nicotinamide

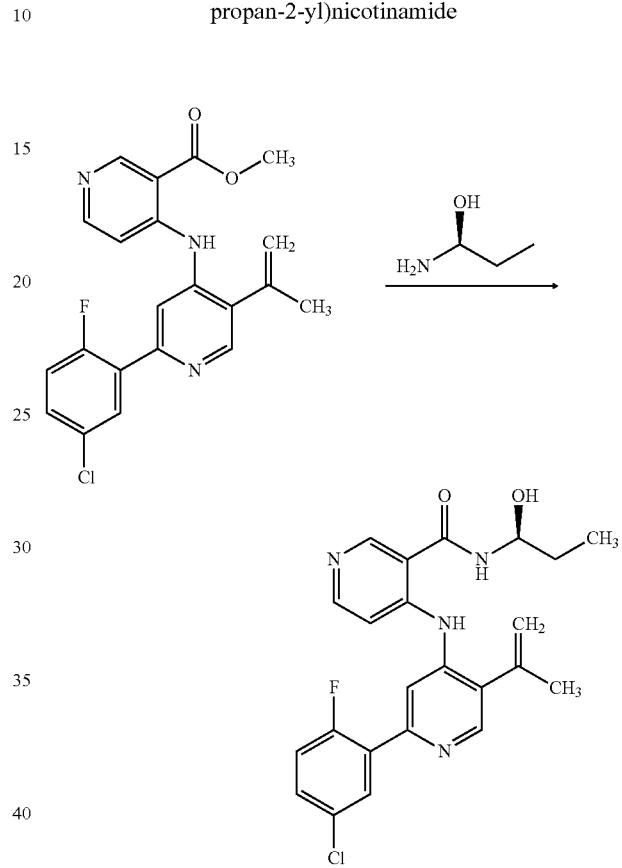

Steps 1 to 4 are the same as in Example 2

Step 5: Synthesis of (S)-4-(2-(5-chloro-2-fluorophenyl)-5-(prop-1-en-2-yl)pyridin-4-ylamino)-N-(1-hydroxypropan-2-yl)nicotinamide A suspension of (S)-2-aminopropan-1-ol (45 mg, 0.601 mmol) and tert-butoxide (68 mg, 0.601 mmol) in DCM (5 mL) was stirred for 5 min. The reaction mixture turned yellow. To this reaction mixture was added a solution of methyl 4-[[2-(5-chloro-2-fluoro-phenyl)-5-isopropenyl-4-pyridyl]amino]pyridine-3-carboxylate (200 mg, 0.501 mmol) in DCM (5 mL). Then, the reaction mixture was heated in a closed reagent bottle at 55° C. for 1 h. The progress of reaction was monitored by TLC and LCMS. After completion of the reaction, the mixture was diluted with DCM (15 mL) and water (5 mL). The DCM layer was separated. The aqueous layer was again extracted with DCM (15 mL). The combined organic layer was dried over anhydrous sodium sulfate. Removal of DCM under reduced pressure afforded a crude product which was purified by reverse phase HPLC to afford (5)-4-(2-(5-chloro-2-fluorophenyl)-5-(prop-1-en-2-yl)pyridin-4-ylamino)-N-(1-hydroxypropan-2-yl)nicotinamide (66 mg) as a white solid.

NMR: $^1$H NMR (400 MHz, DMSO-d6) δ (ppm): 10.78 (s, 1H), 8.84 (s, 1H), 8.66 (d, J=7.9 Hz, 1H), 8.56 (s, 1H), 8.40 (d, J=6.2 Hz, 1H), 8.00 (dd, J=6.8, 2.8 Hz, 1H), 7.85 (s, 1H), 7.57 (dt, J=8.7, 3.6 Hz, 1H), 7.47-7.37 (m, 2H), 5.47 (s, 1H), 5.22 (s, 1H), 4.84-4.74 (m, 1H), 4.03 (m, 1H), 3.50-3.35 (m, 1H), 2.08 (s, 3H), 1.13 (d, J=6.7 Hz, 3H).

Example 7b. Preparation of Compound No. 7b

Synthesis of 4-[[2-(5-chloro-2-fluoro-phenyl)-5-isopropenyl-4-pyridyl]amino]-N-(2-hydroxy-1-methyl-ethyl)pyridine-3-carboxamide

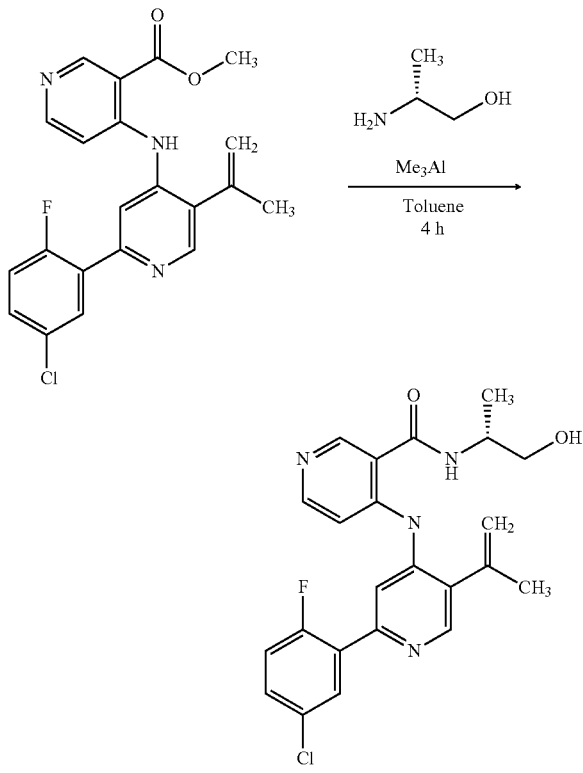

Steps 1 to 4 are the same as in Example 2

Step 5: Synthesis of (2R)-4-[[2-(5-chloro-2-fluoro-phenyl)-5-isopropenyl-4-pyridyl]amino]-N-(2-hydroxy-1-methyl-ethyl)pyridine-3-carboxamide To methyl 4-[[2-(5-chloro-2-fluoro-phenyl)-5-isopropenyl-4-pyridyl]amino]pyridine-3-carboxylate (100 mg, 0.25 mmol) and (2R)-2-aminopropan-1-ol (37 mg, 0.5 mmol) in toluene (4 mL) was added Me$_3$Al (1.0 mL, 1.00 mmol). The reaction mixture was heated at 140° C. for 4 h. The progress of reaction was monitored by LCMS. After completion reaction, the mixture was quenched with a saturated aqueous solution of NaHCO$_3$ (20 mL) and the product was extracted with EtOAc (2×70 mL). The combined organic layer was washed with brine (30 mL), dried over sodium sulfate and concentrated under reduced pressure to give a crude product. The crude product was purified by preparative HPLC to afford (2R)-4-[[2-(5-chloro-2-fluoro-phenyl)-5-isopropenyl-4-pyridyl]amino]-N-(2-hydroxy-1-methyl-ethyl)pyridine-3-carboxamide (13.25 mg).

NMR: $^1$H NMR (400 MHz, CDCl$_3$) δ (ppm): 10.55 (s, 1H), 8.94 (s, 1H), 8.54 (s, 1H), 8.32 (d, J=6.4 Hz, 1H), 8.03 (dd, J=6.7, 2.7 Hz, 1H), 7.79 (d, J=1.7 Hz, 1H), 7.39-7.25 (m, 3H), 7.09 (dd, J=10.7, 8.7 Hz, 1H), 5.50 (d, J=2.2 Hz, 1H), 5.23 (s, 1H), 4.28 (m, 1H), 3.82 (dd, J=11.4, 3.5 Hz, 1H), 3.70 (dd, J=11.3, 5.6 Hz, 1H), 2.13 (s, 3H), 1.32 (d, J=6.7 Hz, 3H). LCMS: 441.2 (M+1).

Example 8. Preparation of Compound No. 8

Synthesis of 4-[[2-(5-chloro-2-fluoro-phenyl)-5-isopropenyl-4-pyridyl]amino]-N-(2-hydroxy-1,1-dimethyl-ethyl)pyridine-3-carboxamide

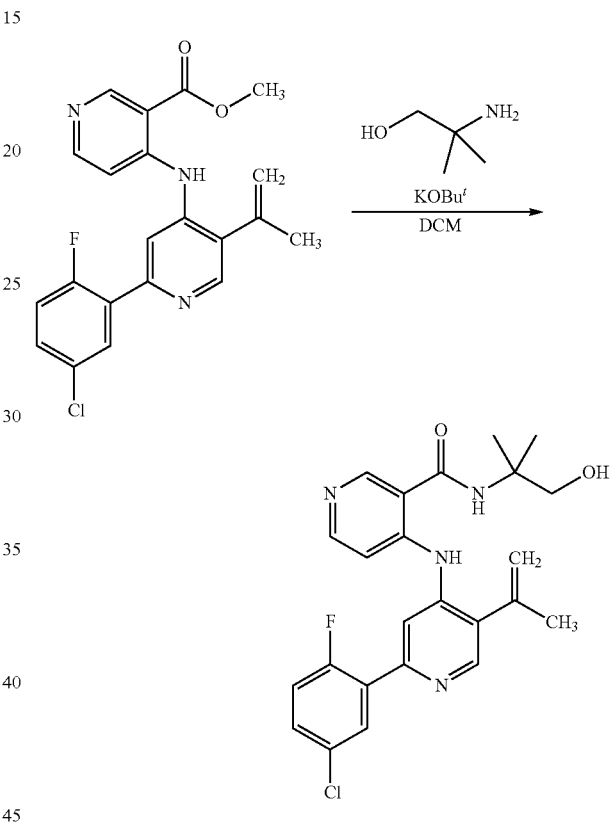

Steps 1 to 4 are the same as in Example 2

Step 5: Synthesis of 4-[[2-(5-chloro-2-fluoro-phenyl)-5-isopropenyl-4-pyridyl]amino]-N-(2-hydroxy-1,1-dimethyl-ethyl)pyridine-3-carboxamide To a solution of 2-amino-2-methyl-propan-1-ol (24 mg, 0.27 mmol) in DCM (3 mL) was added potassium tertiary butoxide (33 mg, 0.30 mmol). The reaction mixture was stirred at RT for 20 min. To the stirred reaction mixture was added a solution of methyl 4-[[2-(5-chloro-2-fluoro-phenyl)-5-isopropenyl-4-pyridyl]amino]pyridine-3-carboxylate (100 mg, 0.25 mmol) in DCM (5 mL) dropwise at RT. The reaction mixture was heated at 50° C. for 1 h. After completion of reaction, water (50 mL) was added and the mixture was diluted with DCM (50 mL). The organic layer was washed with brine (20 mL) and concentrated under reduced pressure to give a crude product which was purified by reverse phase HPLC to give of 4-[[2-(5-chloro-2-fluoro-phenyl)-5-isopropenyl-4-pyridyl]amino]-N-(2-hydroxy-1,1-dimethyl-ethyl)pyridine-3-carboxamide (17.96 mg) as a white solid.

NMR: ¹H NMR (400 MHz; CD₃OD) δ (ppm): 8.65 (s, 1H), 8.42 (s, 1H), 8.35 (d, J=5.9 Hz, 1H), 7.90 (dd, J=6.7, 2.7 Hz, 1H), 7.82 (s, 1H), 7.46 (m, 2H), 7.26 (m, 1H), 5.53 (s, 1H), 5.23 (s, 1H), 3.72 (s, 2H), 2.15 (s, 3H), 1.40 (s, 6H).

Example 9. Preparation of Compound No. 9

Synthesis of [4-[[2-(5-chloro-2-fluoro-phenyl)-5-isopropyl-4-pyridyl]amino]-3-pyridyl]-(4-hydroxy-1-piperidyl)methanone

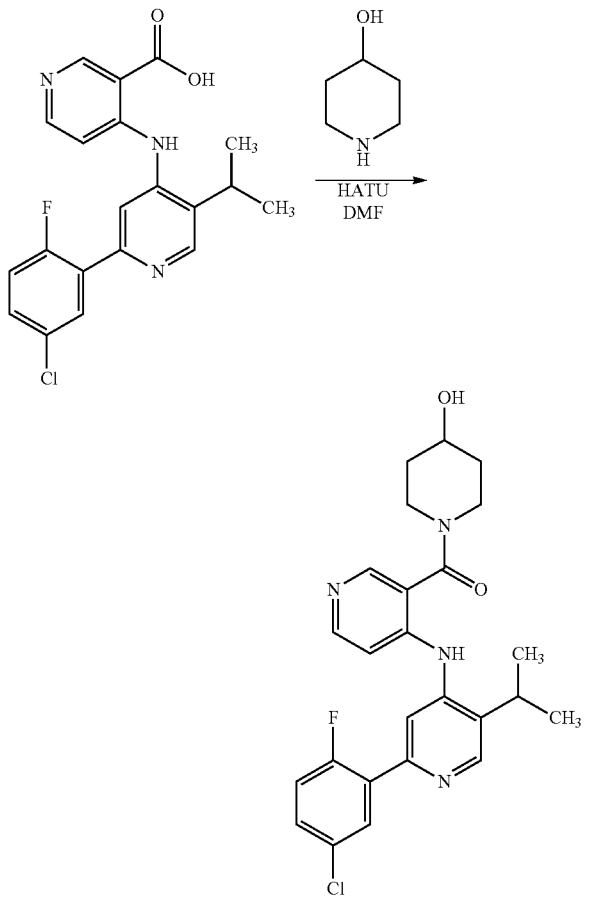

Steps 1 to 8 are the same as in Comparative Example 1

Step 9: Synthesis of [4-[[2-(5-chloro-2-fluoro-phenyl)-5-isopropyl-4-pyridyl]amino]-3-pyridyl]-(4-hydroxy-1-piperidyl)methanone To a solution of 4-[[2-(5-chloro-2-fluoro-phenyl)-5-isopropyl-4-pyridyl]amino] pyridine-3-carboxylic acid (140 mg, 0.343 mmol) in DMF (4 mL) was added N,N-diisopropylethyl amine (0.23 mL, 1.37 mmol) and HATU (254 mg, 0.686 mmol). The reaction mixture was stirred at RT for 15 min under nitrogen atmosphere. To this stirred reaction mixture was added piperidin-4-ol (41 mg, 0.411 mmol) in DMF (1 mL) and the reaction mixture was stirred at RT overnight. The progress of reaction was monitored by TLC. After completion of the reaction, the mixture was diluted with water and extracted with EtOAc (50 mL). The organic layer was washed with water (2×10 mL) and brine solution (10 mL). The combined organic layer was dried over anhydrous sodium sulfate and evaporated under reduced pressure to obtain oily crude compound that was purified by reverse phase HPLC to afford [4-[[2-(5-chloro-2-fluoro-phenyl)-5-isopropyl-4-pyridyl]amino]-3-pyridyl]-(4-hydroxy-1-piperidyl)methanone (9 mg).

NMR: ¹H NMR (400 MHz, CDCl₃) δ (ppm): 8.76 (s, 1H), 8.60 (s, 1H), 8.40 (d, J=14.5 Hz, 2H), 8.02 (dd, J=6.8, 2.7 Hz, 1H), 7.76 (s, 1H), 7.39-7.27 (m, 2H), 7.09 (dd, J=10.7, 8.8 Hz, 1H), 4.10-4.01 (m, 3H), 3.51 (m, 2H), 3.13 (p, J=6.9 Hz, 1H), 1.99 (m, 2H), 1.7 (m, 2H), 1.38 (d, J=6.8 Hz, 6H).

Example 10. Preparation of Compound Nos. 10, 10a and 10b

Synthesis of (S)-4-(2-(5-chloro-2-fluorophenyl)-5-vinylpyridin-4-ylamino)-N-(2-hydroxypropyl)nicotinamide

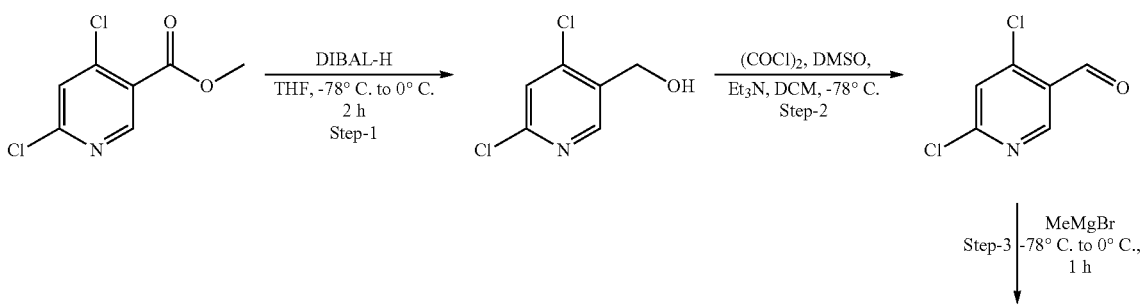

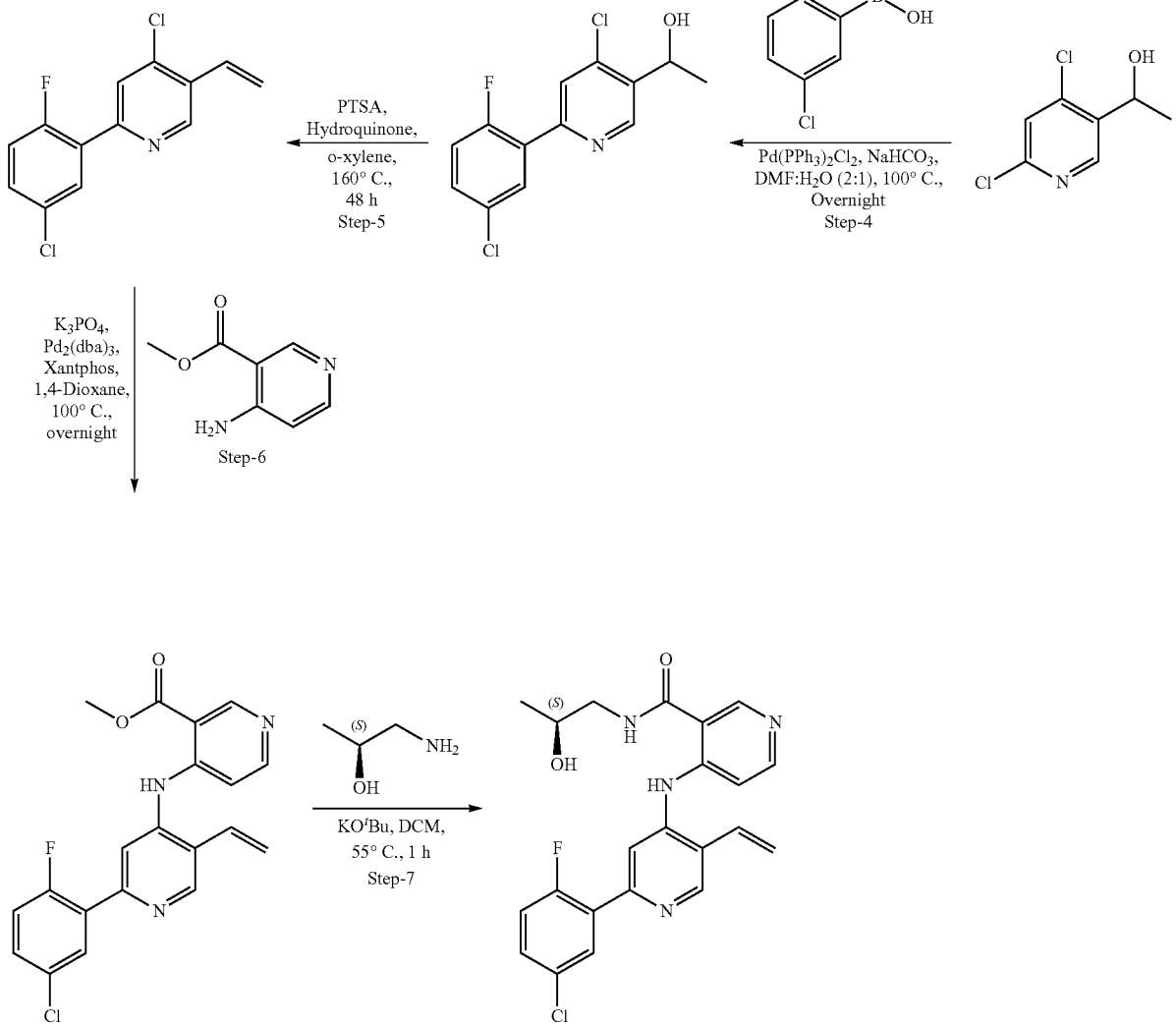

Step 1: Synthesis of (4,6-dichloro-3-pyridyl)methanol

To a solution of methyl 4,6-dichloropyridine-3-carboxylate (1 g, 4.854 mmol) in anhydrous THF (25 mL) was added a 1 M solution of diisobutylaluminium hydride in toluene (14.5 mL, 14.5 mmol) dropwise under nitrogen atmosphere at −78° C. The reaction mixture was stirred for 2 h during which reaction mixture slowly warmed to 0° C. The progress of reaction was monitored by TLC. After completion of reaction, the mixture was quenched with saturated ammonium chloride solution (20 mL). EtOAc (100 mL) was added to the reaction mixture which was filtered. The filtrate was washed with water (30 mL) followed by brine wash (30 mL). The organic layer was separated, dried over anhydrous sodium sulfate and concentrated under reduced pressure to afford (4,6-dichloro-3-pyridyl)methanol (820 mg) as a white solid.

Step 2: Synthesis of 4,6-dichloropyridine-3-carbaldehyde

A solution of oxalyl chloride (2.32 mL, 26.963 mmol) in DCM (30 mL) was cooled down to −78° C. To this solution was added DMSO (3.83 mL, 53.922 mmol) dropwise under nitrogen atmosphere. The reaction mixture was stirred at the same temperature for another 30 min. To this reaction mixture was added a solution of (4,6-dichloro-3-pyridyl)methanol (1.6 g, 8.987 mmol) in DCM (10 mL), and then the reaction mixture was stirred for 30 min. Then, to this stirred reaction mixture was added triethylamine (11.2 mL, 80.883 mmol). The reaction mixture was stirred at the same temperature for another 30 min. The progress of reaction was monitored by TLC. After completion of reaction, the mixture was quenched with saturated sodium bicarbonate solution (30 mL). The product was extracted using DCM (2×50 mL). The combined organic layer was again washed with water (3×30 mL) and finally with brine solution (30 mL). The organic layer was separated, dried over anhydrous sodium sulfate and concentrated under reduced pressure to afford 4,6-dichloropyridine-3-carbaldehyde (1.53 g) as a light yellow solid.

Step 3: Synthesis of 1-(4,6-dichloro-3-pyridyl)ethanol

To a solution of 4,6-dichloropyridine-3-carbaldehyde (1.53 g, 8.693 mmol) in anhydrous THF (15 mL) was added a 3M solution of methylmagnesium bromide in diethyl ether (5.8 mL, 17.386 mmol) dropwise under nitrogen atmosphere at −78° C. The reaction mixture was stirred for 1 h during which the reaction mixture slowly warmed to 0° C. The progress of reaction was monitored by TLC. After completion of reaction, the mixture was quenched with saturated ammonium chloride solution (15 mL). The product was extracted using EtOAc (2×25 mL). The combined organic layer was again washed with water (20 mL) and finally with brine solution (20 mL). The organic layer was separated, dried over anhydrous sodium sulfate and concentrated under reduced pressure to afford 1-(4,6-dichloro-3-pyridyl)ethanol (1.56 g) as a light brown liquid.

Step 4: Synthesis of 1-[4-chloro-6-(5-chloro-2-fluoro-phenyl)-3-pyridyl]ethanol A mixture of 1-(4,6-dichloro-3-pyridyl)ethanol (1.56 g, 8.123 mmol), (5-chloro-2-fluoro-phenyl)boronic acid (2.12 g, 12.184 mmol) and sodium bicarbonate (1.36 g, 16.246 mmol) in a 2:1 mixture of DMF:H$_2$O (21 mL) was purged with nitrogen gas for 40 min. To this reaction mixture was added bis(triphenylphosphine)palladium(II) dichloride (285 mg, 0.406 mmol) and then was purged with nitrogen gas for another 5 min. The reaction mixture was heated at 100° C. overnight. The progress of reaction was monitored by TLC and LCMS. After completion of reaction, water (20 mL) was added to the reaction mixture and product was extracted with EtOAc (2×25 mL). The combined organic layer was washed with water (3×25 mL) and finally with brine solution (25 mL). The organic layer was separated, dried over anhydrous sodium sulfate and concentrated under reduced pressure to afford crude product which was purified by column chromatography on silica gel (100-200 mesh) using 6% EtOAc:Hexane system as eluent to afford 1-[4-chloro-6-(5-chloro-2-fluoro-phenyl)-3-pyridyl]ethanol (1.2 g) as a light brown liquid.

Step 5: Synthesis of 4-chloro-2-(5-chloro-2-fluoro-phenyl)-5-vinyl-pyridine

To a stirred solution of 1-[4-chloro-6-(5-chloro-2-fluoro-phenyl)-3-pyridyl]ethanol (1.2 g, 4.193 mmol) in o-Xylene (10 mL) was added p-toluenesulfonic acid monohydrate (80 mg, 0.419 mmol) and hydroquinone (46 mg, 0.419 mmol). The reaction mixture was heated at 160° C. in a Dean-Stark apparatus for 48 h. The progress of reaction was monitored by TLC. After completion of the reaction, the mixture was concentrated under reduced pressure to remove o-Xylene. To the residue was added water (50 mL) and product was extracted with EtOAc (2×50 mL). The combined organic layer was again washed with water (40 mL) and brine solution (40 mL). The organic layer was separated, dried over anhydrous sodium sulfate and concentrated under reduced pressure to afford crude product which was purified by CombiFlash® chromatography using 0.5% EtOAc-hexane system as eluent to afford 4-chloro-2-(5-chloro-2-fluoro-phenyl)-5-vinyl-pyridine (270 mg) as a light yellow solid.

Step 6: Synthesis of methyl 4-[[2-(5-chloro-2-fluoro-phenyl)-5-vinyl-4-pyridyl]amino]pyridine-3-carboxylate To a mixture of 4-chloro-2-(5-chloro-2-fluoro-phenyl)-5-vinyl-pyridine (270 mg, 1.007 mmol), methyl 4-aminopyridine-3-carboxylate (169 mg, 1.107 mmol) and potassium phosphate (tribasic) (428 mg, 2.014 mmol) in 1,4-dioxane (10 mL) was purged with nitrogen gas for 30 min. To this reaction mixture was added tris(dibenzylidineacetone)dipalladium(0) (92 mg, 0.100 mmol) and Xantphos (87 mg, 0.151 mmol) and then the reaction mixture was purged with nitrogen for another 5 min. Then, the reaction mixture was heated at 100° C. overnight. The progress of reaction was monitored by TLC and LCMS. After completion of reaction, reaction mixture was diluted with EtOAc (50 mL) and filtered through a celite bed. The filtrate was washed with water (20 mL) and finally with brine solution (20 mL). The organic layer was separated, dried over anhydrous sodium sulfate and concentrated under reduced pressure to afford crude product which was purified by CombiFlash® chromatography using 20% EtOAc-hexane system as eluent to afford methyl 4-[[2-(5-chloro-2-fluoro-phenyl)-5-vinyl-4-pyridyl]amino]pyridine-3-carboxylate (100 mg) as an off-white solid.

Step 7: Synthesis of (S)-4-(2-(5-chloro-2-fluorophenyl)-5-vinylpyridin-4-ylamino)-N-(2-hydroxypropyl)nicotinamide To a stirred solution of (S)-1-amino-propan-2-ol (14 mg, 0.187 mmol) in DCM (2 mL) was added potassium tert-butoxide (21 mg, 0.187 mmol) under nitrogen atmosphere at 0° C. The reaction mixture was stirred at RT for 15 min. Then, to this reaction mixture was added a solution of methyl 4-[[2-(5-chloro-2-fluoro-phenyl)-5-vinyl-4-pyridyl]amino]pyridine-3-carboxylate (60 mg, 0.156 mmol) in DCM (3 mL) dropwise. The reaction mixture was heated at 55° C. for 1 h. The progress of reaction was monitored by TLC. After completion of reaction, the mixture was diluted with DCM (15 mL). The organic layer washed with saturated solution of sodium bicarbonate solution (10 mL), water (10 mL) and finally with brine solution (10 mL). The organic layer was separated, dried over anhydrous sodium sulfate and concentrated under reduced pressure to obtain the crude product which was purified by reverse phase preparative HPLC to afford (S)-4-(2-(5-chloro-2-fluorophenyl)-5-vinylpyridin-4-ylamino)-N-(2-hydroxy propyl)nicotinamide (2 mg) as an off-white solid. The (R) enantiomer can be synthesized utilizing (R)-1-aminopropan-2-ol in this step.

NMR: $^1$H NMR (400 MHz, CD$_3$OD) δ (ppm): 8.76 (d, J=6.6 Hz, 2H), 8.35 (s, 1H), 7.94 (dd, J=6.7, 2.8 Hz, 1H), 7.84 (s, 1H), 7.51-7.37 (m, 2H), 7.26 (dd, J=10.7, 8.8 Hz, 1H), 6.92 (dd, J=17.6, 11.2 Hz, 2H), 5.98 (d, J=17.5 Hz, 1H), 5.60 (d, J=11.3 Hz, 1H), 3.97 (p, J=6.5 Hz, 1H), 3.56 (dd, J=10.7, 5.5 Hz, 1H), 3.44 (dd, J=13.6, 4.6 Hz, 1H), 1.22 (d, J=6.4 Hz, 3H). LCMS: 427.0 (M+1).

Example 11. Preparation of Compound Nos. 11, 11a and 11b
Synthesis of (S)-4-(2-(5-chloro-2-fluorophenyl)-5-ethylpyridin-4-ylamino)-N-(2-hydroxy propyl)nicotinamide
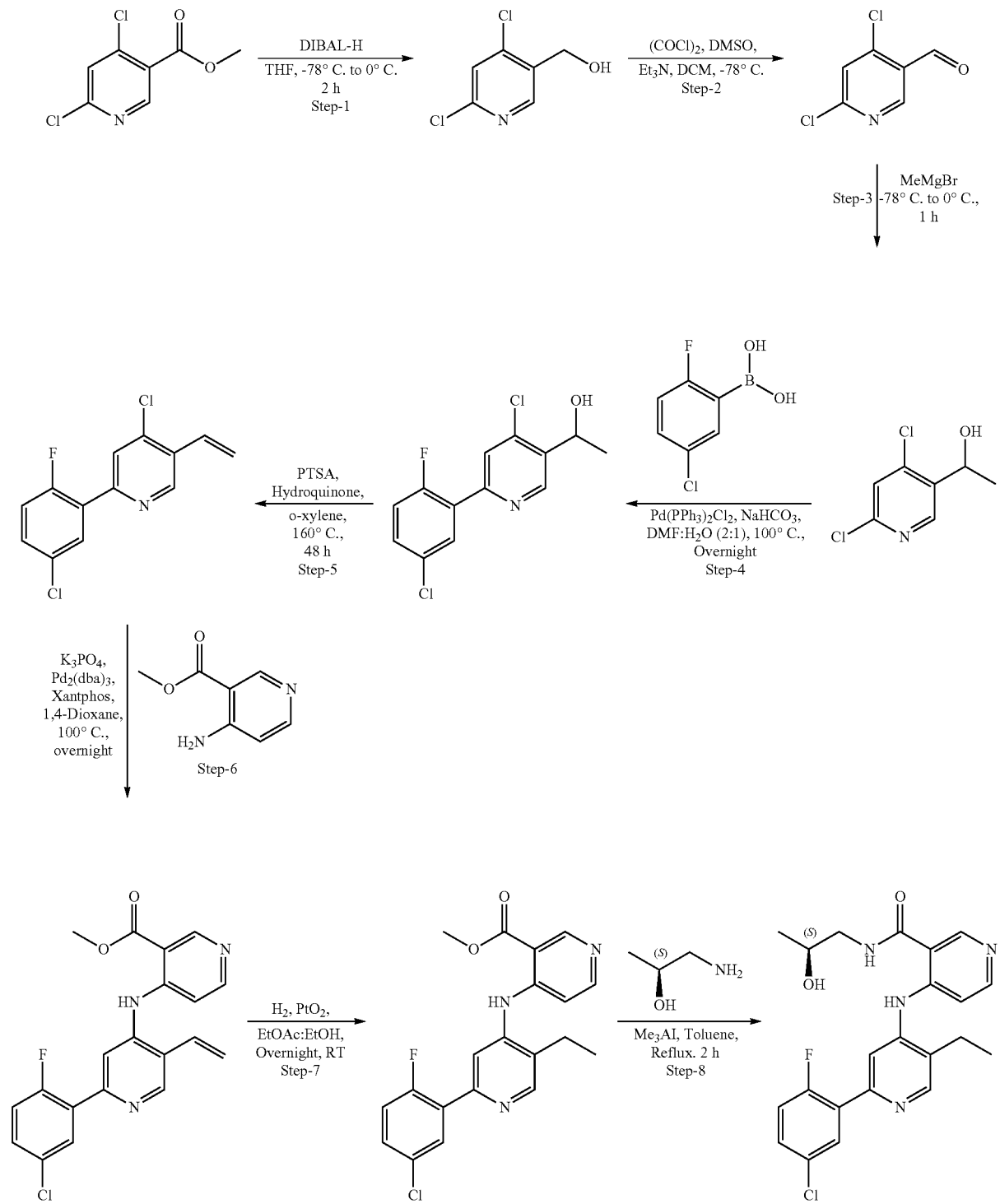

Step 1: Synthesis of (4,6-dichloro-3-pyridyl)methanol

To a solution of methyl 4,6-dichloropyridine-3-carboxylate (1 g, 4.854 mmol) in anhydrous THF (25 mL) was added a 1 M solution of diisobutylaluminium hydride in toluene (14.5 mL, 14.5 mmol) dropwise under nitrogen atmosphere at −78° C. The reaction mixture was stirred for 2 h during which the reaction mixture slowly warmed to 0° C. The progress of reaction was monitored by TLC. After completion of reaction, the mixture was quenched with saturated ammonium chloride solution (20 mL). EtOAc (100 mL) was added to the reaction mixture and filtered. The filtrate was washed with water (30 mL) followed by brine wash (30 mL). The organic layer was separated, dried over anhydrous sodium sulfate and concentrated under reduced pressure to afford (4,6-dichloro-3-pyridyl)methanol (820 mg) as a white solid.

Step 2: Synthesis of 4,6-dichloropyridine-3-carbaldehyde

A solution of oxalyl chloride (2.32 mL, 26.963 mmol) in DCM (30 mL) was cooled to −78° C. To this solution was added DMSO (3.83 mL, 53.922 mmol) dropwise under nitrogen atmosphere. The reaction mixture was stirred at the same temperature for another 30 min. To this reaction mixture was added a solution of (4,6-dichloro-3-pyridyl) methanol (1.6 g, 8.987 mmol) in DCM (10 mL) and then the reaction mixture was stirred for 30 min. Then, to this stirred reaction mixture was added triethylamine (11.2 mL, 80.883 mmol). The reaction mixture was stirred at the same temperature for another 30 min. The progress of reaction was monitored by TLC. After completion of reaction, the mixture was quenched with saturated sodium bicarbonate solution (30 mL). The product was extracted using DCM (2×50 mL). The combined organic layer was washed with water (3×30 mL) and finally with brine solution (30 mL). The organic layer was separated, dried over anhydrous sodium sulfate and concentrated under reduced pressure to afford 4,6-dichloropyridine-3-carbaldehyde (1.53 g) as a light yellow solid.

Step 3: Synthesis of 1-(4,6-dichloro-3-pyridyl)ethanol

To a solution of 4,6-dichloropyridine-3-carbaldehyde (1.53 g, 8.693 mmol) in anhydrous THF (15 mL) was added a 3M solution of methylmagnesium bromide in diethyl ether (5.8 mL, 17.386 mmol) dropwise under nitrogen atmosphere at −78° C. The reaction mixture was stirred for 1 h during which the reaction mixture slowly warmed to 0° C. The progress of reaction was monitored by TLC. After completion of reaction, the mixture was quenched with saturated ammonium chloride solution (15 mL). The product was extracted using EtOAc (2×25 mL). The combined organic layer was washed with water (20 mL) and finally with brine solution (20 mL). The organic layer was separated, dried over anhydrous sodium sulfate and concentrated under reduced pressure to afford 1-(4,6-dichloro-3-pyridyl)ethanol (1.56 g) as a light brown liquid.

Step 4: Synthesis of 1-[4-chloro-6-(5-chloro-2-fluoro-phenyl)-3-pyridyl]ethanol To a mixture of 1-(4,6-dichloro-3-pyridyl)ethanol (1.56 g, 8.123 mmol). (5-chloro-2-fluoro-phenyl)boronic acid (2.12 g, 12.184 mmol) and sodium bicarbonate (1.36 g, 16.246 mmol) in 2:1 mixture of DMF:$H_2O$ (21 mL) was purged with nitrogen gas for 40 min. To this reaction mixture was added bis(triphenylphosphine)palladium(II) dichloride (285 mg, 0.406 mmol) and to the reaction mixture was purged with nitrogen gas for another 5 min. The reaction mixture was then heated at 100° C. overnight. The progress of reaction was monitored by TLC and LCMS. After completion of reaction, water (20 mL) was added to the reaction mixture and product was extracted with EtOAc (2×25 mL). The combined organic layer was washed with water (3×25 mL) and finally with brine solution (25 mL). The organic layer was separated, dried over anhydrous sodium sulfate and concentrated under reduced pressure to afford crude product which was purified by column chromatography on silica gel (100-200 mesh) using 6% EtOAc:Hexane system as eluent to afford 1-[4-chloro-6-(5-chloro-2-fluoro-phenyl)-3-pyridyl]ethanol (1.2 g) as a light brown liquid.

Step 5: Synthesis of 4-chloro-2-(5-chloro-2-fluoro-phenyl)-5-vinyl-pyridine

To a stirred solution of 1-[4-chloro-6-(5-chloro-2-fluoro-phenyl)-3-pyridyl]ethanol (1.2 g, 4.193 mmol) in o-Xylene (10 mL) was added p-toluenesulfonic acid monohydrate (80 mg, 0.419 mmol) and hydroquinone (46 mg, 0.419 mmol). The reaction mixture was heated at 160° C. in a Dean-Stark apparatus for 48 h. The progress of reaction was monitored by TLC. After completion of reaction, the mixture was concentrated under reduced pressure to remove o-Xylene. To the residue was added water (50 mL) and product was extracted with EtOAc (2×50 mL). The combined organic layer was washed with water (40 mL) and brine solution (40 mL). The organic layer was separated, dried over anhydrous sodium sulfate and concentrated under reduced pressure to afford crude product which was purified by CombiFlash® chromatography using 0.5% EtOAc-hexane system as eluent to afford 4-chloro-2-(5-chloro-2-fluoro-phenyl)-5-vinyl-pyridine (270 mg) as a light yellow solid.

Step 6: Synthesis of methyl 4-[[2-(5-chloro-2-fluoro-phenyl)-5-vinyl-4-pyridyl]amino]pyridine-3-carboxylate To a mixture of 4-chloro-2-(5-chloro-2-fluoro-phenyl)-5-vinyl-pyridine (270 mg, 1.007 mmol), methyl 4-aminopyridine-3-carboxylate (169 mg, 1.107 mmol) and potassium phosphate (tribasic) (428 mg, 2.014 mmol) in 1,4-dioxane (10 mL) was purged with nitrogen gas for 30 min. To this reaction mixture was added tris(dibenzylidineacetone)dipalladium(0) (92 mg, 0.100 mmol) and Xantphos (87 mg, 0.151 mmol) and the reaction mixture was purged with nitrogen gas for another 5 min. The reaction mixture was then heated at 100° C. overnight. The progress of reaction was monitored by TLC and LCMS. After completion of reaction, the mixture was diluted with EtOAc (50 mL) and filtered through a celite bed. The filtrate was washed with water (20 mL) and finally with brine solution (20 mL). The organic layer was separated, dried over anhydrous sodium sulfate and concentrated under reduced pressure to afford crude product which was purified by CombiFlash® chromatography using 20% EtOAc-hexane system as eluent to afford methyl 4-[[2-(5-chloro-2-fluoro-phenyl)-5-vinyl-4-pyridyl]amino]pyridine-3-carboxylate (100 mg) as an off-white solid.

Step 7: Synthesis of methyl 4-[[2-(5-chloro-2-fluoro-phenyl)-5-ethyl-4-pyridyl]amino]pyridine-3-carboxylate To a stirred solution of 4-[[2-(5-chloro-2-fluoro-phenyl)-5-vinyl-4-pyridyl]amino]pyridine-3-carboxylate (70 mg, 0.182 mmol) in a 1:1 mixture of EtOAc:EtOH (6 mL) was added platinum dioxide (30 mg). The reaction mixture was agitated under hydrogen atmosphere using hydrogen bladder at RT overnight. The progress of reaction was monitored by ¹H NMR. After completion of reaction, reaction mixture was filtered through a celite bed and filtrate was concentrated under reduced pressure to afford methyl 4-[[2-(5-chloro-2-fluoro-phenyl)-5-ethyl-4-pyridyl]amino]pyridine-3-carboxylate (65 mg) as an off-white solid.

Step 8: Synthesis of (S)-4-(2-(5-chloro-2-fluorophenyl)-5-ethylpyridin-4-ylamino)-N-(2-hydroxy propyl)nicotinamide To a stirred solution of methyl 4-[[2-(5-chloro-2-fluoro-phenyl)-5-ethyl-4-pyridyl]amino]pyridine-3-carboxylate (65 mg, 0.168 mmol) and (S)-1-amino-propan-2-ol (19 mg, 0.252 mmol) in toluene (6 mL) was added a 1 M solution of trimethylaluminium in heptane (0.67 mL, 0.67 mmol) at RT. The reaction mixture was heated at reflux for 2 h. The progress of reaction was monitored by TLC. After completion of reaction, reaction mixture was diluted with EtOAc (20 mL) and washed with saturated solution of sodium bicarbonate (15 mL), water (10 mL) followed by brine wash (10 mL). The organic layer was separated, dried over anhydrous sodium sulfate and concentrated under reduced pressure to obtain the crude product which was purified by reverse phase preparative HPLC to afford (S)-4-(2-(5-chloro-2-fluorophenyl)-5-ethylpyridin-4-ylamino)-N-(2-hydroxy propyl)nicotinamide (12 mg) as an off-white solid. The (R) enantiomer can be synthesized utilizing (R)-1-aminopropan-2-ol in this step.

NMR: ¹H NMR (400 MHz, CD₃OD) δ (ppm): 8.76 (s, 1H), 8.46 (s, 1H), 8.37-8.25 (m, 1H), 7.84 (dd, J=6.7, 2.8 Hz, 1H), 7.76 (s, 1H), 7.52-7.35 (m, 2H), 7.23 (dd, J=10.7, 8.8 Hz, 1H), 4.00 (td, J=6.8, 4.7 Hz, 1H), 3.50-3.33 (m, 2H), 2.77 (q, J=7.5 Hz, 2H), 1.32 (t, J=7.5 Hz, 3H), 1.22 (d, J=6.3 Hz, 3H). LCMS: 429.3 (M+1).

Example 12. Preparation of Compound Nos. 12, 12a and 12b

Synthesis of (S)-4-(2-(5-chloro-2-fluorophenyl)-5-isopropylpyridin-4-ylamino)-N-(2-hydroxypropyl)pyrimidine-5-carboxamide

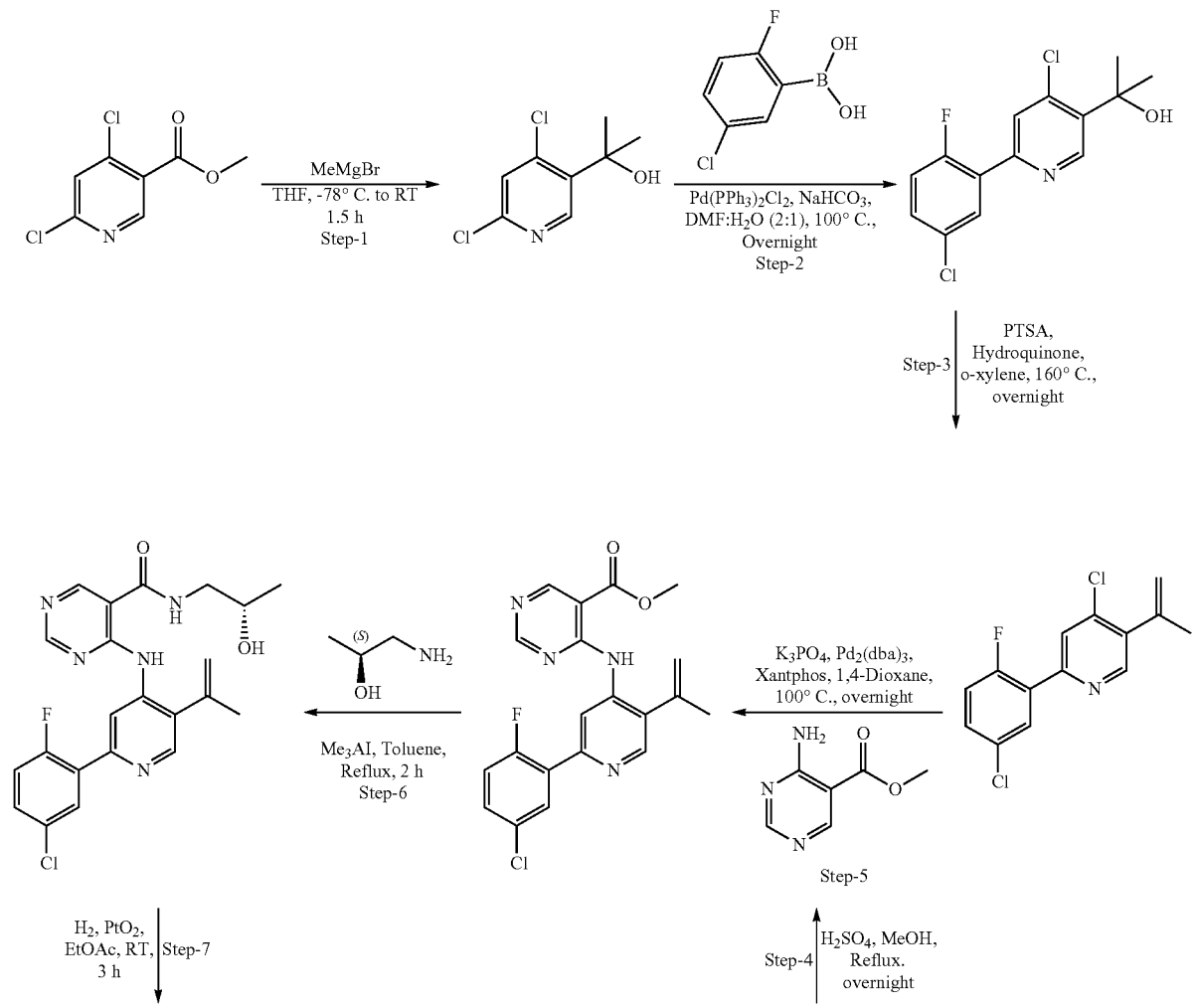

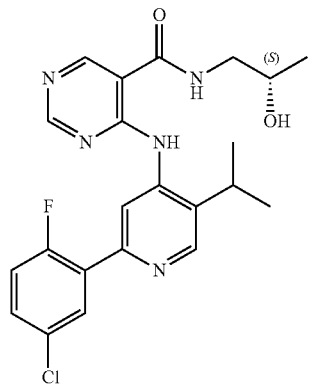

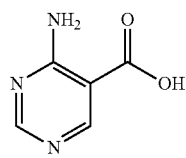

Steps 1 to 6 are the same as in Example 4.

Step 7: Synthesis of (S)-4-(2-(5-chloro-2-fluorophenyl)-5-isopropylpyridin-4-ylamino)-N-(2-hydroxypropyl)pyrimidine-5-carboxamide To a stirred solution of (S)-4-(2-(5-chloro-2-fluorophenyl)-5-(prop-1-en-2-yl)pyridin-4-ylamino)-N-(2-hydroxypropyl)pyrimidine-5-carboxamide (120 mg, 0.271 mmol) in EtOAc (4 mL) was added platinum oxide (20 mg). The reaction mixture was stirred under hydrogen atmosphere using hydrogen bladder at RT for 3 h. The progress of reaction was monitored by LCMS. After completion of the reaction, the mixture was diluted with EtOAc (20 mL) and filtered through a celite bed. The filtrate was concentrated under reduced pressure to obtain the crude product which was purified by reverse phase preparative HPLC to afford (S)-4-(2-(5-chloro-2-fluorophenyl)-5-isopropylpyridin-4-ylamino)-N-(2-hydroxypropyl)pyrimidine-5-carboxamide (36 mg) TFA salt as a white solid. The (R) enantiomer can be synthesized utilizing (R)-1-aminopropan-2-ol in this step.

NMR: $^1$H NMR (400 MHz, CD$_3$OD) δ (ppm): 9.64 (s, 1H), 9.13 (s, 1H), 9.04 (s, 1H), 8.52 (s, 1H), 7.86 (dd, J=6.3, 2.7 Hz, 1H), 7.73 (ddd, J=8.9, 4.3, 2.6 Hz, 1H), 7.46 (t, J=9.5 Hz, 1H), 4.02 (td, J=6.8, 4.6 Hz, 1H), 3.47 (m, 3H), 1.59-1.48 (d, J=8.0 Hz, 6H), 1.24 (d, J=6.3 Hz, 3H). LCMS: 443.8 (M+1).

Example 13. Preparation of Compound Nos. 13, 13a and 13b

Synthesis of 4-[[2-(5-chloro-2-fluoro-phenyl)-5-methoxy-4-pyridyl]amino]-N-[(2S)-2-hydroxypropyl]pyridine-3-carboxamide

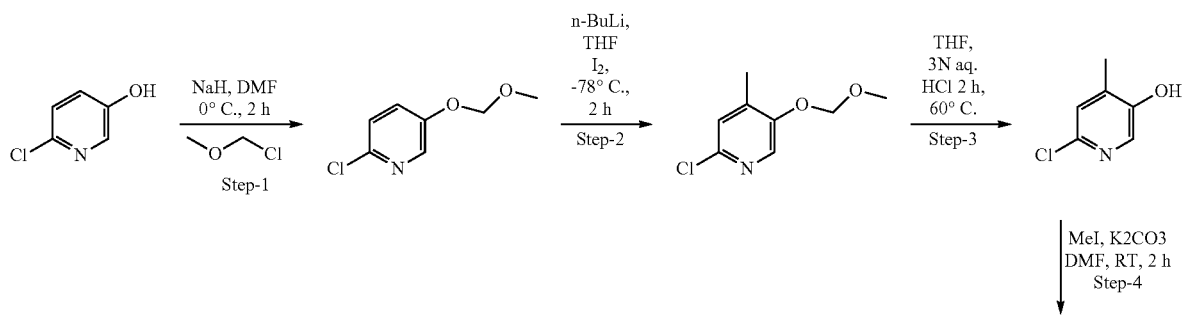

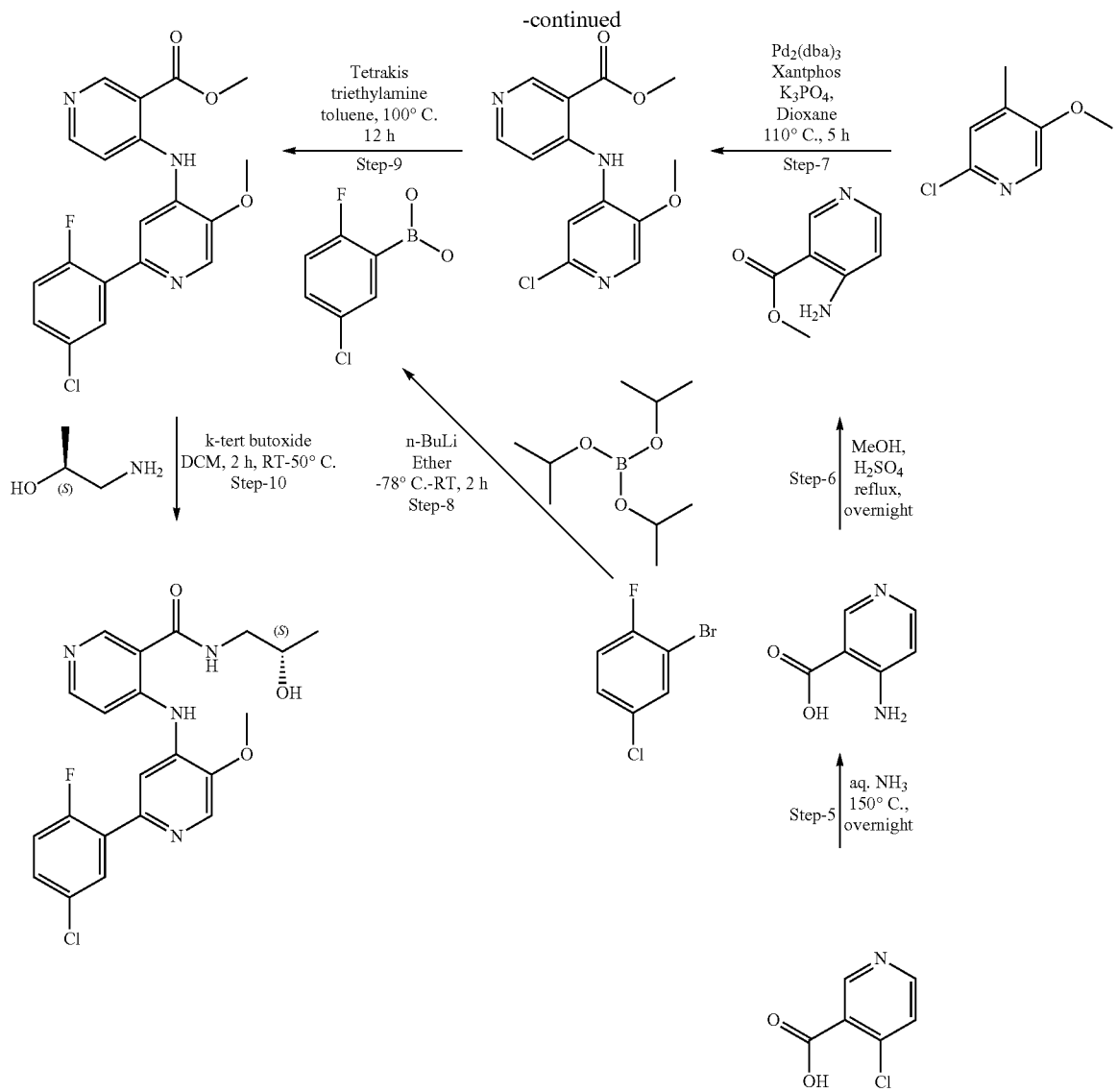

Step 1: Synthesis of 2-chloro-5-(methoxymethoxy)pyridine

To a solution of 6-chloropyridin-3-ol (2 g, 15.439 mmol) in DMF (10 mL) was added NaH (0.960 g, 23.200 mmol) under nitrogen atmosphere at 0° C. The reaction mixture was stirred at 0° C. for 30 min. Then, to this reaction mixture was added a solution of chloro(methoxy)methane (1.62 g, 20.121 mmol) in DMF (2 mL) dropwise. This reaction mixture was stirred at 0° C. for 30 min. The progress of reaction was monitored by TLC. After completion reaction, the mixture was quenched with ice-cold water (20 mL), extracted with EtOAc (2×50 mL). The combined organic layer was washed with water (2×75 mL) and brine (75 mL), dried over anhydrous sodium sulfate and concentrated under reduced pressure to afford 2-chloro-5-(methoxymethoxy)pyridine (2.8 g) as a brown liquid.

Step 2: Synthesis of 2-chloro-4-iodo-5-(methoxymethoxy)pyridine

To a solution of 2-chloro-5-(methoxymethoxy)pyridine (2.1 g, 12.096 mmol) in THF (20 mL) was added a 1.6 M solution of n-BuLi in hexane (8.3 mL) under nitrogen atmosphere at −78° C. dropwise. The reaction mixture was stirred at −78° C. for 1 h. Then, to this reaction mixture was added a solution of iodine (3.6 g, 14.184 mmol) in THF (5 mL) dropwise. The reaction mixture was stirred at −78° C. for 15 min. The progress of reaction was monitored by TLC. After completion of the reaction, the mixture was quenched with a saturated aqueous solution of NH₄Cl (50 mL) and saturated aqueous solution of Na₂S₂O₃ (50 mL), and the product was extracted with EtOAc (2×150 mL). The combined organic layer was dried over anhydrous sodium sulfate and concentrated under reduced pressure to afford 2-chloro-4-iodo-5-(methoxymethoxy)pyridine (4 g) as a yellow solid.

Step 3: Synthesis of 6-chloro-4-iodo-pyridin-3-ol

A mixture of solution of 2-chloro-4-iodo-5-(methoxymethoxy)pyridine (4.4 g, 14.691 mmol) in THF (50 mL) and 3 N aqueous HCl (50 mL) was heated at 60° C. for 2 h. The progress of reaction was monitored by TLC. After completion of the reaction, the mixture was basified using saturated aqueous solution of NaHCO₃ (200 mL) and extracted with EtOAc (3×200 mL). The combined organic layer was dried over anhydrous sodium sulfate and concentrated under reduced pressure to afford 6-chloro-4-iodo-pyridin-3-ol (3.7 g) as a yellow solid.

Step 4: Synthesis of 2-chloro-4-iodo-5-methoxy-pyridine

To a solution of 6-chloro-4-iodo-pyridin-3-ol (300 mg, 1.174 mmol) in DMF (5 mL) was added methyl iodide (0.1 mL, 1.606 mmol) and $K_2CO_3$ (325 mg, 2.351 mmol). The reaction mixture was stirred at RT for 2 h. The progress of reaction was monitored by TLC. After completion of the reaction, the mixture was diluted with water (20 mL) and extracted with EtOAc (2×50 mL). The combined organic layer was washed with water (2×75 mL) and brine (50 mL), dried over anhydrous sodium sulfate and concentrated under reduced pressure to afford 2-chloro-4-iodo-5-methoxy-pyridine (250 mg) as a white solid.

Step 5: Synthesis of 4-aminopyridine-3-carboxylic acid

A solution of 4-chloropyridine-3-carboxylic acid (15 g, 0.095 mol) in aqueous $NH_3$ (600 mL) was heated in a pressure vessel at 150° C. overnight. The progress of reaction was monitored by TLC. After completion of reaction, the mixture was concentrated under reduced pressure. To this reaction mixture was added toluene (2×100 mL) to obtain 4-aminopyridine-3-carboxylic acid (17 g) as a white solid.

Step 6: Synthesis of methyl 4-aminopyridine-3-carboxylate

To a solution of 4-aminopyridine-3-carboxylic acid (17 g, 0.123 mol) in MeOH (300 mL) was added $H_2SO_4$ (45 mL) dropwise at 0° C. The reaction mixture was heated to reflux at 85° C. overnight. The progress of reaction was monitored by TLC. After completion of the reaction, the mixture was concentrated under reduced pressure to remove MeOH, residue was basified with a saturated aqueous solution of $Na_2CO_3$ (400 mL), extracted with EtOAc (3×500 mL). The combined organic layer was dried over anhydrous sodium sulfate and concentrated under reduced pressure to afford methyl 4-aminopyridine-3-carboxylate (10.3 g) as a white solid.

Step 7: Synthesis of methyl 4-aminopyridine-3-carboxylate

To a mixture of 2-chloro-4-iodo-5-methoxy-pyridine (5 g, 0.0185 mol), methyl 4-aminopyridine-3-carboxylate (2.26 g, 0.0148 mol) and $K_3PO_4$ (7.88 g, 0.0371 mol) in dioxane (200 mL) was purged with nitrogen for 20 min. To this reaction mixture was added $Pd_2(dba)_3$ (1.7 g, 0.0018 mol) and Xantphos (2.15 G, 0.0037 mol) and the reaction mixture was purged with nitrogen gas for 5 min. The reaction mixture was heated at reflux overnight at 110° C. The progress of reaction was monitored by TLC. After completion of reaction, the mixture was diluted with water (250 mL) and extracted with EtOAc (3×400 mL). The combined organic layer was dried over anhydrous sodium sulfate and concentrated under reduced pressure to afford crude product. The crude product was purified by column chromatography on silica gel (100-200 mesh) using 70% EtOAc-hexane system as eluent to obtain methyl 4-aminopyridine-3-carboxylate (400 mg) as a yellow solid.

Step 8: Synthesis of 2(5-chloro-2-fluoro-phenyl)boronic acid

To a solution of 2-bromo-4-chloro-1-fluoro-benzene (25 g, 0.122 mol) in dry diethyl ether (250 mL) was added n-BuLi (2.5 M in hexane, 53 mL) was added dropwise at −70° C. under nitrogen atmosphere. The reaction mixture was stirred at the same temperature for 30 min, followed by slow addition of triisopropyl borate (30.3 mL, 0.134 mol). The reaction mixture turned to a white slurry, which was further stirred for 30 min at the same temperature. Then, the reaction mixture was warmed to RT and stirred for 1 h. The progress of reaction was monitored by TLC. After completion of reaction, the mixture was cooled to 0° C., quenched with aqueous 6 N HCl (400 mL), stirred at RT for 1 h and extracted with EtOAc (2×500 mL). The combined organic layer was dried over anhydrous sodium sulfate and concentrated under reduced pressure to obtain the crude product. The crude product was purified by washing with pentane to afford 2(5-chloro-2-fluoro-phenyl)boronic acid (19.5 g) as a white solid.

Step 9: Synthesis of methyl 4-[[2-(5-chloro-2-fluoro-phenyl)-5-methoxy-4-pyridyl]amino]pyridine-3-carboxylate A solution of methyl 4-[(2-chloro-5-methoxy-4-pyridyl)amino]pyridine-3-carboxylate (360 mg, 1.225 mmol), (5-chloro-2-fluoro-phenyl)boronic acid (853 mg, 4.902 mmol) and triethylamine (0.85 mL, 6.106 mmol) in toluene (25 mL) was purged with nitrogen for 20 min. To this reaction mixture was added tetrakis (142 mg, 0.122 mmol) and then again the reaction mixture was purged for 5 min with nitrogen. The reaction mixture was heated at 100° C. for 12 h. The progress of reaction was monitored by TLC. After completion of reaction, the mixture was diluted with water (50 mL) and extracted with EtOAc (2×100 mL). The combined organic layer was dried over anhydrous sodium sulfate and concentrated under reduced pressure to afford a crude product. The crude product was purified by column chromatography on silica gel (230-400 mesh) using 40% acetone-hexane system as eluent to obtain methyl 4-[[2-(5-chloro-2-fluoro-phenyl)-5-methoxy-4-pyridyl]amino]pyridine-3-carboxylate (100 mg) as a brown solid.

Step 10: Synthesis of 4-[[2-(5-chloro-2-fluoro-phenyl)-5-methoxy-4-pyridyl]amino]-N-[(2S)-2-hydroxypropyl]pyridine-3-carboxamide A solution of (S)-1-aminopropan-2-ol (48 mg, 0.639 mmol) and potassium tert-butoxide (46 mg, 0.410 mmol) in DCM (3 mL) was stirred at RT for 30 min. To this stirred reaction mixture was added a solution of methyl 4-[[2-(5-chloro-2-fluoro-phenyl)-5-methoxy-4-pyridyl]amino]pyridine-3-carboxylate (100 mg, 0.258 mmol) in DCM (3 mL). The reaction mixture was heated at 50° C. for 2 h. The progress of reaction was monitored by TLC. After completion of reaction, reaction mixture was diluted with water (25 mL) and extracted with EtOAc (3×100 mL). The combined organic layer was dried over anhydrous sodium sulfate and concentrated under reduced pressure to afford a crude product. The crude product was purified by reverse phase CombiFlash® using 50% MeOH in 0.05% aqueous TFA as eluent to obtain 4-[[2-(5-chloro-2-fluoro-phenyl)-5-methoxy-4- pyridyl]amino]-N-[(2S)-2-hydroxypropyl]pyridine-3-carboxamide (20 mg) TFA salt as a white solid. The (R) enantiomer can be synthesized utilizing (R)-1-aminopropan-2-ol in this step.

NMR: $^1$H NMR (400 MHz, CD$_3$OD) δ (ppm): 8.90 (s, 1H), 8.58 (s, 1H), 8.41 (s, 1H), 8.03-7.86 (m, 2H), 7.55 (d, J=6.7 Hz, 1H), 7.47 (ddd, J=8.8, 4.2, 2.6 Hz, 1H), 7.27 (dd, J=10.7, 8.8 Hz, 1H), 4.12 (s, 3H), 4.00 (pd, J=6.4, 4.2 Hz, 1H), 3.48 (m, 2H), 3.40-3.33 (m, 1H), 1.24 (d, J=6.2 Hz, 3H).

Example 14. Preparation of Compound No. 14

Synthesis of N-(2-acetamidoethyl)-4-[[2-(5-chloro-2-fluoro-phenyl)-5-isopropyl-4-pyridyl]amino]pyridine-3-carboxamide

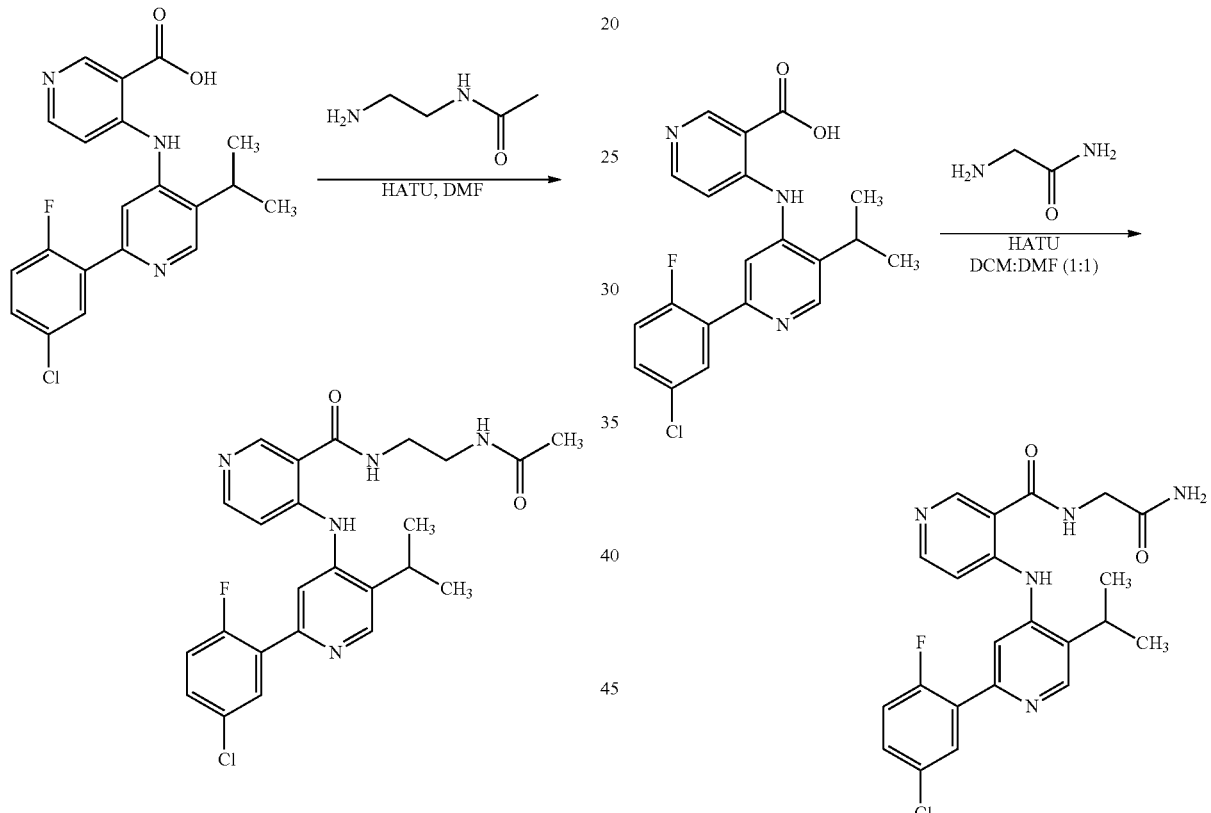

Steps 1 to 8 are the same as in Comparative Example 1

Step 9: Synthesis of N-(2-acetamidoethyl)-4-[[2-(5-chloro-2-fluoro-phenyl)-5-isopropyl-4-pyridyl]amino]pyridine-3-carboxamide To a solution of 4-[[2-(5-chloro-2-fluoro-phenyl)-5-isopropyl-4-pyridyl]amino]pyridine-3-carboxylic acid (200 mg, 0.518 mmol) in DMF (7 mL) was added N,N-diisopropylethyl amine (0.45 mL, 2.59 mmol) and HATU (317 mg, 0.829 mmol) and the reaction mixture was stirred at RT for 15 min under nitrogen atmosphere. To the reaction mixture was added a solution of N-(2-aminoethyl)acetamide (132 mg, 1.295 mmol) in DMF (3 mL) and the reaction mixture was stirred at RT overnight. The progress of reaction was monitored by TLC. After completion of the reaction, the mixture was diluted with water and extracted with EtOAc (50 mL). The organic layer was washed with water (2×10 mL) and brine solution (10 mL), dried over anhydrous sodium sulfate and concentrated under reduced pressure to obtain the crude product. The crude product was purified by reverse phase HPLC to afford N-(2-acetamidoethyl)-4-[[2-(5-chloro-2-fluoro-phenyl)-5-isopropyl-4-pyridyl]amino] pyridine-3-carboxamide (19 mg).

NMR: $^1$H NMR (400 MHz, CD$_3$OD) δ (ppm): 8.72 (s, 1H), 8.59 (s, 1H), 8.32 (d, J=6.0 Hz, 1H), 7.89 (dd, J=6.7, 2.7 Hz, 1H), 7.80 (s, 1H), 7.45 (ddd, J=8.8, 4.3, 2.8 Hz, 1H), 7.37 (d, J=6.0 Hz, 1H), 7.25 (dd, J=10.7, 8.8 Hz, 1H), 3.52 (dd, J=6.7, 5.1 Hz, 2H), 3.42 (t, J=5.9 Hz, 2H), 3.30-3.18 (m, 1H), 1.94 (s, 3H), 1.41 (d, J=6.9 Hz, 6H).

Example 15. Preparation of Compound No. 15

Synthesis of N-(2-amino-2-oxo-ethyl)-4-[[2-(5-chloro-2-fluoro-phenyl)-5-isopropyl-4-pyridyl]amino]pyridine-3-carboxamide Steps 1 to 8 are the same as in Comparative Example 1

Step 9: Synthesis of N-(2-amino-2-oxo-ethyl)-4-[[2-(5-chloro-2-fluoro-phenyl)-5-isopropyl-4-pyridyl]amino]pyridine-3-carboxamide To a solution of 4-[[2-(5-chloro-2-fluoro-phenyl)-5-isopropyl-4-pyridyl]amino]pyridine-3-carboxylic acid (200 mg, 0.518 mmol) in a 10:1 mixture of DCM:DMF (10 mL) was added N,N-diisopropylethyl amine (0.45 mL, 2.59 mmol) and HATU (317 mg, 0.829 mmol) and the reaction mixture was stirred at RT for 15 min under nitrogen atmosphere. To this stirred reaction mixture was added 2-aminoacetamide hydrochloride (143 mg, 1.295 mmol) the reaction mixture was again stirred at RT overnight. The progress of reaction was monitored by TLC. After completion of reaction, the mixture was diluted with water and extracted with EtOAc (50 mL). The organic layer was washed with water (2×10 mL) and brine solution (10 mL), dried over anhydrous sodium sulfate and concentrated under reduced pressure to obtain the crude product. The crude product was purified by reverse phase HPLC to afford N-(2-amino-2-oxo-ethyl)-4-[[2-(5-chloro-2-fluoro-phenyl)-5-isopropyl-4-pyridyl]amino]pyridine-3-carboxamide (115 mg) as a white solid.

NMR: $^1$H NMR (400 MHz, DMSO-d6) δ (ppm): 10.67 (s, 1H), 9.14 (t, J=5.9 Hz, 1H), 8.87 (s, 1H), 8.64 (s, 1H), 8.36 (d, J=5.9 Hz, 1H), 7.99 (dd, J=6.7, 2.8 Hz, 1H), 7.78 (d, J=1.4 Hz, 1H), 7.58-7.45 (m, 2H), 7.45-7.26 (m, 2H), 7.09 (s, 1H), 3.85 (d, J=5.9 Hz, 2H), 3.14 (m, 1H), 1.32 (d, J=6.8 Hz, 6H).

Example 16. Preparation of Compound Nos. 16, 16a and 16b

Synthesis of (S)-4-(2-(5-chloro-2-fluorophenyl)-5-(dimethylamino)pyridin-4-ylamino)-N-(2-hydroxypropyl)nicotinamide

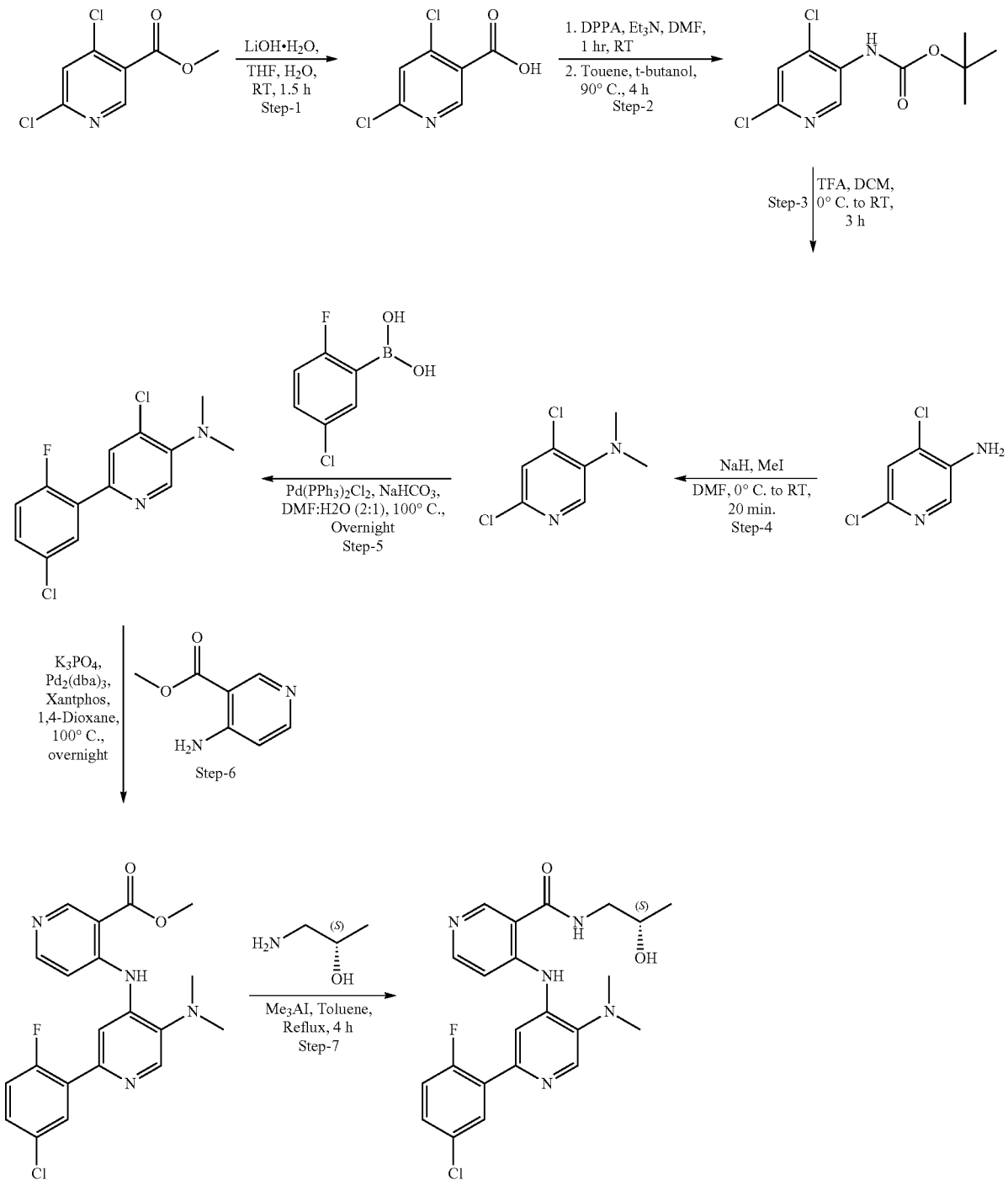

Step 1: Synthesis of 4,6-dichloropyridine-3-carboxylic acid

To a stirred solution of methyl 4,6-dichloropyridine-3-carboxylate (3.5 g, 16.990 mmol) in THF (30 mL) was added a solution of lithium hydroxide monohydrate (3.56 g, 84.951 mmol) in water (15 mL). The reaction mixture was stirred at RT for 1.5 h. The progress of reaction was monitored by TLC. After completion of reaction, the pH of the aqueous layer was adjusted to 2 by the addition of 2 N HCl (aq.) and the product was extracted with EtOAc (2×50 mL). The organic layer was separated, dried over anhydrous sodium sulfate and concentrated under reduced pressure to afford 4,6-dichloropyridine-3-carboxylic acid (3.2 g) as a white solid.

Step 2: Synthesis of tert-butyl N-(4,6-dichloro-3-pyridyl)carbamate

To a solution of 4,6-dichloropyridine-3-carboxylic acid (2.8 g, 14.58 mmol) in dry DMF (10 mL) was added triethylamine (2.24 mL, 16.04 mmol) at 0° C. followed by addition of diphenylphosphoryl azide (3.45 mL, 16.04 mmol). The reaction mixture was stirred at RT for 1 h and poured onto a mixture of ice-water-EtOAc. The product was extracted with EtOAc (2×50 mL). The combined extracts were washed with water (50 mL), saturated solution of sodium bicarbonate (50 mL) and finally with brine solution (50 mL). The organic layer was separated, dried over anhydrous sodium sulfate and concentrated under reduced pressure to afford light yellow solid which was dissolved in dry toluene (30 mL) and heated to reflux for 2 h. Then the reaction mixture was cooled to RT and t-butanol (8.36 mL, 87.48 mmol) was added. The reaction mixture was heated at 90° C. for 4 h. The reaction was monitored by TLC. After completion, the reaction mixture was concentrated under reduced pressure, water was added to the residue and product was extracted with EtOAc (2×100 mL). Removal of EtOAc under reduced pressure afforded an oily residue that was purified by column chromatography on silica gel (100-200) mesh) using 1% EtOAc-hexane system as eluent to afford tert-butyl N-(4,6-dichloro-3-pyridyl)carbamate (3.8 g) as a light yellow liquid.

Step 3: Synthesis of 4,6-dichloropyridin-3-amine

To a stirred solution of tert-butyl N-(4,6-dichloro-3-pyridyl)carbamate (3.8 g, 14.44 mmol) in DCM (15 mL) was added trifluoroacetic acid (5 mL) dropwise at 0° C. The reaction mixture was slowly warmed to RT and stirred for 3 h. The progress of reaction was monitored by TLC. After completion of reaction, the mixture was concentrated under reduced pressure. To the residue was added saturated solution of sodium bicarbonate (30 mL) and product was extracted with EtOAc (100 mL). The organic layer was again washed with water (30 mL) and brine solution (30 mL). The organic layer was separated, dried over anhydrous sodium sulfate. Removal of EtOAc under reduced pressure afforded product which was again washed with n-pentane and dried to afford 4,6-dichloropyridin-3-amine (1.9 g) as a light brown solid.

Step 4: Synthesis of 4,6-dichloro-N-methyl-pyridin-3-amine

To a stirred solution of 4,6-dichloropyridin-3-amine (1.42 g, 8.712 mmol) in dry DMF (8 mL) was added a 60% suspension of sodium hydride in mineral oil (767 mg, 19.166 mmol) under nitrogen atmosphere at 0° C. The reaction mixture was stirred at this temperature for 5-10 min. To this stirred reaction mixture was added a solution of methyl iodide (1.2 mL, 19.166 mmol) in dry DMF (2 mL) dropwise. Then, the reaction mixture was stirred at RT for 20 min. The progress of reaction was monitored by TLC. After completion of the reaction, the mixture was quenched by addition of ice-water and product was extracted with EtOAc (50 mL). The organic layer was again washed with water (2×20 mL) and brine solution (20 mL). The organic layer was separated, dried over anhydrous sodium sulfate and concentrated under reduced pressure to afford 4,6-dichloro-N-methyl-pyridin-3-amine (1.6 g) as a light brown solid.

Step 5: Synthesis of 4-chloro-6-(5-chloro-2-fluoro-phenyl)-N,N-dimethyl-pyridin-3-amine A mixture of 4,6-dichloro-N-methyl-pyridin-3-amine (1.6 g, 8.374 mmol), (5-chloro-2-fluoro-phenyl)boronic acid (2.19 g, 12.561 mmol) and sodium bicarbonate (1.4 g, 16.748 mmol) in a 2:1 mixture DMF:$H_2O$ (21 mL) was purged with nitrogen gas for 40 min. To this reaction mixture was added bis(triphenylphosphine)palladium(II) dichloride (294 mg, 0.418 mmol) and the reaction mixture was purged with nitrogen gas for another 5 min. Then, the reaction mixture was heated at 100° C. overnight. The progress of reaction was monitored by TLC and LCMS. After completion of reaction, water (20 mL) was added to the reaction mixture and product was extracted with EtOAc (2×25 mL). The combined organic layer was washed with water (3×25 mL) and finally with brine solution (25 mL). The organic layer was separated, dried over anhydrous sodium sulfate and concentrated under reduced pressure to afford 4-chloro-6-(5-chloro-2-fluoro-phenyl)-N,N-dimethyl-pyridin-3-amine (1.2 g) as an off-white solid.

Step 6: Synthesis of methyl 4-[[2-(5-chloro-2-fluoro-phenyl)-5-(dimethylamino)-4-pyridyl]amino]pyridine-3-carboxylate A mixture of 4-chloro-6-(5-chloro-2-fluoro-phenyl)-N,N-dimethyl-pyridin-3-amine (980 mg, 3.436 mmol), methyl 4-aminopyridine-3-carboxylate (272 mg, 1.787 mmol) and potassium phosphate (tribasic) (693 mg, 3.264 mmol) in 1,4-dioxane (20 mL) was purged with nitrogen gas for 30 min. To this reaction mixture was added tris(dibenzylidineacetone)dipalladium(0) (151 mg, 0.165 mmol) and Xantphos (139 mg, 0.240 mmol) and the reaction mixture was purged with nitrogen gas for another 5 min. The reaction mixture was then heated at 100° C. overnight. The progress of reaction was monitored by TLC and LCMS. After completion of the reaction, the mixture was diluted with EtOAc (50 mL) and filtered through a celite bed. The filtrate was washed with water (20 mL) and finally with brine solution (20 mL). The organic layer was separated, dried over anhydrous sodium sulfate and concentrated under reduced pressure to afford a crude product which was purified by CombiFlash®® chromatography using 25% EtOAc-hexane system as eluent to afford methyl 4-[[2-(5-chloro-2-fluoro-phenyl)-5-(dimethylamino)-4-pyridyl]amino]pyridine-3-carboxylate (98 mg) as an off-white solid.

Step 7: Synthesis of (S)-4-(2-(5-chloro-2-fluorophenyl)-5-(dimethylamino)pyridin-4-ylamino)-N-(2-hydroxypropyl)nicotinamide To a stirred solution of methyl 4-[[2-(5-chloro-2-fluoro-phenyl)-5-(dimethylamino)-4-pyridyl]amino]pyridine-3- carboxylate (98 mg, 0.244 mmol) and (S)-1-amino-propan-2-ol (28 mg, 0.366 mmol) in toluene (6 mL) was added a 1 M solution of trimethylaluminium in heptane (0.98 mL, 0.98 mmol) at RT. The reaction mixture was heated at reflux for 4 h. The progress of reaction was monitored by TLC. After completion of the reaction, the mixture was diluted with EtOAc (30 mL) and washed with saturated solution of sodium bicarbonate (15 mL), water (15 mL) followed by brine wash (15 mL). The organic layer was separated, dried over anhydrous sodium sulfate and concentrated under reduced pressure to obtain the crude product which was purified by CombiFlash® chromatography using 6% MeOH-DCM system as eluent to afford (S)-4-(2-(5-chloro-2-fluorophenyl)-5-(dimethylamino)pyridin-4-ylamino)-N-(2-hydroxypropyl)nicotinamide (30 mg) as an off-white solid. The (R) enantiomer can be synthesized utilizing (R)-1-aminopropan-2-ol in this step.

NMR: $^1$H NMR (400 MHz, CDCl$_3$) δ (ppm): 10.21 (s, 1H), 8.71 (s, 1H), 8.41 (d, J=9.0 Hz, 2H), 7.99 (dd, J=6.8, 2.8 Hz, 1H), 7.78 (d, J=1.9 Hz, 1H), 7.43 (d, J=5.9 Hz, 1H), 7.29 (ddd, J=8.5, 4.1, 2.6 Hz, 1H), 7.08 (dd, J=10.7, 8.7 Hz, 1H), 6.88 (bs, 1H), 4.14-4.02 (m, 1H), 3.72 (ddd, J=14.0, 6.7, 3.1 Hz, 1H), 3.30 (ddd, J=13.4, 8.0, 4.7 Hz, 1H), 2.85 (s, 6H), 1.29 (d, J=6.3 Hz, 3H). LCMS: 444.2 (M+1).

Example 17. Preparation of Compound Nos. 17, 17a and 17b

Synthesis of 4-[[2-(5-chloro-2-fluoro-phenyl)-5-(1-methoxy-1-methyl-ethyl)-4-pyridyl]amino]-N-(2-hydroxypropyl)pyridine-3-carboxamide

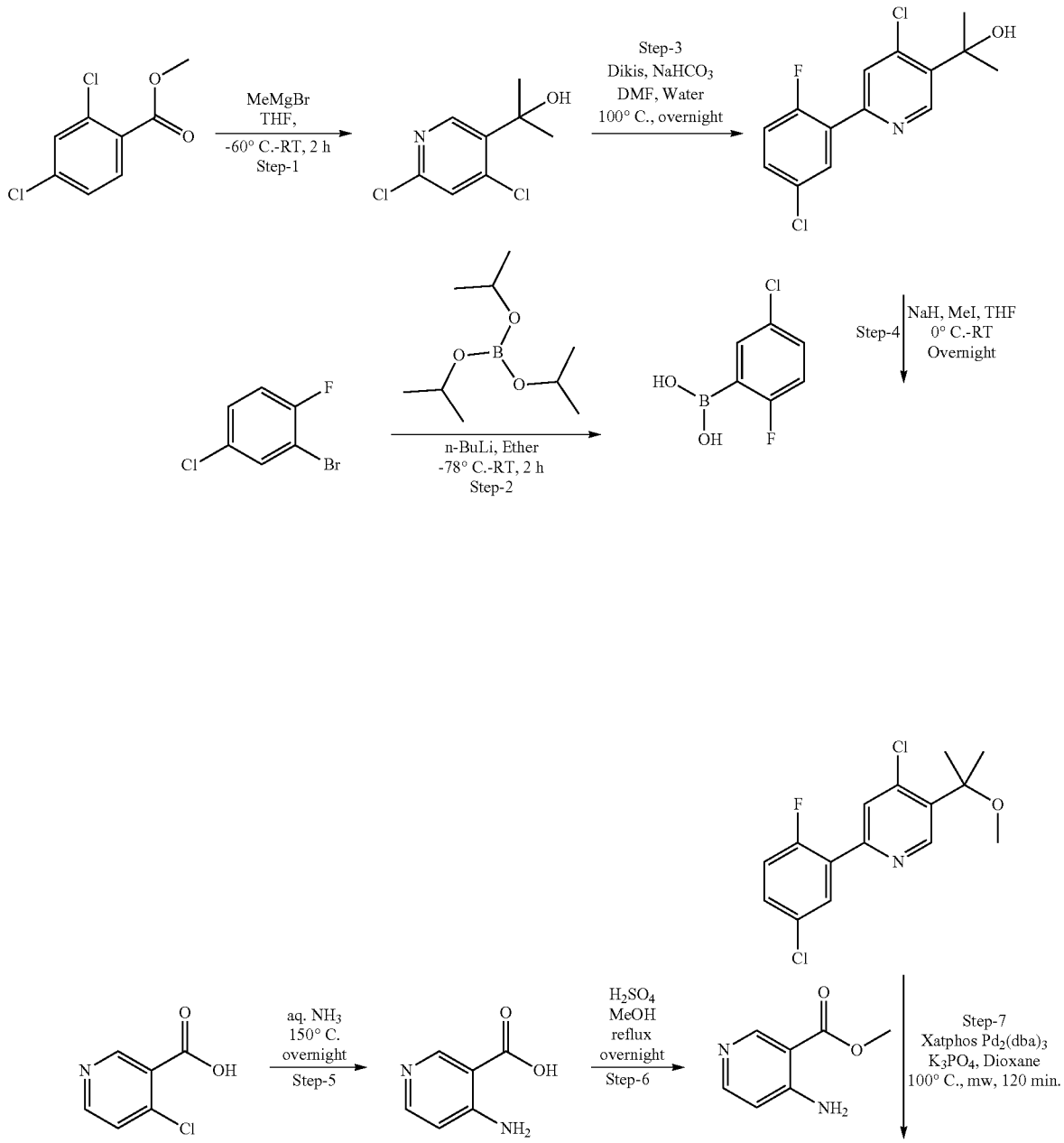

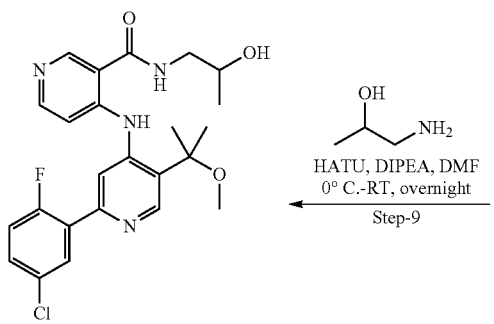 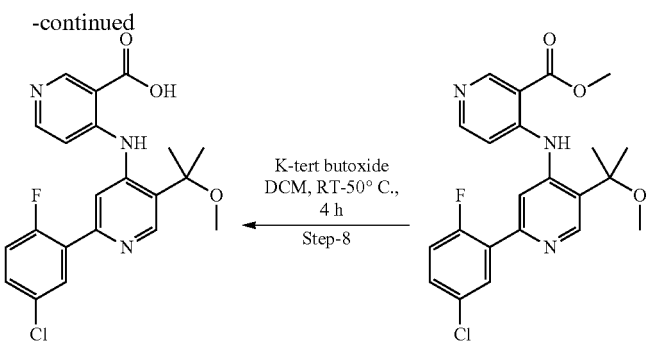

Step 1: Synthesis of 2-(4,6-dichloro-3-pyridyl)propan-2-ol)

A solution of methyl 4,6-dichloropyridine-3-carboxylate (5 g, 0.0243 mol) in dry THF (60 mL) was cooled to −60° C. under nitrogen atmosphere. To this reaction mixture was added methylmagnesium bromide (3 M in THF, 28.3 mL). The reaction mixture was warmed to RT and stirred for 2 h. The progress of reaction was monitored by TLC. After completion of reaction, the mixture was cooled to 0° C. and quenched with saturated aqueous ammonium chloride solution (200 mL) and extracted with EtOAc (2×300 mL). The organic layer was dried over anhydrous sodium sulfate and concentrated under reduced pressure to afford 2-(4,6-dichloro-3-pyridyl)propan-2-ol (4.91 g) as a yellow liquid.

Step 2: Synthesis of 2(5-chloro-2-fluoro-phenyl)boronic acid

1 To a solution of 2-bromo-4-chloro-1-fluoro-benzene (25 G, 0.122 mol) in dry diethyl ether (250 mL) was added n-BuLi (2.5 M in hexane, 53 mL) dropwise at −70° C. under nitrogen atmosphere. The reaction mixture was stirred at the same temperature for 30 min, followed by slow addition of triisopropyl borate (30.3 mL, 0.134 mol). Formation of a white slurry was observed, which was stirred for 30 min at the same temperature. Then, the reaction mixture was warmed to RT and stirred for 1 h. The progress of reaction was monitored by TLC. After the completion of the reaction, the mixture was cooled to 0° C. and quenched with aqueous 6 N HCl (400 mL), stirred at RT for 1 h and then extracted with EtOAc (2×500 mL). The organic layer was dried over anhydrous sodium sulfate and concentrated under reduced pressure to obtain the crude product. The crude product was purified by washing with pentane to afford 2(5-chloro-2-fluoro-phenyl)boronic acid (19.5 g) as a white solid.

Step 3: Synthesis of 2-[4-chloro-6-(5-chloro-2-fluoro-phenyl)-3-pyridyl]propan-2-ol A solution of methyl 2-(4,6-dichloro-3-pyridyl)propan-2-ol (800 mg, 3.882 mmol), (5-chloro-2-fluoro-phenyl)boronic acid (1.150 g, 6.595 mmol) in DMF (18 mL) was mixed with solution of NaHCO$_3$ (625 mg, 7.761 mmol) in water (9 mL). The reaction mixture was purged with nitrogen for 15 min followed by addition of palladium dichloro diphenyl phosphine (136 mg, 0.193 mmol). The reaction mixture was again purged for 5 min and heated at 100° C. overnight. The progress of reaction was monitored by TLC. After completion of reaction, the mixture was diluted with water (60 mL) and extracted with EtOAc (3×125 mL). The organic layers were washed with water (2×300 mL) and brine (150 mL), dried over anhydrous sodium sulfate and concentrated under reduced pressure to afford a crude product. The crude product was purified by CombiFlash® using 10% EtOAc-hexane system as eluent to obtain 2-[4-chloro-6-(5-chloro-2-fluoro-phenyl)-3-pyridyl]propan-2-ol (750 mg) as a pale yellow sticky material.

Step 4: Synthesis of 4-chloro-2-(5-chloro-2-fluoro-phenyl)-5-(1-methoxy-1-methyl-ethyl)pyridine To a solution of 2-[4-chloro-6-(5-chloro-2-fluoro-phenyl)-3-pyridyl]propan-2-ol (110 mg, 0.366 mmol) in THF (5 mL) was added NaH (33 mg, 0.797 mmol) and MeI (0.03 mL, 0.481 mmol) at 0° C. under nitrogen atmosphere. The reaction mixture was warmed to RT and stirred overnight. The progress of reaction was monitored by TLC. After completion of reaction, the mixture was quenched with ice-cold water (10 mL) and extracted with EtOAc (2×15 mL). The organic layers were dried over anhydrous sodium sulfate and concentrated under reduced pressure to afford 4-chloro-2-(5-chloro-2-fluoro-phenyl)-5-(1-methoxy-1-methyl-ethyl)pyridine (100 mg) as a brown semisolid.

Step 5: Synthesis of 4-aminopyridine-3-carboxylic acid

A solution of 4-chloropyridine-3-carboxylic acid (15 g, 0.095 mol) in aqueous NH$_3$ (600 mL) was heated in a pressure vessel at 150° C. overnight. The progress of reaction was monitored by TLC. After completion of reaction, the mixture was concentrated under reduced pressure. To this reaction mixture was added toluene (2×100 mL) to obtain 4-aminopyridine-3-carboxylic acid (17 g) as a white solid.

Step 6: Synthesis of methyl 4-aminopyridine-3-carboxylate

To a solution of 4-aminopyridine-3-carboxylic acid (17 g, 0.123 mol) in MeOH (300 mL) was added H$_2$SO$_4$ (45 mL) dropwise at 0° C. The reaction mixture was heated to reflux at 85° C. overnight. The progress of reaction was monitored by TLC. After completion of the reaction, the mixture was concentrated under reduced pressure. The residue was basified with saturated aqueous Na$_2$CO$_3$ solution (400 mL), and extracted with EtOAc (3×500 mL). The organic layers were dried over anhydrous sodium sulfate and concentrated under reduced pressure to afford methyl 4-aminopyridine-3-carboxylate (10.3 g) as a white solid.

Step 7: Synthesis of methyl 4-[[2-(5-chloro-2-fluoro-phenyl)-5-(1-methoxy-1-methyl-ethyl)-4-pyridyl]amino] pyridine-3-carboxylate A mixture of 4-chloro-2-(5-chloro-2-fluoro-phenyl)-5-(1-methoxy-1-methyl-ethyl)pyridine (200 mg, 0.636 mmol), methyl 4-aminopyridine-3-carboxylate (107 mg, 0.703 mmol) and K₃PO₄ (270 mg, 1.271 mmol) in dioxane (1.5 mL) was purged with nitrogen for 10 min, followed by addition of Pd₂(dba)₃ (58 mg, 0.063 m mol) and Xantphos (74 mg, 0.127 mmol) and again purged for 2 min. The reaction mixture was heated in a microwave at 100° C. for 2 h. The progress of reaction was monitored by TLC and LCMS. After completion of reaction, the mixture was diluted with EtOAc (15 mL) and washed with water (2×10 mL). The organic layer was dried over anhydrous sodium sulfate and concentrated under reduced pressure to afford a crude product. The crude product was purified by Combi-Flash® using 25% EtOAc-hexane as eluent to obtain methyl 4-[[2-(5-chloro-2-fluoro-phenyl)-5-(1-methoxy-1-methyl-ethyl)-4-pyridyl]amino]pyridine-3-carboxylate (42 mg).

Step 8: Synthesis of 4-[[2-(5-chloro-2-fluoro-phenyl)-5-(1-methoxy-1-methyl-ethyl)-4-pyridyl]amino] pyridine-3-carboxylic acid To a stirred solution of potassium tert-butoxide (21 mg, 0.197 mmol) in DCM (2 mL) was added a solution of methyl 4-[[2-(5-chloro-2-fluoro-phenyl)-5-(1-methoxy-1-methyl-ethyl)-4-pyridyl]amino]pyridine-3-carboxylate (50 mg, 0.116 mmol) in DCM (2 mL). The reaction mixture was heated at 50° C. for 4 h. The progress of reaction was monitored by TLC and LCMS. After completion of the reaction, the mixture was diluted with DCM (20 mL) and washed with water (2×10 mL). The organic layer was dried over anhydrous sodium sulfate and concentrated under reduced pressure to obtain 4-[[2-(5-chloro-2-fluoro-phenyl)-5-(1-methoxy-1-methyl-ethyl)-4-pyridyl]amino]pyridine-3-carboxylic acid (50 mg) as a yellow solid.

Step 9: Synthesis of 4-[[2-(5-chloro-2-fluoro-phenyl)-5-(1-methoxy-1-methyl-ethyl)-4-pyridyl] amino]-N-(2-hydroxypropyl)pyridine-3-carboxamide To a solution of 4-[[2-(5-chloro-2-fluoro-phenyl)-5-(1-methoxy-1-methyl-ethyl)-4-pyridyl]amino]pyridine-3-carboxylic acid (50 mg, 0.120 mmol) in DMF (2 mL) was added HATU (91 mg, 0.289 mmol) and DIPEA (0.13 mL, 0.746 mmol) at 0° C. under nitrogen atmosphere. The reaction mixture was stirred at 0° C. for 15 min followed by addition of (S)-1-aminopropan-2-ol (18 mg, 0.239 mmol) in DMF (1 mL). Then, the reaction mixture was warmed to RT and stirred overnight. The progress of reaction was monitored by TLC. After completion of the reaction, the mixture was diluted with EtOAc (25 mL) and washed with water (2×15 mL), saturated aqueous NaHCO₃ solution (15 mL), saturated aqueous NH₄Cl solution (15 mL) and brine (15 mL). The organic layers were dried over anhydrous sodium sulfate and concentrated under reduced pressure to obtain the crude product. The crude product was purified by reverse phase preparative HPLC to obtain 4-[[2-(5-chloro-2-fluoro-phenyl)-5-(1-methoxy-1-methyl-ethyl)-4-pyridyl]amino]-N-(2-hydroxypropyl)pyridine-3-carboxamide (19.8 mg) as a white solid. The (R) enantiomer can be synthesized utilizing (R)-1-aminopropan-2-ol in this step.
NMR: ¹H NMR (400 MHz, CD₃OD) δ (ppm): 8.70 (s, 1H), 8.52 (s, 1H), 8.36 (d, J=6.0 Hz, 1H), 7.89 (dd, J=6.7, 2.8 Hz, 1H), 7.83 (d, J=1.8 Hz., 1H), 7.53 (d, J=6.0 Hz, 1H), 7.46 (ddd, J=8.8, 4.3, 2.8 Hz, 1H), 7.25 (d, J=10.7, 8.8 Hz, 1H), 3.98 (td, J=6.7, 4.8 Hz, 1H), 3.44 (m, 2H), 3.23 (s, 3H), 1.70 (s, 6H), 1.25 (d, J=6.2, 3H).

Example 18. Preparation of Compound No. 18

Synthesis of 4-[[2-(5-chloro-2-fluoro-phenyl)-5-isopropyl-4-pyridyl]amino]-N-[2-(methane sulfonamido)ethyl]pyridine-3-carboxamide

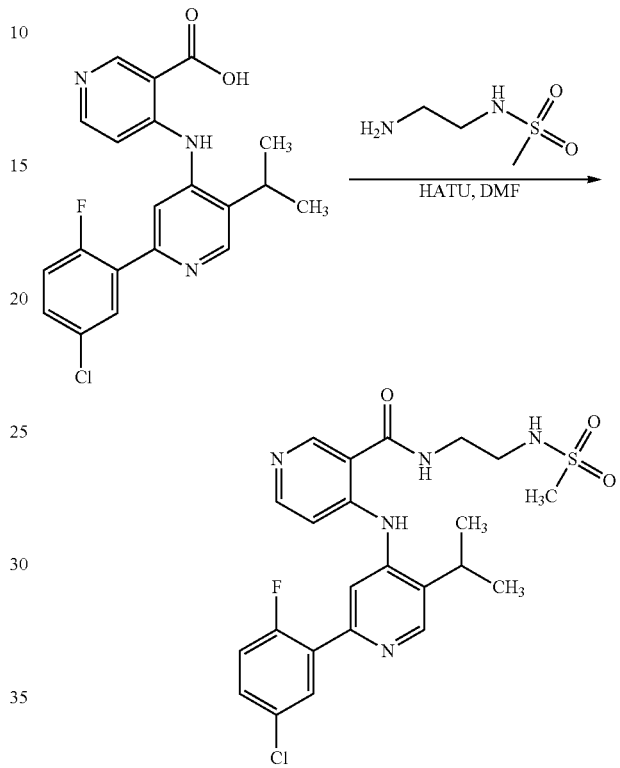

Steps 1 to 8 are the same as in Comparative Example 1

Step 9: Synthesis of 4-[[2-(5-chloro-2-fluoro-phenyl)-5-isopropyl-4-pyridyl]amino]-N-[2-(methanesulfonamido)ethyl]pyridine-3-carboxamide To a solution of 4-[[2-(5-chloro-2-fluoro-phenyl)-5-isopropyl-4-pyridyl]amino]pyridine-3-carboxylic acid (100 mg, 0.245 mmol) in DMF (4 mL) was added N,N-diisopropylethyl amine (0.17 mL, 0.98 mmol) and HATU (149 mg, 0.39 mmol) and stirred at RT for 15 min under nitrogen atmosphere. Then, to this reaction mixture was added N-(2-aminoethyl)methanesulfonamide hydrochloride (107 mg, 0.613 mmol) and the reaction mixture was stirred at RT overnight. The progress of reaction was monitored by TLC. After completion of reaction, the mixture was diluted with water and extracted with EtOAc (50 mL). The organic layer was washed with water (2×10 mL) and brine solution (10 mL), dried over anhydrous sodium sulfate and concentrated under reduced pressure to obtain the crude product. The crude product was purified by reverse phase HPLC to afford 4-[[2-(5-chloro-2-fluoro-phenyl)-5-isopropyl-4-pyridyl] amino]-N-[2-(methane sulfonamido)ethyl]pyridine-3-carboxamide (25 mg) as a white solid.
NMR: ¹H NMR (400 MHz CD₃OD) δ (ppm): 8.76 (s, 1H), 8.57 (s, 1H), 8.31 (d, J=5.9 Hz, 1H), 7.88 (dd, J=6.7, 2.7 Hz, 1H), 7.78 (s, 1H), 7.45 (ddd, J=8.8, 4.2, 2.7 Hz, 1H), 7.36 (d, J=5.3 Hz, 1H), 7.25 (dd, J=10.7, 8.8 Hz, 1H), 3.55 (d, J=6.0 Hz, 2H), 3.37-3.17 (m, 3H), 2.96 (s, 3H), 1.40 (d, J=6.9 Hz; 6H).

Example 19. Preparation of Compound No. 19

Synthesis of N-(2-aminoethyl)-4-[[2-(5-chloro-2-fluoro-phenyl)-5-isopropyl-4-pyridyl]amino] pyridine-3-carboxamide

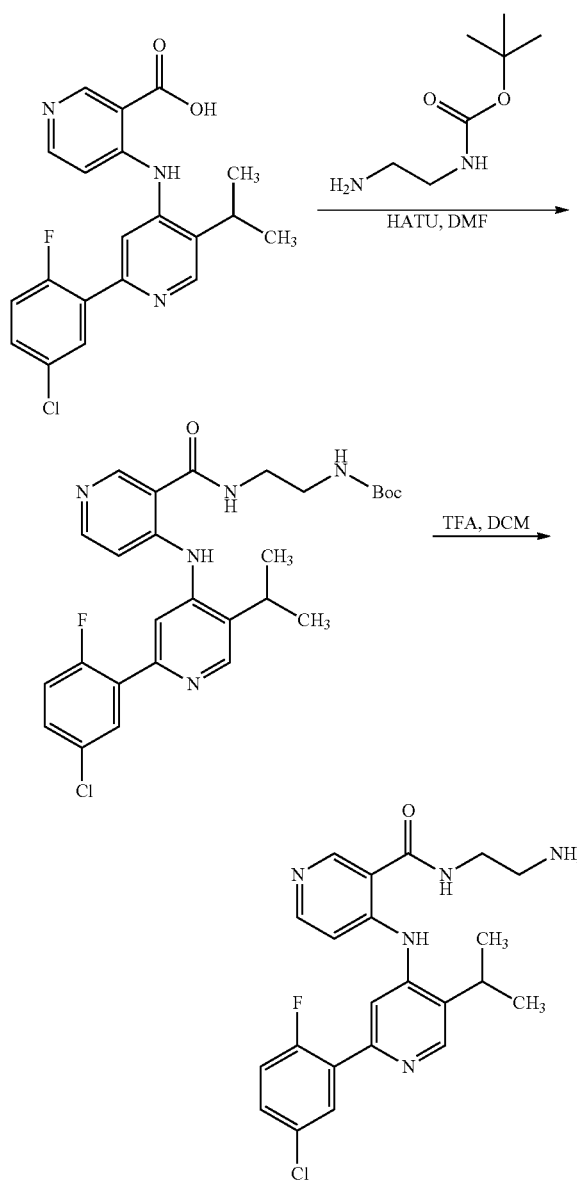

Steps 1 to 8 are the same as in Comparative Example 1

Step 9: Synthesis of tert-butyl N-[2-[[4-[[2-(5-chloro-2-fluoro-phenyl)-5-isopropyl-4-pyridyl]amino]pyridine-3-carbonyl]amino]ethyl]carbamate To a solution of 4-[[2-(5-chloro-2-fluoro-phenyl)-5-isopropyl-4-pyridyl]amino]pyridine-3-carboxylic acid (150 mg, 0.367 mmol) in DMF (4 mL) was add N,N-diisopropylethyl amine (0.26 mL, 1.47 mmol) and HATU (224 mg, 0.588 mmol) and stirred at RT for 15 min under nitrogen atmosphere. Then, to this reaction mixture was added tert-butyl N-(2-aminoethyl)carbamate hydrochloride (147 mg, 0.919 mmol) and the reaction mixture was stirred at RT overnight. The progress of reaction was monitored by TLC. After completion of reaction, the mixture was diluted with water and extracted with EtOAc (50 mL). The organic layer was washed with water (2×10 mL) and brine solution (10 mL), dried over anhydrous sodium sulfate and concentrated under reduced pressure to obtain the crude product. The crude product was purified by column chromatography on silica gel (100:200 mesh) using 80% EtOAc-hexane system as eluent to afford tert-butyl N-[2-[[4-[[2-(5-chloro-2-fluoro-phenyl)-5-isopropyl-4-pyridyl]amino]pyridine-3-carbonyl]amino]ethyl]carbamate (75 mg).

Step 10: Synthesis of N-(2-aminoethyl)-4-[[2-(5-chloro-2-fluoro-phenyl)-5-isopropyl-4-pyridyl]amino]pyridine-3-carboxamide To a stirred solution of tert-butyl N-[2-[[4-[[2-(5-chloro-2-fluoro-phenyl)-5-isopropyl-4-pyridyl]amino]pyridine-3-carbonyl]amino]ethyl]carbamate (75 mg, 0.142 mmol) in DCM (4 mL) was added TFA (1.5 mL) and stirred at RT for 1 h. The progress of reaction was monitored by TLC and NMR. After completion of reaction, the mixture was concentrated under reduced pressure to obtain the crude product. The crude product was triturated with diethyl ether and dried to obtain a crude residue, which was purified by reverse phase HPLC to afford N-(2-aminoethyl)-4-[[2-(5-chloro-2-fluoro-phenyl)-5-isopropyl-4-pyridyl]amino]pyridine-3-carboxamide (6 mg) as an off white solid.

NMR: $^1$H NMR (400 MHz, CD$_3$OD) δ (ppm): 8.77 (s, 1H), 8.60 (s, 1H), 8.32 (d, J=6.0 Hz, 1H), 7.90 (dt, J=6.7, 3.3 Hz, 1H), 7.80 (d, J=1.9 Hz, 1H), 7.46 (ddd, J=8.8, 4.3, 2.6 Hz, 1H), 7.36 (d, J=6.1 Hz 1H), 7.25 (t, J=9.75 Hz, 1H), 3.65 (t, J=6.0 Hz, 2H), 3.12 (t, J=6.0 Hz, 2H), 1.40 (d, J=6.9 Hz, 6H).

Example 20. Preparation of Compound Nos. 20, 20a and 20b

Synthesis of 3-[[2-(5-chloro-2-fluoro-phenyl)-5-isopropenyl-4-pyridyl]amino]-N-(2-hydroxypropyl)-1H-pyrazole-4-carboxamide

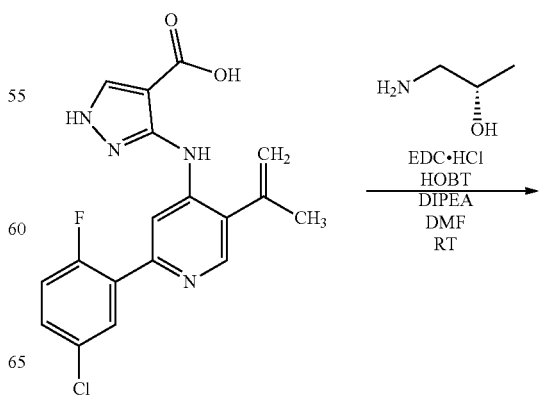

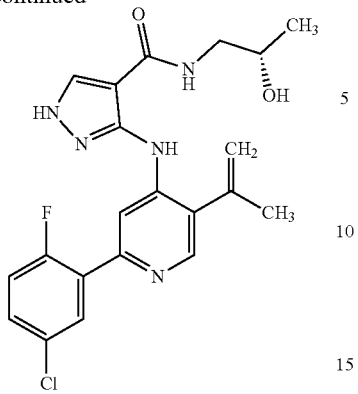

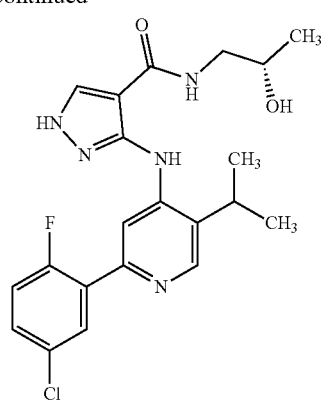

To a solution of 3-[[2-(5-chloro-2-fluoro-phenyl)-5-isopropenyl-4-pyridyl]amino]-1H-pyrazole-4-carboxylic acid (160 mg, 0.42 mmol) in DMF (4 mL) was added EDC.HCl (164 mg, 0.85 mmol), HOBT (115 mg, 0.85 mmol) and followed by the addition of DIPEA (0.37 mL, 2.14 mmol). The reaction mixture was stirred at RT for 15 min. Then, to this reaction mixture was added a solution of (S)-1-aminopropan-2-ol (96 mg 1.28 mmol) in DMF (1 mL) and the reaction mixture was stirred at RT overnight. The progress of reaction was monitored by LCMS. After completion of the reaction, the mixture was diluted with water (15 mL) and the product was extracted with EtOAc (2×100 mL). The organic layers were washed with water (2×40 mL), dried over sodium sulfate and concentrated under reduced pressure to get the crude product. The crude product was purified by preparative HPLC to afford (S)-3-[[2-(5-chloro-2-fluoro-phenyl)-5-isopropenyl-4-pyridyl]amino]-N-(2-hydroxypropyl)-1H-pyrazole-4-carboxamide (7.08 mg). The (R) enantiomer can be synthesized utilizing (R)-1-aminopropan-2-ol in this step.

NMR: $^1$H NMR (400 MHz, CD$_3$OD) δ (ppm): 8.79 (s, 1H), 8.15 (d, J=15.8 Hz, 2H), 7.75 (dd, J=6.5, 2.7 Hz, 1H), 7.44 (m, 1H), 7.24 (dd, J=10.2, 8.8 Hz, 1H), 5.64 (s, 1H), 5.25 (s, 1H), 3.92 (m, 1H), 3.46-3.32 (m, 2H), 2.20 (s, 3H), 1.20 (d, J=6.2 Hz, 3H). LCMS: 430.6 (M+1).

Example 21. Preparation of Compound Nos. 21, 21a and 21b

Synthesis of 3-[[2-(5-chloro-2-fluoro-phenyl)-5-isopropyl-4-pyridyl]amino]-N-(2-hydroxy propyl)-1H-pyrazole-4-carboxamide To (S)-3-[[2-(5-chloro-2-fluoro-phenyl)-5-isopropenyl-4-pyridyl]amino]-N-(2-hydroxy propyl)-1H-pyrazole-4-carboxamide (10 mg, 0.023 mmol) in MeOH (1.5 mL) was added PtO$_2$ (2 mg) and conc. HCl (1 drop), and the reaction mixture was hydrogenated using a hydrogen bladder for 90 min. The progress of reaction was monitored by NMR. After completion the reaction, the mixture was filtered through a celite bed. The filtrate was washed with MeOH and concentrated under reduced pressure to get crude product. The crude product was purified by preparative HPLC giving 3-[[2-(5-chloro-2-fluoro-phenyl)-5-isopropyl-4-pyridyl]amino]-N-(2-hydroxypropyl)-1H-pyrazole-4-carboxamide (2.1 mg). The (R) enantiomer can be synthesized utilizing the (R)-enantiomeric starting material.

NMR: $^1$H NMR (400 MHz, CD$_3$OD) δ (ppm): 8.75 (s, 1H), 8.30 (s, 1H), 8.16 (s, 1H), 7.73 (dd, J=6.5, 2.7 Hz, 1H), 7.43 (m, 1H), 7.23 (dd, J=10.2, 8.8 Hz, 1H), 3.95 (td, J=6.8, 4.8 Hz, 1H), 3.42 (dd, J=13.7, 4.6 Hz, 2H), 3.31-3.15 (m, 2H), 1.44 (d, J=6.8 Hz, 6H), 1.21 (d, J=6.3 Hz, 4H). LCMS: 432.5 (M+1).

Example 22. Preparation of Compound No. 22

Synthesis of 4-[[2-(5-chloro-2-fluoro-phenyl)-5-isopropyl-4-pyridyl]amino]-N-[2-hydroxy-1-(hydroxymethyl)ethyl]pyridine-3-carboxamide

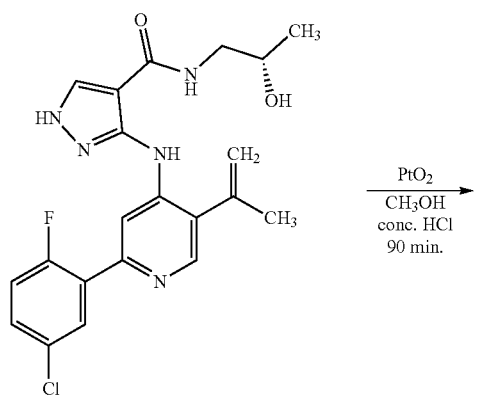

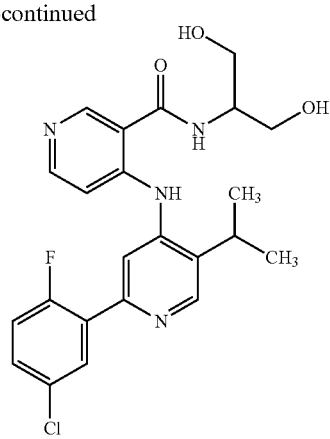

Steps 1 to 8 are the same as in Comparative Example 1

Step 9: Synthesis of 4-[[2-(5-chloro-2-fluoro-phenyl)-5-isopropyl-4-pyridyl]amino]-N-[2-hydroxy-1-(hydroxymethyl)ethyl] pyridine-3-carboxamide To a solution of 4-[[2-(5-chloro-2-fluoro-phenyl)-5-isopropyl-4-pyridyl]amino]pyridine-3-carboxylic acid (100 mg, 0.245 mmol) in DMF (4 mL) was added N,N-diisopropylethyl amine (0.17 mL, 0.98 mmol) and PYBOP (254 mg, 0.829 mmol) and the reaction mixture was stirred at RT for 15 min under nitrogen atmosphere. Then, to this reaction mixture was added a solution of 2-aminopropane-1,3-diol (33 mg, 0.367 mmol) in DMF (1 mL) and the reaction mixture was stirred at RT overnight. The progress of reaction was monitored by TLC. After completion of reaction, the mixture was diluted with water and extracted with EtOAc (50 mL). The organic layer was washed with water (2×10 mL) and brine solution (10 mL). The combined organic layer was dried over anhydrous sodium sulfate and evaporated under reduced pressure to obtain oily crude compound which was purified by reverse phase HPLC to afford 4-[[2-(5-chloro-2-fluoro-phenyl)-5-isopropyl-4-pyridyl]amino]-N-[2-hydroxy-1-(hydroxymethyl)ethyl]pyridine-3-carboxamide (10 mg).

NMR: $^1$H NMR (400 MHz, CD$_3$OD) δ (ppm): 8.80 (s, 1H), 8.58 (s, 1H), 8.32 (d, J=6.0 Hz, 1H), 7.89 (dd, J=6.6, 2.8 Hz, 1H), 7.80 (d, J=1.8 Hz, 1H), 7.50-7.34 (m, 2H), 7.25 (dd, J=10.7, 8.8 Hz, 1H), 4.24 (p, J=5.7 Hz, 1H), 3.82-3.68 (m, 4H), 3.30-3.18 (m, 1H), 1.40 (d, J=6.9 Hz, 6H).

Example 23. Preparation of Compound Nos. 23, 23a and 23b

Synthesis of 4-[[2-amino-6-(5-chloro-2-fluoro-phenyl)-3-isopropenyl-4-pyridyl]amino]-N-[(2S)-2-hydroxypropyl] pyridine-3-carboxamide

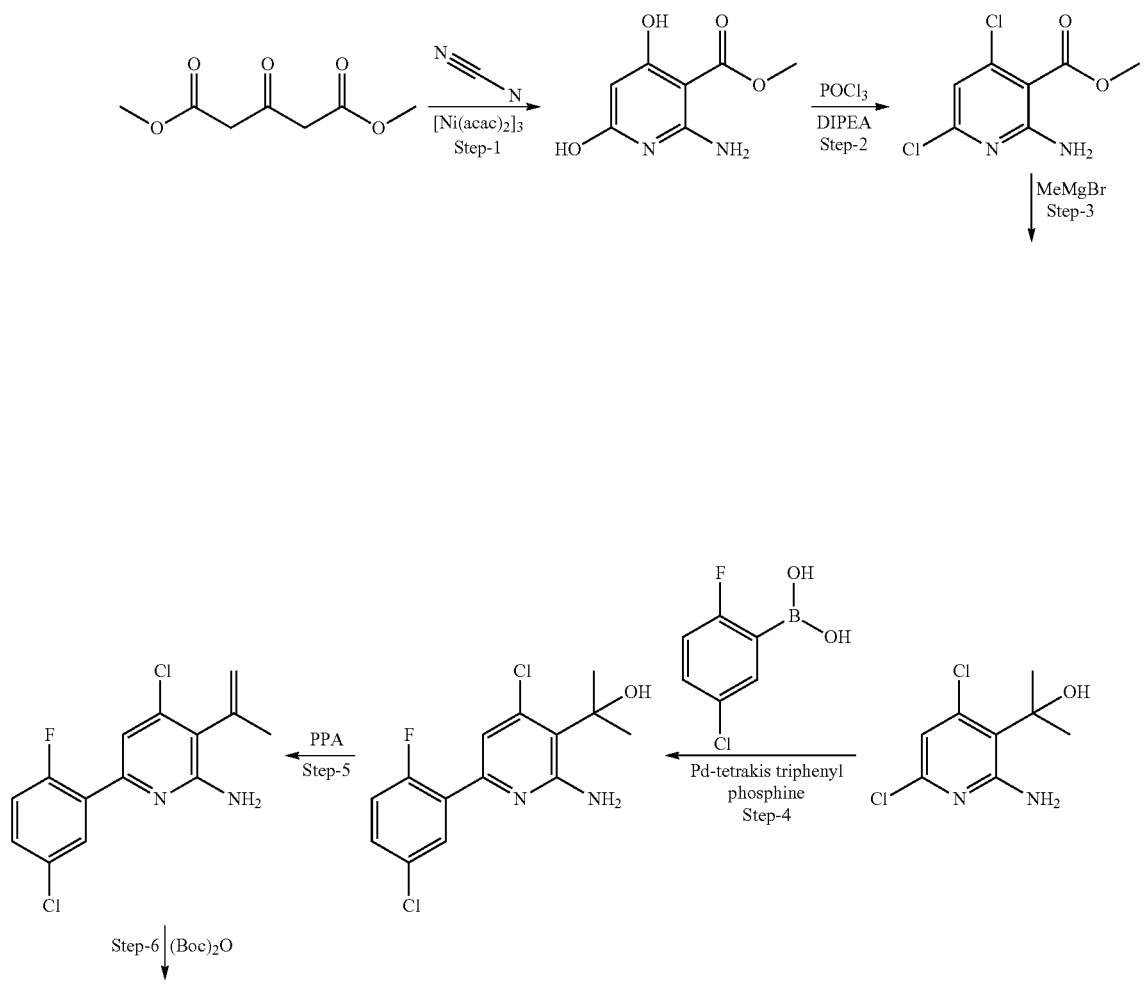

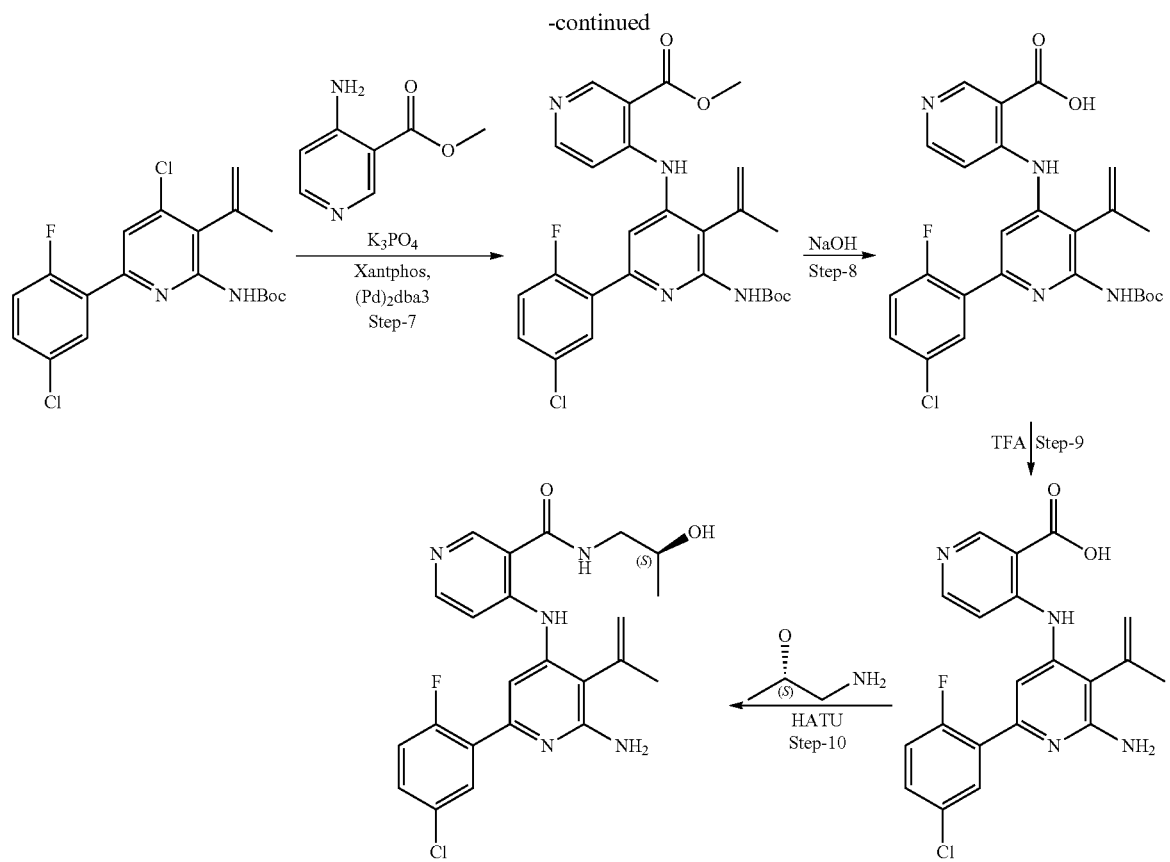

Step 1: Synthesis of methyl 2-amino-4,6-dihydroxy-pyridine-3-carboxylate

A mixture of dimethyl 1,3-acetonedicarboxylate (50 g, 0.287 mol), cyanamide (36.17 g, 0.861 mol) and nickel(II) acetylacetonate (7.376 g, 0.0287 mol) in 1,4-dioxane (300 mL) was heated to reflux for 16 h. Then, the reaction mixture was cooled to RT and stirred for 1 h. The reaction mixture was filtered and the resulting residue was filtered. The residue was mixed with MeOH (100 mL) and stirred for 1 h and filtered to afford methyl 2-amino-4,6-dihydroxy-pyridine-3-carboxylate (44 g) as a yellow solid.

Step 2: Synthesis of methyl 2-amino-4,6-dichloro-pyridine-3-carboxylate

Phosphorous oxychloride (225 mL) was added to methyl 2-amino-4,6-dihydroxy-pyridine-3-carboxylate (44 g, 0.239 mol) at 0° C. under nitrogen atmosphere. To this reaction mixture was added N,N-diisopropylethyl amine (44 mL) at the same temperature and the reaction mixture was stirred at RT for 3 d. The progress of reaction monitored by TLC and LCMS. After completion of reaction, the reaction mixture was concentrated under reduced pressure to obtain a sticky compound which was cooled to 0° C. and MeOH (40 mL) and water (200 mL) were added. The reaction mixture was stirred at RT for 1 h. The resulting solid was filtered off and purified by column chromatography on silica (100:200 mesh) using 10% EtOAc-hexane system as eluent to afford methyl 2-amino-4,6-dichloro-pyridine-3-carboxylate (20 g).

Step 3: Synthesis of 2-(2-amino-4,6-dichloro-3-pyridyl)propan-2-ol

To a solution of methyl 2-amino-4,6-dichloro-pyridine-3-carboxylate (300 mg, 1.357 mmol) in dry THF (7 mL) was added a 3M solution of methylmagnesium bromide in diethyl ether (1.58 mL, 4.75 mmol) dropwise under nitrogen at −60° C. The reaction mixture was stirred at −60° C. to 0° C. for 1 h. The progress of reaction was monitored by TLC & $^1$H NMR. After completion of reaction, the mixture was quenched using aqueous saturated solution of ammonium chloride and extracted with EtOAc. The organic layer was washed with water and brine, dried over anhydrous sodium sulfate and concentrated under reduced pressure to obtain the crude product. The crude product was purified by column chromatography on silica (100:200 mesh) using 10% EtOAc-hexane system as eluent to afford 2-(2-amino-4,6-dichloro-3-pyridyl)propan-2-ol (263 mg).

Step 4: Synthesis of 2-[2-amino-4-chloro-6-(5-chloro-2-fluoro-phenyl)-3-pyridyl]propan-2-ol A suspension of 2-(2-amino-4,6-dichloro-3-pyridyl)propan-2-ol (3.5 g, 0.0158 mole); (5-chloro-2-fluoro-phenyl) boronic acid (4.409 g, 0.0253 mol) and cesium carbonate (10.32 g, 0.0316 mol) in 2:1 mixture of DMF:H$_2$O (50 mL). This mixture was purged with nitrogen for 45 min. Then, to this reaction mixture was added Pd(PPh$_3$)$_4$ (1.829 g, 0.00158 mol) and purging continued with nitrogen for further 10 min. The resulting reaction mixture was heated at 95° C. overnight. After completion of reaction, the reaction mixture was diluted with water, extracted with EtOAc. The organic layer was washed with water and brine solution, dried over anhydrous sodium sulfate and concentrated under reduced pressure to obtain the crude product. The crude product was purified by column chromatography on silica (100:200 mesh) using 8% EtOAc-hexane system as eluent to afford 2-[2-amino-4-chloro-6-(5-chloro-2-fluoro-phenyl)-3-pyridyl]propan-2-ol (1.38 g) pure compound as a sticky yellow solid.

Step 5: Synthesis of 4-chloro-6-(5-chloro-2-fluoro-phenyl)-3-isopropenyl-pyridin-2-amine 2-[2-amino-4-chloro-6-(5-chloro-2-fluoro-phenyl)-3-pyridyl]propan-2-ol (1.04 g, 0.0033 mol) in polyphosphoric acid (10 g) was heated at 120° C. for 2 h. The progress of reaction was monitored by TLC and LCMS. After completion of reaction, the mixture was cooled to 0° C., diluted with water, basified with a saturated aqueous solution of sodium hydroxide (pH 10-12) and extracted with EtOAc. The organic layer was washed with water and brine solution, dried over anhydrous sodium sulfate and concentrated under reduced pressure to afford 4-chloro-6-(5-chloro-2-fluoro-phenyl)-3-isopropenyl-pyridin-2-amine (850 mg) as a pure compound.

Step 6: Synthesis of tert-butyl N-[4-chloro-6-(5-chloro-2-fluoro-phenyl)-3-isopropenyl-2-pyridyl]carbamate To a solution of 4-chloro-6-(5-chloro-2-fluoro-phenyl)-3-isopropenyl-pyridin-2-amine (3.25 g, 0.019 mol) in DCM (30 mL) was added TEA (3 mL) followed by DMAP (0.267 g, 0.00218 mol) under nitrogen atmosphere and stirred at RT for 15 min. To this reaction mixture was added (BOC)$_2$O (3.104 g, 0.01425 mol) and stirred overnight at RT. The progress of reaction was monitored by TLC and LCMS. After completion of reaction, the mixture was diluted with DCM and washed with water and brine solution. The organic layer was dried over anhydrous sodium sulfate and concentrated under reduced pressure to obtain the crude which was purified by column chromatography on silica gel (100:200 mesh) using 1% EtOAc-hexane system as eluent to afford tert-butyl N-[4-chloro-6-(5-chloro-2-fluoro-phenyl)-3-isopropenyl-2-pyridyl]carbamate (3.2 g).

Step 7: Synthesis of methyl 4-[[2-(tert-butoxycarbonylamino)-6-(5-chloro-2-fluoro-phenyl)-3-isopropenyl-4-pyridyl]amino] pyridine-3-carboxylate A suspension of tert-butyl N-[4-chloro-6-(5-chloro-2-fluoro-phenyl)-3-isopropenyl-2-pyridyl]carbamate (3.2 g, 0.0062 mol), methyl 4-aminopyridine-3-carboxylate (1.137 g, 0.0074 mol) and potassium phosphate tribasic (2.64 g, 0.01247 mol) in dioxane (40 mL) was purged with nitrogen for 45 min. To this reaction mixture was added Xantphos (0.721 g, 0.001247 mol) and Pd$_2$(dba)$_3$ (0.856 g, 0.00093 mol) and purging continued with nitrogen for 10 min. The resulting mixture was heated at 100° C. for 18 h. The progress of reaction was monitored by TLC and LCMS. After completion of reaction, the mixture was filtered through a celite bed. The filtrate was concentrated under reduced pressure to obtain oily crude compound that was purified by column chromatography on silica gel (100:200 mesh) using 25-30% EtOAc-hexane system as eluent to afford methyl 4-[[2-(tert-butoxycarbonylamino)-6-(5-chloro-2-fluoro-phenyl)-3-isopropenyl-4-pyridyl]amino] pyridine-3-carboxylate (0.84 g) pure compound as a yellow solid.

Step 8: Synthesis of 4-[[2-(tert-butoxycarbonylamino)-6-(5-chloro-2-fluoro-phenyl)-3-isopropenyl-4-pyridyl]amino]pyridine-3-carboxylic acid To a suspension of methyl 4-[[2-(tert-butoxycarbonylamino)-6-(5-chloro-2-fluoro-phenyl)-3-isopropenyl-4-pyridyl]amino]pyridine-3-carboxylate (500 mg, 0.814 mmol) in MeOH (10 mL) was added NaOH (52 mg, 1.3 mmol) in water (1 mL) and heated at 80° C. for 2 h. The progress of reaction was monitored by TLC. After completion of reaction, the mixture was concentrated under reduced pressure to obtain a sticky compound. To this was added toluene (3×10 mL) to obtain a solid compound which was triturated with diethyl ether (10 mL) to afford 4-[[2-(tert-butoxycarbonylamino)-6-(5-chloro-2-fluoro-phenyl)-3-isopropenyl-4-pyridyl]amino] pyridine-3-carboxylic acid (500 mg) as a light yellow solid.

Step 9: Synthesis of afforded 4-[[2-amino-6-(5-chloro-2-fluoro-phenyl)-3-isopropenyl-4-pyridyl]amino]pyridine-3-carboxylic acid To a suspension of 4-[[2-(tert-butoxycarbonylamino)-6-(5-chloro-2-fluoro-phenyl)-3-isopropenyl-4-pyridyl]amino] pyridine-3-carboxylic acid (100 mg, 0.16 mmol) in 10:1 mixture of DCM:DMF (10 mL) was added TFA (1 mL) and stirred for 2 h. The progress of reaction was monitored by TLC and LCMS. After completion of reaction, the mixture was concentrated under reduced pressure to obtain the crude product. The crude product was triturated with diethylether and dried in vacuo to afford 4-[[2-amino-6-(5-chloro-2-fluoro-phenyl)-3-isopropenyl-4-pyridyl]amino]pyridine-3-carboxylic acid (80 mg).

Step 10: Synthesis of 4-[[2-amino-6-(5-chloro-2-fluoro-phenyl)-3-isopropenyl-4-pyridyl]amino]-N-[(2S)-2-hydroxypropyl]pyridine-3-carboxamide To a stirred solution of 4-[[2-amino-6-(5-chloro-2-fluoro-phenyl)-3-isopropenyl-4-pyridyl]amino]pyridine-3-carboxylic acid (80 mg, 0.127 mmol) in DMF (4 mL) added N,N-diisopropylethyl amine (0.09 mL, 0.51 mmol) and HATU (78 mg, 0.204 mmol) and stirred for 15 min at RT under nitrogen atmosphere. To this reaction mixture was added (S)-1-aminopropan-2-ol (24 mg, 0.318 mmol) and the reaction mixture was stirred at RT for 4 h. The progress of reaction was monitored by TLC and LCMS. After completion of reaction, the mixture was diluted with water and extracted with EtOAc. The organic layer was washed with brine and water, dried over anhydrous sodium sulfate and concentrated under reduced pressure to obtain the crude product. The crude product was purified by reverse phase HPLC to afford 4-[[2-amino-6-(5-chloro-2-fluoro-phenyl)-3-isopropenyl-4-pyridyl]amino]-N-[(2S)-2-hydroxypropyl] pyridine-3-carboxamide (6.5 mg) as a white solid. The (R) enantiomer can be synthesized utilizing (R)-1-aminopropan-2-ol in this step.

NMR: $^1$H NMR (400 MHz, CDCl$_3$) δ (ppm): 10.12 (s, 1H), 8.73 (s, 1H), 8.34 (s, 1H), 7.97 (dd, J=6.7, 2.8 Hz, 1H), 7.36 (s, 1H), 7.33-7.22 (m, 2H), 7.06 (dd, J=10.6, 8.7 Hz, 1H), 6.96 (s, 1H), 5.64 (d, J=2.2 Hz, 1H), 5.22 (s, 1H), 4.69

(s, 2H), 4.06 (m, 1H), 3.67 (d, J=13.8 Hz, 1H), 3.34-3.24 (m, 1H), 2.05 (s, 3H), 1.27 (t, J=6.2 Hz, 3H).

Example 24. Preparation of Compound Nos. 24, 24a and 24b

Synthesis of 4-[[2-(5-chloro-2-fluoro-phenyl)-5-isopropenyl-4-pyridyl]amino]-N-[(1S)-1-(hydroxymethyl)propyl]pyridine-3-carboxamide

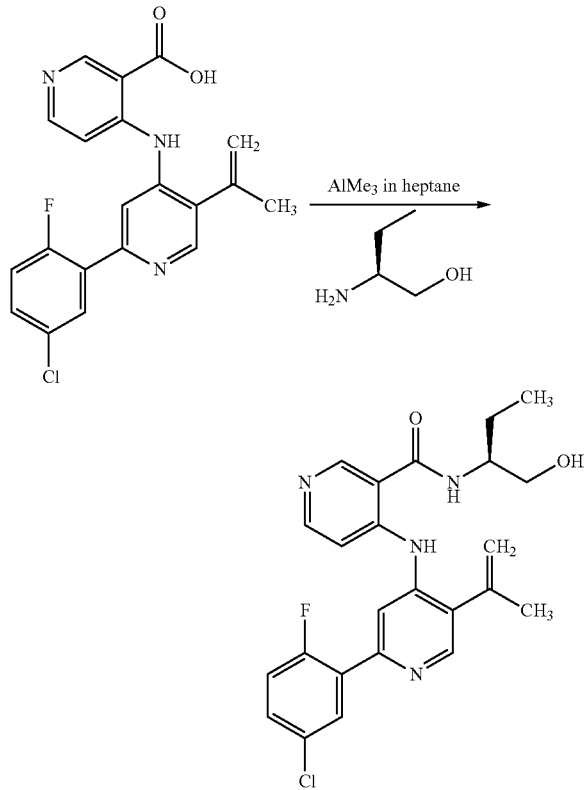

To a solution of methyl 4-[[2-(5-chloro-2-fluoro-phenyl)-5-isopropenyl-4-pyridyl]amino]pyridine-3-carboxylate (100 mg, 0.25 mmol) and (2S)-2-aminobutan-1-ol (45 mg, 0.5 mmol) in toluene (5 mL) was added a 1 M solution of trimethylaluminium) in heptane (1 mL, 1.005 mmol) and heated at 120° C. for 4 h. The progress of reaction was monitored by TLC and LCMS. After completion of reaction, the mixture was cooled to RT and diluted with water and EtOAc. The organic layer was washed with water and brine solution, dried over anhydrous sodium sulfate and concentrated under reduced pressure to obtain the crude product. The crude product was purified by CombiFlash® chromatography to afford a residue which was triturated with n-pentane and dried under vacuum to afford 4-[[2-(5-chloro-2-fluoro-phenyl)-5-isopropenyl-4-pyridyl]amino]-N-[(1S)-1-(hydroxymethyl)propyl]pyridine-3-carboxamide (43 mg). The (R) enantiomer can be synthesized utilizing (2R)-2-aminobutan-1-ol in this step.

NMR: $^1$H NMR (400 MHz, DMSO-d6) (ppm): 10.42 (s, 1H), 8.81 (s, 1H), 8.46 (d, J=9.3 Hz, 2H), 8.39 (d, J=5.8 Hz, 1H), 7.99 (dd, J=6.7, 2.8 Hz, 1H), 7.84 (s, 1H), 7.60-7.49 (m, 1H), 7.41 (dd, J=11.9, 7.4 Hz, 2H), 5.48 (s, 1H), 5.20 (s, 1H), 4.70 (t, J=5.8 Hz, 1H), 3.88 (td, J=8.6, 4.5 Hz, 1H), 3.43 (m, 2H), 2.09 (s, 3H), 1.65 (m, 1H), 1.53-1.37 (m, 1H), 0.88 (t, J=7.5 Hz, 3H).

Example 25a. Preparation of Compound No. 25a

Synthesis of 4-[[2-(5-chloro-2-fluoro-phenyl)-5-vinyl-4-pyridyl]amino]-N-[(1R)-1-(hydroxy methyl)-2-methyl-propyl]pyridine-3-carboxamide

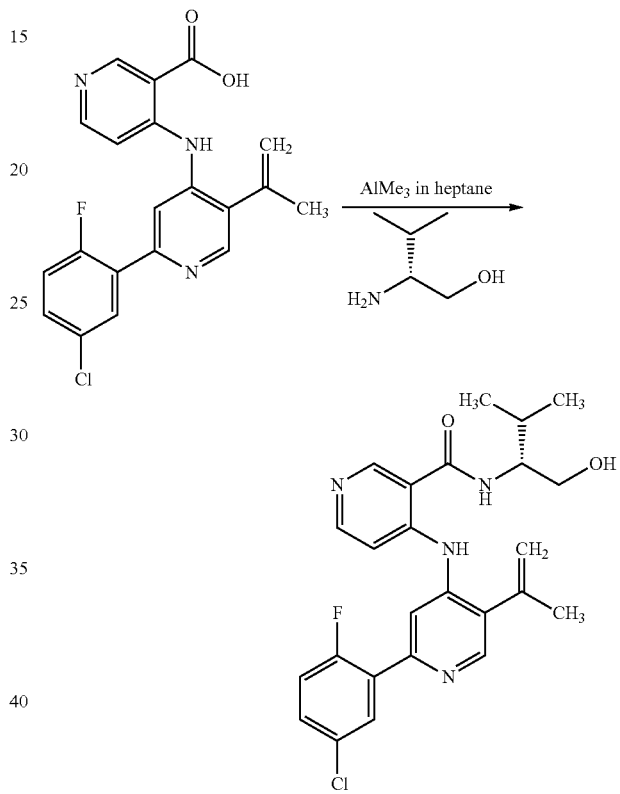

To a solution of methyl 4-[[2-(5-chloro-2-fluoro-phenyl)-5-isopropenyl-4-pyridyl]amino]pyridine-3-carboxylate (100 mg, 0.25 mmol) and ((2R)-2-amino-3-methyl-butan-1-ol (52 mg, 0.502 mmol) in toluene (5 mL) was added a 1 M solution of trimethylaluminium in heptane (1 mL, 1.005 mmol) and heated at 120° C. for 4 h. The progress of reaction was monitored by TLC and LCMS. After completion of reaction, the mixture was cooled to RT and diluted with water and EtOAc. The organic layer was washed with water and brine solution, dried over anhydrous sodium sulfate and concentrated under reduced pressure to obtain the crude product. The crude product was purified by reverse phase HPLC to afford 4-[[2-(5-chloro-2-fluoro-phenyl)-5-vinyl-4-pyridyl]amino]-N-[(1R)-1-(hydroxymethyl)-2-methyl-propyl]pyridine-3-carboxamide (13.8 mg).

NMR: $^1$H NMR (400) MHz, CDCl$_3$) δ (ppm): 10.13 (s, 1H), 8.68 (s, 1H), 8.50 (s, 1H), 8.39 (d, J=5.9 Hz, 1H), 8.02 (dd, J=6.8, 2.7 Hz, 1H), 7.84-7.78 (m, 1H), 7.41-7.21 (m, 2H), 7.10 (dd, J=10.7, 8.7 Hz, 1H), 6.57 (d, J=8.8 Hz, 1H), 5.47 (s, 1H), 5.21 (s, 1H), 3.96 (m, 1H), 3.82 (d, J=4.3 Hz, 2H), 2.15-1.97 (m, 4H), 1.04 (t, J=6.9 Hz, 6H).

Example 25b. Preparation of Compound No. 25b

Synthesis of 4-[[2-(5-chloro-2-fluoro-phenyl)-5-vinyl-4-pyridyl]amino]-N-[(1S)-1-(hydroxy methyl)-2-methyl-propyl]pyridine-3-carboxamide

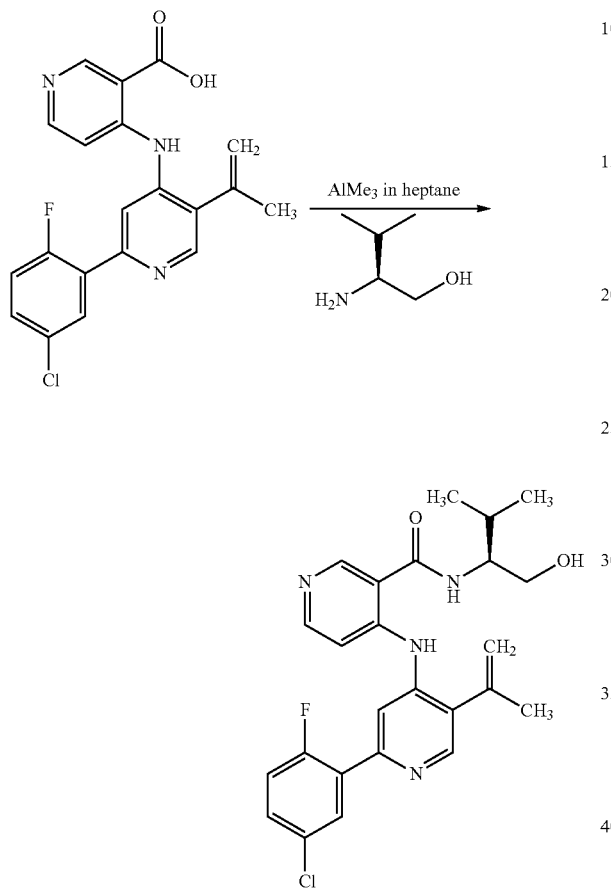

To a solution of methyl 4-[[2-(5-chloro-2-fluoro-phenyl)-5-isopropenyl-4-pyridyl]amino]pyridine-3-carboxylate (100 mg, 0.25 mmol) and ((2R)-2-amino-3-methyl-butan-1-ol (52 mg, 0.502 mmol) in toluene (5 mL) was added a 1 M solution of trimethylaluminium in heptane (1 mL, 1.005 mmol) and heated at 120° C. for 4 h. The progress of reaction was monitored by TLC and LCMS. After completion of reaction, the mixture was cooled to RT and diluted with water and EtOAc. The organic layer was separated, washed with water and brine solution, dried over anhydrous sodium sulfate and concentrated under reduced pressure to obtain the crude product. The crude product was purified by reverse phase HPLC to afford 4-[[2-(5-chloro-2-fluoro-phenyl)-5-vinyl-4-pyridyl]amino]-N-[(1S)-1-(hydroxymethyl)-2-methyl-propyl]pyridine-3-carboxamide (14.58 mg).

NMR: $^1$H NMR (400 MHz, CDCl$_3$) δ (ppm): 10.13 (s, 1H), 8.68 (s, 1H), 8.50 (s, 1H), 8.40 (d, J=5.9 Hz, 1H), 8.02 (dd, J=6.8, 2.7 Hz, 1H), 7.81 (d, J=1.7 Hz, 1H), 7.41-7.27 (m, 2H), 7.10 (dd, J=10.7, 8.7 Hz, 1H), 6.57 (d, J=8.7 Hz, 1H), 5.47 (s, 1H), 5.21 (s, 1H), 3.97 (m, 1H), 3.82 (d, J=4.3 Hz, 2H), 2.15-1.97 (m, 4H), 1.04 (t, J=6.9 Hz 6H). Example 26.

Preparation of Compound No. 26

Synthesis of 4-[[2-(5-chloro-2-fluoro-phenyl)-5-isopropenyl-4-pyridyl]amino]-N-(2-hydroxy ethyl) pyridine-3-carboxamide

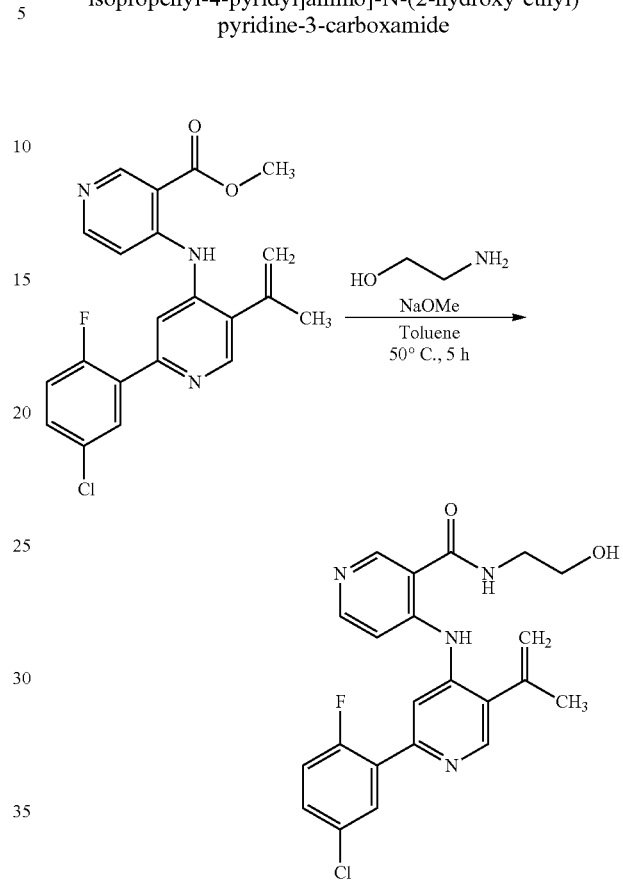

Steps 1 to 4 are the same as in Example 2

Step 5: Synthesis of 4-[[2-(5-chloro-2-fluoro-phenyl)-5-isopropenyl-4-pyridyl]amino]-N-(2-hydroxyethyl)pyridine-3-carboxamide To 2-aminoethanol (30 mg, 0.5 mmol) in toluene (4 mL) was added sodium methoxide (13 mg, 0.25 mmol). The reaction mixture was stirred at RT for 5 min. Then, to this reaction mixture was added methyl 4-[[2-(5-chloro-2-fluoro-phenyl)-5-isopropenyl-4-pyridyl]amino]pyridine-3-carboxylate (100 mg, 0.25 mmol) and the reaction mixture was heated at 50° C. for 5 h. The progress of reaction was monitored by LCMS. After completion of the reaction, the mixture was quenched with ice-cold water (15 mL) and the product was extracted with EtOAc (2×250 mL). The combined organic layer was washed with brine (50 mL), dried over sodium sulfate and concentrated under reduced pressure to give a crude product. The crude product was purified by preparative HPLC to afford 4-[[2-(5-chloro-2-fluoro-phenyl)-5-isopropenyl-4-pyridyl]amino]-N-(2-hydroxy ethyl)pyridine-3-carboxamide (29.28 mg) as the TFA salt.

NMR: $^1$H NMR (400 MHz, CD$_3$OD) δ (ppm): 8.88 (s, 1H), 8.68 (s, 1H), 8.36 (d, J=7.2 Hz, 1H), 8.02-7.91 (m, 2H), 7.56-7.44 (m, 2H), 7.29 (dd, J=10.7, 8.8 Hz, 1H), 5.53-5.45 (m, 1H), 5.29 (s, 1H), 3.75 (t, J=5.6 Hz, 2H), 3.55 (t, J=5.5 Hz, 2H), 2.13 (s, 3H) LCMS: 425.4 (m−1).

Example 27. Preparation of Compound No. 27

Synthesis of 4-[[2-(5-chloro-2-fluoro-phenyl)-5-isopropenyl-4-pyridyl]amino]-N-cyclopropyl-pyridine-3-carboxamide

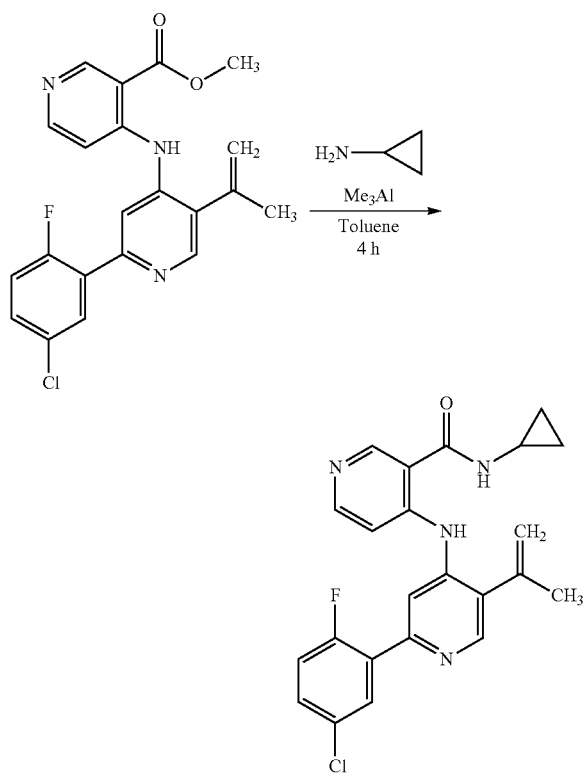

Steps 1 to 4 are the same as in Example 2

Step 5: Synthesis of 4-[[2-(5-chloro-2-fluoro-phenyl)-5-isopropenyl-4-pyridyl]amino]-N-cyclopropyl-pyridine-3-carboxamide To methyl 4-[[2-(5-chloro-2-fluoro-phenyl)-5-isopropenyl-4-pyridyl]amino]pyridine-3-carboxylate (100 mg, 0.25 mmol) and cyclopropanamine (28 mg, 0.5 mmol) in toluene (4 mL) was added Me$_3$Al (1.0 mL, 1.00 mmol) and the reaction was heated at 140° C. for 4 h. The progress of reaction was monitored by LCMS. After completion of reaction, the mixture was quenched with a saturated aqueous solution of NaHCO$_3$ (20 mL) and the product was extracted with EtOAc (2×70 mL). The combined organic layer was washed with brine (30 mL), dried over sodium sulfate and concentrated under reduced pressure to give a crude product. The crude compound was purified by preparative HPLC to afford 4-[[2-(5-chloro-2-fluoro-phenyl)-5-isopropenyl-4-pyridyl]amino]-N-cyclopropyl-pyridine-3-carboxamide (34.85 mg).

NMR: $^1$H NMR (400 MHz, CD$_3$OD) δ (ppm): 8.79 (s, 1H), 8.68 (s, 1H), 8.34 (d, J=7.2 Hz, 1H), 7.99 (dd, J=6.7, 2.8 Hz, 1H), 7.92 (s, 1H), 7.56-7.36 (m, 2H), 7.29 (dd, J=10.8, 8.8 Hz, 1H), 5.54-5.48 (m, 1H), 5.29 (s, 1H), 2.92 (tt, J=7.4, 3.9 Hz, 1H), 2.14 (s, 3H), 0.86 (m, 2H), 0.80-0.65 (m, 2H). LCMS: 423.4 (M+1).

Example 28. Preparation of Compound Nos. 28, 28a and 28b

Synthesis of N-[(2S)-2-hydroxy propyl]-4-{[2-phenyl-5-(propan-2-yl)pyridin-4-yl]amino}pyridine-3-carboxamide

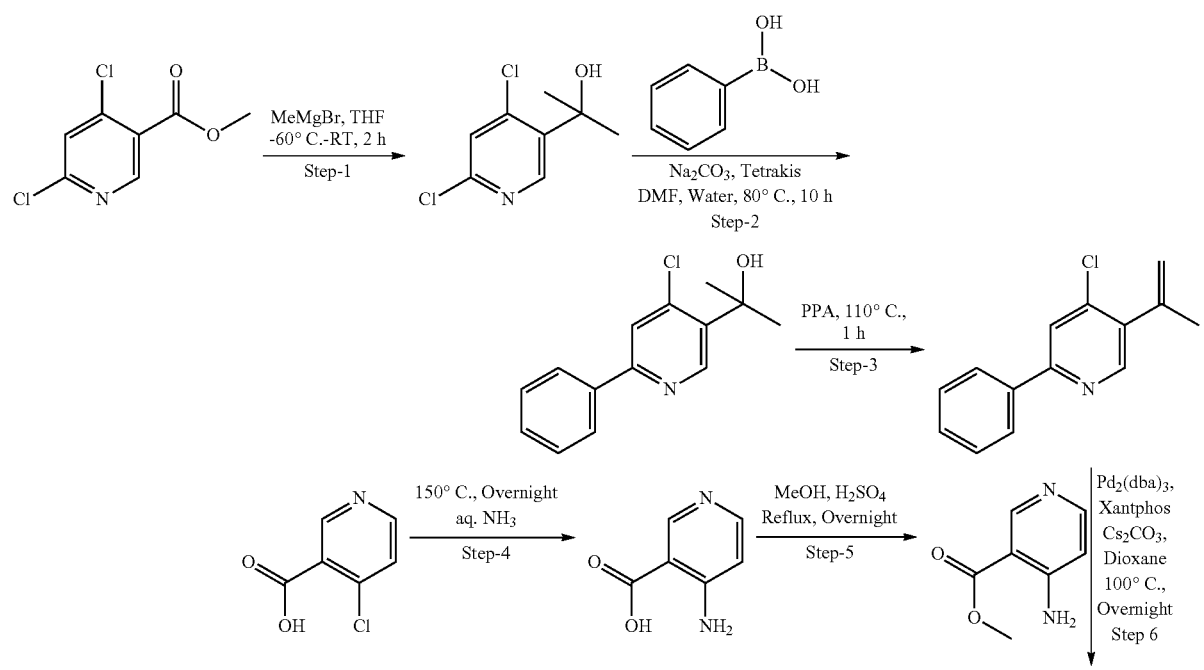

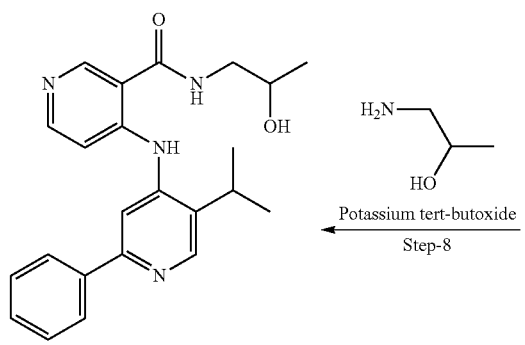
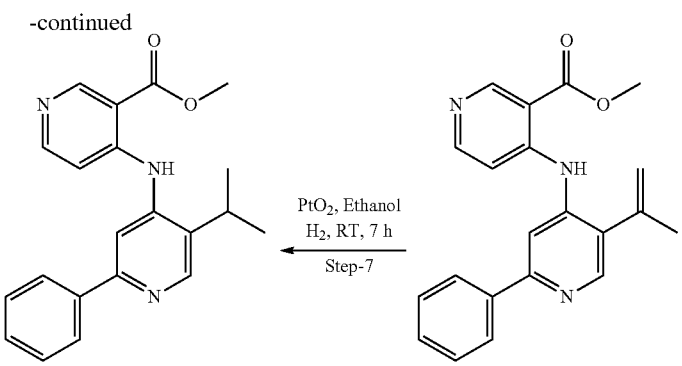

Step 1: Synthesis of 2-(4,6-dichloro-3-pyridyl)propan-2-ol

To a solution of methyl 4,6-dichloropyridine-3-carboxylate (5 g, 0.0243 mol) in dry THF (60 mL) was added MeMgBr (3 M in THF, 28.3 mL) dropwise at −60° C. under nitrogen atmosphere. The resultant reaction mixture was allowed to warm to RT and stirred for 2 h. The progress of reaction was monitored over TLC. After completion of reaction, the reaction mixture was cooled to 0° C. and quenched with saturated aqueous solution of ammonium chloride solution (200 mL) and extracted with EtOAc (2×300 mL). The combined organic layer was dried over anhydrous sodium sulfate and concentrated under reduced pressure to afford 2-(4,6-dichloro-3-pyridyl)propan-2-ol (4.91 g) as a yellow liquid.

Step 2: Synthesis of 2-(4-chloro-6-phenyl-3-pyridyl)propan-2-ol

To a solution of methyl 2-(4,6-dichloro-3-pyridyl)propan-2-ol (1.5 g, 7.279 mmol), phenylboronic acid (1.150 g, 9.431 mmol) in DMF (24 mL) was added a solution of $Na_2CO_3$ (1.54 g, 14.529 mmol) in water (12 mL). The resultant reaction mixture was purged with nitrogen for 30 min, followed by addition of tetrakis (673 mg, 0.582 mmol). The reaction mixture was again purged for 10 min and heated at 80° C. for 10 h. The progress of reaction was monitored over TLC & LCMS. After completion of reaction, the reaction mixture was diluted with water (300 mL) and extracted with EtOAc (2×300) mL), dried over anhydrous sodium sulfate and concentrated under reduced pressure to afford a crude product, which was purified by column chromatography on silica gel (100-200 mesh) using 110/EtOAc-hexane as eluent to obtain 2-(4-chloro-6-phenyl-3-pyridyl)propan-2-ol (3.2 g) as an off white semi-solid.

Step 3: Synthesis of 4-chloro-5-isopropenyl-2-phenyl-pyridine

A mixture of 2-(4-chloro-6-phenyl-3-pyridyl)propan-2-ol (100 mg, 0.403 mmol) and poly phosphoric acid (PPA, 1 g) was heated at 110° C. for 1 h. The progress of reaction was monitored by TLC. After the completion of reaction, the reaction mixture was basified with aqueous KOH solution and extracted with EtOAc (2×20 mL). The combined organic layer was dried over anhydrous sodium sulfate and concentrated under reduced pressure to afford 4-chloro-5-isopropenyl-2-phenyl-pyridine (75 mg) as an off white sticky solid.

Step 4: Synthesis of 4-aminopyridine-3-carboxylic acid

A solution of 4-chloropyridine-3-carboxylic acid (15 g, 0.095 mol) in aqueous $NH_3$ (600 mL) was heated in a pressure vessel at 150° C. overnight. The progress of reaction was monitored by TLC. After completion of the reaction, the reaction mixture was concentrated under reduced pressure. To this concentrated reaction mixture was added toluene to (2×100 mL) to obtain 4-aminopyridine-3-carboxylic acid (17 g) as a white solid.

Step 5: Synthesis of methyl 4-aminopyridine-3-carboxylate

To a solution 4-aminopyridine-3-carboxylic acid (17 g, 0.123 mol) in methanol (300 mL) was added sulfuric acid (45 mL) dropwise at 0° C. The resultant reaction mixture was heated to reflux at 85° C. overnight. The progress of reaction was monitored by TLC. After the completion of the reaction, the reaction mixture was concentrated under reduced pressure to remove methanol, the residue was basified with saturated aqueous solution of sodium carbonate (400 mL), and extracted with EtOAc (3×500 mL). The combined organic layer was dried over anhydrous sodium sulfate and concentrated under reduced pressure to afford of methyl 4-aminopyridine-3-carboxylate (10.3 g) as a white solid.

Step 6: Synthesis of methyl 4-[(5-isopropenyl-2-phenyl-4-pyridyl)amino]pyridine-3-carboxylate A mixture of 4-chloro-5-isopropenyl-2-phenyl-pyridine (1.2 g, 5.24 mmol), methyl 4-aminopyridine-3-carboxylate (795 mg, 5.225 mmol) and Cs2CO3 (3.40 g, 10.435 mmol) in dioxane (30 mL) was purged with nitrogen for 30 min, followed by addition of $Pd_2(dba)_3$ (478 mg, 0.521 mmol) and xantphos (604 mg, 1.043 mmol) and again purged with nitrogen for 5 min. The reaction mixture was heated at 100° C. overnight. The progress of reaction was monitored over LCMS. After completion of the reaction, the reaction mixture was diluted with water (100 mL) and extracted with EtOAc (2×150 mL). The combined organic layer was dried over anhydrous sodium sulfate and concentrated under reduced pressure to afford a crude product, which was purified by column chromatography on silica gel (100-200 mesh) using 20% EtOAc-hexane as eluent to obtain methyl 4-[(5-isopropenyl-2-phenyl-4-pyridyl)amino]pyridine-3-carboxylate (500 mg) as a yellow sticky semi-solid.

Step 7: Synthesis of methyl 4-[(5-isopropyl-2-phenyl-4-pyridyl)amino]pyridine-3-carboxylate To a solution of methyl 4-[(5-isopropenyl-2-phenyl-4-pyridyl)amino]pyridine-3-carboxylate (1 g, 2.895 mmol) in ethanol (30 mL) was added PtO$_2$ (225 mg). The resultant reaction mixture was allowed to stir at RT under hydrogen atmosphere (using a hydrogen bladder) for 7 h. The progress of reaction was monitored over $^1$HNMR. After completion of reaction, the reaction mixture was filtered through a celite bed. The organic layer was concentrated under reduced pressure to afford methyl 4-[(5-isopropyl-2-phenyl-4-pyridyl)amino]pyridine-3-carboxylate (890 mg) as a brown semi-solid.

Step 8: Synthesis of N-(2-hydroxypropyl)-4-[(5-isopropyl-2-phenyl-4-pyridyl)amino]pyridine-3-carboxamide A solution of (S)-1-aminopropan-2-ol (162 mg, 2.156 mmol) and (155 mg, 1.381 mmol) in DCM (8 mL) was allowed to stir at RT for 30 min. To this reaction mixture was added a solution of methyl 4-[(5-isopropyl-2-phenyl-4-pyridyl)amino]pyridine-3-carboxylate (300 mg, 0.863 mmol) in DCM (2 mL). The reaction mixture was heated at 50° C. for 90 min. The progress of reaction was monitored over LCMS. After completion of the reaction, the reaction mixture was diluted with water (50 mL) and extracted with EtOAc (2×100 mL). The organic layer was dried over anhydrous sodium sulfate and concentrated under reduced pressure to afford a crude product, which was purified by reverse phase preparative HPLC to obtain N-(2-hydroxypropyl)-4-[(5-isopropyl-2-phenyl-4-pyridyl)amino]pyridine-3-carboxamide (57 mg) as a white solid. The (R) enantiomer can be synthesized utilizing (R)-1-aminopropan-2-ol in this step.

$^1$H NMR: (400 MHz, DMSO-d6) δ (ppm): 10.59 (s, 1H), 8.84 (m, 2H), 8.59 (s, 1H), 8.34 (d, J=5.9 Hz, 1H), 8.13-7.87 (m, 2H), 7.81 (s, 1H), 7.45 (m, 2H), 7.33-7.15 (m, 1H), 3.82 (h, J=6.2 Hz, 1H), 3.11 (m, 3H), 1.31 (d, J=6.8 Hz, 6H), 1.09 (d, J=6.2 Hz, 3H).

Example 29. Preparation of Compound No. 29

Synthesis of 2-(3-fluoropyridin-2-yl)-5-(propan-2-yl)-N-{1H-pyrrolo[2,3-b]pyridin-4-yl}pyridin-4-amine

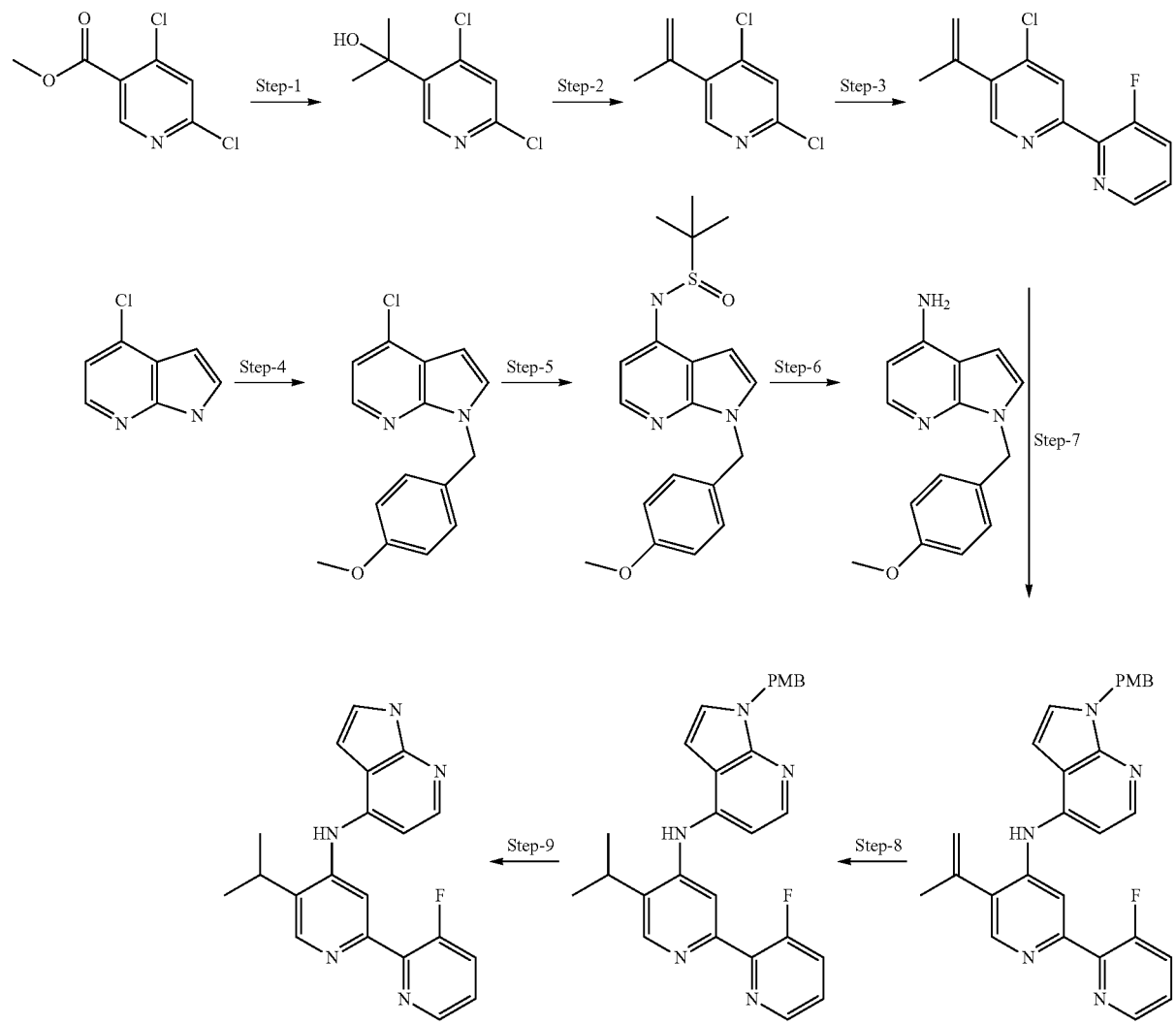

Step-1: Synthesis of 2-(4, 6-dichloro-3-pyridyl)propan-2-ol

To a solution of methyl 4,6-dichloropyridine-3-carboxylate (5 g, 0.0243 mol) in dry THF (60 mL) was added 3M solution of methyl magnesium bromide in diethyl ether (28.3 mL, 0.0848 mol) dropwise under nitrogen atmosphere at −60° C. The resultant mixture was stirred at −60° C. to 0° C. for 2 h. The reaction was monitored by TLC & NMR. After completion of reaction, the reaction mixture was quenched using aq. saturated ammonium chloride solution and extracted with EtOAc. The organic layer washed with water and brine solution, dried over anhydrous sodium sulfate and concentrated under reduced pressure afforded 2-(4,6-dichloro-3-pyridyl)propan-2-ol (4.96 g) as a yellow oil.

Step-2: Synthesis of 2,4-dichloro-5-isopropenyl-pyridine

To 2-(4,6-dichloro-3-pyridyl)propan-2-ol (200 mg, 0.97 mmol) was added PPA (2 g) and heated at 120° C. for 90 min. The reaction was monitored by TLC & LCMS. After completion of reaction, the reaction mixture was cooled to RT, basified with a saturated solution of NaOH solution up to pH 12-14 and extracted with EtOAc (2×50 mL). The organic layer washed with water (100 mL) and brine, dried over anhydrous sodium sulfate and concentrated under reduced pressure to obtain the crude compound which was purified by column chromatography using silica 100:200 mesh and eluent 1% EtOAc in Hexane to afford 2,4-dichloro-5-isopropenyl-pyridine (150 mg).

Step-3: Synthesis of 4-chloro-2-(3-fluoro-2-pyridyl)-5-isopropenyl-pyridine 2,4-Dichloro-5-isopropenyl-pyridine (900 mg, 4.787 mmol) and (3-fluoro-2-pyridyl) boronic acid (1.011 g, 7.180 mmol) were dissolved in DMF (15 mL). To the stirred solution were added $CsCO_3$ (3.12 g, 9.574 mmol). CuCl (236 mg, 2.393 mmol) and Pd(dppf) (26.87 mg, 0.1196 mmol) slowly at RT for 5 min. Then $Pd(OAc)_2$ (132.6 mg, 0.239 mmol) was added and the resultant reaction mixture was kept at 100° C. overnight. The progress of the reaction was monitored by LCMS. On completion of reaction, the reaction mixture was diluted with water (150 mL) and the reaction mixture was extracted with EtOAc (2×200 mL). The combined organic layer was washed with water (2×100 mL), brine solution (200 mL), dried over anhydrous sodium sulfate and concentrated under reduced pressure to obtain the crude compound, which was further purified by column chromatography using silica gel 100:200 mesh, compound eluting with 40% EtOAc:hexane to give pure 4-chloro-2-(3-fluoro-2-pyridyl)-5-isopropenyl-pyridine (700 mg).

Step-4: Synthesis of 4-chloro-1-[(4-methoxyphenyl)methyl]pyrrolo[2,3-b]pyridine To a solution of 4-chloro-1H-pyrrolo[2,3-b]pyridine (7 g, 0.026 mmol) in DMF (5 mL) was added sodium hydride (55-60%) (1.56 g, 0.039 mmol) portionwise at 0° C. The reaction mixture was stirred at 0° C. to 10° C. for 30 min, followed by the slow addition of Para-methoxybenzyl chloride (5.319g, 0.0338 mmol) in DMF (5 mL). The reaction mixture was allowed to stir at 0° C. to 10° C. for 2 h. The reaction was monitored by TLC and LCMS. After completion of reaction, ice cold water (100 mL) was added to the reaction mixture and product was extracted with EtOAc (2×200 mL). The combined organic layer was again washed with water (3×100 mL) and finally with brine solution (2×75 mL). The organic layer was separated, dried over anhydrous sodium sulfate and concentrated under reduced pressure to afford a crude product which was purified by column chromatography with silica gel 100:200 mesh in EtOAc:hexane product elutes at 5% to give 4-chloro-1-[(4-methoxyphenyl)methyl]pyrrolo[2,3-b]pyridine as an off-white solid (7 g).

Step 5: Synthesis of N-[1-[(4-methoxyphenyl)methyl]pyrrolo[2,3-b]pyridin-4-yl]-2-methyl-propane-2-sulfinamide To a solution of 4-chloro-1-[(4-methoxyphenyl)methyl] pyrrolo[2,3-b]pyridine (5g, 0.0183 mmol) was added cesium carbonate (2.66g, 0.0219 mmol) in dioxane (40 mL) then purged with nitrogen for 5 min. To this was added xantphos (0.634 g, 0.0010 mmol) and palladium acetate (12 mg, 0.0005 mmol). The reaction mixture was heated in a reagent bottle at 100° C. overnight. The reaction was monitored by TLC and LCMS. After completion of reaction, the reaction mixture was filtered through celite, the celite bed was washed with EtOAc (2×100 mL). The filtrate obtained was concentrated under reduced pressure. The crude product obtained was purified by column chromatography on silica gel 100:200 mesh. The product elutes at 20% EtOAc: Hexane to give N-[1-[(4-methoxyphenyl)methyl]pyrrolo[2, 3-b]pyridin-4-yl]-2-methyl-propane-2-sulfinamide (2 g).

Step-6: Synthesis of 1-[(4-methoxyphenyl)methyl] pyrrolo[2,3-b]pyridin-4-amine To a solution of N-[1-[(4-methoxyphenyl)methyl]pyrrolo[2,3-b]pyridin-4-yl]-2-methyl-was added 4M HCl in dioxane (15 mL) dropwise at 0° C. under nitrogen atmosphere. The reaction mixture was kept at RT for 1 h. The reaction was monitored by TLC and LCMS. After completion of reaction, the reaction mixture was neutralized by $NaHCO_3$ to pH 6-7. Then the product was extracted with EtOAc (2×100 mL). The combined organic layer was again washed with water (100 mL) and finally with brine solution (2×75 mL). The organic layer was separated, dried over anhydrous sodium sulfate and concentrated under reduced pressure to afford crude 1-[(4-methoxyphenyl)methyl]pyrrolo[2,3-b]pyridin-4-amine (2.5 g).

Step-7: Synthesis of N-[2-(3-fluoro-2-pyridyl)-5-isopropenyl-4-pyridyl]-1-[(4-methoxyphenyl)methyl]pyrrolo[2,3-b]pyridin-4-amine A suspension of 1-[(4-methoxyphenyl) methyl]pyrrolo[2, 3-b]pyridin-4-amine (430 mg, 1.699 mmol), 4-chloro-2-(3-fluoro-2-pyridyl)-5-isopropenyl-pyridine (424 mg, 1.699 mmol) and cesium carbonate (1.104 g, 3.398 mmol) in dioxane (15 mL) was purged for 20 min and xantphos (147.303 mg: 0.2548 moles), Pd$_2$(dba)$_3$ (311.18 mg, 0.339 mmol) were added and the mixture purged for 5 min. The reaction mixture was heated in a reagent bottle at 100° C. overnight. The reaction was monitored by TLC and LCMS. After completion of reaction mixture was filtered through celite, the celite bed was washed with EtOAc (2×100 mL). The filtrate obtained was concentrated under reduced pressure. The crude product was purified by column chromatography on silica gel 100:200 mesh. The product elutes at 55% EtOAc:hexane to give N-[2-(3-fluoro-2-pyridyl)-5-isopropenyl-4-pyridyl]-1-[(4-methoxyphenyl) methyl]pyrrolo[2,3-b]pyridin-4-amine (490 mg).

Step-8: Synthesis of N-[2-(3-fluoro-2-pyridyl)-5-isopropyl-4-pyridyl]-1-[(4-methoxyphenyl) methyl]pyrrolo[2,3-b]pyridin-4-amine To a stirred solution of N-[2-(3-fluoro-2-pyridyl)-5-isopropenyl-4-pyridyl]-1-[(4-methoxyphenyl)methyl]pyrrolo[2,3-b]pyridin-4-amine (480 mg, 0.953 mmol) in ethanol (5 mL) and EtOAc (0.4 mL), PtO$_2$ (100 mg) was added at RT under H$_2$ atmosphere using a hydrogen bladder. The reaction was kept on continuous stirring overnight. Completion of reaction was monitored by LCMS and NMR. On completion of reaction, the reaction mixture was filtered through a celite bed. The filtrate obtained was concentrated under reduced pressure to obtain N-[2-(3-fluoro-2-pyridyl)-5-isopropyl-4-pyridyl]-1-[(4-methoxyphenyl)methyl]pyrrolo [2,3-b]pyridin-4-amine was obtained (450 mg).

Step-9: Synthesis of N-[2-(3-fluoro-2-pyridyl)-5-isopropyl-4-pyridyl]-1H-pyrrolo[2,3-b]pyridin-4-amine N-[2-(3-Fluoro-2-pyridyl)-5-isopropyl-4-pyridyl]-1-[(4-methoxyphenyl)methyl]pyrrolo [2,3-b]pyridin-4-amine (450 mg, 0.963 mmol) in TFA (8 mL) was added triflic acid (3 mL) and the reaction was heated at 60° C. for 1 h. Completion of reaction was monitored by TLC and LCMS. On completion of reaction, the reaction mixture was concentrated under reduced pressure to obtain an oily compound which was neutralized by aq. saturated NaHCO$_3$ and extracted with EtOAc (2×100 mL). The organic layer was again washed with brine, dried over anhydrous sodium sulfate and concentrated under reduced pressure to afford a crude product which was purified by reverse phase HPLC to obtain N-[2-(3-fluoro-2-pyridyl)-5-isopropyl-4-pyridyl]-1H-pyrrolo[2,3-b]pyridin-4-amine (95 mg) as an off-white solid. This was dissolved in ethanolic HCl (10 mL) and concentrated under reduced pressure to give N-[2-(3-fluoro-2-pyridyl)-5-isopropyl-4-pyridyl]-1H-pyrrolo[2,3-b]pyridin-4-amine hydrochloride salt (96 mg) as an off-white solid.

$^1$H NMR: (400 MHz, Methanol-d4) δ (ppm): 8.96 (s, 1H), 8.84 (s, 1H), 8.77 (d, J=5.3 Hz, 1H), 8.29 (d, J=6.7 Hz, 1H), 8.20 (t, J=6.1 Hz, 1H), 7.96 (s, 1H), 7.57 (d, J=3.5 Hz, 1H), 7.27 (d, J=6.7 Hz, 1H), 6.76 (d, J=3.7 Hz, 1H), 3.56 (h, J=6.8 Hz, 1H), 1.46 (d, J=6.8 Hz, 6H). LCMS: 348 (M+1).

Example 30. Preparation of Compound No. 30

Synthesis of 2-(3-fluoropyridin-2-yl)-5-(propan-2-yl)-N-{7H-pyrrolo[2,3-d]pyrimidin-4-yl}pyridin-4-amine

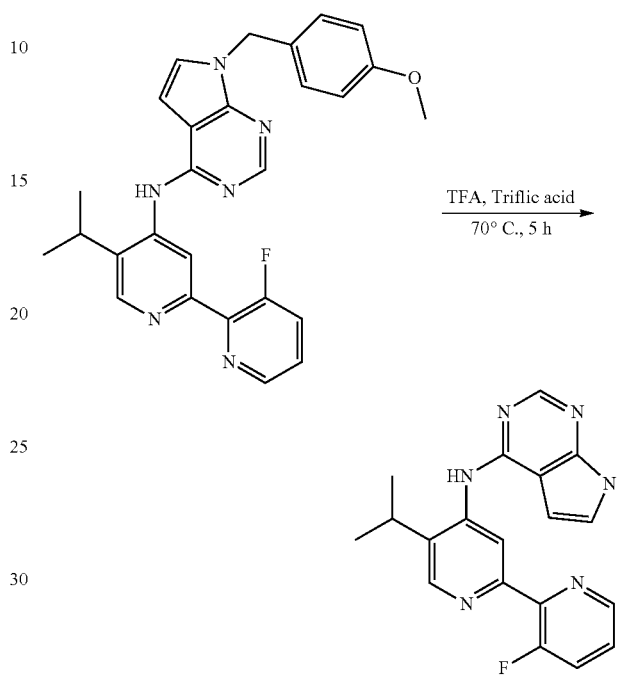

Steps 1-8: Synthesis of N-[2-(3-fluoro-2-pyridyl)-5-isopropyl-4-pyridyl]-7-[(4-methoxyphenyl) methyl]pyrrolo[2,3-d]pyrimidin-4-amine See Example 29.

Step 9: Synthesis of N-[2-(3-fluoro-2-pyridyl)-5-isopropyl-4-pyridyl]-7H-pyrrolo[2,3-d]pyrimidin-4-amine A solution of N-[2-(3-fluoro-2-pyridyl)-5-isopropyl-4-pyridyl]-7-[(4-methoxyphenyl) methyl]pyrrolo[2,3-d]pyrimidin-4-amine (290 mg, 0.618 mmol) in TFA (5 mL) and triflic acid (2.5 mL) was heated at 70° C. for 5 h. Progress of the reaction was monitored by TLC & LCMS. After completion of reaction, the reaction mixture was cooled to RT and concentrated under reduced pressure to obtain an oily compound which was neutralized using aq. saturated sodium bicarbonate and extracted with EtOAc (2×100 mL). The combined organic layer was washed with brine solution (50 mL) and dried over anhydrous sodium sulfate and concentrate under reduced pressure to obtain the crude compound, which was purified by reverse phase HPLC to obtain N-[2-(3-fluoro-2-pyridyl)-5-isopropyl-4-pyridyl]-7H-pyrrolo[2,3-d]pyrimidin-4-amine (15 mg).

$^1$H NMR: (400 MHz; Methanol-d4) δ (ppm): 8.70 (s, 1H), 8.56 (d, J=3.1 Hz, 1H), 8.51 (d, J=5.1 Hz, 1H), 8.25 (d, J=5.1 Hz, 2H), 7.99 (dd, J=6.8, 5.1 Hz, 1H), 7.25 (d, J=3.6 Hz, 1H), 6.66 (d, J=3.6 Hz, 1H), 3.43 (p, J=6.9 Hz, 1H), 1.38 (d, J=6.9 Hz, 6H). LCMS: 349 (M+1).

Example 31. Preparation of Compound Nos. 31, 31a and 31b

Synthesis of 4-{[2-(5-chloro-2-fluorophenyl)-5-cyclopropylpyridin-4-yl]amino}-N-[(2S)-2-hydroxypropyl]pyridine-3-carboxamide

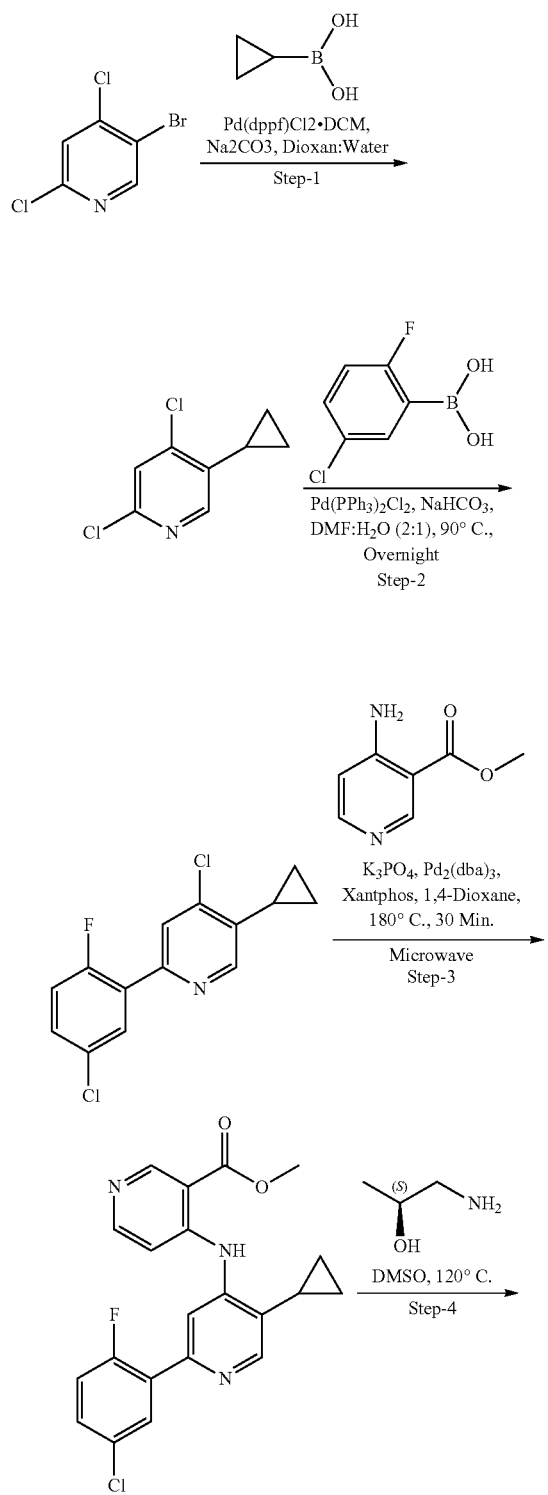

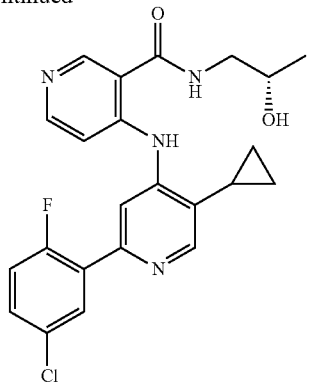

STEP-1: Synthesis of 2,4-dichloro-5-cyclopropyl-pyridine

5-Bromo-2,4-dichloro-pyridine (1.5 g, 6.60 mmol), cyclopropyl boronic acid (1.14 g, 13.2 mmol) and sodium carbonate (2.1 g, 19.82 mmol) were dissolved in 1,4-dioxane:Water (20:5 mL). Nitrogen gas was purged for 10 min. Then Pd(dppf)Cl$_2$.DCM (270 mg, 0.330 mmol) was added and the resulting mixture was heated at 100° C. for 3 h. Product formation was confirmed by TLC and LCMS. Then the reaction mixture was diluted with water (50 mL) and extracted with EtOAc (2×100 mL). The combined organic layer was dried over anhydrous sodium sulfate and concentrated. The crude product was passed through the CombiFlash® chromatography to afford 700 mg of 2,4-dichloro-5-cyclopropyl-pyridine.

STEP-2: Synthesis of 4-chloro-2-(5-chloro-2-fluoro-phenyl)-5-cyclopropyl-pyridine 2,4-Dichloro-5-cyclopropyl-pyridine (700 mg, 3.72 mmol), (5-chloro-2-fluoro-phenyl)boronic acid (1.3 g, 7.44 mmol) and sodium bicarbonate (626 mg, 7.44 mmol) were dissolved in DMF:Water (10:5 mL) and nitrogen was purged for 10 min. Then Pd(PPh$_3$)$_2$.Cl$_2$ and heated at 90° C. for 12 h. Product formation was confirmed by TLC and LCMS. Then the reaction mixture was diluted with water (50 mL) and extracted with EtOAc (2×100 mL). The combined organic layer was washed with water (5×50 mL) and dried over anhydrous sodium sulfate, and concentrated. The crude product was passed through CombiFlash® chromatography to afford 400 mg of 4-chloro-2-(5-chloro-2-fluoro-phenyl)-5-cyclopropyl-pyridine.

STEP-3: Synthesis of 4-[[2-(5-chloro-2-fluoro-phenyl)-5-cyclopropyl-4-pyridyl]amino]pyridine-3-carboxylate 4-Chloro-2-(5-chloro-2-fluoro-phenyl)-5-cyclopropyl-pyridine (300 mg, 1.06 mmol), methyl 4-aminopyridine-3-carboxylate (244 mg, 1.60 mmol) and potassium phosphate tribasic (566 mg, 2.66 mmol) were dissolved in 1,4-dioxane (5 mL). Nitrogen gas was purged for 10 min. Then Pd$_2$(dba)$_3$ (49 mg, 0.053 mmol) and xantphos (31 mg, 0.053 mmol) were added and the resulting mixture was heated at 180° C. in a microwave reactor for 30 min. Product formation was confirmed by TLC and LCMS. Then the reaction mixture was diluted with water (50 mL) and extracted with EtOAc (2×100 mL). The combined organic layer was dried over anhydrous sodium sulfate and concentrated. The crude product was passed through the CombiFlash® chromatography to afford 200 mg of methyl 4-[[2-(5-chloro-2-fluoro-phenyl)-5-cyclopropyl-4-pyridyl]amino] pyridine-3-carboxylate.

STEP-4: Synthesis of 4-[[2-(5-chloro-2-fluoro-phenyl)-5-cyclopropyl-4-pyridyl]amino]-N-[(2S)-2-hydroxypropyl]pyridine-3-carboxamide Methyl 4-[[2-(5-chloro-2-fluoro-phenyl)-5-cyclopropyl-4-pyridyl]amino]pyridine-3-carboxylate (200 mg, 0.503 mmol) and (S)-1-aminopropan-2-ol (227 mg, 3.00 mmol) were dissolved in 2 mL of DMSO and heated at 120° C. for 4 h. Product formation was confirmed by LCMS. Then the reaction mixture was diluted with water (50 mL) and extracted with EtOAc (2×50 mL). The combined organic layer was washed with water (5×20 mL) and dried over anhydrous sodium sulfate, and concentrated. The crude product was passed over reverse phase HPLC to afford 45 mg of 4-[[2-(5-chloro-2-fluoro-phenyl)-5-cyclopropyl-4-pyridyl]amino]-N-[(2S)-2-hydroxypropyl]pyridine-3-carboxamide. The (R) enantiomer can be synthesized utilizing (R)-1-aminopropan-2-ol in this step.

$^1$H NMR: (400 MHz, CDCl$_3$): δ (ppm): 10.58 (bs, 1H), 8.75 (s, 1H), 8.42 (m, 2H), 7.99 (m, 1H), 7.78 (s, 1H), 7.42 (d, 1H), 7.30 (m, 1H), 7.08 (t, 1H), 6.92 (bs, 1H), 4.08 (m, 1H), 3.70 (m 1H), 3.32 (m 1H), 1.88 (m, 1H), 1.30 (d, 3H), 1.18 (m, 2H), 0.75 (m, 2H).

Example 32. Preparation of Compound No. 32

Synthesis of 2-(5-chloro-2-fluorophenyl)-5-cyclopropyl-N-{1H-pyrrolo[2,3-b]pyridin-4-yl}pyridin-4-amine

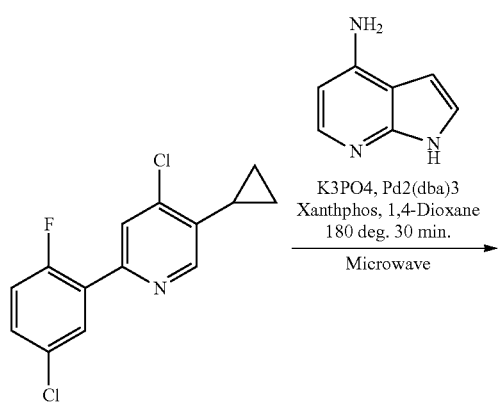

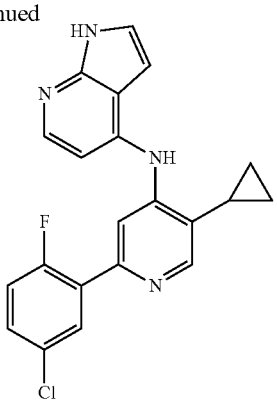

4-Chloro-2-(5-chloro-2-fluoro-phenyl)-5-cyclopropyl-pyridine (200 mg, 0.709 mmol), 1H-pyrrolo[2,3-b]pyridin-4-amine (189 mg, 1.41 mmol) and potassium phosphate tribasic (376 mg, 1.77 mmol) were dissolved in 1,4-dioxane (5 mL). Nitrogen gas was purged for 10 min. Then Pd$_2$(dba)$_3$ (33 mg, 0.035 mmol) and xantphos (21 mg, 0.035 mmol) were added and the resulting mixture was heated at 180° C. in microwave reactor for 30 min. Product formation was confirmed by LCMS. Then the reaction mixture was diluted with water (50 mL) and extracted with EtOAc (2×50 mL). The combined organic layer was dried over anhydrous sodium sulfate and concentrated. The crude product was passed through reverse phase HPLC to afford 50 mg of N-[2-(5-chloro-2-fluoro-phenyl)-5-cyclopropyl-4-pyridyl]-1H-pyrrolo[2,3-b]pyridin-4-amine.

$^1$H NMR: (400 MHz, CDCl$_3$): δ (ppm): 10.58 (bs, 1H), 8.75 (s, 1H), 8.42 (m, 2H), 7.99 (m, 1H), 7.78 (s, 1H), 7.42 (d, 1H), 7.30 (m, 1H), 7.08 (t, 1H), 6.92 (bs, 1H), 4.08 (m, 1H), 3.70 (m, 1H), 3.32 (m, 1H), 1.88 (m, 1H), 1.30 (d, 3H), 1.18 (m, 2H), 0.75 (m, 2H).

Example 33. Preparation of Compound No. 33

Synthesis of 4-{[2-(5-chloro-2-fluorophenyl)-5-(pyrrolidin-1-yl)pyridin-4-yl]amino}-N-(1,3-dihydroxypropan-2-yl)pyridine-3-carboxamide

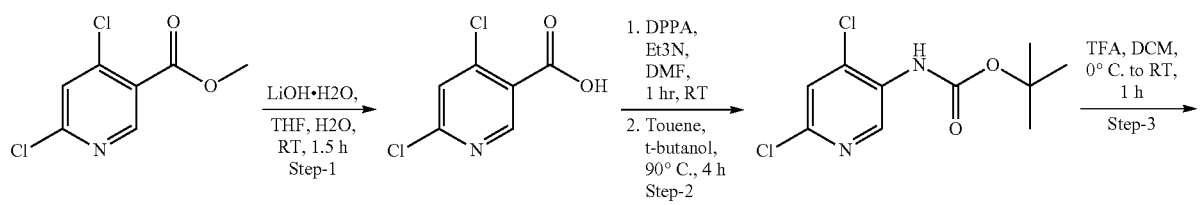

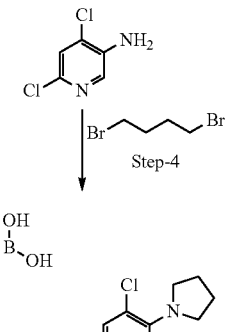

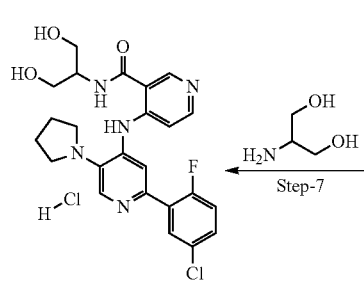

Step-1: Synthesis of 4,6-dichloropyridine-3-carboxylic acid

To a stirred solution of methyl 4,6-dichloropyridine-3-carboxylate (15 g, 0.0728 mol) in THF (100 mL) was added a solution of lithium hydroxide monohydrate (8.737 g, 0.364 mol) in water (50 mL). The resultant reaction mixture was stirred at RT for 1.5 h. The reaction was monitored by TLC. After completion of reaction, the pH of the aqueous layer was adjusted to 2 by the addition of 2 N HCl (aq.) and product was extracted with EtOAc (2×500 mL). The organic layer was separated, dried over anhydrous sodium sulfate and concentrated under reduced pressure to afford 4,6-dichloropyridine-3-carboxylic acid (13.5 g) as a white solid.

Step-2: Synthesis of tert-butyl N-(4,6-dichloro-3-pyridyl)carbamate

To a solution of 4,6-dichloropyridine-3-carboxylic acid (8.4 g, 43.75 mmol) in dry DMF (30 mL) was added triethylamine (6.5 mL, 48.12 mmol) at 0° C. followed by diphenylphosphoryl azide (10.37 mL, 48.12 mmol). The resultant reaction mixture was stirred at RT for 1 h and poured onto a mixture of ice-water-EtOAc. The product was extracted with EtOAc (2×200 mL). The combined extracts were washed with water (2×100 mL), a saturated solution of sodium bicarbonate (50 mL) and finally with brine solution (50 mL). The organic layer was separated, dried over anhydrous sodium sulfate and concentrated under reduced pressure to afford a light yellow solid which was dissolved in 80 mL of dry toluene and heated to reflux for 2 h. Then the reaction mixture was cooled to RT and t-butanol (25.1 mL, 262.5 mmol) was added. The resultant reaction mixture was heated at 90° C. for 4 h. The reaction was monitored by TLC. After completion, the reaction mixture was concentrated under reduced pressure, water was added to the residue and the product was extracted with EtOAc (2×250 mL). Removal of EtOAc under reduced pressure afforded an oily residue that was purified by column chromatography on silica gel (100-200 mesh) using 1% EtOAc-hexane system as eluent to afford tert-butyl N-(4,6-dichloro-3-pyridyl)carbamate (6.9 g) as a light yellow liquid.

Step-3: Synthesis of 4,6-dichloropyridin-3-amine

To a stirred solution of tert-butyl N-(4, 6-dichloro-3-pyridyl)carbamate (6.9 g, 0.0262 mol) in DCM (20 mL) was added trifluoroacetic acid (8 mL) dropwise at 0° C. The reaction mixture was slowly warmed to RT and stirred for 90 min. The reaction was monitored by TLC. After completion of reaction, reaction mixture was concentrated under reduced pressure. To the residue was added saturated solution of sodium bicarbonate (30 mL) and product was extracted with EtOAc (2×200 mL). The organic layer was again washed with water (30 mL) and brine solution (30 mL). The organic layer was separated, dried over anhydrous sodium sulfate. Removal of EtOAc under reduced pressure afforded product which was again washed with n-pentane and dried to afford 4,6-dichloropyridin-3-amine (3.8 g) as a light brown solid.

Step-4: Synthesis of 2,4-dichloro-5-pyrrolidin-1-yl-pyridine

To a stirred solution of 4,6-dichloropyridin-3-amine (3.9 g, 0.0239 mol) in dry DMF (35 mL) was added sodium hydride (1.914 g, 0.0478 mol, 60% suspension in mineral oil) under nitrogen atmosphere at 0° C. The reaction mixture was stirred at this temperature for 30 min. Then 1,4-dibromobutane (4.134 g, 0.0191 mol) was added dropwise. The reaction mixture was stirred at RT overnight. The reaction was monitored by TLC and LCMS. After completion of reaction, the reaction was quenched by addition of ice-water (50 mL) and the product was extracted with EtOAc (2×150 mL). The organic layer was again washed with water (2×50 mL) and brine solution (50 mL). The organic layer was separated, dried over anhydrous sodium sulfate and concentrated under reduced pressure to affored an oily residue that was purified by column chromatography on silica gel (100-200 mesh) using 0.5-1% EtOAc-hexane to afford 2,4-dichloro-5-pyrrolidin-1-yl-pyridine (3.711 g) as an off-white solid.

Step-5: Synthesis of 4-chloro-2-(5-chloro-2-fluoro-phenyl)-5-pyrrolidin-1-yl-pyridine To a stirred solution of 2,4-dichloro-5-pyrrolidin-1-yl-pyridine (3.5 g, 0.0161 mol), (5-chloro-2-fluoro-phenyl) boronic acid (3.36 g, 0.01963 mol) in DMF (15 mL) was added a suspension of sodium bicarbonate (2.7 g, 0.0322 mol) in water (15 mL) was purged nitrogen for 30 min. Then bis(triphenylphosphine)palladium(II) dichloride (566 mg, 0.000806 mmol) was added to the reaction mixture and nitrogen gas was purged through it for another 5 min. The reaction mixture was then heated at 80° C. overnight. The reaction was monitored by TLC and LCMS. After completion of reaction, the reaction mixture was cooled to RT and water (50 mL) was added to the reaction mixture and product was extracted with EtOAc (2×100 mL). The combined organic layer was washed with water (3×50 mL) and finally with brine solution (50 mL). The organic layer was separated, dried over anhydrous sodium sulfate and concentrated under reduced pressure to obtain the crude compound which was purified by combi flash chromatography using 5% EtOAc in hexane elute to afford 4-chloro-2-(5-chloro-2-fluoro-phenyl)-5-pyrrolidin-1-yl-pyridine (1.615 g) as an off-white solid and also recover unreacted starting material (2,4-dichloro-5-pyrrolidin-1-yl-pyridine, 1.8 g).

Step-6: Synthesis of methyl 4-[[2-(5-chloro-2-fluoro-phenyl)-5-pyrrolidin-1-yl-4-pyridyl]amino]pyridine-3-carboxylate A stirred solution of 4-chloro-2-(5-chloro-2-fluoro-phenyl)-5-pyrrolidin-1-yl-pyridine (1.2 g, 3.85 mmol), methyl 4-aminopyridine-3-carboxylate (645 mg, 4.24 mmol) and potassium phosphate (tribasic) (1.635 g, 7.712 mmol) in 1,4-dioxane (20 mL) was purged with nitrogen for 30 min. Then tris(dibenzylidineacetone)dipalladium(0) (353 mg, 0.385 mmol) and xantphos (335 mg, 0.578 mmol) were added to the reaction mixture. Nitrogen gas was purged through it for another 5 min. The resulting reaction mixture was then heated at 100° C. overnight. The reaction was monitored by TLC and LCMS. After completion of reaction, reaction mixture was filtered through a celite bed. The celite bed was washed with EtOAc (2×100 mL). The filtrate was concentrated under reduced pressure to afford a crude product which was purified by combi-flash chromatography using 25% EtOAc-hexane system as eluent to afford methyl 4-[[2-(5-chloro-2-fluoro-phenyl)-5-pyrrolidin-1-yl-4-pyridyl]amino]pyridine-3-carboxylate (1.056 g) as a light yellow solid.

Step-7: Synthesis of obtain 4-[[2-(5-chloro-2-fluoro-phenyl)-5-pyrrolidin-1-yl-4-pyridyl]amino]-N-[2-hydroxy-1-(hydroxymethyl)ethyl]pyridine-3-carboxamide To a stirred suspension of methyl 4-[[2-(5-chloro-2-fluoro-phenyl)-5-pyrrolidin-1-yl-4-pyridyl]amino]pyridine-3-carboxylate (120 mg, 0.281 mmol) and 2-aminopropane-1,3-diol (128 mg, 1.405 mmol) in DMF (3 mL) The resulting reaction mixture was heated at 90° C. for 5 h. The reaction was monitored by TLC and LCMS. After completion of reaction, reaction mixture was cooled to RT and diluted with water (10 mL) and extracted with EtOAc (2×50 mL), and the organic layer washed with water (15 mL). The organic layer was dried over anhydrous sodium sulfate and concentrated under reduced pressure to obtain the crude product which was purified by reverse phase HPLC to afford 4-[[2-(5-chloro-2-fluoro-phenyl)-5-pyrrolidin-1-yl-4-pyridyl]amino]-N-[2-hydroxy-1-(hydroxy methyl)ethyl]pyridine-3-carboxamide (75 mg) as an off-white solid, which was dissolved in ethanolic HCl (10 mL) and concentrated under reduced pressure to obtain 4-[[2-(5-chloro-2-fluoro-phenyl)-5-pyrrolidin-1-yl-4-pyridyl]amino]-N-[2-hydroxy-1-(hydroxy methyl)ethyl]pyridine-3-carboxamide (76 mg) as the HCl salt.

¹H NMR: (400 MHz, Methanol-d4) δ (ppm): 8.90 (s, 1H), 8.33 (d, J=8.3 Hz, 2H), 7.88 (d, J=11.0 Hz, 2H), 7.51 (m, 1H), 7.30 (t, J=9.7 Hz, 1H), 7.19 (d, J=7.1 Hz, 1H), 4.26 (d, J=6.1 Hz, 1H), 3.76 (qd, J=11.2, 5.7 Hz, 4H), 3.47 (m, 4H), 1.99 (m, 4H). LCMS: 486 (M+1).

Example 34. Preparation of Compound No. 34

Synthesis of 2-(5-chloro-2-fluorophenyl)-5-(prop-1-en-2-yl)-N-[3-(pyrrolidine-1-carbonyl)pyridin-4-yl]pyridin-4-amine

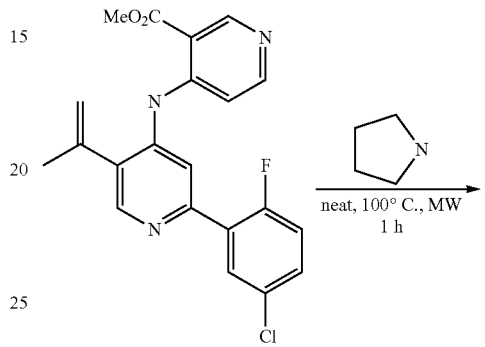

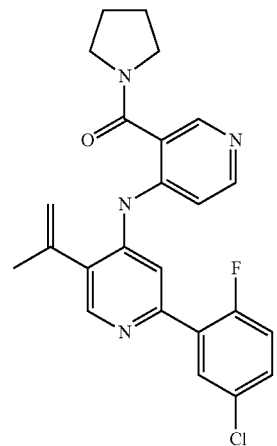

To a solution of methyl 4-[[2-(5-chloro-2-fluoro-phenyl)-5-isopropenyl-4-pyridyl]amino]pyridine-3-carboxylate (700 mg, 1.763 m mol) and added pyrrolidine (1.25 g, 17.63 mmol) and heated at 100° C. for 1 h in a microwave reactor. The progress of the reaction was monitored by TLC and LCMS. After completion of reaction, the mixture was diluted with water (20 mL) extracted with EtOAc (2×100 mL) and washed with water (5×100 mL). The combined organic layer was dried with anhydrous sodium sulfate and concentrated under reduced pressure to afford a crude product, which was purified by reverse phase purification to afford 200 mg 2-(5-chloro-2-fluorophenyl)-5-(prop-1-en-2-yl)-N-[3-(pyrrolidine-1-carbonyl)pyridin-4-yl]pyridin-4-amine.

¹HNMR: (Free Base, DMSO-d6): δ (ppm): 9.15 (bs, 1H) 8.58 (s, 1H), 8.42 (s, 1H), 8.38 (d, 1H), 7.98 (m, 1H), 7.75 (s, 1H), 7.58 (m, 1H), 7.41 (m, 2H), 5.42 (s, 1H) 5.18 (s, 1H), 3.52 (m, 2H), 3.42 (m, 2H), 2.15 (s, 3H), 1.88 (m, 2H), 1.78 (m, 2H).

167

Example 35. Preparation of Compound No. 35

Synthesis of 2-(5-chloro-2-fluorophenyl)-5-(propan-2-yl)-N-{7H-pyrrolo[2,3-d]pyrimidin-4-yl}pyridin-4-amine

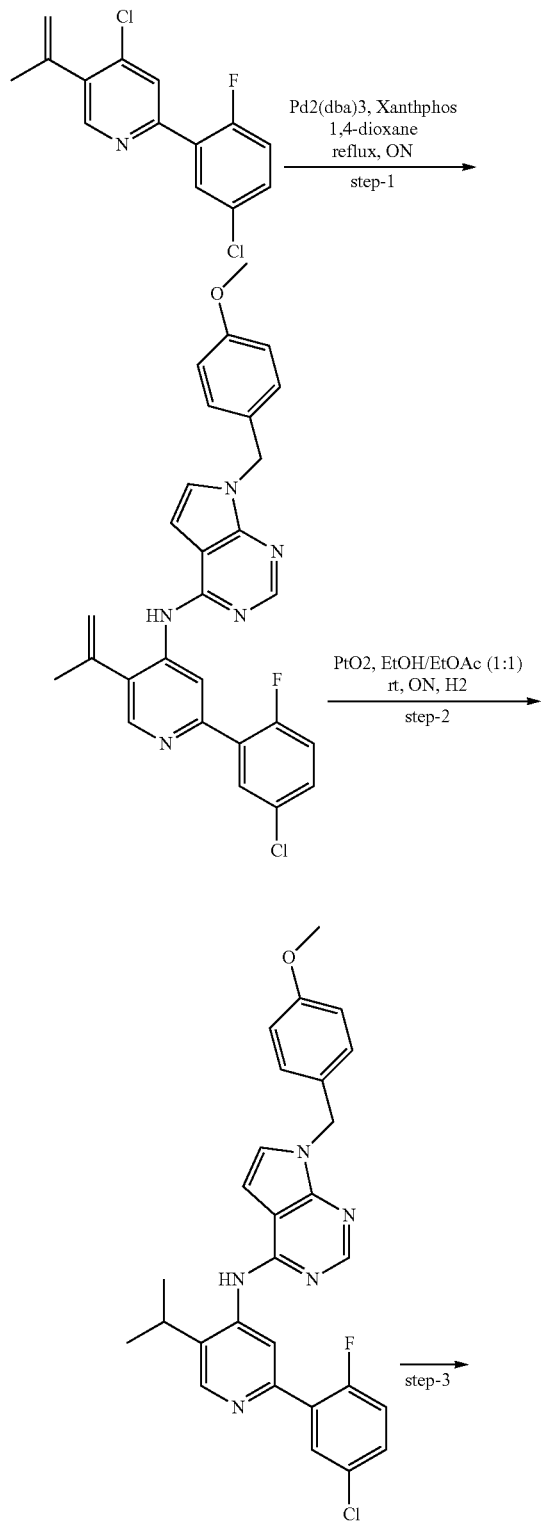

168

-continued

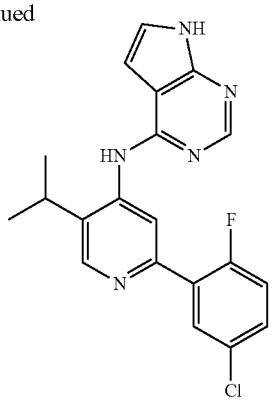

Step-1: Synthesis of N-[2-(5-chloro-2-fluoro-phenyl)-5-isopropenyl-4-pyridyl]-7-[(4-methoxyphenyl)methyl]pyrrolo[2,3-d]pyrimidin-4-amine 4-Chloro-2-(5-chloro-2-fluoro-phenyl)-5-isopropenyl-pyridine (1.0 g, 3.5 mmol), 7-[(4-methoxyphenyl)methyl]pyrrolo[2,3-d]pyrimidin-4-amine (1.35g, 5.3 mmol) potassium phosphate (2.25g, 10.52 mmol) was dissolved in 1,4-dioxane (20 ml)nitrogen gas was purged for 20 min. To it was added tris(dibenzylideneacetone)dipalladium(0) (324 mg, 0.35 mmol) and xantphos (418 mg, 0.72 mmol) and again degassed with nitrogen for 20 min and the reaction mass was heated to reflux overnight. The reaction was monitored by TLC and LCMS. The reaction mass was filtered through a small bed of celite and concentrated under reduced pressure to get the crude product that was purified by chromatography (eluent: 20-40% EtOAc in hexane) to obtain the pure N-[2-(5-chloro-2-fluoro-phenyl)-5-isopropenyl-4-pyridyl]-7-[(4-methoxyphenyl)methyl]pyrrolo[2,3-d]pyrimidin-4-amine (530 mg).

Step-2: Synthesis of N-[2-(5-chloro-2-fluoro-phenyl)-5-isopropyl-4-pyridyl]-7-[(4-methoxyphenyl)methyl]pyrrolo[2,3-d]pyrimidin-4-amine N-[2-(5-Chloro-2-fluoro-phenyl)-5-isopropenyl-4-pyridyl]-7-[(4-methoxyphenyl)methyl] pyrrolo[2,3-d]pyrimidin-4-amine (502 mg, 1 mmol) was dissolved in a solution of ethanol and EtOAc (1:1) (10 mL), and to it was added platinum oxide (45 mg, 0.20 mmol) and the reaction mass was purged by Hydrogen, with Hydrogen gas bladder for 3 h and kept under a hydrogen atmosphere overnight. The reaction was monitored by NMR. The reaction mass was filtered through a small bed of celite and concentrated under reduced pressure to obtain the product that was purified by chromatography (eluent: 50% EtOAc in hexane) to obtain the pure N-[2-(5-chloro-2-fluoro-phenyl)-5-isopropyl-4-pyridyl]-7-[(4-methoxyphenyl)methyl]pyrrolo[2,3-d]pyrimidin-4-amine (340 mg).

Step-3: Synthesis of 2-(5-chloro-2-fluorophenyl)-5-(propan-2-yl)-N-{7H-pyrrolo[2,3-d]pyrimidin-4-yl}pyridin-4-amine N-[2-(5-Chloro-2-fluoro-phenyl)-5-isopropyl-4-pyridyl]-7-[(4-methoxyphenyl)methyl] pyrrolo[2,3-d]pyrimidin-4-amine (250 mg, 0.5 mmol) was dissolved in trifluoroacetic acid (0.8 mL), and to it was added trifluoromethanesulfonic acid (0.2 mL) and the reaction mass was heated in a microwave at 120° C. for 50 min. The reaction was monitored by LCMS. The reaction mass was basified with ice cold saturated sodium hydrogen carbonate (20 mL) and extracted with DCM (2×20 mL). The combined organics were dried over sodium sulfate and concentrated under reduced pressure to obtain the product that was purified by chromatography (mobile phase (0-5% methanol in DCM) to obtain the product (120 mg). This product was again purified with reverse phase HPLC to obtain the pure product 2-(5-chloro-2-fluorophenyl)-5-(propan-2-yl)-N-{7H-pyrrolo[2,3-d]pyrimidin-4-yl}pyridin-4-amine as free base (15 mg).
$^1$HNMR: (400 MHz: DMSO-d6) δ (ppm): 11.8 (bs 1H), 9.02 (s, 1H), 8.82 (s, 1H), 8.2 (s, 1H), 8.04 (s, 1H), 8.0 (d, 1H), 7.44 (m, 1H), 7.40 (m, 1H), 7.22 (s, 1H), 6.6 (s, 1H), 3.4 (m, 1H), 1.2 (d, 6H).

Example 36. Preparation of Compound No. 36

Synthesis of 2-(5-chloro-2-fluorophenyl)-5-(propan-2-yl)-N-{1H-pyrazolo[3,4-d]pyrimidin-4-yl}pyridin-4-amine

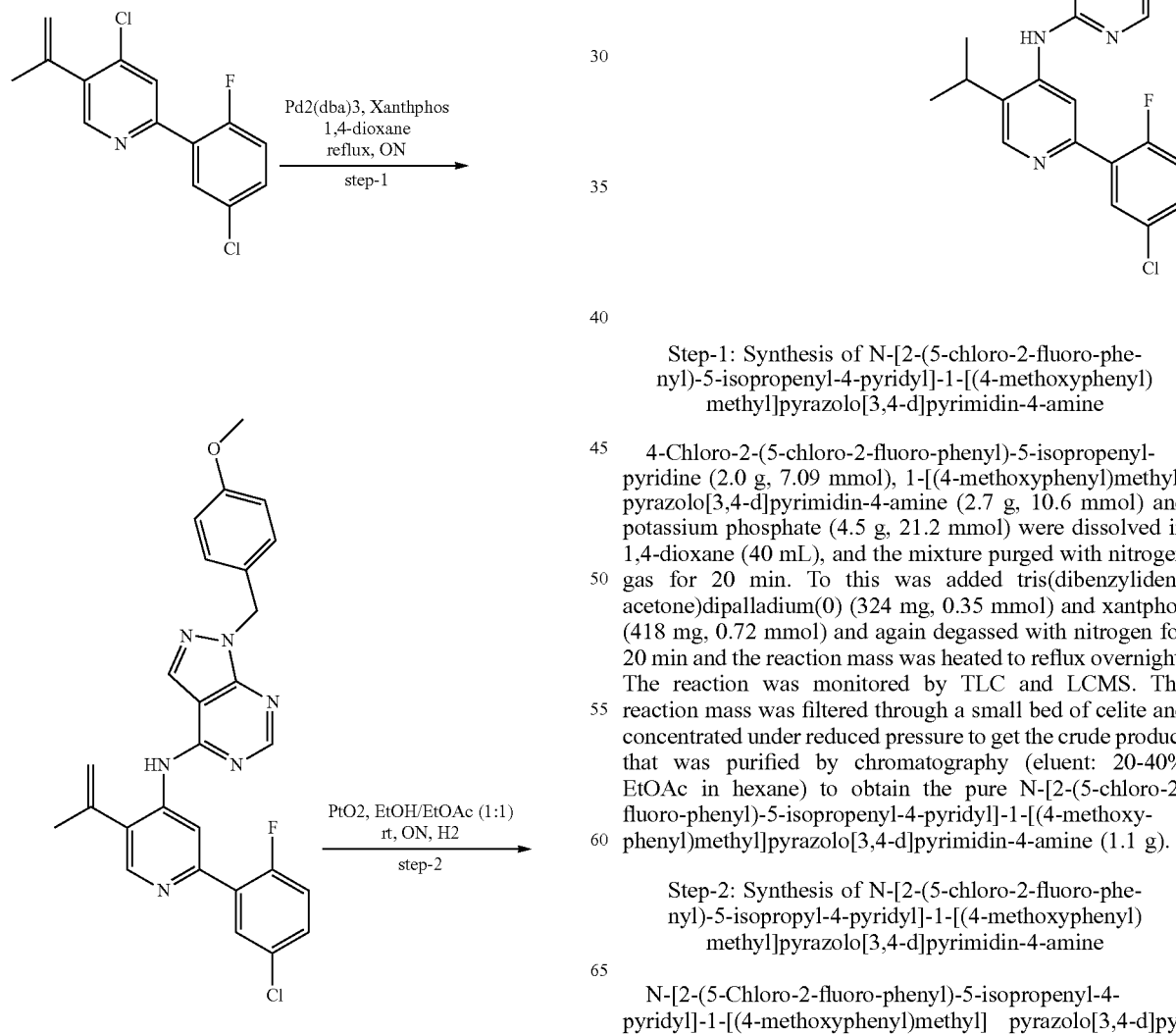

Step-1: Synthesis of N-[2-(5-chloro-2-fluoro-phenyl)-5-isopropenyl-4-pyridyl]-1-[(4-methoxyphenyl)methyl]pyrazolo[3,4-d]pyrimidin-4-amine 4-Chloro-2-(5-chloro-2-fluoro-phenyl)-5-isopropenyl-pyridine (2.0 g, 7.09 mmol), 1-[(4-methoxyphenyl)methyl]pyrazolo[3,4-d]pyrimidin-4-amine (2.7 g, 10.6 mmol) and potassium phosphate (4.5 g, 21.2 mmol) were dissolved in 1,4-dioxane (40 mL), and the mixture purged with nitrogen gas for 20 min. To this was added tris(dibenzylidene acetone)dipalladium(0) (324 mg, 0.35 mmol) and xantphos (418 mg, 0.72 mmol) and again degassed with nitrogen for 20 min and the reaction mass was heated to reflux overnight. The reaction was monitored by TLC and LCMS. The reaction mass was filtered through a small bed of celite and concentrated under reduced pressure to get the crude product that was purified by chromatography (eluent: 20-40% EtOAc in hexane) to obtain the pure N-[2-(5-chloro-2-fluoro-phenyl)-5-isopropenyl-4-pyridyl]-1-[(4-methoxyphenyl)methyl]pyrazolo[3,4-d]pyrimidin-4-amine (1.1 g).

Step-2: Synthesis of N-[2-(5-chloro-2-fluoro-phenyl)-5-isopropyl-4-pyridyl]-1-[(4-methoxyphenyl)methyl]pyrazolo[3,4-d]pyrimidin-4-amine N-[2-(5-Chloro-2-fluoro-phenyl)-5-isopropenyl-4-pyridyl]-1-[(4-methoxyphenyl)methyl] pyrazolo[3,4-d]pyrimidin-4-amine (1.0 g, 2.0 mmol) was dissolved in a solution of ethanol and EtOAc (1:1) (20 mL), and to it was added platinum oxide (90 mg, 0.39 mmol) and the reaction mass was purged with hydrogen gas, by bladder, for 3 h and kept under a hydrogen atmosphere overnight. The reaction was monitored by NMR. The reaction mass was filtered through a small bed of celite and concentrated under reduced pressure to obtain the product which was purified by chromatography (eluent: 50% EtOAc in hexane) to obtain the pure form of N-[2-(5-chloro-2-fluoro-phenyl)-5-isopropyl-4-pyridyl]-1-[(4-methoxyphenyl)methyl]pyrazolo[3,4-d]pyrimidin-4-amine (650 mg).

Step-3: Synthesis of 2-(5-chloro-2-fluorophenyl)-5-(propan-2-yl)-N-{1H-pyrazolo[3,4-d]pyrimidin-4-yl}pyridin-4-amine N-[2-(5-Chloro-2-fluoro-phenyl)-5-isopropyl-4-pyridyl]-1-[(4-methoxyphenyl)methyl] pyrazolo[3,4-d]pyrimidin-4-amine (503 mg, 1.0 mmol) was dissolved in trifluoroacetic acid (0.8 mL), and to it was added trifluoromethanesulfonic acid (0.2 mL) and the reaction mass was heated in a microwave at 120° C. for 50 min. The reaction was monitored by LCMS. The reaction mass was basified with ice cold saturated sodium hydrogen carbonate (20 mL) and extracted with DCM (2×20 mL). The combined organics were dried over sodium sulfate and concentrated under reduced pressure to obtain the product that was purified by chromatography (mobile phase (0-5% methanol in DCM) to obtain the product (270 mg). that was again purified with reverse phase HPLC to obtain the pure product 2-(5-chloro-2-fluorophenyl)-5-(propan-2-yl)-N-{1H-pyrazolo[3,4-d]pyrimidin-4-yl}pyridin-4-amine as formate salt (52 mg).

$^1$HNMR: (400 MHz: DMSO-d6) δ (ppm): 13.8-13.6 (bs, 1H) 10.0-9.8 (bs, 1H) 8.8 (s, 1H), 8.2 (s, 1H), 8.14-8.0 (bs, 1H), 8.0 (d, 1H), 7.98 (s, 1H), 7.6 (m, 1H), 7.4 (m, 1H), 3.2 (m, 1H), 1.2 (d, 6H).

Example 37. Preparation of Compound Nos. 37, 37a and 37b

Synthesis of 4-{[2-(2-fluorophenyl)-5-(prop-1-en-2-yl)pyridin-4-yl]amino}-N-[(2S)-2-hydroxypropyl] pyridine-3-carboxamide

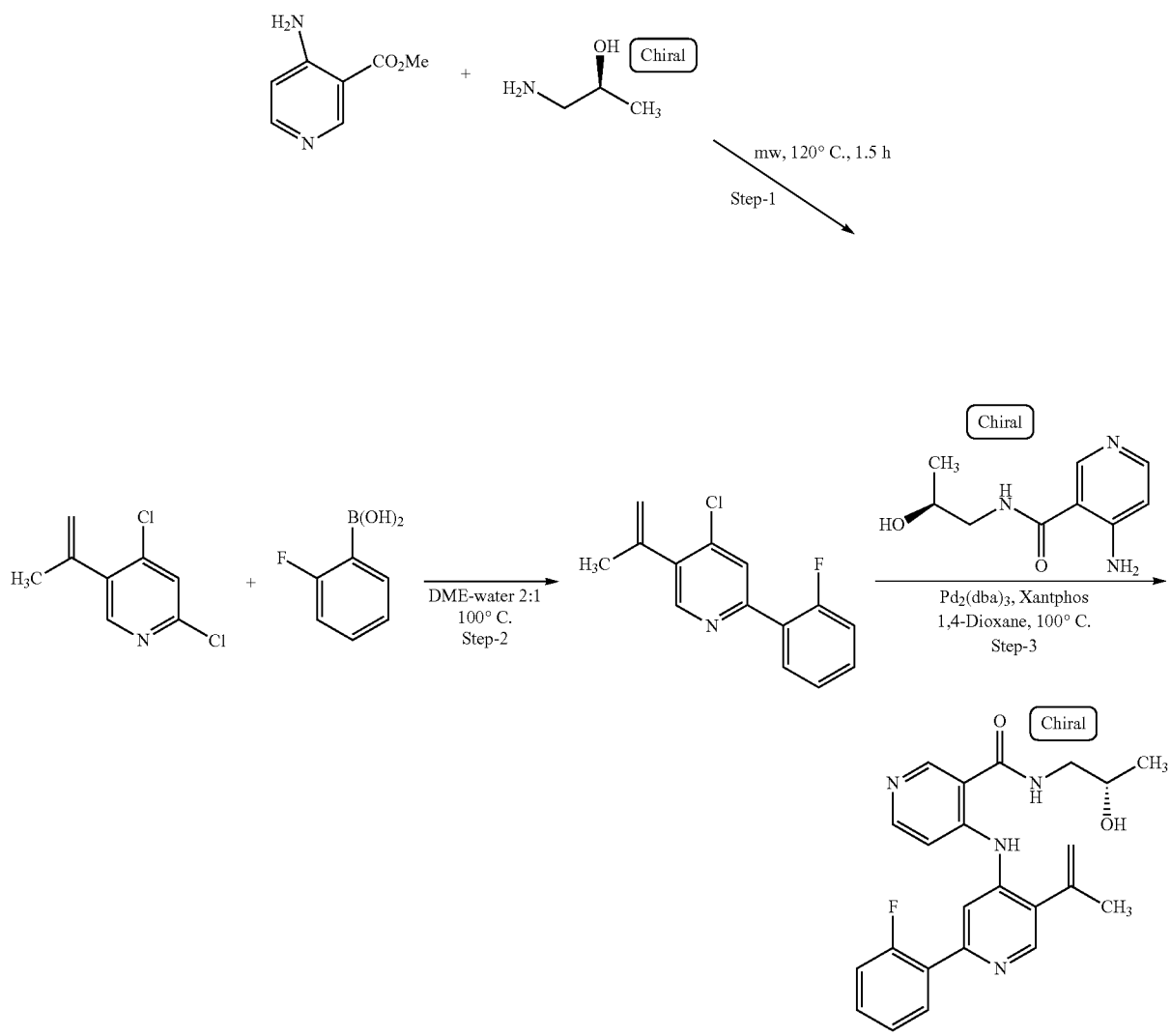

Step-1: Synthesis of 4-amino-N-[(2S)-2-hydroxypropyl]pyridine-3-carboxamide (S)-1-Amino-2-propanol (2.0 g, 13.1 mmol) was added to methyl-4-aminonicotinate (3.0 g, 39.9 mmol) in a microwave tube and the resulting mixture was heated in a microwave reactor at 120° C. for 1.5 h. The product formation was confirmed by TLC and LCMS. The crude product was purified by chromatography to afford 1.03 g of the product 4-amino-N-[(2S)-2-hydroxpropyl]pyridine-3-carboxamide as white crystals.

Step-2: Synthesis of 4-chloro-2-(2-fluorophenyl)-5-isopropenyl-pyridine

A 100 mL screw cap bottle was charged with 2,4-dichloro-5-isopropenyl-pyridine (2.0 g, 10.6 mmol), 2-fluorophenylboronic acid (1.1 g, 8.0 mmol) and sodium carbonate (3.4 g, 31.8 mmol) DME (20 ml) and water (5 mL) and degassed with nitrogen for 15 min. To it was added Pd (PPh$_3$)$_2$.Cl$_2$ (364 mg, 0.52 mmol) and degassed with nitrogen for another 10 min. The resulting mixture was heated at 100° C. for 3 h. The reaction was monitored by TLC and LCMS. Then the reaction mixture was passed through a celite bed, diluted with water (25 mL) and EtOAc (25 mL). The layers were separated, and the aqueous layer was again extracted with EtOAc (50 mL). The combined organics were dried over anhydrous sodium sulfate and concentrated under reduced pressure to obtain the product, which was purified by chromatography (eluent: hexane) to afford 1.24 g of product 4-chloro-2-(2-fluorophenyl)-5-isopropenyl-pyridine as white crystals.

Step-3: Synthesis of 4-[[2-(2-fluorophenyl)-5-isopropenyl-4-pyridyl]amino]-N-[(2S)-2-hydroxypropyl]pyridine-3-carboxamide A 25 mL screw cap bottle was charged with 4-chloro-2-(2-fluorophenyl)-5-isopropenyl-pyridine (500 mg, 2.0 mmol), 4-amino-N-[(2S)-2-hydroxypropyl]pyridine-3-carboxamide (433 mg, 2.2 mmol), K$_3$PO$_4$ (849 mg, 4.0 mmol) and 1,4-dioxane (10 mL) and degassed with nitrogen for 20 min. Then Xantphos (174 mg, 0.3 mmol) and Pd$_2$(dba)$_3$ (183 mg, 0.2 mmol) were added and again degassed with nitrogen for a further 15 min. The resulting mixture was heated at 100° C. overnight. The product formation was confirmed by LCMS. Then the reaction mixture was passed through a celite bed and concentrated under reduced pressure to obtain the product, which was purified with reverse phase HPLC to afford 85 mg of product 4-[[2-(2-fluorophenyl)-5-isopropenyl-4-pyridyl]amino]-N-[(2S)-2-hydroxypropyl]pyridine-3-carboxamide as a white solid. The (R) enantiomer can be synthesized utilizing (R)-1-aminopropan-2-ol in Step-1.

$^1$HNMR: (400 MHz, DMSO): δ (ppm): 10.43 (bs, 1H), 8.83-8.81 (m, 2H), 8.47 (m, 1H), 7.99 (m, 1H), 7.78 (s, 1H), 7.42 (d, 1H), 7.30 (m, 1H), 7.08 (t, 1H), 6.92 (bs, 1H), 4.08 (m, 1H), 3.70 (m, 1H), 3.32 (m, 1H), 1.88 (m, 1H), 1.30 (d, 3H), 1.18 (m, 2H), 0.75 (m, 2H).

Example 38. Preparation of Compound Nos. 38, 38a and 38b

Synthesis of 4-{[2-(4-fluorophenyl)-5-(prop-1-en-2-yl)pyridin-4-yl]amino}-N-[(2S)-2-hydroxypropyl]pyridine-3-carboxamide

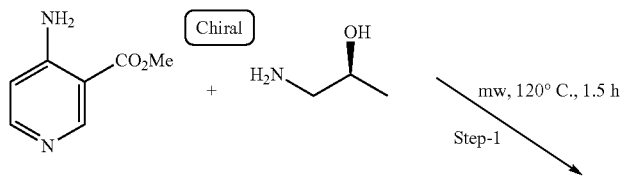

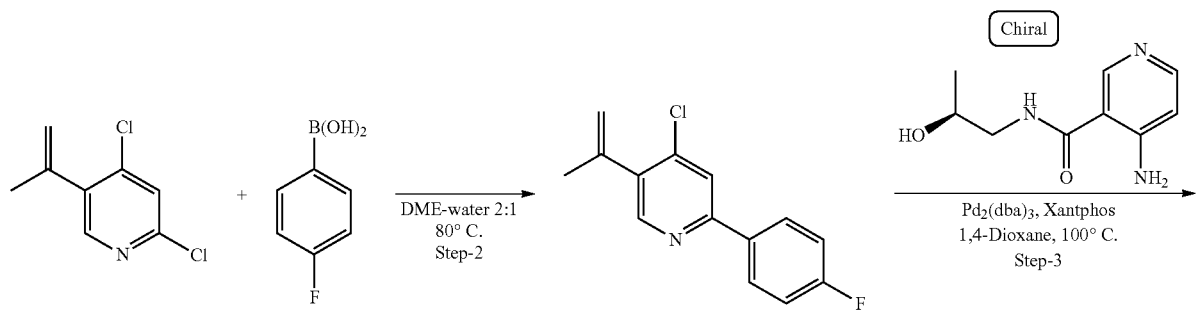

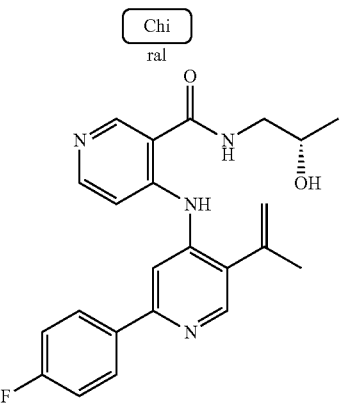

Step-1: Synthesis of 4-amino-N-[(2S)-2-hydroxypropyl]pyridine-3-carboxamide

See Example 37.

Step-2: Synthesis of 4-chloro-2-(4-fluorophenyl)-5-isopropenyl-pyridine

A 100 mL screw cap bottle was charged with 2,4-dichloro-5-isopropenyl-pyridine (2.0 g, 10.6 mmol), 2-fluorophenylboronic acid (1.1 g, 8.0 mmol) and sodium carbonate (3.4 g, 31.8 mmol) in a mixture of DME (20 mL) and water (5 mL) and degassed with nitrogen for 15 min. Then Pd(PPh$_3$)$_2$.Cl$_2$ (364 mg, 0.52 mmol) was added and again degassed with nitrogen for a another 10 min. The resulting mixture was heated at 100) ° C. for 3 h. The reaction was monitored by LCMS formation TLC and LCMS. Then the reaction mixture was passed through a celite bed, diluted with water (25 mL) and extracted with EtOAc (2×50 mL). The combined organic layer was dried over anhydrous sodium sulfate and concentrated under reduced pressure. The crude product was passed through the CombiFlash® chromatography to afford 1.41 g of product 4-chloro-2-(4-fluorophenyl)-5-isopropenyl-pyridine as white crystals.

Step-3: Synthesis of 4-{[2-(4-fluorophenyl)-5-(prop-1-en-2-yl)pyridin-4-yl]amino}-N-[(2S)-2-hydroxypropyl]pyridine-3-carboxamide A 25 mL screw cap bottle was charged with 4-chloro-2-(4-fluorophenyl)-5-isopropenyl-pyridine (500 mg, 2.0 mmol) and 4-amino-N-[(2S)-2-hydroxypropyl]pyridine-3-carboxamide (433 mg, 2.2 mmol) and K$_3$PO$_4$ (849 mg, 4.0 mmol) and 1,4-dioxane (10 mL) and degassed with nitrogen for 30 min. Then Xantphos (174 mg, 0.3 mmol) and Pd$_2$(dba)$_3$ (183 mg, 0.2 mmol) were added and nitrogen was purged for further 15 min. The resulting mixture was heated at 100° C. overnight. The reaction was monitored by LCMS. Then the reaction mixture was passed through a celite bed and extracted with EtOAc (2×50 mL) and concentrated under reduced pressure to obtain the product, which was purified with reverse phase HPLC to afford 169 mg of product 4-[[2-(2-fluorophenyl)-5-isopropenyl-4-pyridyl]amino]-N-[(2S)-2-hydroxypropyl]pyridine-3-carboxamide as a white solid. The (R) enantiomer can be synthesized utilizing (R)-1-aminopropan-2-ol in Step-1.

$^1$HNMR: (400 MHz, CDCl$_3$): δ (ppm): 10.58 (bs, 1H), 8.75 (s, 1H), 8.42 (m, 2H), 7.99 (m, 1H), 7.78 (s, 1H), 7.42 (d, 1H), 7.30 (m, 1H), 7.08 (t, 1H), 6.92 (bs, 1H), 4.08 (m, 1H), 3.70 (m, 1H), 3.32 (m, 1H), 1.88 (m, 1H), 1.30 (d, 3H), 1.18 (m, 2H), 0.75 (m, 2H).

Example 39. Preparation of Compound Nos. 39, 39a and 39b

Synthesis of 4-{[2-(3-chlorophenyl)-5-(prop-1-en-2-yl)pyridin-4-yl]amino}-N-[(2S)-2-hydroxypropyl]pyridine-3-carboxamide

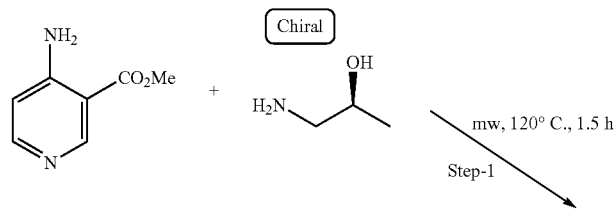

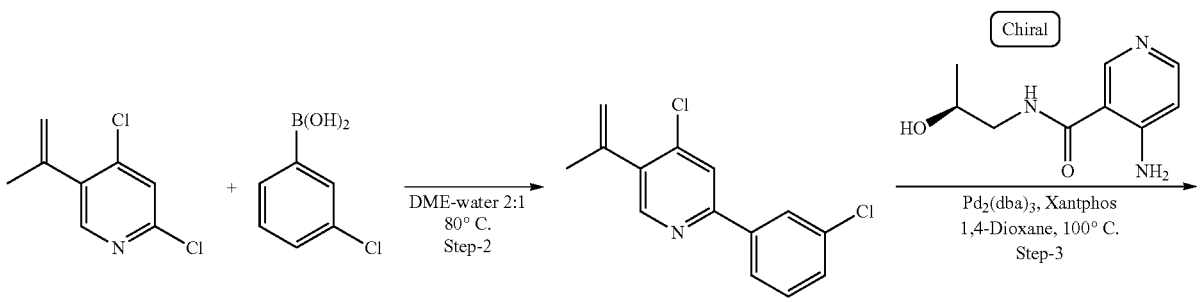

Step-1: Synthesis of 4-amino-N-[(2S)-2-hydroxypropyl]pyridine-3-carboxamide

See Example 37.

Step-2: Synthesis of 4-chloro-2-(3-chlorophenyl)-5-isopropenyl-pyridine

A 100 mL screw cap bottle was charged with 2,4-dichloro-5-isopropenyl-pyridine (1.5 g, 8.0 mmol), 2-fluorophenylboronic acid (837 mg, 6.0 mmol) and sodium carbonate (2.5 g, 24.0 mmol) in a mixture of DME (20 mL) and water (5 mL) and degassed with nitrogen for 15 min. Then Pd(PPh$_3$)$_2$.Cl$_2$ (280 mg, 0.40 mmol) and again degassed with nitrogen for another 10 min. The resulting mixture was heated at 100° C. for 3 h. The reaction was monitored by LCMS. Then the reaction mixture was passed through a celite bed, diluted with water (25 mL) and extracted with EtOAc (2×50 mL). The combined organic layer was dried over anhydrous sodium sulfate and concentrated under reduced pressure. The crude product was passed through the CombiFlash® chromatography to afford 935 mg of product 4-chloro-2-(3-chlorophenyl)-5-isopropenyl-pyridine as a colorless thick liquid.

Step-3: Synthesis of 4-{[2-(3-chlorophenyl)-5-(prop-1-en-2-yl)pyridin-4-yl]amino}-N-[(2S)-2-hydroxypropyl]pyridine-3-carboxamide

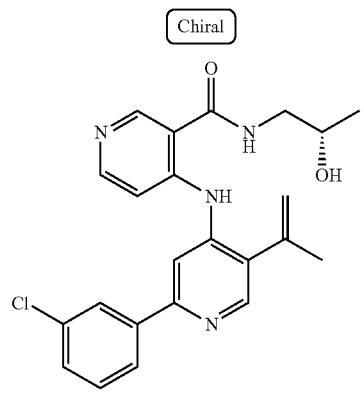

A 25 mL screw cap bottle was charged with 4-chloro-2-(3-chlorophenyl)-5-isopropenyl-pyridine (500 mg, 2.0 mmol) and 4-amino-N-[(2S)-2-hydroxypropyl]pyridine-3-carboxamide (433 mg, 2.2 mmol) and K$_3$PO$_4$ (849 mg, 4.0 mmol) and 1,4-dioxane (10 mL) and degassed with nitrogen for 15 min. Then xantphos (174 mg, 0.3 mmol) and Pd$_2$(dba)$_3$ (183 mg, 0.2 mmol) were added and degassed with nitrogen for a further 15 min. The resulting mixture was heated at 100° C. overnight. The product formation was confirmed by LCMS. Then the reaction mixture was passed through a celite bed and extracted with EtOAc (2×50 mL) extracted with EtOAc (2×50 mL) and concentrated under reduced pressure to obtain the product, which was purified with reverse phase HPLC to obtain 52 mg of 4-[[2-(3-chlorophenyl)-5-isopropenyl-4-pyridyl]amino]-N-[(2S)-2-hydroxypropyl]pyridine-3-carboxamide as a white solid. The (R) enantiomer can be synthesized utilizing (R)-1-aminopropan-2-ol in Step-1.

$^1$HNMR: (400 MHz, CDCl$_3$): δ (ppm): 10.58 (bs, 1H), 8.75 (s, 1H), 8.42 (m, 2H), 7.99 (m, 1H), 7.78 (s, 1H), 7.42 (d, 1H), 7.30 (m, 1H), 7.08 (t, 1H), 6.92 (bs, 1H), 4.08 (m, 1H), 3.70 (m, 1H), 3.32 (m, 1H), 1.88 (m, 1H), 1.30 (d, 3H), 1.18 (m, 2H), 0.75 (m, 2H).

Example 40. Preparation of Compound Nos. 40, 40a and 40b

Synthesis of N-[(2S)-2-hydroxypropyl]-4-{[5-(prop-1-en-2-yl)-2-[3-(trifluoromethyl)phenyl]pyridin-4-yl]amino}pyridine-3-carboxamide

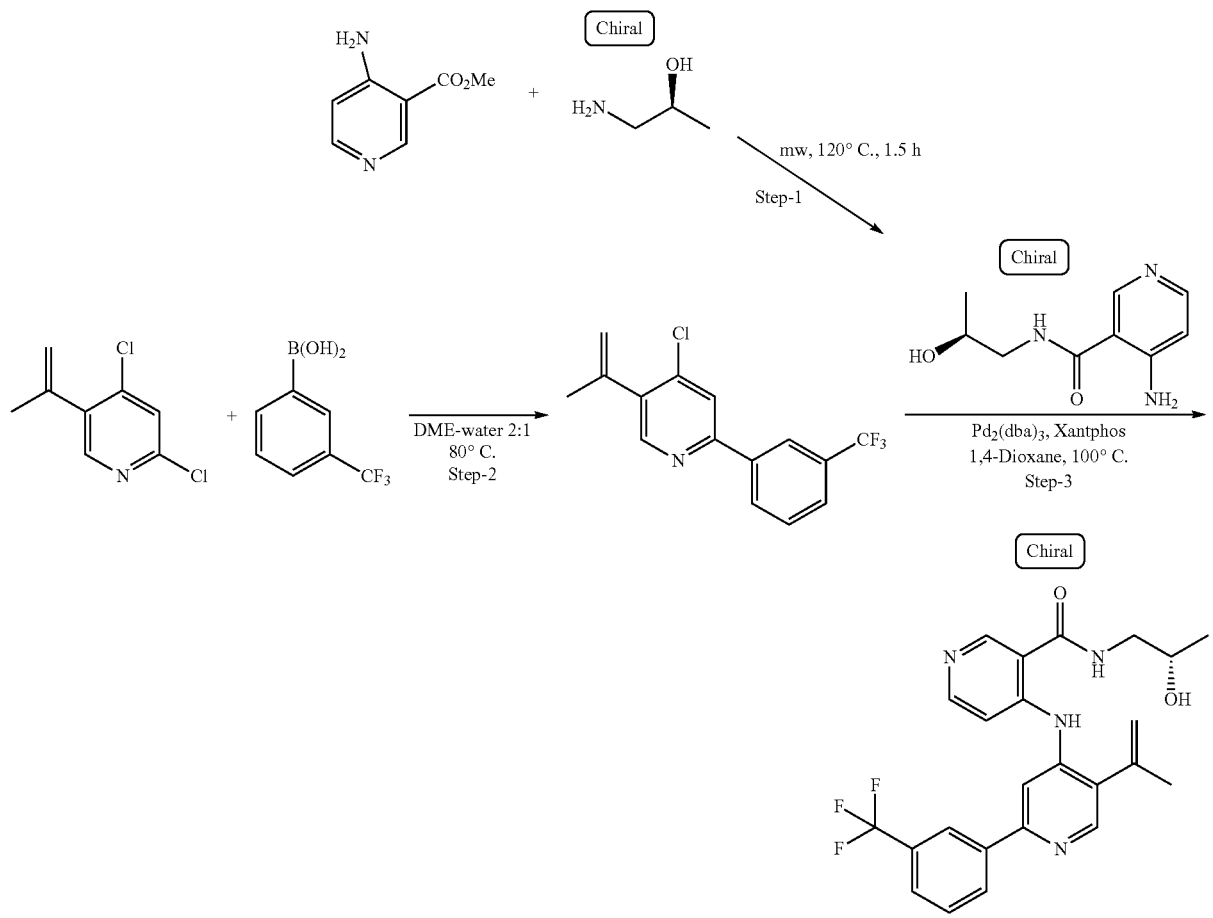

Step-1: Synthesis of 4-amino-N-[(2S)-2-hydroxypropyl]pyridine-3-carboxamide

See Example 37.

Step-2: Synthesis of 4-chloro-5-isopropenyl-2-[3-(trifluoromethyl)phenyl]pyridine A 100 mL screw cap bottle was charged with 2,4-dichloro-5-isopropenyl-pyridine (800 mg, 4.26 mmol), [3-(trifluoromethyl)phenyl]boronic acid (606 mg, 3.19 mmol) and sodium carbonate (1.3g, 12.8 mmol) in a mixture of DME (5 mL) and water (2.5 mL) and degassed with nitrogen for 15 min. Then Pd(PPh$_3$)$_2$.Cl$_2$ (147 mg, 0.21 mmol) and again degassed with nitrogen for another 10 min. The resulting mixture was heated at 100° C. for 3 h. The reaction was monitored by LCMS. Then the reaction mixture was passed through a celite bed, diluted with water (25 mL) and extracted with EtOAc (2×50 mL). The combined organic layer was dried over anhydrous sodium sulfate and concentrated under reduced pressure to obtain the product, which was purified by chromatography to obtain the product (250 mg) as an oil.

Step-3: Synthesis of N-[(2S)-2-hydroxypropyl]-4-{[5-(prop-1-en-2-yl)-2-[3-(trifluoromethyl)phenyl]pyridin-4-yl]amino}pyridine-3-carboxamide A 25 mL screw cap bottle was charged with 4-chloro-5-isopropenyl-2-[3-(trifluoro methyl)phenyl]pyridine (250 mg, 0.84 mmol) and 4-amino-N-[(2S)-2-hydroxypropyl]pyridine-3-carboxamide (180 mg, 0.92 mmol) and K$_3$PO$_4$ (356 mg, 1.7 mmol) and 1,4-dioxane (10 mL) and degassed with nitrogen for 15 min. Then xantphos (73 mg, 0.13 mmol) and Pd$_2$(dba)$_3$ (77 mg, 0.08 mmol) were added and degassed with nitrogen for a further 15 min. The resulting mixture was heated at 100° C. overnight. The product formation was confirmed by LCMS. Then the reaction mixture was passed through a celite bed and extracted with EtOAc (2×50 mL) and concentrated under reduced pressure to obtain the product that was purified with reverse phase HPLC to obtain the product 4-[[2-(3-chlorophenyl)-5-isopropenyl-4- pyridyl]amino]-N-[(2S)-2-hydroxypropyl]pyridine-3-carboxamide as a white solid (40 mg). The (R) enantiomer can be synthesized utilizing (R)-1-aminopropan-2-ol in Step-1.

¹HNMR: (400 MHz, DMSO-d6): δ (ppm): 10.47 (bs, 1H), 8.86 (s, 1H), 8.48 (m, 2H), 8.4-8.3 (m, 2H), 8.0 (s, 1H), 7.79 (d, 1H), 7.74-7.720 (m, 1H), 7.44 (d, 1H), 5.44 (s, 1H), 5.18 (s, 1H) 4.78 (d, 1H), 3.80 (m, 1H), 3.32 (m, 1H), 2.06 (s, 3H), 1.07 (d, 3H).

Example 41. Preparation of Compound No. 41

Synthesis of N-[2-(5-chloro-2-fluorophenyl)-5-(prop-1-en-2-yl)pyridin-4-yl]quinolin-4-amine

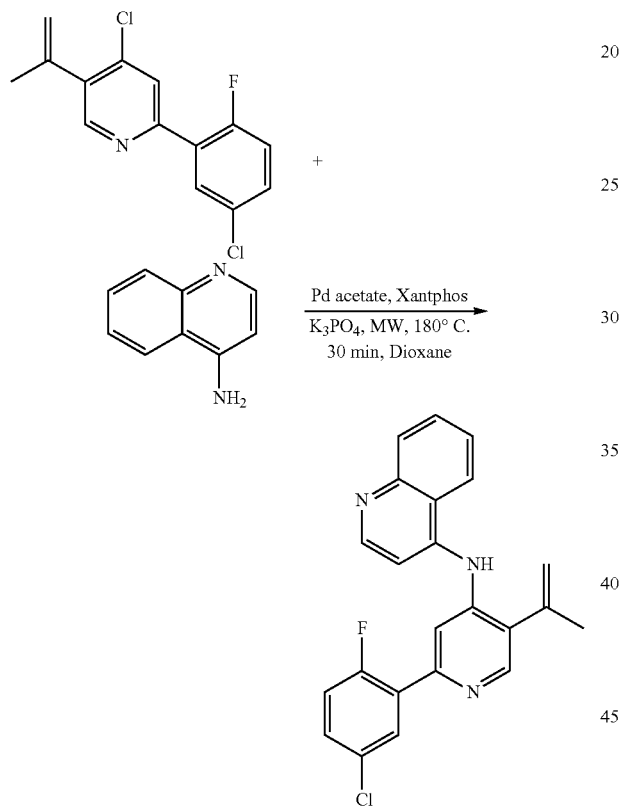

Quinolin-4-amine (500 mg, 3.47 mmol) and 4-chloro-2-(5-chloro-2-fluoro-phenyl)-5-isopropenyl-pyridine (1.1g, 3.82 mmol) were dissolved in 5 mL dioxane. N₂ gas was purged for 10 min. Palladium acetate (78 mg, 0.347 mmol), xantphos (200 mg, 0.347 mmol), K₃PO₄ (2.2 g, 10.41 mmol) were added. Again N₂ gas was purged for 10 min. The reaction was irradiated at 180° C. temperature for 30 min. The progress of reaction was monitored by LCMS. After completion of reaction, the solvent was removed under reduced pressure. The residue was diluted with 30 mL of water and extracted with DCM (3×50 mL). The combined organic layer was washed with water (2×20 mL), dried over anhydrous sodium sulfate and concentrated under reduced pressure. The crude product was purified by reverse phase HPLC to obtain 150 mg of the free base of N-[2-(5-chloro-2-fluoro-phenyl)-5-isopropenyl-4-pyridyl]quinolin-4-amine.

¹HNMR: (Free Base, CD₃OD): δ (ppm): 8.50 (m, 2H), 8.20 (d, 1H), 7.95 (d, 1H), 7.90 (d, 1H), 7.80 (t, 1H), 7.60 (m, 2H), 7.42 (m, 1H), 7.20 (m, 1H), 6.95 (bs, 1H), 5.30 (s, 2H), 2.05 (s, 3H).

Example 42. Preparation of Compound No. 42

Synthesis of N-[2-(5-chloro-2-fluorophenyl)-5-(prop-1-en-2-yl)pyridin-4-yl]quinolin-5-amine

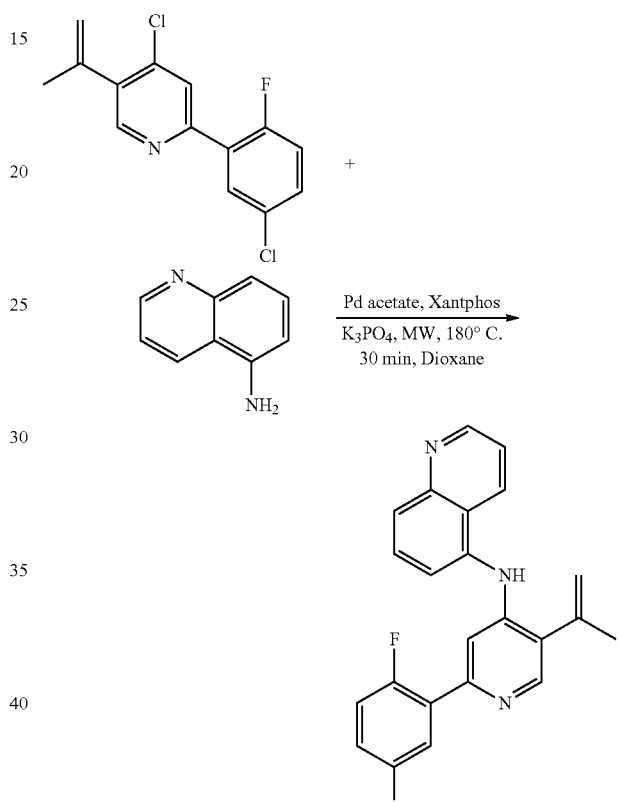

Quinolin-5-amine (300 mg, 2.10 mmol) and 4-chloro-2-(5-chloro-2-fluoro-phenyl)-5-isopropenyl-pyridine (644 mg, 2.30 mmol) were dissolved in 5 mL of dioxane. N₂ gas was purged for 10 min. Palladium acetate (47 mg, 0.21 mmol), xantphos (127 mg, 0.21 mmol), K₃PO₄ (1.34 g, 6.30 mmol) were added. Again N₂ gas was purged for 10 min. The reaction was irradiated at 180° C. temperature for 30 min. Progress of reaction was monitored by LCMS. After completion of reaction, solvent was removed under reduced pressure. The residue was diluted with 30 mL of water and extracted with DCM (3×50 mL). The combined organic layer was washed with water (2×20 mL), dried over anhydrous sodium sulfate and concentrated under reduce pressure. The crude product was purified by reverse phase HPLC to obtain 25 mg free base of N-[2-(5-chloro-2-fluoro-phenyl)-5-isopropenyl-4-pyridyl]quinolin-5-amine.

¹HNMR: (Free Base, CD₃OD): δ (ppm): 8.95 (s, 1H), 8.30 (m, 3H), 7.90 (m, 2H), 7.75 (t, 1H), 7.55 (m, 1H), 7.42 (m, 2H), 7.20 (t, 1H), 6.80 (s, 1H), 5.40 (s, 1H), 5.30 (s, 1H), 2.15 (s, 3H).

Example 43. Preparation of Compound Nos. 43, 43a and 43b

Synthesis of 4-{[2-(5-chloro-2-fluorophenyl)-5-(propan-2-yl)pyridin-4-yl]amino}-N-[(2S)-1-hydroxybutan-2-yl]pyridine-3-carboxamide

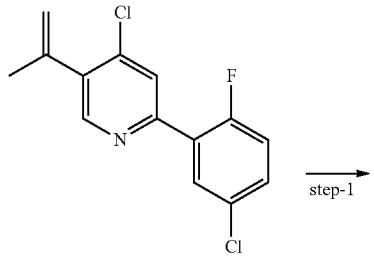

step-1

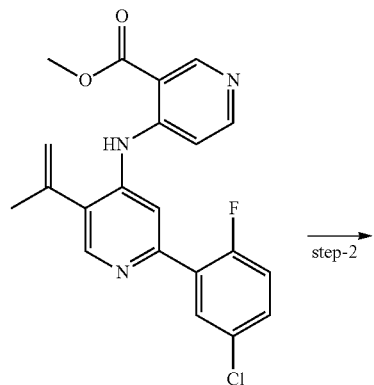

step-2

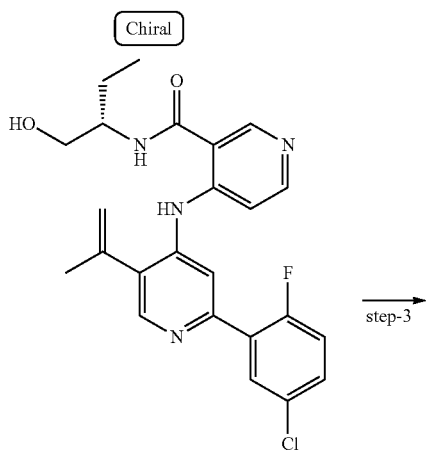

step-3

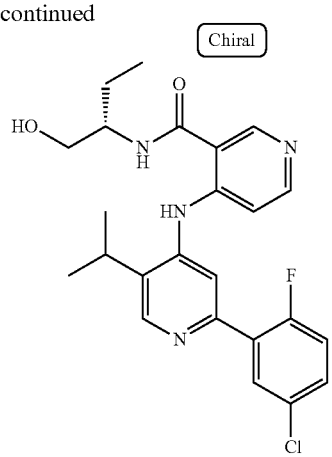

Step-1: Synthesis of methyl 2-[[2-(5-chloro-2-fluoro-phenyl)-5-isopropenyl-4-pyridyl]amino]pyridine-3-carboxylate A 250 mL screw cap bottle was charged 4-chloro-2-(5-chloro-2-fluoro-phenyl)-5-isopropenyl-pyridine (5 g, 17.7 mmol), methyl 2-aminopyridine-3-carboxylate (4.0 g, 26.5 mmol), potassium phosphate tribasic (11.2 g, 53.1 mmol) and 1,4-dioxane (60 mL). The resultant mixture was degassed with nitrogen for 15 min. To it was added Pd$_2$dba$_3$ (811 mg, 0.88 mmol) and xantphos (1.02 g, 1.77 mmol) and again degassed with nitrogen for 15 min. The reaction mass was heated at 100° C. for 12 h. The reaction was monitored by LCMS. The reaction mass was cooled to RT, diluted with DCM (20 mL) filtered through a small celite bed and concentrated under reduced pressure to obtain the product, which was purified by chromatography (eluent: 30% EtOAc in hexane) to obtain the pure methyl 2-[[2-(5-chloro-2-fluoro-phenyl)-5-isopropenyl-4-pyridyl]amino] pyridine-3-carboxylate (2.1 g).

Step-2: Synthesis of 2-[[2-(5-chloro-2-fluoro-phenyl)-5-isopropenyl-4-pyridyl]amino]-N-[(1S)-1-(hydroxymethyl)propyl]pyridine-3-carboxamide A heterogeneous mixture of methyl 2-[[2-(5-chloro-2-fluoro-phenyl)-5-isopropenyl-4-pyridyl]amino]pyridine-3-carboxylate (1 g, 2.5 mmol) and (S)-2-aminobutan-1-ol was irradiated by microwave at 120° C. for 1 h. The reaction mass became a homogenous solution. The reaction was monitored by LCMS and TLC. The reaction mass was purified by chromatography using combi flash (eluent: 5% methanol in DCM) to obtain 2-[[2-(5-chloro-2-fluoro-phenyl)-5-isopropenyl-4-pyridyl]amino]-N-[(1S)-1-(hydroxymethyl) propyl]pyridine-3-carboxamide (500 mg).

Step-3: Synthesis of 4-{[2-(5-chloro-2-fluorophenyl)-5-(propan-2-yl)pyridin-4-yl]amino}-N-[(2S)-1-hydroxybutan-2-yl]pyridine-3-carboxamide To a solution of 2-[[2-(5-chloro-2-fluoro-phenyl)-5-isopropenyl-4-pyridyl]amino]-N-[1-(hydroxymethyl)propyl]pyridine-3-carboxamide (500 mg, 1.09 mmol) in EtOAc (10 mL) and ethanol (5 mL) was added platinum oxide (90 mg 0.3 mmol) and bubbled with hydrogen gas for 3 h at RT. The reaction was monitored by $^1$H NMR and TLC. The reaction mass was filtered through a celite bed and concentrated under reduced pressure to obtain the product, which was purified by chromatography two times (eluent: 3% methanol in DCM) to obtain pure 4-{[2-(5-chloro-2-fluorophenyl)-5-(propan-2-yl)pyridin-4-yl]amino}-N-[(2S)-1-hydroxybutan-2-yl]pyridine-3-carboxamide (50 mg). This compound was converted to the HCl salt (46 mg). The (R) enantiomer can be synthesized utilizing (R)-2-aminobutan-1-ol in Step-2.

$^1$HNMR: (400 MHz, DMSO-d6): δ (ppm): 11.5 (bs, 1H), 9.0 (s, 1H), 8.9 (d, 1H), 8.8 (s 1H), 8.38 (d, 1H), 8.0 (d, 1H), 7.78 (s, 1H), 7.76 (m, 1H), 7.42 (t, 1H), 7.24 (d, 1H), 3.90 (m, 1H), 3.32 (m, 1H), 1.7 (m, 1H), 1.5 (m, 1H), 1.30 (d, 6H), 0.9 (t, 3H).

Example 44. Preparation of Compound Nos. 44, 44a and 44b

Synthesis of 4-{[2-(5-chloro-2-fluorophenyl)-5-(trifluoromethyl)pyridin-4-yl]amino}-N-[(2S)-2-hydroxypropyl]pyridine-3-carboxamide

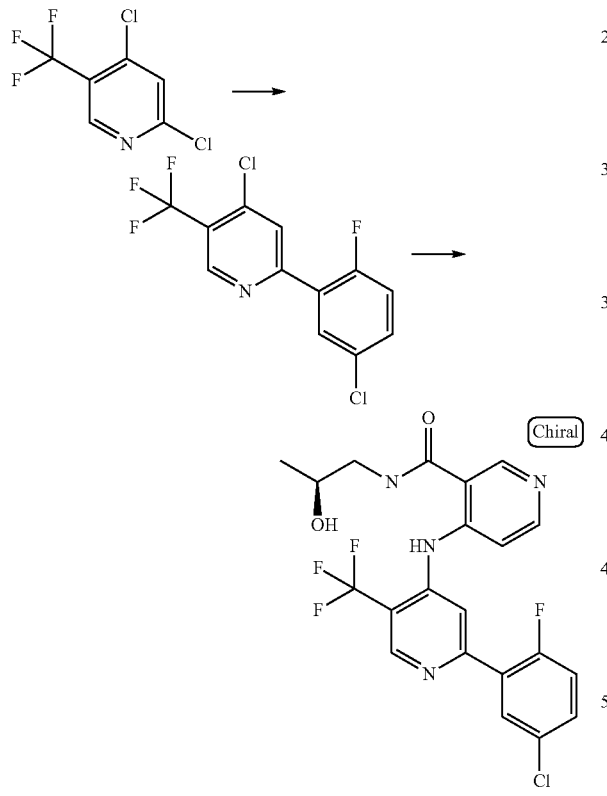

Step-1: Synthesis of 4-chloro-2-(5-chloro-2-fluorophenyl)-5-(trifluoromethyl)pyridine A two neck round bottom flask (100 mL) was charged with 2,4-dichloro-5-(trifluoromethyl)pyridine (2.16 g, 10 mmol), (5-chloro-2-fluoro-phenyl)boronic acid (1.04 g, 6.0 mmol), sodium carbonate (3.18 g, 30 mmol), 1,2-dimethoxy ethane (20 mL) and water (4 mL) degassed with nitrogen for 15 min. To it was added bis(triphenylphosphine)palladium (II) dichloride (140 mg, 0.2 mmol) again degassed with nitrogen for 10 min. The reaction mass was heated at 90° C.

for 90 min. The reaction was monitored by LCMS. The reaction mass was cooled to RT, filtered through a small bed of celite, and diluted with EtOAc (50 mL) and water (50 mL). The layers were separated, aqueous layer was again extracted with EtOAc (50 mL), the combined organics were dried over sodium sulfate and concentrated under reduced pressure to obtain the product, which was purified by chromatography (eluent: hexane) to obtain 1.2 g pure 4-chloro-2-(5-chloro-2-fluoro-phenyl)-5-(trifluoromethyl)pyridine.

Step-2: Synthesis of 4-{[2-(5-chloro-2-fluorophenyl)-5-(trifluoromethyl)pyridin-4-yl]amino}-N-[(2S)-2-hydroxypropyl]pyridine-3-carboxamide A 25 mL screw cap bottle was charged with 4-chloro-2-(5-chloro-2-fluoro-phenyl)-5-(trifluoromethyl)pyridine (500 mg, 1.60 mmol), (S)-2-amino-N-(2-hydroxypropyl)benzamide (469 mg, 2.4 mmol), potassium phosphate tribasic (1.02 g, 4.89 mmol) and 1,4-dioxane (20 mL). The resultant mixture was degassed with nitrogen for 15 min. To it was added Pd$_2$dba$_3$ (74 mg, 0.08 mmol) and xantphos (93 mg, 0.160 mmol) and again degassed with nitrogen for 15 min. The reaction mass was heated at 100° C. for 12 h. The reaction was monitored by LCMS. The reaction mass was cooled to room temperature, diluted with DCM (20 mL), filtered through a small celite bed and concentrated under reduced pressure to obtain the product, which was purified by chromatography and with reverse phase HPLC to obtain the pure 4-{[2-(5-chloro-2-fluorophenyl)-5-(trifluoromethyl)pyridin-4-yl]amino}-N-[(2S)-2-hydroxypropyl]pyridine-3-carboxamide (50 mg). The (R) enantiomer can be synthesized utilizing the (R)-2-amino-N-(2-hydroxypropyl)benzamide in this step.

$^1$HNMR: (400 MHz, CD$_3$OD): δ (ppm): 8.86-8.84 (d, 1H), 8.4 (d, 1H), 8.0 (s, 2H), 7.56 (d, 1H), 7.50 (bs, 1H), 7.28 (t, 1H), 3.98 (m, 1H), 3.43-3.41 (m, 2H), 1.25 (d, 3H).

Example 45. Preparation of Compound Nos. 45

Synthesis of 4-{[2-(5-chloro-2-fluorophenyl)-5-(prop-1-en-2-yl)pyridin-4-yl]amino}-N-(oxetan-3-yl)pyridine-3-carboxamide

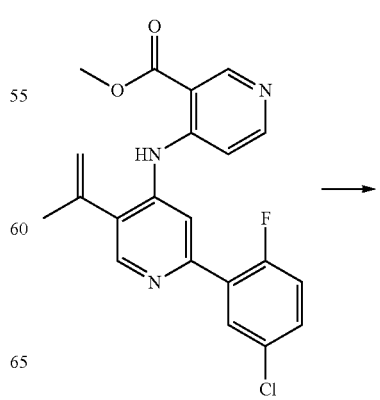

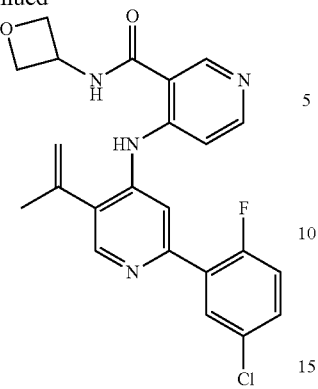
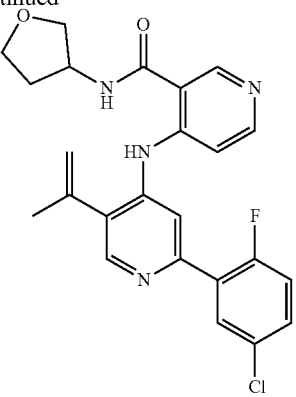

A heterogeneous mixture of methyl 2-[[2-(5-chloro-2-fluoro-phenyl)-5-isopropenyl-4-pyridyl]amino]pyridine-3-carboxylate (500 mg, 1.25 mmol) and 3-oxetane amine (1 mL) was irradiated by microwave at 120° C. for 1 h. The reaction mass became a homogenous solution. The reaction was monitored by LCMS and TLC. The reaction mass was purified by chromatography using combi flash (eluent: 5% methanol in DCM) to obtain the product, which was triturated with EtOAc to obtain pure 4-{[2-(5-chloro-2-fluoro-phenyl)-5-(prop-1-en-2-yl)pyridin-4-yl]amino}-N-(oxetan-3-yl)pyridine-3-carboxamide (35 mg).

$^1$HNMR: (400 MHz, DMSO-d6): δ (ppm): 10.3 (s, 1H), 9.47 (d, 1H), 8.9 (s, 1H), 8.46 (s, 1H), 8.41 (d, 1H), 8.0 (d, 1H,) 7.8 (s, 1H), 7.55 (m, 1H), 7.40 (m, 2H), 5.46 (s, 1H), 5.19 (s, 1H), 5.0 (m, 1H), 4.7 (m, 2H), 4.6 (m, 2H), 2.0 (s, 3H).

Example 46. Preparation of Compound Nos. 46, 46a and 46b

Synthesis of 4-{[2-(5-chloro-2-fluorophenyl)-5-(prop-1-en-2-yl)pyridin-4-yl]amino}-N-(oxolan-3-yl)pyridine-3-carboxamide

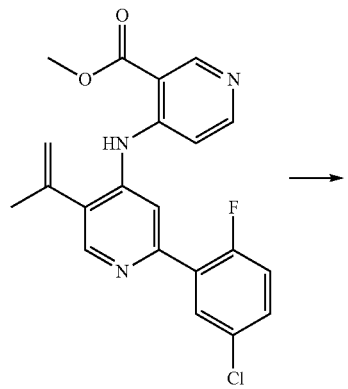

A heterogeneous mixture of methyl 2-[[2-(5-chloro-2-fluoro-phenyl)-5-isopropenyl-4-pyridyl]amino]pyridine-3-carboxylate (250 mg, 0.62 mmol) and tetrahydrofuran-3-amine) was irradiated by microwave at 120° C. for 1 h. The reaction mass became a homogenous solution. The reaction was monitored by LCMS and TLC. The reaction mass was purified by chromatography using combi flash (eluent: 5% methanol in DCM) to obtain product, which was triturated with EtOAc to obtain pure 4-{[2-(5-chloro-2-fluorophenyl)-5-(prop-1-en-2-yl)pyridin-4-yl]amino}-N-(oxolan-3-yl) pyridine-3-carboxamide (17 mg) as a racemate. Chiral HPLC will resolve the enantiomers into the individual (R) and (S) forms.

$^1$HNMR: (400 MHz, DMSO-d6): δ (ppm): 10.3 (s, 1H), 8.96 (d, 1H), 8.79 (s, 1H), 8.44 (s, 1H), 8.40 (d, 1H), 8.0 (d, 1H,) 7.8 (s, 1H), 7.5 (m, 1H), 7.4 (m, 2H), 5.48 (s, 1H), 5.2 (s, 1H), 4.46 (bs, 1H), 3.86-3.84 (m, 2H), 3.7 (m, 1H), 3.6 (m, 1H), 2.1 (m, 1H), 2.0 (s, 3H), 1.9 (m, 1H).

Example 47. Preparation of Compound Nos. 47, 47a and 47b

Synthesis of 4-({2-[2-fluoro-5-(trifluoromethoxy) phenyl]-5-(prop-1-en-2-yl)pyridin-4-yl}amino)-N-[(2S)-2-hydroxypropyl]pyridine-3-carboxamide

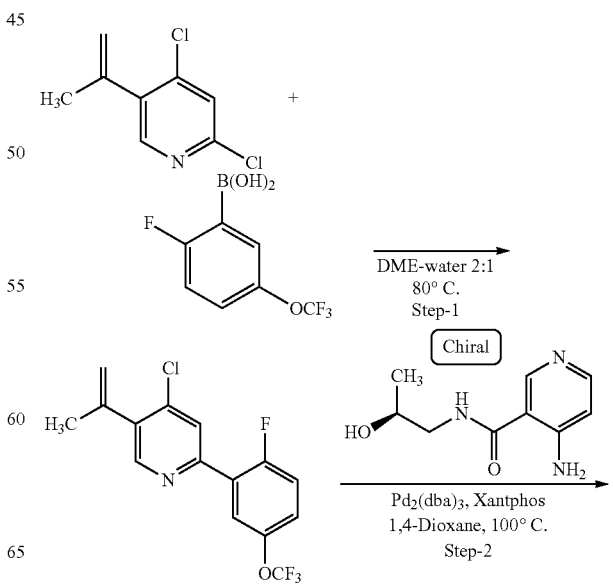

-continued

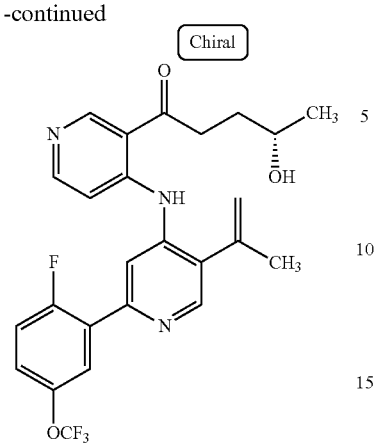

Step-1: Synthesis of 4-chloro-2-[2-fluoro-5-(trifluoromethoxy)phenyl]-5-isopropenyl-pyridine A 100 mL screw cap bottle was charged with 2,4-dichloro-5-isopropenyl-pyridine (800 mg, 4.26 mmol [4-fluoro-3-(trifluoromethoxy)phenyl]boronic acid (606 mg, 3.1 mmol) and sodium carbonate (1.3 g, 12.8 mmol) in a mixture of DME (5 mL) and water (2.5 mL) and degassed with nitrogen for 15 min. Then Pd(PPh$_3$)$_2$.Cl$_2$ (147 mg, 0.21 mmol) and again degassed with nitrogen for another 10 min. The resulting mixture was heated at 100° C. for 3 h. The reaction was monitored by LCMS. Then the reaction mixture was passed through a celite bed, diluted with water (25 mL) and extracted with EtOAc (2×50 mL). The combined organic layer was dried over anhydrous sodium sulfate and concentrated under reduced pressure to obtain the product, which was purified by chromatography to obtain 4-chloro-2-[2-fluoro-5-(trifluoromethoxy)phenyl]-5-isopropenyl-pyridine (250 mg) as an oil.

Step-2: Synthesis of 4-({2-[2-fluoro-5-(trifluoromethoxy)phenyl]-5-(prop-1-en-2-yl)pyridin-4-yl}amino)-N-[(2S)-2-hydroxypropyl]pyridine-3-carboxamide A 25 mL screw cap bottle was charged with 4-chloro-2-[2-fluoro-5-(trifluoro methoxy)phenyl]-5-isopropenyl-pyridine (250 mg, 0.84 mmol), 4-amino-N-[(2S)-2-hydroxypropyl]pyridine-3-carboxamide (180 mg, 0.92 mmol), K$_3$PO$_4$ (356 mg, 1.7 mmol) and 1,4-dioxane (10 mL) and degassed with nitrogen for 15 min. Then Xantphos (73 mg, 0.13 mmol) and Pd$_2$(dba)$_3$ (77 mg, 0.08 mmol) were added and the mixture degassed with nitrogen for 15 min. The resulting mixture was heated at 100° C. overnight. Product formation was confirmed by LCMS. The reaction mixture was passed through a celite bed and extracted with EtOAc (2×50 mL) and concentrated under reduced pressure to obtain the product that was purified with reverse phase HPLC to obtain 4-({2-[2-fluoro-5-(trifluoromethoxy)phenyl]-5-(prop-1-en-2-yl)pyridin-4-yl}amino)-N-[(2S)-2-hydroxypropyl]pyridine-3-carboxamide as a free base (15 mg). The (R) enantiomer can be synthesized utilizing (R)-2-aminobutan-1-ol in this step.

$^1$H NMR: (400 MHz, DMSO-D6): δ (ppm): 10.42 (bs, 1H), 8.86 (m, 2H), 8.5 (s, 1H), 8.4 (d, 2H), 8.0 (d, 1H), 7.90 (s, 1H), 7.58 (m, 2H), 7.40 (d, 1H), 5.44 (s, 1H), 5.20 (s, 1H) 4.78 (d, 1H), 3.80 (m, 1H), 3.18 (m, 1H), 2.06 (s, 3H), 1.07 (d, 3H).

Example 48. Preparation of Compound No. 48

Synthesis of 4-{[2-(5-chloro-2-fluorophenyl)-5-(propan-2-yl)pyridin-4-yl]amino}-N-(oxetan-3-yl)pyridine-3-carboxamide

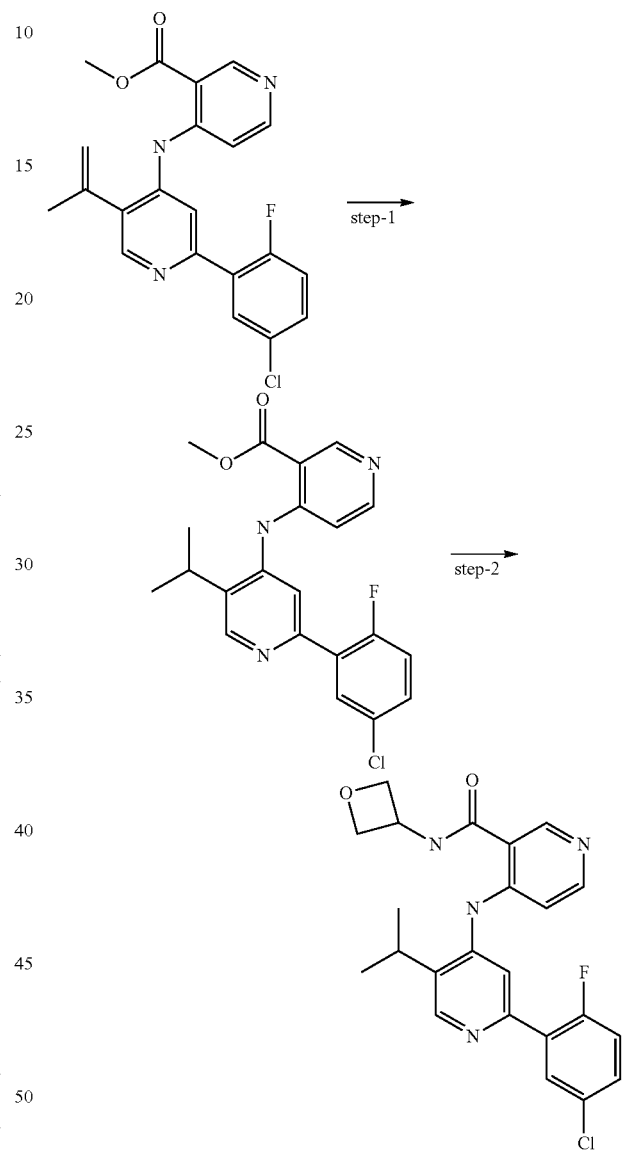

Step-1: Synthesis of methyl 4-[[2-(5-chloro-2-fluoro-phenyl)-5-isopropyl-4-pyridyl]amino]pyridine-3-carboxylate To a solution of methyl 4-[[2-(5-chloro-2-fluoro-phenyl)-5-isopropyl-4-pyridyl]amino]pyridine-3-carboxylate (398 mg, 1.0 mmol) in EtOAc (10 mL) and ethanol (5 mL) was added platinum oxide (60 mg, 0.2 mmol) and bubbled with hydrogen gas for 3 h at RT. The reaction was monitored by $^1$H NMR and TLC. The reaction mass was filtered through a celite bed and concentrated under reduced pressure to obtain the product, which was purified by chromatography (5% MeOH in DCM) to obtain methyl 4-[[2-(5-chloro-2-fluoro-phenyl)-5-isopropyl-4-pyridyl]amino]pyridine-3-carboxylate (180 mg).

Step-2: Synthesis of 4-{[2-(5-chloro-2-fluorophenyl)-5-(propan-2-yl)pyridin-4-yl]amino}-N-(oxetan-3-yl)pyridine-3-carboxamide A heterogeneous mixture of methyl 4-[[2-(5-chloro-2-fluoro-phenyl)-5-isopropyl-4-pyridyl]amino]pyridine-3-carboxylate (180 mg, 0.45 mmol) and 3-oxitane amine (1 mL) was irradiated by microwave at 120° C. for 1 h. The reaction mass became a homogenous solution. The reaction was monitored by LCMS and TLC. The reaction mass purified by chromatography (eluent: 5% MeOH in DCM) to obtain the product, which was triturated with EtOAc to obtain 4-{[2-(5-chloro-2-fluorophenyl)-5-(propan-2-yl)pyridin-4-yl] amino}-N-(oxetan-3-yl)pyridine-3-carboxamide (10 mg).

$^1$H NMR: (400 MHz, DMSO-D6): δ (ppm): 10.5 (s, 1H), 9.47 (d, 1H), 8.9 (s, 1H), 8.62 (s, 1H), 8.38 (d, 1H), 8.0 (d, 1H,) 7.8 (s, 1H), 7.55 (m, 1H), 7.40 (m, 2H), 7.30 (d, 1H), 5.0 (m, 1H), 4.8 (t, 2H), 4.60 (t, 2H), 3.10 (m, 1H), 1.24 (d, 6H).

Example 49. Preparation of Compound No. 49

Synthesis of N-[2-(5-chloro-2-fluorophenyl)-5-(propan-2-yl)pyridin-4-yl]quinolin-4-amine N-[2-(5-Chloro-2-fluoro-phenyl)-5-isopropenyl-4-pyridyl]quinolin-4-amine (100 mg, 0.257 mmol) was dissolved in EtOAc:EtOH (10 mL), and purged with $N_2$ gas for 10 min. $PtO_2$ (20 mg) was added, and the mixture now purged with $H_2$ gas for 10 min. The reaction was stirred at RT for 5 h. The progress of reaction was monitored by LCMS. After completion of reaction, the $PtO_2$ was removed by filtration, and the solvent removed under reduced pressure. The residue was purified by flash chromatography using MeOH:DCM to obtain 70 mg free base of N-[2-(5-chloro-2-fluoro-phenyl)-5-isopropyl-4-pyridyl]quinolin-4-amine.

$^1$H NMR: (Free Base, CD$_3$OD): δ (ppm): 8.65 (m, 1H), 8.50 (s, 1H), 8.25 (d, 1H), 7.95 (m, 1H), 7.85 (d, 1H), 7.75 (t, 1H), 7.60 (t, 1H), 7.50 (s, 1H), 7.40 (m, 1H), 7.20 (t, 1H), 6.80 (s, 1H), 3.45 (m, 1H), 1.19 (m, 6H).

Example 50. Preparation of Compound No. 50

Synthesis of 2-N-[2-(5-chloro-2-fluorophenyl)-5-(prop-1-en-2-yl)pyridin-4-yl]-2-N-methyl pyridine-2,4-diamine

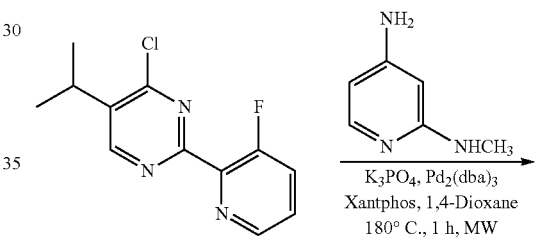

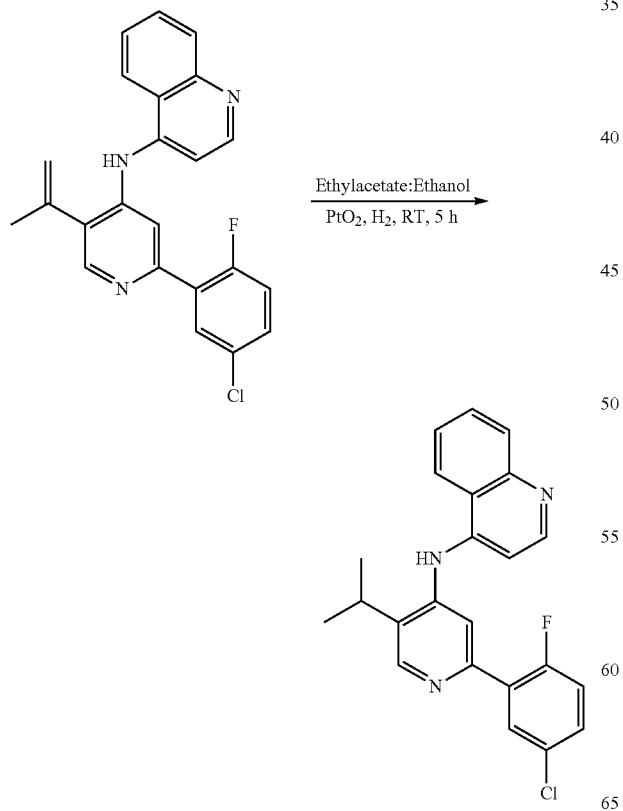

PK-1

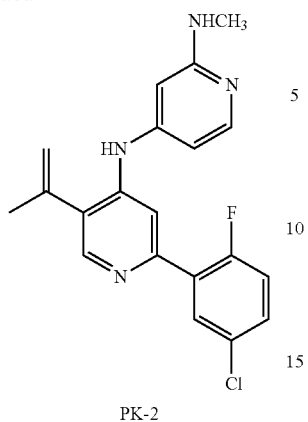

PK-2

Nitrogen gas was purged in a mixture of 4-chloro-2-(5-chloro-2-fluoro-phenyl)-5-isopropenyl-pyridine (300 mg, 1.06 mmol), N-2-methylpyridine-2,4-diamine (157 mg, 1.27 mmol) and potassium phosphate (tribasic) (449 mg, 2.12 mmol) in 1,4-dioxane (15 mL) for 15 min. Then tris(dibenzylidineacetone) dipalladium(0) (97 mg, 0.12 mmol) and Xantphos (92 mg, 0.16 mmol) were added to the reaction mixture. Nitrogen gas was purged through it for another 5 min. The reaction mixture was irradiated by microwave at 180° C. for 1 h. The reaction was monitored by TLC and LCMS. After completion of reaction, the mixture was diluted with EtOAc (100 mL) and filtered through a celite bed. The filtrate was washed with water (25 mL), and the organic layer was separated, dried over anhydrous sodium sulfate and concentrated under reduced pressure to afford a crude product which was purified by reverse phase purification to get N-2-[2-(5-chloro-2-fluoro-phenyl)-5-isopropenyl-4-pyridyl]-N-2-methyl-pyridine-2,4-diamine (Peak 1) as a semi-solid (26 mg) and N4-[2-(5-chloro-2-fluoro-phenyl)-5-isopropenyl-4-pyridyl]-N2-methyl-pyridine-2,4-diamine (Peak 2) (44 mg) as a white solid.

¹H NMR: (400 MHz, DMSO-d6): δ (ppm): 8.59 (s, 1H), 7.99 (s, 1H), 7.62 (m, 2H), 7.59 (s, 1H), 7.38 (m, 1H), 6.00 (d, 1H), 5.70 (m, 3H), 5.15 (m, 2H), 3.23 (s, 3H), 1.90 (s, 3H).

Example 51. Preparation of Compound Nos. 51, 51a and 51b

Synthesis of 4-{[2-(2,5-difluorophenyl)-5-(prop-1-en-2-yl)pyridin-4-yl]amino}-N-[(2S)-2-hydroxypropyl]pyridine-3-carboxamide

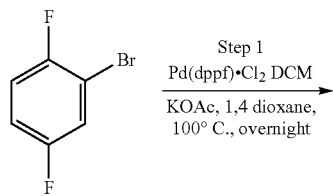

Step 1
Pd(dppf)·Cl₂ DCM
KOAc, 1,4 dioxane, 100° C., overnight

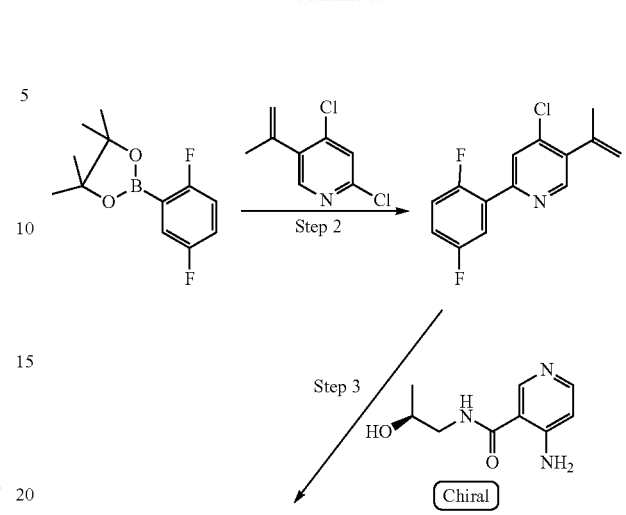

Step-1: Synthesis of 2-(2,5-difluorophenyl)-4,4,5,5-tetramethyl-1,3,2-dioxaborolane A 250 mL screw cap bottle was charged with 2-bromo-1,4-difluoro-benzene (1.0 g, 5.18 mmol), bis(pinacolato)diboroncarbonate and potassium acetate (1.52 g, 15.54 mmol) in 1,4-dioxane (20 mL) and degassed with nitrogen for 20 min. Then Pd(dppf)Cl₂.DCM (634 mg, 0.77 mmol) was added, and the mixture again degassed with nitrogen for another 10 min. The resulting mixture was heated at 100° C. overnight. The reaction was monitored by TLC and LCMS. The reaction mixture was passed through a celite bed, diluted with water (100 mL) and extracted with EtOAc (3×50 mL) and washed with water (2×50 mL). The combined organic layer was dried over anhydrous sodium sulfate and concentrated under reduced pressure to obtain the product, which was purified by chromatography to obtain 2-(2,5-difluorophenyl)-4,4,5,5-tetramethyl-1,3,2-dioxaborolane (500 mg) as a semisolid.

Step-2: Synthesis of 4-chloro-2-(2,5-difluorophenyl)-5-isopropenyl-pyridine

A 100 mL screw cap bottle was charged with 2,4-dichloro-5-isopropenyl-pyridine (1.5 g, 7.97 mmol) and to is was added 2-(2,5-difluorophenyl)-4,4,5,5-tetramethyl-1,3,2-dioxaborolane (2.29 mg, 9.57 mmol) and sodium carbonate (2.53 g, 23.91 mmol) in a mixture of DME (15 mL) and water (7 mL), and the mixture degassed with nitrogen for 20 min. Then Pd(PPh$_3$)$_2$.Cl$_2$ (279 mg, 0.398 mmol) was added and the mixture again degassed with nitrogen for another 10 min. The resulting mixture was heated at 100° C. for 3 h. The reaction was monitored by TLC and LCMS. Then the reaction mixture was passed through a celite bed, diluted with water (50 mL) and extracted with EtOAc (4×150 mL). The combined organic layer was washed with water (2×150 mL), dried over anhydrous sodium sulfate and concentrated under reduced pressure to obtain the product, which was purified with combiflash chromatography to obtain 4-chloro-2-(2,5-difluoro phenyl)-5-isopropenyl-pyridine (1.0 g) as a semi solid.

Step-3: Synthesis of 4-{[2-(2,5-difluorophenyl)-5-(prop-1-en-2-yl)pyridin-4-yl]amino}-N-[(2S)-2-hydroxypropyl]pyridine-3-carboxamide A 30 mL microwave vial was charged with 4-chloro-2-(2,5-difluorophenyl)-5-isopropenyl-pyridine (500 mg, 1.886 mmol), 4-amino-N-[(2S)-2-hydroxypropyl]pyridine-3-carboxamide (400 mg, 2.07 mmol), K$_3$PO$_4$ (797 mg, 3.76 mmol) and 1,4-dioxane (10 mL) and the mixture degassed with nitrogen for 20 min. Then Xantphos (163 mg, 0.28 mmol) and Pd$_2$(dba)$_3$ (172 mg, 0.188 mmol) were added and degassed with nitrogen for a further 10 min. The resulting mixture was heated at 140° C. in a microwave. Product formation was confirmed by TLC and LCMS. The reaction mixture was passed through a celite bed, diluted with water (50 mL), extracted with EtOAc (2×100 mL) and washed with water (2×50 mL). The organic layer was dried over anhydrous sodium sulfate, and concentrated under reduced pressure to obtain the product that was purified by reverse phase HPLC to obtain 4-{[2-(2,5-difluorophenyl)-5-(prop-1-en-2-yl)pyridin-4-yl]amino}-N-[(2S)-2-hydroxypropyl]pyridine-3-carboxamide as the free base (70 mg). The (R) enantiomer can be synthesized utilizing the (R)-enantiomeric reagent in this step.

$^1$H NMR: (400 MHz, DMSO-D6): δ (ppm): 10.45 (bs, 1H), 8.82 (m, 2H), 8.45 (s, 1H), 8.39 (d, 1H), 7.82 (s, 1H), 7.78 (bs, 1H), 7.42 (m, 2H), 7.39 (m, 1H), 5.43 (s, 1H), 5.20 (s, 1H), 4.78 (d, 1H), 3.78 (m, 1H), 3.19 (m, 2H), 2.06 (s, 3H), 1.12 (d, 3H).

Example 52. Preparation of Compound Nos. 52, 52a and 52b

Synthesis of 4-{[2-(2,5-difluorophenyl)-5-(propan-2-yl)pyridin-4-yl]amino}-N-[(2S)-2-hydroxypropyl]pyridine-3-carboxamide

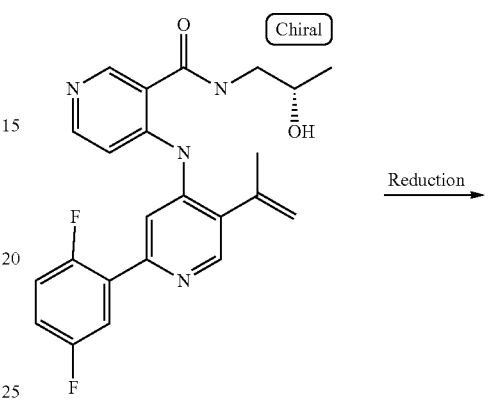

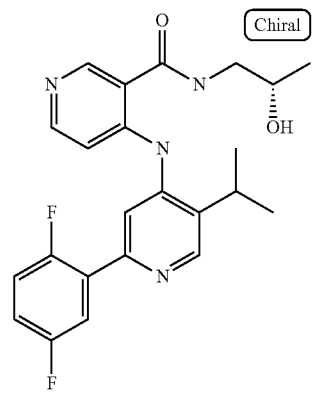

To a solution of 4-[[2-(2,5-difluorophenyl)-5-isopropenyl-4-pyridyl]amino]-N-[(2S)-2-hydroxypropyl]pyridine-3-carboxamide (50 mg, 0.117 mmol) in EtOAc (5 mL) and ethanol (5 mL) was added platinum oxide (20 mg, 0.2 mmol) and bubbled with hydrogen gas for 4 h at RT. The reaction was monitored by $^1$H NMR and TLC. The reaction mass was filtered through a celite bed and concentrated under reduced pressure to obtain the product, which was purified by chromatography (5% MeOH in DCM) to obtain 4-[[2-(2,5-difluorophenyl)-5-isopropyl-4-pyridyl]amino]-N-[(2S)-2-hydroxy propyl]pyridine-3-carboxamide (20 mg). The (R) enantiomer can be synthesized utilizing (R)-2-aminobutan-1-ol in this step.

$^1$H NMR: (400 MHz. CDCl$_3$): δ (ppm): 10.39 (s, 1H), 8.70 (s, 1H), 8.62 (s, 1H), 8.39 (d, 1H), 7.79 (m, 2H), 7.28 (d, 1H,) 7.15 (m, 2H), 6.98 (bs, 1H), 4.15 (m, 1H), 3.71 (m, 1H), 3.31 (m, 1H), 3.21 (m, 1H), 1.40 (d, 6H), 1.21 (d, 3H).

Example 53. Preparation of Compound Nos. 53, 53a and 53b

Synthesis of 4-({2-[2-fluoro-5-(trifluoromethyl)phenyl]-5-(prop-1-en-2-yl)pyridin-4-yl}amino)-N-[(2S)-2-hydroxypropyl]pyridine-3-carboxamide

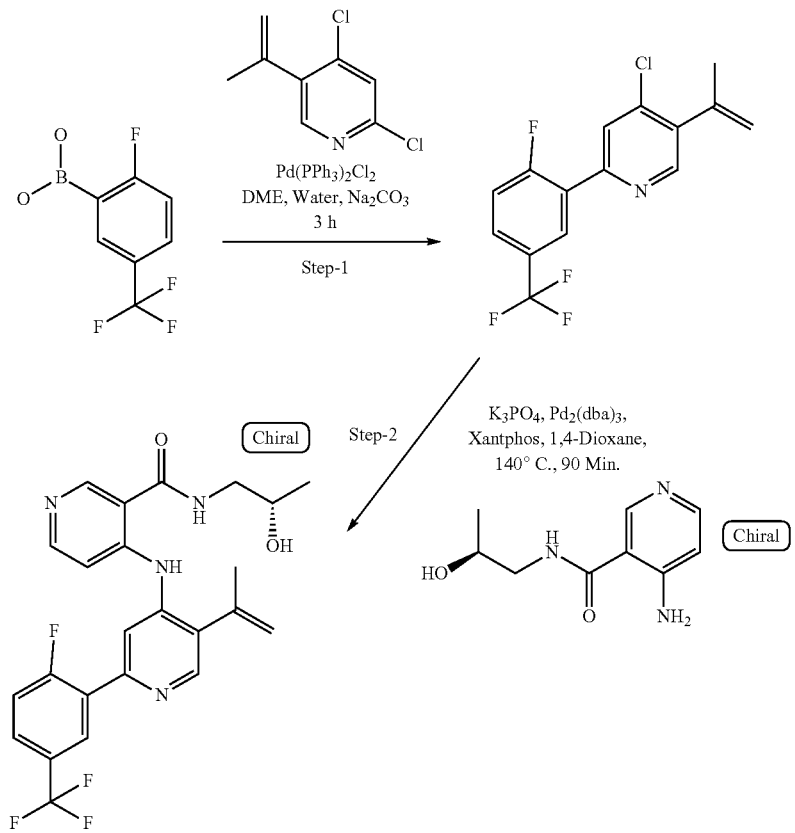 [SMILES: OB(O)c1cc(C(F)(F)F)ccc1F ; C=C(C)c1cnc(Cl)cc1Cl ; C=C(C)c1cnc(-c2cc(C(F)(F)F)ccc2F)cc1Cl ; C=C(C)c1cnc(-c2cc(C(F)(F)F)ccc2F)cc1Nc1ccncc1C(=O)NC[C@H](C)O ; C[C@H](O)CNC(=O)c1cnccc1N]

Step-1: Synthesis of 4-chloro-2-[2-fluoro-5-(trifluoromethyl)phenyl]-5-isopropenyl-pyridine A 100 mL screw cap bottle was charged with 2,4-dichloro-5-isopropenyl-pyridine (1.0 g, 5.31 mmol), [2-fluoro-5-(trifluoromethyl)phenyl]boronic acid (1.65 g, 7.97 mmol) and sodium carbonate (1.68 g, 15.93 mmol) in a mixture of DME (10 mL) and water (5 mL), and the mixture degassed with nitrogen for 20 min. Then Pd(PPh)$_2$.Cl$_2$ (186 mg, 0.265 mmol) and again degassed with nitrogen for another 10 min. The resulting mixture was heated at 100° C. for 3 h. The reaction was monitored by TLC and LCMS. Then the reaction mixture was passed through a celite bed, diluted with water (50 mL) and extracted with EtOAc (3×100 mL). The combined organic layer was washed with water (2×150 mL) dried over anhydrous sodium sulfate and concentrated under reduced pressure to obtain the product that was purified by chromatography to obtain 4-chloro-2-[2-fluoro-5-(trifluoromethyl)phenyl]-5-isopropenyl-pyridine (500 mg) as a semi solid.

Step-2: Synthesis of 4-({2-[2-fluoro-5-(trifluoromethyl)phenyl]-5-(prop-1-en-2-yl)pyridin-4-yl}amino)-N-[(2S)-2-hydroxypropyl]pyridine-3-carboxamide A 30 mL microwave vial was charged with 4-chloro-2-[2-fluoro-5-(trifluoromethyl) phenyl]-5-isopropenyl-pyridine (500 mg, 1.58 mmol) and 4-amino-N-[(2S)-2-hydroxypropyl]pyridine-3-carboxamide (340 mg, 1.74 mmol) and K$_3$PO$_4$ (669 mg, 3.16 mmol) and 1,4-dioxane (5 mL) and degassed with nitrogen for 20 min. Then Xantphos (137 mg, 0.237 mmol) and Pd$_2$(dba)$_3$ (144 mg, 0.158 mmol) were added and degassed with nitrogen for a further 10 min. The resulting mixture was heated at 140° C. by microwave. Product formation was confirmed by TLC and LCMS. Then the reaction mixture was passed through a celite bed and diluted with water (50 mL), extracted with EtOAc (2×100 mL) and washed with water (2×50 mL). The organic layer was dried over anhydrous sodium sulfate and concentrated under reduced pressure to obtain the product that was purified by HPLC to obtain 4-({2-[2-fluoro-5-(trifluoromethyl)phenyl]-5-(prop-1-en-2-yl)pyridin-4-yl}amino)-N-[(2S)-2-hydroxypropyl]pyridine-3-carboxamide as free base (30 mg). The (R) enantiomer can be synthesized utilizing (R)-2-aminobutan-1-ol in this step.

$^1$H NMR: (400 MHz, DMSO-D6): δ (ppm): 10.45 (bs, 1H), 8.82 (m, 2H), 8.45 (s, 1H), 8.39 (d, 1H), 8.32 (d, 1H), 7.82 (bs, 2H), 7.61 (t, 1H), 7.41 (d, 1H), 5.42 (s, 1H), 5.20 (s, 1H), 4.78 (d, 1H), 3.79 (m, 1H), 3.19 (m, 2H), 2.06 (s, 3H), 1.12 (d, 3H).

Example 54. Preparation of Compound No. 54

Synthesis of 4-{[2-(5-chloro-2-fluorophenyl)-5-cyclopropylpyridin-4-yl]amino}-N-(1,3-dihydroxy-propan-2-yl)pyridine-3-carboxamide

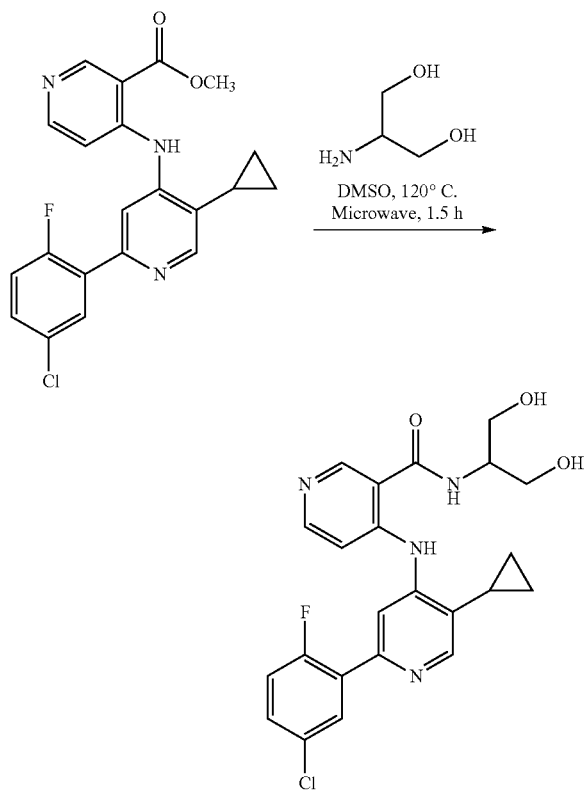

Methyl 4-[[2-(5-chloro-2-fluoro-phenyl)-5-cyclopropyl-4-pyridyl]amino]pyridine-3-carboxylate (100 mg, 0.251 mmol) and 2-aminopropane-1,3-diol (92 mg, 1.00 mmol) were dissolved in 1 mL of DMSO and heated at 120° C. in a microwave for 1.5 h. Product formation was confirmed by LCMS. Then the reaction mixture was diluted with water (50 mL), and the resultant precipitate filtered and dried. This crude product was purified by chromatography to obtain 20 mg of 4-[[2-(5-chloro-2-fluoro-phenyl)-5-cyclopropyl-4-pyridyl]amino]-N-[2-hydroxy-1-(hydroxymethyl)ethyl]pyridine-3-carboxamide.

$^1$H NMR: (400 MHz, DMSO-d6): δ (ppm): 10.78 (bs, 1H), 8.85 (s, 1H), 8.48 (s, 1H), 8.40 (m, 2H), 7.98 (d, 1H), 7.80 (s, 1H), 7.55-7.42 (m, 2H), 7.40 (t, 1H), 4.70 (t, 2H), 4.00 (m, 1H), 3.58 (m, 4H), 1.80 (m 1H), 1.05 (m, 2H), 0.75 (n, 2H).

Example P1. Preparation of Compound Nos. 2.1 to 2.35

Compound nos. 2.1 to 2.35 can be prepared according to the methods presented herein using appropriately functionalized starting materials and reagents.

Example B1: p-SMAD2 Inhibition

Compounds of the invention were screened for inhibition of p-SMAD2, using Western Blot Analysis, using the following protocol. On Day 1, MDA-MB-231 cells were seeded at 150,000 cells/well in a 12-well plate using DMEM plus antibiotics (Pen/Strepto) plus FBS 10%. On Day 2, the medium was changed to a serum-free version (DMEM plus Ab) and left overnight. On Day 3, the cells were treated with Compounds of the invention for 30 min (pre-treatment) at two concentrations of 0.1 µM and 0.5 µM (prepared with serum-free medium). Then. TGFβ was added to a final concentration of 2 ng/mL for 1.5 h.

Western Blot Analysis: Lysis buffer plus proteases and phosphatise inhibitors were added to the cells (100 µL), then the cells were collected with a cell scraper and placed into an Eppendorf tube. The sample was sonicated for 3 min, then centrifuged for 15 min at 13,000 rpm at 4° C. The proteins were quantified with the BCA Protein Assay Kit (Pierce, #23225), and SDS-PAGE electrophoresis with 10% acrylamide gel was used to separate the samples (20 µg of protein loaded). The proteins were transferred in a PDVF membrane overnight at 50 mA and 4° C., then the membrane was blocked with 5% milk solution for 1 h. The primary antibody was added (p-SMAD2, cell signalling #3108: SMAD2, cell signalling #3103: or β-Actin, Sigma #A5441) at 4° C. overnight, or for 2 h at RT. The membrane was washed with TBS-TWEEN® (0.1%) three times over 10 min. The second antibody was added for h at RT, and then the membrane washed again with TBS-TWEEN® (0.1%) for 10 min. Signal development was performed using an ECL Western Blotting Substrate (Pierce #32106), and the image acquired using the Gel Logic 6000 Pro. Quantification was performed using ImageJ software, and the average % inhibition was obtained and presented in Table B1.

TABLE B1

Inhibition of p-SMAD (samples run in triplicate)

| Compound Number | Average p-SMAD2 inhibition @ 0.1 µM (% Inh) | Average p-SMAD2 inhibition @ 0.5 µM (% Inh) |
| --- | --- | --- |
| CE-1 | 15.67 | 17.00 |
| 1a | 31.33 | 64.33 |
| 2a | 26.33 | 77.67 |
| 3a | 45.67 | 78.00 |
| 4a | 72.67 | 99.67 |
| 5a | 14.33 | 41.33 |
| 6a | 53.67 | 98.33 |
| 7a | 74.33 | 99.33 |
| 7b | 36.33 | 78.67 |
| 8 | 58.67 | 94.33 |
| 9 | 6.00 | 12.67 |
| 10a | 0 | 64.33 |
| 11a | 44.67 | 96.00 |
| 12a | 64.33 | 93.00 |
| 13a | 59.00 | 93.67 |
| 14 | 45.00 | 92.33 |
| 15 | 80.33 | 97.33 |
| 16a | 58.33 | 88.00 |
| 17a | 25.33 | 81.67 |
| 18 | 31.33 | 82.67 |
| 19 | 74.67 | 93.00 |
| 20a | 0 | 3.67 |
| 21a | 4.67 | 7.67 |
| 22 | 50.00 | 93.67 |
| 23a | 46.33 | 93.67 |
| 24a | 17.00 | 68.33 |
| 25a | 15.33 | 18.67 |
| 25b | 14.33 | 12.67 |
| 26 | 64.00 | 89.00 |
| 27 | 29.33 | 81.33 |
| 28 | 2.33 | 51.33 |
| 29 | 58.00 | 67.67 |
| 30 | 59.67 | 70.33 |

Example B2: In Vitro Kinase Assay—Inhibition of ALK1/2/3/4/5/6 Kinases

Compound of the invention were screened in an in vitro kinase assay against several members of the TGFβ family of Ser/Thr kinases. The kinases tested were ALK1 (ACVRL1), ALK2 (ACVR1), ALK3 (BMPR1A), ALK4 (ACVR1B), ALK5 (TGFBR1), and ALK6 (BMPR1B). Standard kinase testing conditions and techniques were employed. For each case, specific kinase/substrate pairs along with required cofactors were prepared in reaction buffer. Compound of the invention were delivered into the reaction, followed 15-20 min later by addition of a mixture of ATP and $^{33}$P ATP to a final concentration of 10 μM. Reactions were carried out at RT for 120 min, followed by spotting of the reactions onto P81 ion exchange filter paper. Unbound phosphate was removed by extensive washing of filters in 0.75% phosphoric acid. Kinase activity data was expressed as the percent of remaining kinase activity in test samples compared to vehicle. $IC_{50}$ values were generated from activity values performed at multiple concentrations, and the results are presented in Table B2.

TABLE B2

| | In vitro Kinase Assay | | | | | |
|---|---|---|---|---|---|---|
| Compound Number | Inhibition of ALK1 ($IC_{50}$ μM) | Inhibition of ALK2 ($IC_{50}$ μM) | Inhibition of ALK3 ($IC_{50}$ μM) | Inhibition of ALK4 ($IC_{50}$ μM) | Inhibition of ALK5 ($IC_{50}$ μM) | Inhibition of ALK6 ($IC_{50}$ μM) |
| CE-1 | >100 | >100 | >100 | >100 | >100 | >100 |
| 1a | >100 | >100 | >100 | 93.2 | 0.25 | >100 |
| 2a | 10 | >100 | >100 | 0.0325 | 0.0204 | >100 |
| 3a | 8.41 | >100 | >100 | 0.0315 | 0.0452 | >100 |
| 4a | 3.44 | 10.6 | >100 | 0.0424 | 0.0281 | — |
| 6a | 5.01 | 10.4 | >100 | 0.0086 | 0.0157 | — |
| 7a | 6.57 | 10.9 | >100 | 0.0130 | 0.0162 | — |
| 7b | 16.50 | >100 | >100 | 0.1710 | 0.0539 | >100 |
| 8 | >100 | >100 | >100 | 0.5020 | 0.0992 | — |
| 11a | 6.75 | >100 | >100 | 0.0868 | 0.0335 | — |
| 12a | 1.53 | 9.97 | >100 | 0.0304 | 0.0175 | — |
| 13a | 9.12 | >100 | >100 | 0.0235 | 0.0715 | — |
| 14 | 5.85 | >100 | >100 | 0.0451 | 0.0239 | — |
| 15 | 4.59 | 11.4 | 15.4 | 0.0117 | 0.0155 | — |
| 16a | 7.3 | >1000 | >1000 | 0.1140 | 0.0422 | >1000 |
| 17a | 4.67 | >1000 | >1000 | 0.0401 | 0.0508 | >1000 |
| 18 | 6.92 | >1000 | >1000 | 0.1050 | 0.0345 | >1000 |
| 19 | 2.13 | >1000 | >1000 | 0.0110 | 0.0068 | >1000 |
| 20a | >100 | >1000 | >1000 | >1000 | >100 | >1000 |
| 21a | >100 | >1000 | >1000 | >1000 | >100 | >1000 |
| 22 | 7.29 | >1000 | >1000 | 0.0567 | 0.0247 | >1000 |
| 23a | 5.67 | >100 | >100 | 0.0331 | 0.0169 | >100 |
| 24a | >100 | >100 | >100 | 0.2300 | 0.0653 | >100 |
| 25a | >100 | >100 | >100 | >100 | 2.8000 | >100 |
| 25b | >100 | >100 | >100 | 5.02 | 0.9880 | >100 |
| 26 | 5.20 | >100 | >100 | 0.0115 | 0.0103 | >100 |
| 27 | 13.10 | >100 | >100 | 0.0402 | 0.0281 | >100 |
| 28 | >100 | >1000 | >1000 | 1.1000 | 0.5510 | >1000 |
| 29 | 8.20 | 60.60 | >10 | 0.0105 | 0.0164 | 15.30 |
| 30 | 5.90 | 73.00 | >10 | 0.0237 | 0.0264 | 13.50 |
| 31 | >10 | >10 | >10 | 0.0048 | 0.0105 | >10 |
| 32 | 2.54 | 5.84 | 333 | 0.0027 | 0.0061 | >10 |
| 33 | >10 | >10 | >10 | 0.0896 | 0.0788 | >10 |
| 34 | >10 | >10 | >10 | 0.1490 | 0.0773 | >10 |
| 35 | 1.94 | 5.45 | 871 | 0.0037 | 0.0082 | 9.62 |
| 36 | 3.7 | 8.93 | >10 | 0.0037 | 0.0177 | >10 |

Example B3: Pharmacokinetics and Bioavailability for Compounds of the Invention

The pharmacokinetics and bioavailability of compounds in male mice were determined after a single dose, administered either intravenously (2 mg/kg) or orally (10 mg/kg). Compounds were formulated at 1 mg/mL in 50% PEG-400 or 20% HPβCD. Parameters were generated using WinNonlin non-compartment analysis with no weighting, and are presented in Tables B3a and B3b.

TABLE B3a

Intravenous Administration, 2 mg/kg, n = 3 mice/timepoint,

| Compound No. | $C_{max}$ (μM) | $AUC_{last}$ (μM*h) | Terminal $t_{1/2}$ (h) | CL (L/h/kg) | V (L/kg) |
|---|---|---|---|---|---|
| 2a | 0.544 | 1.19 | 1.80 | 1.60 | 4.14 |
| 3a | 0.602 | 2.56 | 3.86 | 0.77 | 1.29 |
| 8 | 1.24 | 0.709 | 1.68 | 6.15 | 14.9 |
| 11a | 3.61 | 3.15 | 1.02 | 1.48 | 2.17 |
| 12a | 7.15 | 3.69 | 1.63 | 1.19 | 2.80 |
| 13a | 1.42 | 1.56 | 2.09 | 1.24 | 3.72 |
| 14 | 3.01 | 1.57 | 0.987 | 2.71 | 3.86 |
| 16a | 3.40 | 4.41 | 0.655 | 1.02 | 0.967 |
| 19 | 0.52 | 1.19 | 6.12 | 2.39 | 21.1 |
| 22 | 2.46 | 3.77 | 1.53 | 1.10 | 2.43 |
| 23a | 2.56 | 1.11 | 0.607 | 3.96 | 3.47 |
| 26 | 3.00 | 1.76 | 1.62 | 2.66 | 6.21 |

TABLE B3b

Oral Administration, 10 mg/kg

| Compound No. | $C_{max}$ (μM) | $T_{max}$ (h) | $AUC_{last}$ (μM*h) | Terminal $t_{1/2}$ (h) | Bioavailability |
|---|---|---|---|---|---|
| 2a | 1.57 | 0.5 | 5.25 | 2.57 | 88% |
| 3a | 1.65 | 0.25 | 10.5 | 3.85 | 82% |
| 8 | 1.06 | 0.25 | 1.31 | 1.26 | 36.9% |
| 11a | 3.48 | 0.25 | 9.79 | 1.65 | 62.2% |
| 12a | 4.28 | 0.5 | 14.5 | 1.72 | 78.3% |
| 13a | 1.60 | 0.25 | 5.64 | 2.85 | 72.3% |
| 14 | 1.88 | 0.5 | 2.54 | 1.60 | 32.5% |
| 16a | 3.42 | 0.5 | 7.50 | 2.36 | 34.1% |
| 19 | 0.198 | 1 | 0.927 | 4.19 | 15.5% |
| 22 | 7.07 | 0.5 | 16.2 | 2.09 | 86.6% |
| 23a | 0.612 | 0.25 | 0.907 | 0.822 | 16.4% |
| 26 | 1.29 | 0.5 | 2.36 | 1.66 | 26.9% |

Plasma and brain concentrations of compounds at 0.5 and 1 h were also analyzed and are presented in Tables B3c and B3d.

TABLE B3c

Plasma and brain concentrations (mg/mL)

| Compound No. | Time (h) | IV (2 mg/kg) | | | PO (10 mg/kg) | | |
|---|---|---|---|---|---|---|---|
| | | Plasma | Brain | % Brain | Plasma | Brain | % Brain |
| 2a | 0.5 | 310 | 73.2 | 24 | 1570 | 202 | 13 |
| | 1 | 366 | 82.4 | 23 | 905 | 114 | 13 |
| 3a | 0.5 | 432 | 173 | 40 | 1280 | 305 | 24 |
| | 1 | 365 | 168 | 46 | 1250 | 406 | 32 |

TABLE B3d

Plasma and brain concentrations (μM).

| Compound No. | Route | Time (h) | Brain Concentration (μM) | Plasma Concentration μM | % of Plasma |
|---|---|---|---|---|---|
| 16a | IV | 0.5 | 0.048 | 3.04 | 1.58% |
| | | 1 | 0.019 | 1.23 | 1.52% |
| | PO | 0.5 | 0.048 | 3.42 | 1.40% |
| | | 1 | 0.025 | 1.69 | 1.50% |
| 19 | IV | 0.5 | 0.004 | 0.280 | 1.49% |
| | | 1 | 0.003 | 0.183 | 1.80% |
| | PO | 0.5 | BLQ | 0.164 | na |
| | | 1 | BLQ | 0.198 | na |
| 22 | IV | 0.5 | 0.007 | 1.69 | 0.41% |
| | | 1 | 0.005 | 0.967 | 0.48% |
| | PO | 0.5 | 0.020 | 7.07 | 0.29% |
| | | 1 | 0.015 | 3.53 | 0.43% |

It is understood that the foregoing examples and embodiments described above are for illustrative purposes only and that various modifications or changes in light thereof will be suggested to persons skilled in the art and are to be included within the spirit and purview of this application and the scope of the appended claims.

The invention claimed is:

1. A method of providing a first or a second line therapy for treating (a) a breast cancer in an individual diagnosed with the breast cancer or (b) a prostate cancer in an individual diagnosed with the prostate cancer, comprising administering to the individual an effective amount of

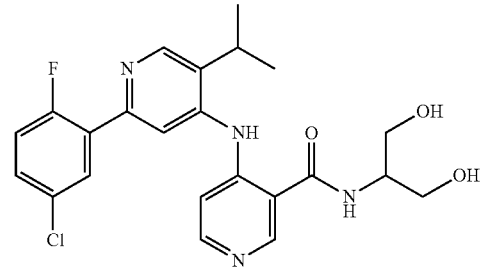 [SMILES: CC(C)c1cnc(-c2cc(Cl)ccc2F)cc1Nc1ccncc1C(=O)NC(CO)CO]

4-(2-(5-chloro-2-fluorophenyl)-5-isopropylpyridin-4-ylamino)-N-(1,3-dihydroxypropan-2-yl)nicotinamide or a pharmaceutically acceptable salt thereof, thereby decreasing number of cancer cells, inhibiting cancer cell growth and/or proliferation, or increasing apoptosis of cancer cells.

2. The method of claim 1, wherein the individual is diagnosed with the breast cancer.

3. The method of claim 2, wherein the breast cancer is selected from the group consisting of ER negative breast carcinoma, ER positive breast carcinoma, primary breast ductal carcinoma, mammary adenocarcinoma, ER positive mammary ductal carcinoma, ER negative mammary ductal carcinoma, HER2 positive mammary ductal carcinoma, HER2 positive breast cancer, luminal breast cancer, triple negative breast cancer (TNBC), and unclassified breast cancer.

4. The method of claim 3, wherein the breast cancer is TNBC, and the TNBC is selected from the group consisting of basal-like TNBC, mesenchymal TNBC, mesenchymal stem-like TNBC, immunomodulatory TNBC, and a luminal androgen receptor TNBC.

5. The method of claim 3, wherein the breast cancer is a luminal breast cancer.

6. The method of claim 1, wherein the individual is diagnosed with the prostate cancer.

7. The method of claim 6, wherein the prostate cancer is prostate adenocarcinoma.

8. The method of claim 1, wherein the treating comprises a reduction of tumor size.

9. The method of claim 1, wherein the treating comprises a slowing of tumor growth.

10. The method of claim 1, wherein the treating comprises slowing of metastasis.

11. The method of claim 1, further comprising administering to the individual a second cancer therapy.

12. The method of claim 11, wherein the second cancer therapy comprises a therapy selected from the group consisting of surgery, radiation, and chemotherapy.

13. The method of claim 12, wherein the second cancer therapy is a chemotherapy.

14. The method of claim 13, wherein the individual is diagnosed with the breast cancer.

15. The method of claim 14, wherein the breast cancer is a luminal breast cancer.

16. The method of claim 14, wherein the breast cancer is TNBC.

17. The method of claim 13, wherein the individual is diagnosed with the prostate cancer.

18. The method of claim 17, wherein the prostate cancer is prostate adenocarcinoma.

19. The method of claim 1, wherein the pharmaceutically acceptable salt is a hydrochloride salt.

* * * * *